(12) United States Patent
Chintakindi et al.

(10) Patent No.: US 12,002,068 B2
(45) Date of Patent: Jun. 4, 2024

(54) DATA PROCESSING SYSTEM WITH MACHINE LEARNING ENGINE TO PROVIDE OUTPUT GENERATION FUNCTIONS

(71) Applicant: Allstate Insurance Company, Northbrook, IL (US)

(72) Inventors: Sunil Chintakindi, Menlo Park, CA (US); Timothy W. Gibson, Barrington, IL (US); Howard Hayes, Glencoe, IL (US); Regina Madigan, Mountain View, CA (US); Soton Ayodele Rosanwo, Chicago, IL (US); Juan Ortiz-Zabala, Buffalo Grove, IL (US)

(73) Assignee: ALLSTATE INSURANCE COMPANY, Northbrook, IL (US)

( * ) Notice: Subject to any disclaimer, the term of this patent is extended or adjusted under 35 U.S.C. 154(b) by 745 days.

(21) Appl. No.: 16/582,611

(22) Filed: Sep. 25, 2019

(65) Prior Publication Data
US 2020/0104744 A1 Apr. 2, 2020

Related U.S. Application Data

(60) Provisional application No. 62/845,560, filed on May 9, 2019, provisional application No. 62/836,114, filed (Continued)

(51) Int. Cl.
G06Q 30/0207 (2023.01)
A61B 5/024 (2006.01)
(Continued)

(52) U.S. Cl.
CPC ......... *G06Q 30/0239* (2013.01); *A61B 5/024* (2013.01); *G06F 16/337* (2019.01);
(Continued)

(58) Field of Classification Search
CPC .......... G06Q 30/0239; G06Q 30/0222; G06Q 30/0236; G06Q 30/0269; G06Q 30/0255;
(Continued)

(56) References Cited

U.S. PATENT DOCUMENTS

| 5,797,134 A | 8/1998 | McMillan et al. |
| 5,809,478 A | 9/1998 | Greco et al. |

(Continued)

FOREIGN PATENT DOCUMENTS

| CN | 103941037 A | 7/2014 |
| EP | 2993619 A1 | 3/2016 |

(Continued)

OTHER PUBLICATIONS

Mar. 9, 2021—U.S. Final Office Action—U.S. Appl. No. 16/582,544.
(Continued)

*Primary Examiner* — Mohamed Barakat
*Assistant Examiner* — Rufus C Point
(74) *Attorney, Agent, or Firm* — Polsinelli PC

(57) ABSTRACT

Methods, computer-readable media, systems, and/or apparatuses for providing offer and output generation functions are provided. For instance, a request for an output may be received by a device. In response, user physical trait data, pre-stored data, location data, and the like, may be extracted and received from a plurality of sources. Machine learning may be used to analyze the data to predict one or more factors associated with the user and the output or offer may be generated based on the predicted factors.

20 Claims, 71 Drawing Sheets

Related U.S. Application Data on Apr. 19, 2019, provisional application No. 62/738,460, filed on Sep. 28, 2018, provisional application No. 62/738,422, filed on Sep. 28, 2018.

(51) Int. Cl.
| | |
|---|---|
| *G06F 16/335* | (2019.01) |
| *G06F 21/31* | (2013.01) |
| *G06F 21/32* | (2013.01) |
| *G06N 20/00* | (2019.01) |
| *G06Q 30/0251* | (2023.01) |
| *G16H 10/60* | (2018.01) |
| *H04W 4/029* | (2018.01) |

(52) U.S. Cl.
CPC .............. *G06F 21/31* (2013.01); *G06F 21/32* (2013.01); *G06N 20/00* (2019.01); *G06Q 30/0222* (2013.01); *G06Q 30/0236* (2013.01); *G06Q 30/0269* (2013.01); *G16H 10/60* (2018.01); *H04W 4/029* (2018.02); *G06Q 30/0255* (2013.01); *G06Q 30/0261* (2013.01)

(58) Field of Classification Search
CPC ........... G06Q 30/0261; G06Q 30/0611; G06Q 40/08; A61B 5/024; A61B 2560/0242; A61B 2562/0219; A61B 2562/0247; A61B 5/0022; A61B 5/02; A61B 5/1112; A61B 5/163; A61B 5/18; A61B 5/6898; A61B 5/7275; G06F 16/337; G06F 21/31; G06F 21/32; G06N 20/00; G16H 10/60; G16H 20/00; G16H 50/30; H04W 4/029; H04W 4/40; H04W 4/021; H04W 4/38

See application file for complete search history.

(56) References Cited

U.S. PATENT DOCUMENTS

| | | | |
|---|---|---|---|
| 8,086,523 | B1 | 12/2011 | Palmer |
| 8,280,752 | B1 | 10/2012 | Cripe et al. |
| 8,332,242 | B1 | 12/2012 | Medina, III |
| 8,332,244 | B1 | 12/2012 | Karam et al. |
| 8,560,436 | B2 | 10/2013 | Ingram et al. |
| 8,620,785 | B1 | 12/2013 | Wilks et al. |
| 8,660,864 | B2 | 2/2014 | Krause et al. |
| 8,838,498 | B2 | 9/2014 | Ross |
| 8,854,199 | B2 | 10/2014 | Cook et al. |
| 8,996,234 | B1 | 3/2015 | Tamari et al. |
| 9,141,995 | B1 | 9/2015 | Brinkmann et al. |
| 9,390,452 | B1 | 7/2016 | Biemer et al. |
| 9,454,786 | B1 | 9/2016 | Srey et al. |
| 9,483,795 | B1 | 11/2016 | Warden et al. |
| 9,754,424 | B2 | 9/2017 | Ling et al. |
| 9,773,281 | B1 | 9/2017 | Hanson |
| 9,818,154 | B1 | 11/2017 | Wilbert et al. |
| 9,830,663 | B2 | 11/2017 | Roberts et al. |
| 9,932,033 | B2 | 4/2018 | Slusar et al. |
| 9,984,419 | B1 | 5/2018 | Manzella et al. |
| 9,984,420 | B1 | 5/2018 | Manzella et al. |
| 9,996,811 | B2 | 6/2018 | Matus et al. |
| 10,140,199 | B1 | 11/2018 | Rugel et al. |
| 10,735,411 | B1 | 8/2020 | Hardt et al. |
| 2007/0016488 | A1 | 1/2007 | Ulenas |
| 2007/0116299 | A1 | 5/2007 | Vanderwall et al. |
| 2008/0132251 | A1 | 6/2008 | Altman et al. |
| 2009/0076912 | A1 | 3/2009 | Rajan et al. |
| 2010/0131300 | A1 | 5/2010 | Collopy et al. |
| 2010/0156834 | A1* | 6/2010 | Sangster .............. G06V 40/173 345/173 |
| 2011/0035284 | A1 | 2/2011 | Moshfeghi |
| 2011/0106370 | A1 | 5/2011 | Duddle et al. |
| 2011/0161100 | A1 | 6/2011 | Peak et al. |
| 2011/0196571 | A1 | 8/2011 | Foladare et al. |
| 2011/0213628 | A1 | 9/2011 | Peak et al. |
| 2011/0276484 | A1* | 11/2011 | Pearson .............. G06Q 20/4014 235/380 |
| 2012/0250938 | A1 | 10/2012 | DeHart |
| 2012/0252485 | A1 | 10/2012 | Wolverton et al. |
| 2013/0006674 | A1 | 1/2013 | Bowne et al. |
| 2013/0018541 | A1 | 1/2013 | Raz et al. |
| 2013/0095459 | A1* | 4/2013 | Tran ........................ G09B 19/00 434/247 |
| 2013/0190967 | A1 | 7/2013 | Hassib et al. |
| 2013/0191270 | A1 | 7/2013 | Carragher |
| 2013/0274955 | A1 | 10/2013 | Rosenbaum |
| 2013/0282271 | A1 | 10/2013 | Rubin et al. |
| 2013/0295901 | A1 | 11/2013 | Abramson et al. |
| 2013/0325517 | A1 | 12/2013 | Berg |
| 2013/0339065 | A1 | 12/2013 | Denning et al. |
| 2014/0019171 | A1 | 1/2014 | Koziol |
| 2014/0081858 | A1* | 3/2014 | Block ................ G06Q 20/1085 705/43 |
| 2014/0108058 | A1* | 4/2014 | Bourne .................. G06Q 40/08 705/4 |
| 2014/0222469 | A1 | 8/2014 | Stahl et al. |
| 2014/0222798 | A1 | 8/2014 | Want et al. |
| 2014/0247154 | A1* | 9/2014 | Proud ...................... H02J 50/80 340/870.09 |
| 2014/0257869 | A1 | 9/2014 | Binion et al. |
| 2015/0004934 | A1 | 1/2015 | Qian et al. |
| 2015/0025917 | A1 | 1/2015 | Stempora |
| 2015/0062354 | A1 | 3/2015 | Zhang |
| 2015/0073695 | A1 | 3/2015 | Groves et al. |
| 2015/0092056 | A1* | 4/2015 | Rau ........................ B60R 11/04 348/148 |
| 2015/0095792 | A1 | 4/2015 | Hashimoto |
| 2015/0112731 | A1 | 4/2015 | Binion et al. |
| 2015/0161738 | A1 | 6/2015 | Stempora |
| 2015/0168174 | A1* | 6/2015 | Abramson ......... G01C 21/3407 701/408 |
| 2015/0312404 | A1* | 10/2015 | Abramson .............. H04W 8/02 455/418 |
| 2015/0363886 | A1 | 12/2015 | Fernandes et al. |
| 2016/0063235 | A1 | 3/2016 | Tussy |
| 2016/0098522 | A1* | 4/2016 | Weinstein .............. G16H 10/60 705/3 |
| 2016/0140332 | A1 | 5/2016 | Pfursich et al. |
| 2016/0205238 | A1* | 7/2016 | Abramson ............ H04W 4/029 455/456.4 |
| 2016/0275518 | A1* | 9/2016 | Bowles ................ G06V 40/166 |
| 2016/0275625 | A1 | 9/2016 | Biemer et al. |
| 2017/0265044 | A1 | 9/2017 | Lundsgaard et al. |
| 2017/0339525 | A1 | 11/2017 | Schrader et al. |
| 2017/0357941 | A1* | 12/2017 | Best ........................ G06Q 10/10 |
| 2018/0047196 | A1* | 2/2018 | Du ............................ G06N 5/02 |
| 2018/0061242 | A1 | 3/2018 | Bavar et al. |
| 2018/0089687 | A1 | 3/2018 | Kohli |
| 2018/0124047 | A1* | 5/2018 | Fisher ................. H04L 63/0861 |
| 2018/0126951 | A1 | 5/2018 | Ricci |
| 2018/0260908 | A1 | 9/2018 | Collopy et al. |
| 2018/0308100 | A1 | 10/2018 | Haukioja et al. |
| 2019/0102826 | A1 | 4/2019 | Rohrssen et al. |
| 2019/0102840 | A1* | 4/2019 | Perl ........................ G06Q 40/08 |
| 2019/0374170 | A1* | 12/2019 | Inoue ...................... A61B 5/743 |
| 2020/0104876 | A1* | 4/2020 | Chintakindi ........... A61B 5/163 |
| 2020/0317216 | A1 | 10/2020 | Konrardy et al. |

FOREIGN PATENT DOCUMENTS

| | | |
|---|---|---|
| KR | 101341986 B1 | 12/2013 |
| WO | WO-2007133991 A2 | 11/2007 |
| WO | 2016028228 A1 | 2/2016 |
| WO | WO-2017074752 A1 | 5/2017 |

OTHER PUBLICATIONS

Nakashima, Ryan, AP Exclusive: Google tracks your movements, like it or not, downloaded from https://apnews.com/article/828aefab64d4411bac257a07c1af0ecb on Mar. 3, 2021, and dated Aug. 13, 2018 (Year: 2018).

(56) References Cited

OTHER PUBLICATIONS

Sep. 25, 2020—U.S. Non-Final Office Action—U.S. Appl. No. 16/582,495.
Saiprasert et al, Driver Behaviour Profiling using Smartphone Sensory Data in a V2I Environment, 2014 International Conference on Connected Vehicles and Expo (ICCVE), pp. 552-557.
Zheng et al, Mining Interesting Locations and Travel Sequences from GPS Trajectories, International World Wide Web Conference 2009 Madrid Spain, pp. 791-800.
Sharma et al, Big data learning and suggestions in modern apps, IOP Conf. Series: Materials Science and Engineering 263 (2017), pp. 1-8.
Zhu et al, Design of Driving Behavior Pattern Measurements Using Smartphone Global Positioning System Data, International Journal of Transportation Science and Technology, vol. 2, No. 4, 2013, pp. 269-288.
Fisher, Social media intelligence and profiling in the insurance industry . . . it's not only the price you pay that will be affected, downloaded from <https://medium.com/privacy-international/social-media-intelligence-and-profiling-in-the-insurance-industry-4958fd11f86f> on Oct. 10, 2018.
Clark, et al., Unleashing the value of advanced analytics in insurance, downloaded from <https://www.mckinsey.com/industries/financial-services/our-insights/unleashing-the-value of-advanced-analytics-in-insurance> on Oct. 10, 2018.
Intel Corporation, Deliver innovative insurance services through predictive analytics, downloaded from <https://www.intel.com/content/dam/www/public/us/en/documents/reference-architectures/innovative-insurance-services-through-predictive-analytics-brief.pdf> on Sep. 25, 2019.
Ha, Young, In Few Years, Social Network Data May Be Used in Underwriting, downloaded from <https://www.insurancejournal.com/news/national/2011/10/13/219764.htm> on Oct. 10, 2018.
May 3, 2021—U.S. Final Office Action—U.S. Appl. No. 16/582,579.
Nov. 23, 2020—U.S. Non-Final Office Action—U.S. Appl. No. 16/582,579.
Dec. 23, 2020—U.S. Non-Final Office Action—U.S. Appl. No. 16/582,544.
Cook, Steve, "How the Selfie is Revolutionizing Mobile Payments!" from Finextra.com, downloaded from https://www.finextra.com/blogposting/12336/how-the-selfie-is-revolutionising-mobile-payments on Dec. 17, 2020, and dated Mar. 8, 2016 (Year: 2016).
Thadani, Trisha, "Companies Try Out Selfies as Password Alternatives", from The Wall Street Journal, downloaded from https://www.wsj.com/articles/companies-try-out-selfies-as-password-alternatives-1476661046 on Dec. 17, 2020, and dated Oct. 17, 2016 )Year: 2016).
Iao, Shannon, "Facebook Uses Selfies as Login Authentication for Suspicious Actifity", from TheVerge.com, downloaded from https://www.theverge.com/2017/11/29/16716278/facebook-tests-selfies-login-verification-face on Dec. 17, 2020, and date Nov. 29, 2017 (Year: 2017).
Vincent, James, "MasterCard Unveils Selfie Security Checks, Says Heartbeat Authentication Could Follow", from TheVerge.com, downloaded from https://wwwtheverge.com/2016/2/23/11098540/mastercard-facial-recognition-heartbeat-security on Dec. 17, 2020, and dated Feb. 23, 2016 (Year: 2016).
Storm, David, "The Rise of the Selfie Authentication as a New Security Factor", from SecurityIntelligence.com downloaded from https://securityintelligence.com/the-rise-of-the-selfie-authentication-as-a-new-security-factor/ on Dec. 17, 2020, and dated Jul. 27, 2016 (Year: 2016).
Jan. 29, 2021—U.S. Final Office Action—U.S. Appl. No. 16/582,495.
Sedzielewski, Mike, "How to Create Advanced Coupon Campaigns", 2017 (Year: 2017).
Mar. 9, 2022—U.S. Notice of Allowance—U.S. Appl. No. 16/582,579, 9 Pages.
Bala Raja, "Driver Monitoring," Computer Vision and Imaging in Intelligent Transportation Systems, 2017, 21 Pages.
Extended European Search Report for Application No. 19864389.2 dated May 13, 2022 (12 pages).
Guilherme Folego et al., Cross-Domain Face Verification: Matching ID Document and Self-Portrait Photographs, arxiv.org, Cornell University Library, 201 Olin Library Cornell University Ithaca, NY 14853, Nov. 17, 2016 (Nov. 17, 2016), XP080732559, (6 pages).
International Preliminary Report on Patentability for International Application No. PCT/US2019/053192, dated Apr. 8, 2021, 27 Pages.
International Search Report and Written Opinion for International Application No. PCT/US2019/053192, dated Jan. 22, 2020, 31 Pages.
Macri D., "Understanding Mobile Coupons," Marketing Dive, 2008, Retrieved from the Internet URL: https://www.marketingdive.com/ex/mobilemarketer/cms/opinion/co1unms/2306.html on Jun. 1, 2021, 9 Pages.
Jul. 1, 2022—U.S. Final Office Action—U.S. Appl. No. 16/582,544, 34 Pages.
Dec. 21, 2022—U.S. Non-Final Office Action—U.S. Appl. No. 16/582,544, 40 Pages.
Aug. 30, 2022—U.S. Notice of Allowance—U.S. Appl. No. 16/582,579, 11 Pages.
Nov. 8, 2022—U.S. Final Office Action—U.S. Appl. No. 16/582,611, 30 Pages.
Here's how selfie passwords will work, CBS News, dated Mar. 29, 2016, downloaded from https://www.cbsnews.com/news/ heres-how-selfie-passwords-will-work/ on Jun. 26, 2022 (Year: 2016).
Nov. 22, 2023—(US) Final Office Action—U.S. Appl. No. 18/086,072, 16 Pages.
May 5, 2023—(US) Non-Final Office Action—U.S. Appl. No. 18/086,072, 29 Pages.
Sep. 8, 2023—(US) Non-Final Office Action—U.S. Appl. No. 17/828,430, 27 Pages.
Dean Macri, Understanding mobile coupons, 2008 (Year: 2008).
Oct. 5, 2023—(US) Non-Final Office Action—U.S. Appl. No. 17/828,430, 45 Pages.
Oct. 11, 2023—(US) Non-Final Office Action—U.S. Appl. No. 17/828,430, 50 Pages.

* cited by examiner

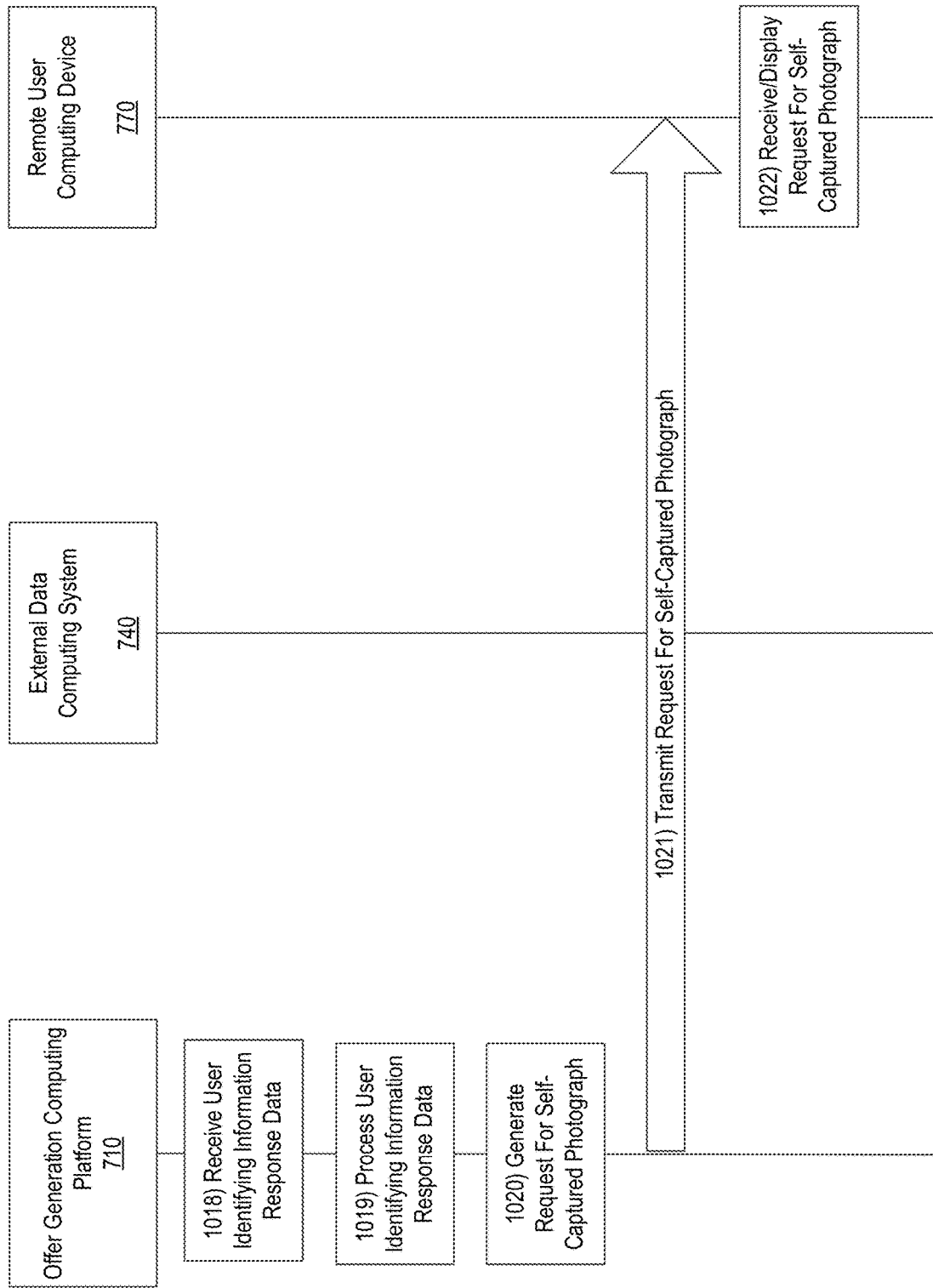

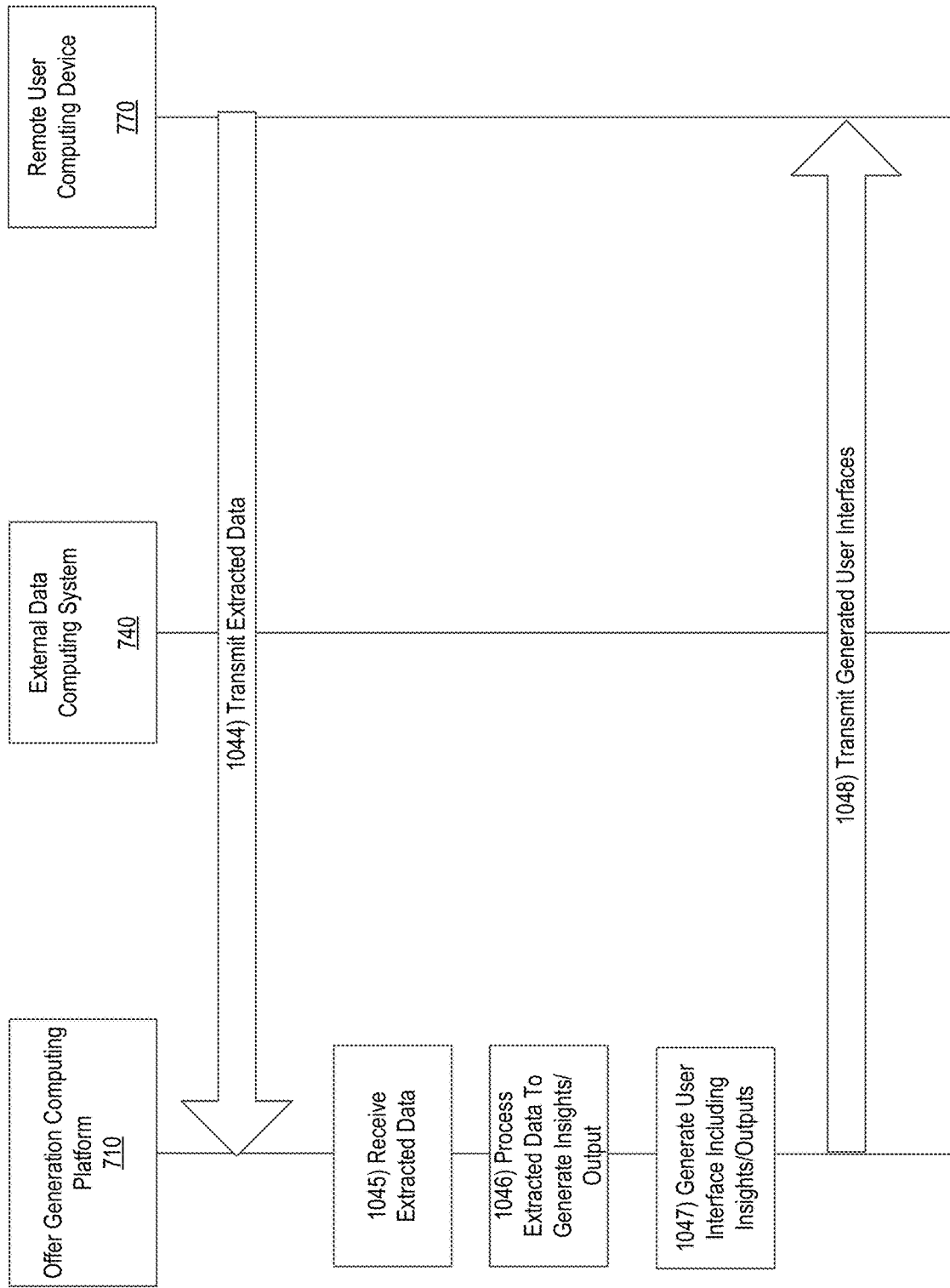

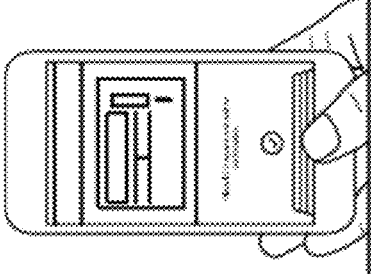

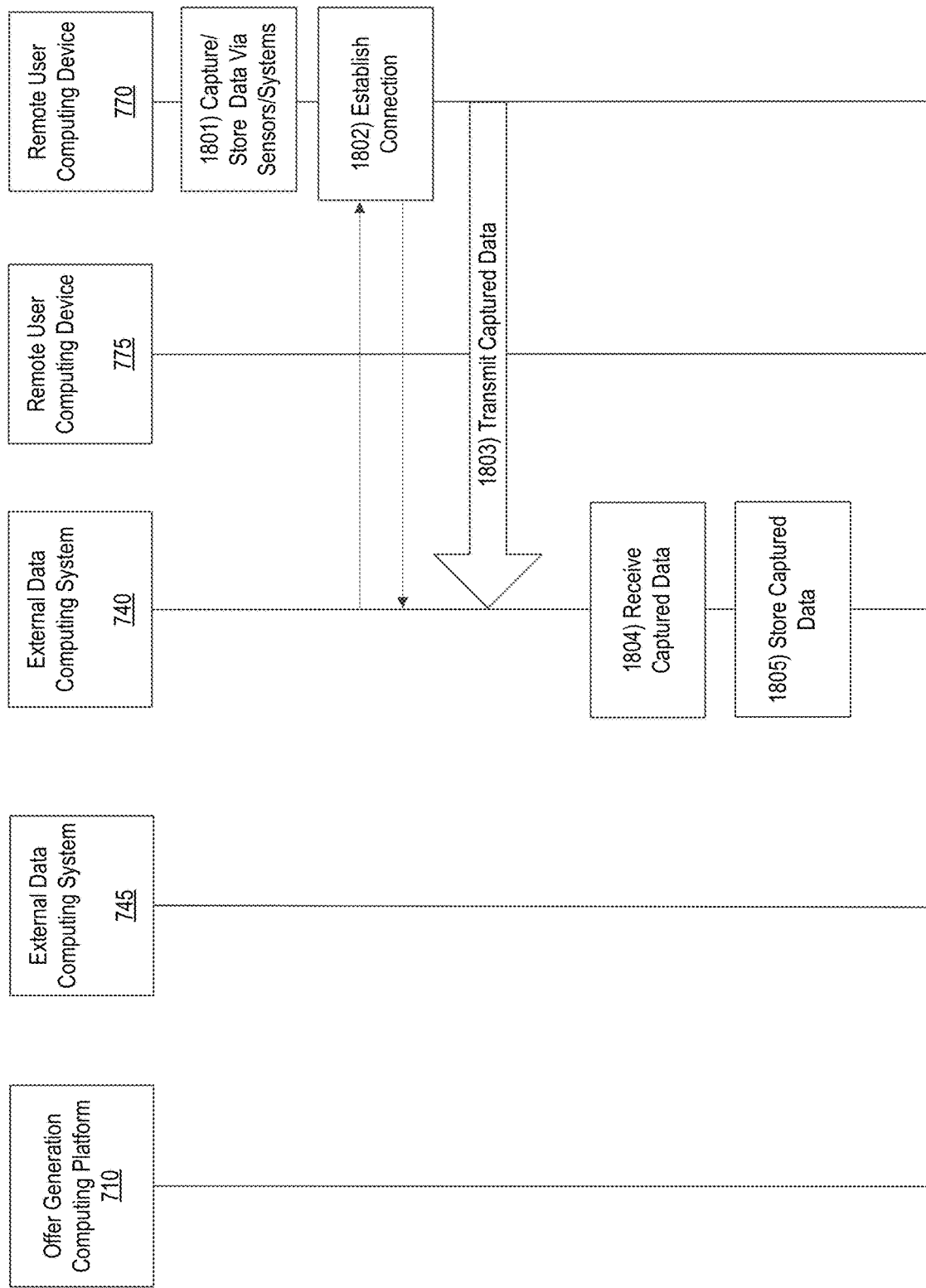

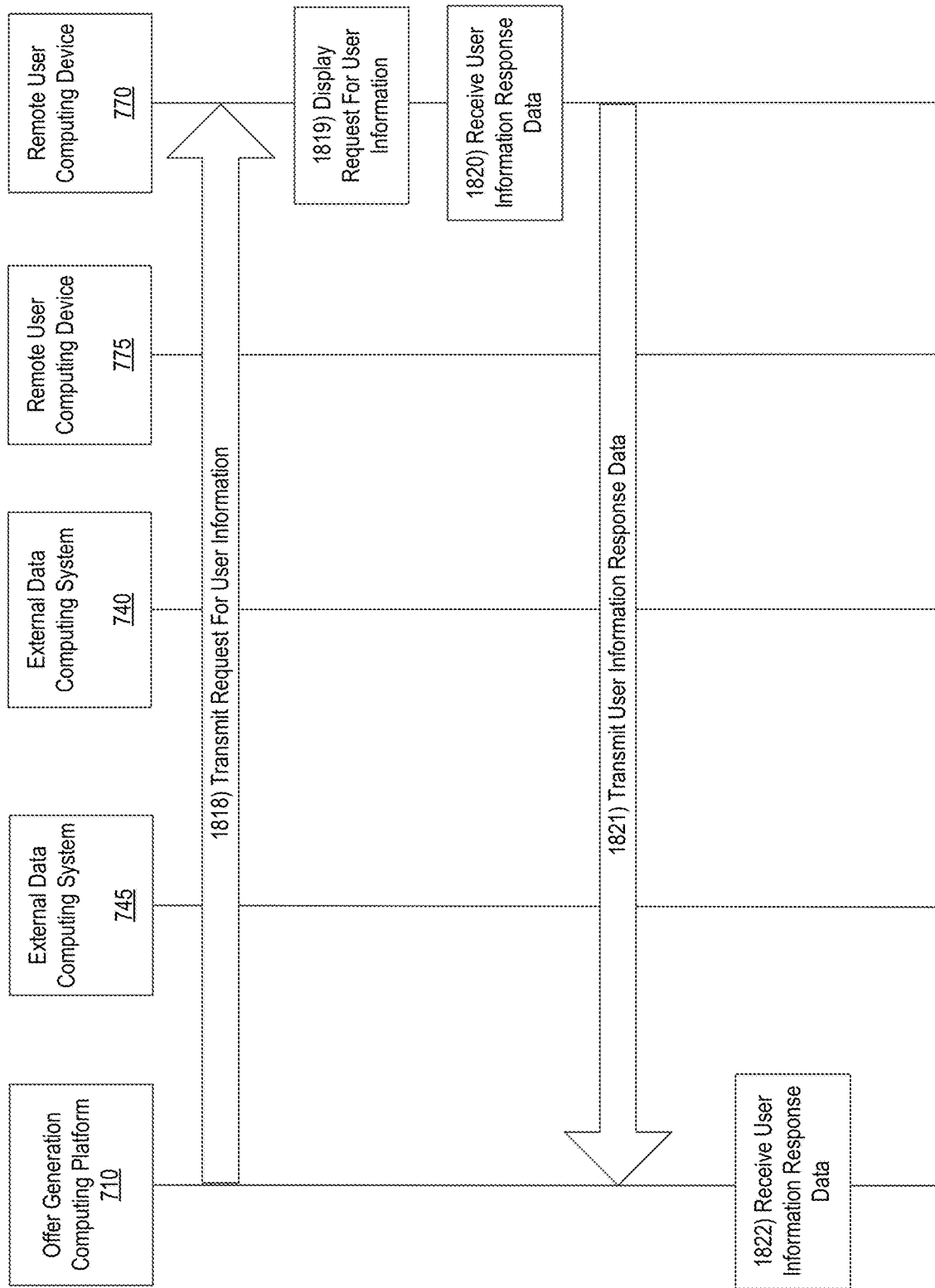

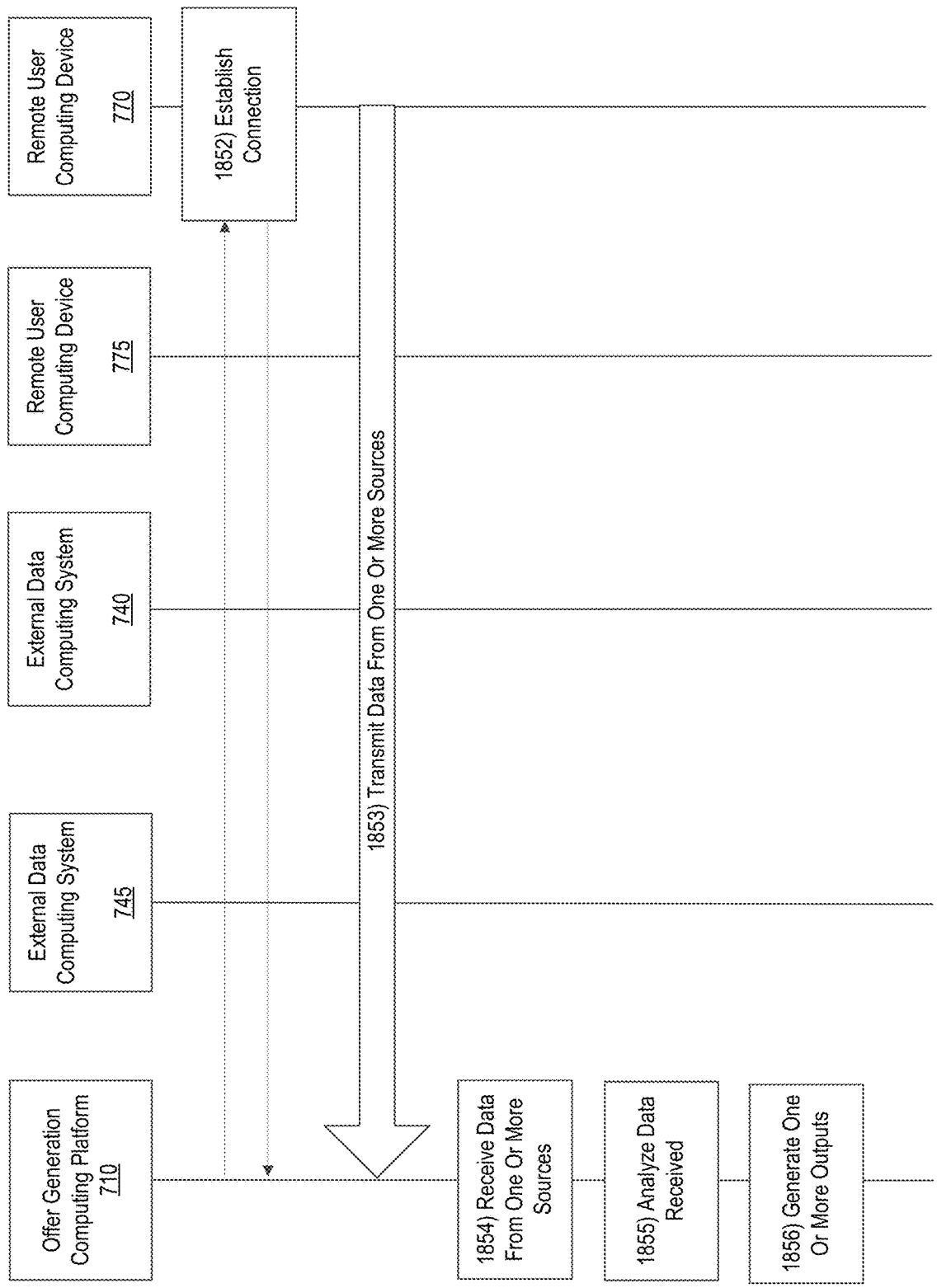

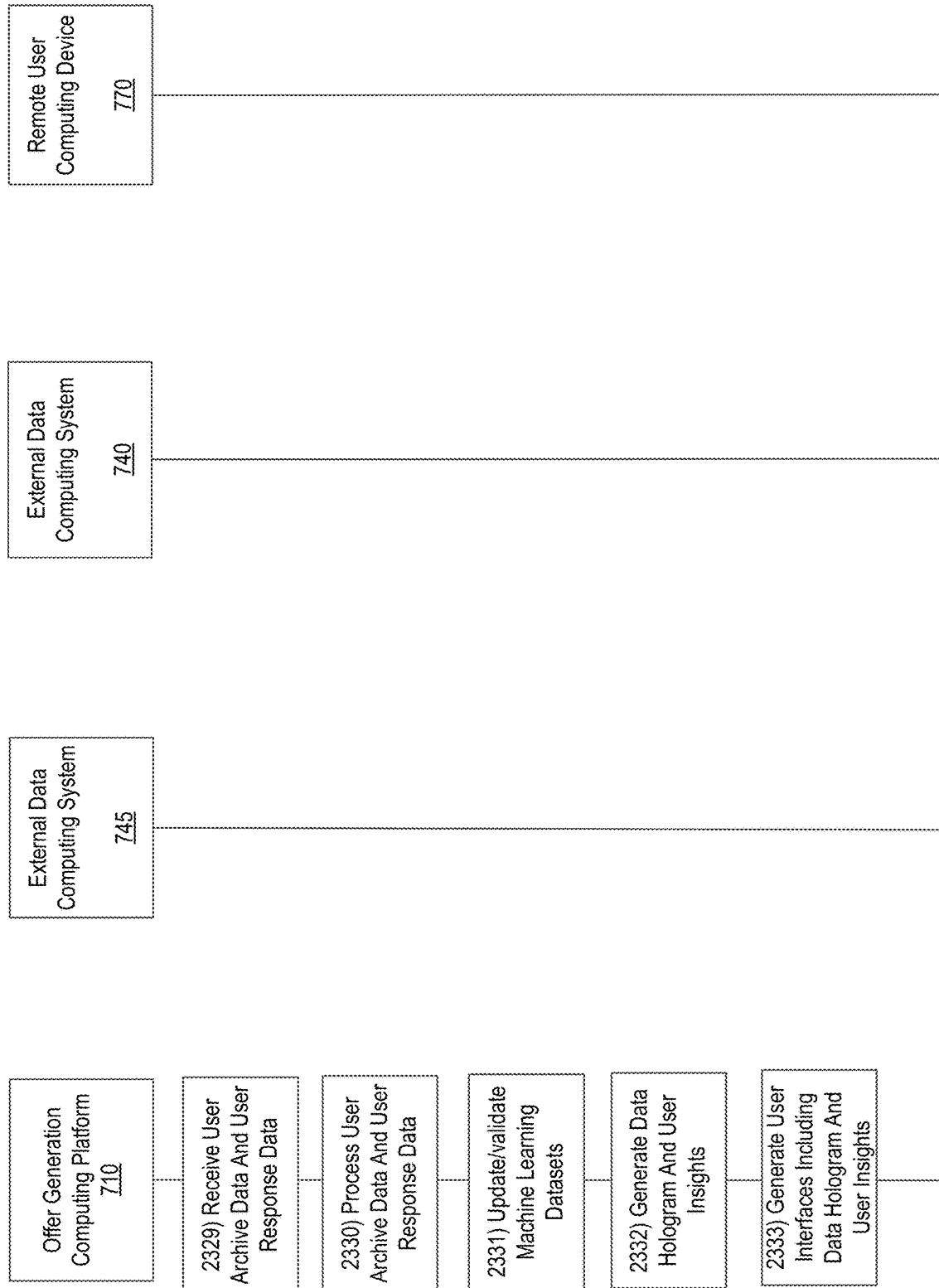

DATA PROCESSING SYSTEM WITH MACHINE LEARNING ENGINE TO PROVIDE OUTPUT GENERATION FUNCTIONS

CROSS REFERENCE TO RELATED APPLICATIONS

This application is a non-provisional of and claims priority to U.S. Provisional Application No. 62/738,460, filed Sep. 28, 2018, and entitled, "Systems and Methods for Mapping Significant Locations Using Mobile Devices," and is a non-provisional of and claims priority to U.S. Provisional Application No. 62/738,422, filed Sep. 28, 2018, and entitled, "Data Processing System with Machine Learning Engine to Provide Output Generation Functions," and is a non-provisional of and claims priority to U.S. Provisional Application No. 62/836,114, filed Apr. 19, 2019 and entitled "Data Processing System with Machine Learning Engine to Provide Output Generation Functions," and is a non-provisional of and claims priority to U.S. Provisional Application No. 62/845,560, filed May 9, 2019, and entitled "Data Processing System with Machine Learning Engine to Provide Output Generation Functions," all of which are incorporated herein by reference in their entirety.

TECHNICAL FIELD

Aspects of the disclosure generally relate to one or more computer systems, servers, and/or other devices including hardware and/or software. In particular, aspects of the disclosure generally relate to capturing data via one or more sensors in a mobile device and aggregating that data with other data to generate an output based, in some examples, on machine learning.

BACKGROUND

Nearly everyone today uses some sort of personal mobile device on a regular basis. For instance, people use smartphones, cell phones, wearable devices such as smart watches and fitness monitors, tablets, laptops, and the like. These personal mobile devices are regularly carried by users throughout the day and can capture a variety of information regarding the user's usage of their personal mobile device, locations visited, and the like.

In addition, user data is collected and stored by a variety of different sources. For instance, user data that is collected by a mobile device, wearable device, or other similar device of a user may be stored via one or more third party systems (e.g., cloud-based environments) or entity systems with the permission of the user (e.g., upon downloading an application, executing an application, or the like). This data may be transmitted to an entity for evaluation and may be useful in evaluating user behaviors and identifying insights that may be helpful to users. In some examples, this data may be useful to other entities to evaluate users and generate offers. However, it is difficult for users to view and/or retrieve this data from the third party or entity. Accordingly, it may be advantageous to retrieve data from the third party and analyze the data to generate and provide outputs to a user.

Further, some conventional processes require human interaction, evaluation, and the like. Given the volume of data captured by the mobile device, stored by one or more entities, and the like, it would be advantageous to perform these processes based on sensor data collected rather than requiring human evaluation.

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of the disclosure relate to methods, computer-readable media, systems, and apparatuses for evaluating device usage, capturing user data, and generating one or more outputs based on the device usage and/or user data. For instance, data from one or more sensors within a mobile device can be received and processed to determine movement associated with the device. In addition, an amount of usage (e.g., hours, minutes, etc.) associated with the device can be received. In some examples, application usage and/or types of applications used can also be received. This data can be processed to determine travel patterns for the user of the device and those travel patterns can be utilized to build a risk profile for the user. The risk profile can be utilized for a variety of purposes, including determining rate information and confirming information provided by the user, as well as for generating other insights.

Additional aspects of the disclosure relate to methods, computer-readable media, systems, and apparatuses for retrieving user data collected by, for example, a mobile device of a user, from a third party system for use in evaluating user behaviors, generating outputs and insights, and the like. In some examples, machine learning may be used to evaluate user data and/or generate one or more outputs.

Aspects of the disclosure relate to methods, computer-readable media, systems, and apparatuses for capturing sensor data associated with physical traits of a user (e.g., heart rate, blood pressure, fitness level, and the like) via one or more sensors in a mobile device of the user. This data may then be aggregated with additional user data obtained from, in some examples, one or more third party systems or devices and may be analyzed, using machine learning, to generate one or more outputs or offers for the user.

These and other features and advantages of the disclosure will be apparent from the additional description provided herein.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein:

FIGS. 10A-10K depict another illustrative event sequence for performing offer/insight generation functions, according to one or more aspects described herein.

FIGS. 18A-18K illustrate another illustrative event sequence for performing offer generation functions according to one or more aspects described herein.

FIGS. 23A-23H illustrate another illustrative event sequence for performing offer generation functions according to one or more aspects described herein.

DETAILED DESCRIPTION

Figure 1:
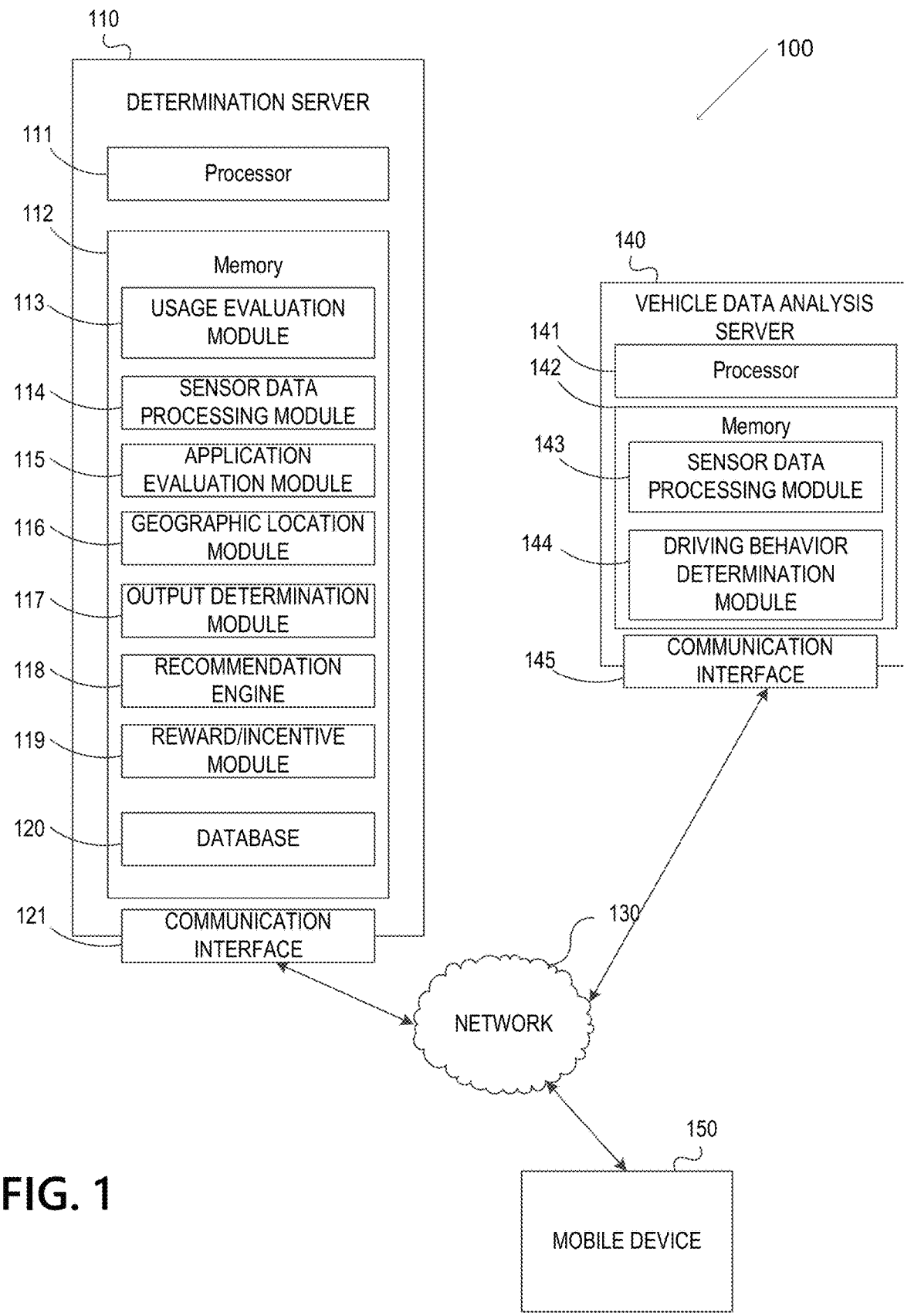
FIG. 1 illustrates an environment including illustrative servers, computing devices, and the like, for performing various device usage analysis functions, generating recommendations, generating incentives, and the like, according to one or more aspects described herein.

In the following description of the various embodiments, reference is made to the accompanying drawings, which form a part hereof, and in which is shown by way of illustration, various embodiments of the disclosure that can be practiced. It is to be understood that other embodiments can be utilized. As will be appreciated by one of skill in the art upon reading the following disclosure, various aspects described herein can be embodied as a method, a computer system, or a computer program product. Accordingly, those aspects can take the form of an entirely hardware embodiment, an entirely software embodiment or an embodiment combining software and hardware aspects. Furthermore, such aspects can take the form of a computer program product stored by one or more computer-readable storage media having computer-readable program code, or instructions, embodied in or on the storage media. Any suitable computer readable storage media can be utilized, including hard disks, CD-ROMs, optical storage devices, magnetic storage devices, and/or any combination thereof. In addition, various signals representing data or events as described herein can be transferred between a source and a destination in the form of electromagnetic waves traveling through signal-conducting media such as metal wires, optical fibers, and/or wireless transmission media (e.g., air and/or space).

One or more aspects described herein may be related to evaluating usage of a device to determine an output. For instance, risk profiles are commonly generated based on information provided by a user. However, this information can be inaccurate and lead to an inaccurate risk profile being generated. By utilizing location data (and/or other data described herein) from the user's mobile device, information provided by the user can be validated and/or the need for the user to provide data can be eliminated. In this way, more accurate risk profiles can be generated. In a variety of embodiments, the risk profile can be generated based on a risk map. A risk map can include data associated with one or more of vehicle accident data, traffic data, vehicle volume data, vehicle density data, road characteristic data, or weather data for a variety of geographical locations. Systems and methods for generating and utilizing risk maps that can be utilized in accordance with embodiments of the invention are disclosed in U.S. Pat. No. 9,581,461, titled "Data Processing System Communicating with a Map Data Processing System to Generate a Display of One or More Segments of One or More Vehicle Routes" and issued Feb. 28, 2017, the disclosure of which is hereby incorporated by reference in its entirety.

These and other aspects will be described more fully herein.

As discussed herein, in order to provide customized insurance options to a user, detailed information about user behaviors (e.g., frequency of driving, time of day, driving behaviors, frequently visited locations, other lifestyle behaviors, and the like) may be used to generate an accurate quote. This information is often unavailable or unknown to the user (e.g., users are often unfamiliar with data captured about their behaviors or with the values associated with the captured data) and, as such, it would be difficult or impossible for the user to provide this information directly and, in some examples, may be difficult or impossible for the user to provide accurately. Accordingly, upon receiving a request for an insurance quote, a software application may be executed on a mobile device of the user to automatically obtain remote sensor data, such as location data, to identify information about the user, driving behaviors, and the like. This may enable accurate and relevant data to be obtained without user input. Accordingly, the user input needed to obtain an accurate quote may be greatly reduced.

FIG. 1 depicts an environment 100 including illustrative servers, computing devices, and the like, for performing various device usage and output determination functions, including, for instance, determining an output based on received sensor and other data, generating one or more risk profiles, generating rate and/or product data, providing notifications, and the like, according to one or more aspects described herein. For instance, the environment 100 includes a determination server 110, a vehicle data analysis server 140, and a mobile device 150. The various devices, servers, and the like, can be connected or in communication with each other via a network 130. The network 130 can be a private network (e.g., a network owned and/or operated by an entity, such as an insurance provider) or can be a public network (e.g., a public network providing, in some examples, secure communication between devices).

The determination server 110 can include one or more processors 111, memory 112, and communication interface 121. A data bus can interconnect processor(s) 111, memory 112, and communication interface 121. Communication interface 121 can be a network interface configured to support communication between determination server 110 and one or more networks (e.g., network 130). Memory 112 can include one or more program modules having instructions that when executed by processor(s) 111 cause determination server 110 to perform one or more functions described herein. In some instances, the one or more program modules and/or databases can be stored by and/or maintained in different memory units of determination server 110 and/or by different computer systems or devices that can form and/or otherwise make up the determination server 110. In some arrangements, different features or processes performed can be performed by different sets of instructions, such that the processor can execute each desired set of instructions to perform different functions described herein.

For example, memory 112 can include a device usage evaluation module 113. The device usage evaluation module 113 can include hardware and/or software configured to perform various functions within the determination server 110. For instance, the device usage evaluation module 113 can monitor usage of one or more computing devices, such as mobile device 150. Monitoring usage can include evaluating a number of minutes, hours, or the like, the device is activated in a particular time period (e.g., one day, one month, etc.). In some arrangements, monitoring usage can include determining how much time (e.g., minutes, hours, etc.) the mobile device 150 was engaged in a particular type of use and/or the location of the mobile device 150. For instance, the device usage evaluation module 113 can determine an amount of time (e.g., minutes, hours, etc.) in a predetermined time period (e.g., one day, one month, etc.) that the device 150 was engaged in texting activities. In another example, the device usage evaluation module 113 can determine an amount of time (e.g., minutes, hours, etc.) in a predetermined time period (e.g., one day, one month, etc.) that the device 150 was engaged in talk or traditional phone call activities. In still another example, the device usage evaluation module 113 can determine an amount of time (e.g., minutes, hours, etc.) in a predetermined time period (e.g., one day, one month, etc.) that the device 150 was engaged in application related activities. In a variety of arrangements, monitoring usage can include determining how much time the mobile device 150 is traveling in a vehicle (such as in a car, train, bus, etc.), is stationary at a particular location, how often a mobile device is detected at a particular location, and the like. In some examples, usage of different types can indicate an increased risk and, accordingly, can result in variations in the determined output, as will be discussed more fully below. In some arrangements, usage data used to determine an amount of usage can be collected by, for instance, a device usage monitor, which can include hardware (e.g., processor, etc.) and/or software configured to monitor the location and/or overall usage and types of usage of the mobile device 150. Accordingly, in some examples, data received from, for instance, third party systems and via a mobile device of the user, may include one or more other types of data, such as sensor data and/or device usage data, as described herein.

The determination server 110 can further include a sensor data processing module 114. The sensor data processing module 114 can include hardware and/or software configured to perform various functions within the determination server 110. For instance, the sensor data processing module 114 can receive raw data from one or more sensors arranged within the mobile device 150. Some example sensors can include accelerometers, gyroscopes, pressure sensors, proximity sensors, location determination devices, global navigation satellite systems (GNSS) such as global positioning system (GPS), Galileo, or the like, receivers, and the like. Signals or data collected by the sensors can be transmitted to the sensor data processing module 114 for processing. The processing of the sensor data can result in data indicating how often there was movement of the mobile device 150, a type of movement, conditions surrounding the mobile device 150, and the like. This can be useful in determining a risk associated with a vehicle traveling in the same location as the mobile device. In some examples, the data can be processed to filter data that can be considered less useful. For instance, if movement data is being collected by one or more sensors on a continuous or nearly continuous basis, the system can filter out data corresponding to times when no or little movement of the device is detected based on sensor data. For instance, in some examples, a minimum threshold amount of movement, as determined from the received data, can be necessary for the data to be processed. In such arrangements, the data associated with movement below the threshold can be removed and/or no further processing can be performed on that data. Instead, any further processing can be focused on the sensor data associated with at least the threshold amount of movement. Accordingly, in some examples, analyzing data to evaluate a user may include filtering data to filter out, for example, data where no movement is detected.

In some examples, processing the received raw data can include evaluating a signature of one or more signals to determine a type of movement associated with the device. For instance, the signature of the signals can be used to determine whether a user was traveling in a vehicle with the mobile device 150 for at least a threshold amount of time. In some examples, signals with a frequency within a specific range (which can be determined dynamically and/or predetermined) can be indicative of a mobile device being located in a moving vehicle. Accordingly, in some arrangements, analyzing data to evaluate a user may include evaluating a signature of one or more signals to determine a type of movement associated with the device.

The determination server 110 can further include an application evaluation module 115. The application evaluation module 115 can include hardware and/or software configured to perform various activities or functions within the determination server 110. For instance, evaluating an amount of time spent interacting with applications, as well as a type of application with which a user is interacting or which is passively operating on a device, can be indicative of driving behaviors. For example, applications in which a user can spend a significant amount of time (e.g., navigation applications, vehicle monitoring applications, music streaming applications, and the like) can have a user interacting with or generally using the mobile device 150 while traveling in a vehicle for longer periods than other applications (such as a weather application, news application, or the like) in which a user can briefly review updated information. Accordingly, the application evaluation module 115 can evaluate an amount of time (e.g., minutes, hours, etc.) that one or more applications are executing on the mobile device 150 in a predetermined time period (e.g., one day, one month, or the like). The application evaluation module 115 can analyze each application downloaded or otherwise provided and/or executing on the mobile device 150 to identify a type of application. For instance, the applications can be categorized as one of types one or two. Alternatively, three or more different types of applications can be identified. The applications can be analyzed to determine what type of application or category each application is associated with. The types of applications or categories of application can be based on an actual or expected amount of time a user can interact with each application in a particular time period, how a user interacts with a particular application (e.g., passive or active), and the like. For instance, as discussed above, applications such as gaming applications and the like with which a user can interact for extended periods can be considered a type or category one application, while applications a user can interact with less, such as news and/or weather applications can be type or category two applications. The type of category of application can be used to evaluate risk to the mobile device 150 and to generate one or more outputs.

The determination server 110 can further include a geographic location module 116. The geographic location module 116 can include hardware and/or software configured to perform various functions within the determination server 110. For instance, the geographic location module 116 can communicate with and/or connect to a global navigation satellite system (GNSS) such as global positioning system (GPS) within or associated with the mobile device 150 to obtain location information associated with the mobile device 150. In some examples, the geographic location module 116 can establish a geo-fence identifying a particular area in which a mobile device 150 typically is located. The geographic location module 116 can determine a current geographic location of the mobile device 150 and can evaluate a risk associated with the current location. GPS data indicating that the mobile device 150 is at or near particular locations above a threshold amount of time can impact one or more generated outputs, as will be discussed more fully herein.

The determination server 110 can further include an output determination module 117. The output determination module 117 can include hardware and/or software configured to perform various functions within the determination server 110. For instance, the output determination module 117 can receive data from one or more other modules, such as usage evaluation module 113, sensor data processing module 114, application evaluation module 115, and/or geographic location module 116 and can evaluate the received data to determine a risk profile associated with the mobile device 150 and/or a hypothetical vehicle having the same travel profile as the mobile device 150. Based on the evaluated data and/or the determined risk profile, the output determination module 117 can identify a premium or rate, such as an insurance premium or rate, for insuring a vehicle and/or validate data provided by a user. Accordingly, the premium or rate can be based on how often the device 150 is used, where the device 150 is located, what types of applications are executed on the device 150, a type or amount of movement associated with the device 150, and the like. In some examples, additional information such as an age of a user, a gender of a user, a credit history of a user, and the like, can also be used in generating the risk profile and/or determining the premium and/or rate. For instance, users in a certain age group or of a certain gender can be known to be more prone to damage or loss of a vehicle than in other age groups or other genders. For instance, this additional information can be retrieved from one or more databases, such as database 120, and can be used to evaluate risk. Further, general information about the vehicle (e.g., make, model, age, mileage, etc.) can also be retrieved (e.g., from one or more databases) and used to generate the risk profile.

In some example arrangements, a user's driving behaviors can also be used to generate the risk profile associated with the mobile device 150. For instance, data associated with driving behaviors can be received from a vehicle data analysis server 140. The vehicle data analysis server 140 can include one or more processors 141, memory 142, and communication interface 145. A data bus can interconnect processor(s) 141, memory 142, and communication interface 145. Communication interface 145 can be a network interface configured to support communication between the vehicle data analysis server 140 and one or more networks (e.g., network 130). Memory 142 can include one or more program modules having instructions that when executed by processor(s) 141 cause vehicle data analysis server 140 to perform one or more functions described herein. In some instances, the one or more program modules and/or databases can be stored by and/or maintained in different memory units of vehicle data analysis server 140 and/or by different computer systems or devices that can form and/or otherwise make up the vehicle data analysis server 140. In some arrangements, different features or processes performed can be performed by different sets of instructions, such that the processor can execute each desired set of instructions to perform different functions described herein.

For example, memory 142 can include a vehicle sensor data processing module 143. The vehicle sensor data processing module 143 can include hardware and/or software configured to perform various functions within the vehicle data analysis server 140. For instance, the vehicle sensor data processing module 143 can receive data from one or more sensors associated with the vehicle. The one or more sensor can detect acceleration, braking, swerving, lane changes, and the like. Data from these sensors can be received by the vehicle sensor data processing module 143 and can be processed. The processed data can be transmitted to a driving behavior determination module 144. The driving behavior determination module 144 can include hardware and/or software configured to perform various functions within the vehicle data analysis server 140. For instance, the driving behavior determination module 144 can receive the processed data and evaluate the data to determine one or more driving behaviors of the user. For instance, the driving behavior determination module 144 can evaluate the data to determine how quickly a user accelerates from a stopped position, whether the user is generally a hard braker (e.g., a number of hard braking occurrences in a time period is over a threshold), how often the user changes lanes (e.g., in a trip, a day, or the like), whether the user maintains his or her lane, and the like. This information can then be used to evaluate a risk associated with the driving behaviors of the user. For instance, each type of behavior can, in some examples, be given a score. Each score for each driving behavior (e.g., acceleration, braking, swerving, lane changes, etc.) can then be summed to determine an overall score for the user. This overall score, any of the individual scores, and/or the driving data itself can be transmitted to the output determination module 117 to generate the risk profile and/or rate information.

The determination server 110 can further include a recommendation engine 118. The recommendation engine 118 can include hardware and/or software configured to perform various functions within the determination server 110. For instance, the recommendation engine 118 can evaluate data from various sources (e.g., usage evaluation module 113, sensor data processing module 114, application evaluation module 115, geographic location module 116, determination server 110, etc.) and can generate one or more recommendations for the user to reduce a risk of damage to the vehicle. In addition to generating a recommendation, a reward/incentive module 119 of the determination server 110 can generate one or more rewards or incentives to offer to a user to implement one or more generated recommendations. For instance, the reward/incentive module 119 can offer a discount on a premium or rate for a next term if one or more recommendations are implemented. In another example, the reward/incentive module 119 can offer a refund of a portion of a premium if one or more recommendations are implemented.

Figure 2:
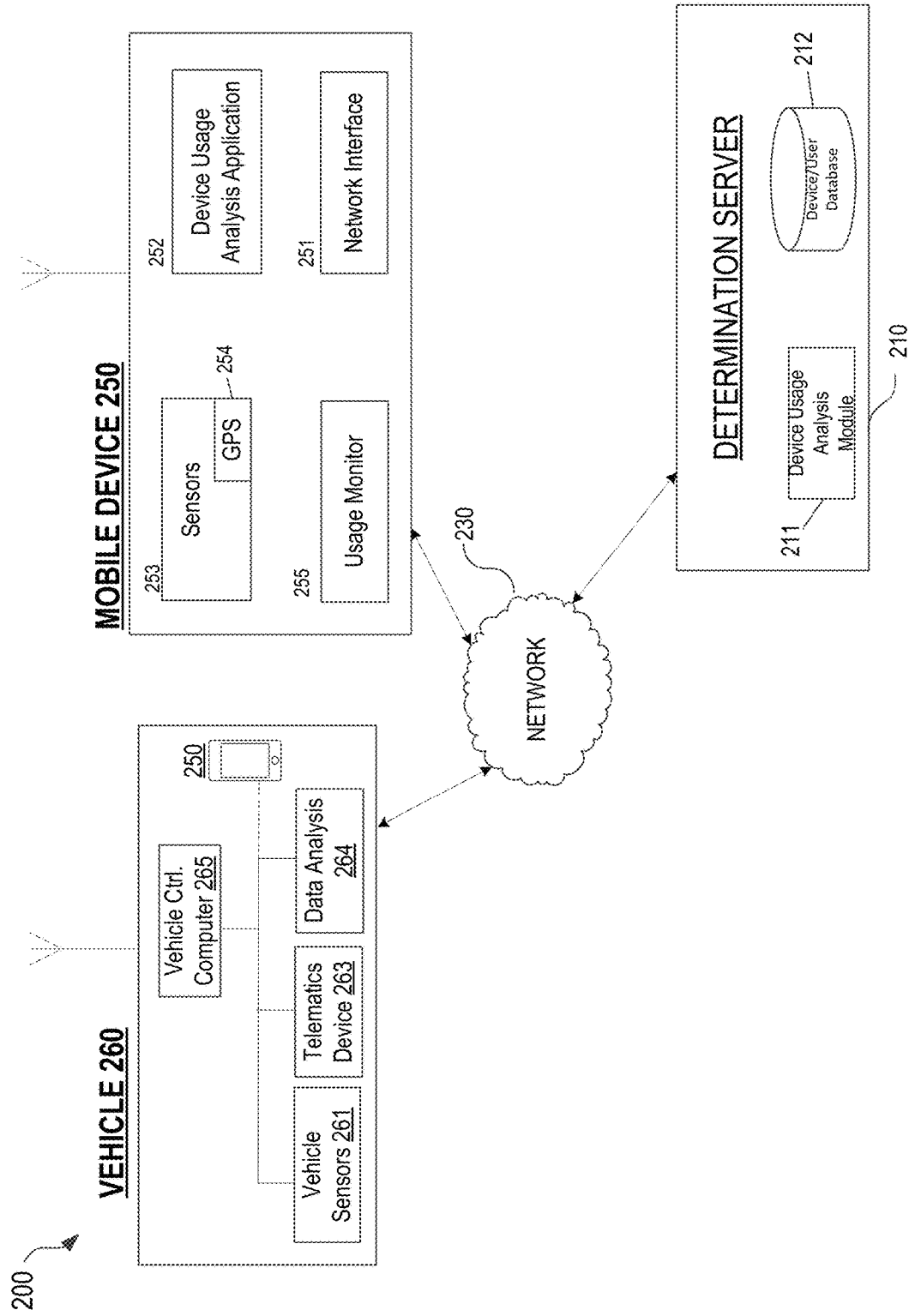
FIG. 2 is a diagram illustrating various components and devices of a device usage and output determination system according to one or more aspects described herein.

FIG. 2 is a diagram of an illustrative device usage and output determination system 200 including a vehicle 260, a mobile device 250, a determination server 210, and additional related components. Each component shown in FIG. 2 can be implemented in hardware, software, or a combination of the two. Additionally, each component of the device usage and output determination system 200 can include a computing device (or system) having some or all of the structural components described herein. The device usage and output determination system 200 can also include or be in communication with one or more servers, devices, and the like, shown and described with respect to FIG. 1.

One or more components shown in FIG. 2, such as the vehicle 260 and the mobile device 250, can communicate with each other via wireless networks or wired connections (e.g., for devices physically docked in vehicles), and each can communicate with one or more additional vehicles, additional mobile computing devices, and/or a number of external computer servers 210, over one or more communication networks 230. In some examples, the mobile device 250 can be paired (e.g., via Bluetooth technology) to one or more other devices (e.g., another mobile device, such as a wearable device, tablet, etc.). If the device is no longer in proximity to be paired, a notification can be generated and displayed on the device.

As discussed herein, the components of device usage and output determination system 200, operating individually or using communication and collaborative interaction, can perform such features and functions such as evaluating overall usage of a device, evaluating applications executing on a device, evaluating sensor data from the device, receiving and analyzing sensor data from a vehicle, determining an output, such as a risk profile and/or an insurance premium, generating one or more recommendations and/or incentives for a user, and the like.

Device usage and output determination system 200 can include one or more mobile devices 250. Mobile device 250 can be, for example, smartphones or other mobile phones, personal digital assistants (PDAs), tablet computers, laptop computers, wearable devices such as smart watches and fitness monitors, and the like. Mobile device 250 can include some or all of the elements described herein with respect to computing devices.

As discussed herein, the travel patterns of and usage of a vehicle can be predicted by analyzing the location and usage history of a mobile device owned by the driver of the vehicle. Accordingly, by monitoring usage of a device, the arrangements described herein can customize an insurance plan for a vehicle 260 based on a variety of factors associated with the mobile device. For instance, some factors that can be used to determine a likelihood of damage and/or loss to the vehicle (and, thus, an insurance premium) can include: age of the user, gender of the user, credit score or history of the user, vehicle driving data and/or behaviors of the user, vehicle insurance claim data of the user, motion of movement of the device, location information (e.g., particular location information, area or region information (e.g., based on zip code), type of area (e.g., urban, suburban, rural) and the like), usage behaviors (e.g., number of text messages sent/received, type of applications executing on the device, number of applications executing on the device), number of hours in movement, WiFi usage, type of WiFi, time of day device is in use, weather conditions, connectivity to other devices, time of day in which the device is used (e.g., devices used late at night or early in the morning, on weekends, etc.), and the like. Various other factors can be considered without departing from the invention. In a number of embodiments, some or all of these factors can be described for one or more geographic locations using a risk map. The risk map can then be utilized to correlate the location(s) of the mobile device to the appropriate risk factors described in the risk map for use in generating risk profiles.

The mobile device 250 can include a network interface 251, which can include various network interface hardware (e.g., adapters, modems, wireless transceivers, etc.) and software components to allow mobile device 250 to communicate with determination server 210, vehicle 260, and various other external computing devices. One or more specialized software applications, such as device usage analysis applications 252 can be stored in the memory of the mobile device 250. The device usage analysis application(s) 252 can be received via network interface 251 from the determination server 210, vehicle 260, or other application providers (e.g., public or private application stores). Certain device usage analysis applications 252 might not include user interface screens while other applications 252 can include user interface screens that support user interaction Such applications 252 and can be configured to run as user-initiated applications or as background applications. The memory of mobile device 250 also can include databases configured to receive and store sensor data received from mobile device sensors, usage type, application usage data, and the like. Although aspects of the device usage analysis software application(s) 252 are described as executing on mobile device 250, in various other implementations, some or all of the device usage analysis functionality described herein can be implemented by determination server 210.

As discussed herein, mobile device 250 can include various components configured to generate and/or receive data associated with usage of the mobile device 250, movement of the mobile device 250, location of the mobile device 250, and the like. For example, using data from sensors 253 (e.g., 1-axis, 2-axis, or 3-axis accelerometers, compasses, speedometers, vibration sensors, gyroscopic sensors, etc.) and/or GPS receivers or other location-based services (LBS) 254, an application 252 (or other device or module, e.g., determination server 210) can determine movement of the mobile device 250 (e.g., in a vehicle, with a user who is walking, with a user who is running, etc.). The sensors 253 and/or GPS receiver or LBS component 254 of a mobile device 250 can also be used to determine driving speeds, routes, accident force and angle of impact, and other accident characteristics and accident-related data. This data may be transmitted to and/or stored by a third party computer system, such as external data computing system 740. Location data, such as GPS coordinates and associated time and date stamps may also be captured and, in some examples, may be stored by an external data computing system, such as a third party system (e.g., external data computing device 740).

Mobile device 250 can further include a usage monitor 255. The usage monitor can be a device (e.g., including a processor, etc.) and can include hardware and/or software configured to monitor various aspects of the usage of the mobile device 250. For instance, the usage monitor 255 can monitor a number of minutes, hours, or the like the device is in use (e.g., based on factors such as device being illuminated, user interacting with or looking at the device, etc.). As described herein, mobile device 250 can execute a variety of applications. Many of these applications include a variety of driving, navigation, vehicle monitoring, and/or other travel-specific applications. Usage of these applications can indicate that the user is traveling in a vehicle while the application is being used. The usage monitor 255 can monitor which applications are used above a threshold amount of time in a predetermined time period (e.g., one day, one week, one month, or the like). In still other examples, the usage monitor 255 can determine a type of motion or speed of motion associated with movement of the mobile device 250, whether the device is maintained within a case, and the like. Additional aspects of device usage can be monitored without departing from the invention. In some examples, data from usage monitor 255 can be accessed by the device usage analysis application 252 for analysis and/or transmission to, for instance, determination server 210. Data from usage monitor 255 can be transmitted directly to the determination server 210.

The mobile device 250 can be configured to establish communication with determination server 210 or other computing system (such as external data computing device 740) via one or more wireless networks (e.g., network 230). The mobile device, when carried in a vehicle, can be used to detect performance and/or operational characteristics of the vehicle 260, similar to the one or more sensors arranged in the vehicle 260. Mobile device 250 can be configured to be paired (e.g., via Bluetooth technology) to one or more other devices, such as vehicle 260 or the like. In a variety of embodiments, the mobile device 250 includes any of the sensors described below and/or is capable of obtaining any of the data described with respect to vehicle 260 without a connection to the vehicle 260 or any device within the vehicle 260.

Device usage and output determination system 200 can further include a vehicle 260. Vehicle 260 can be, for example, automobiles, motorcycles, scooters, buses, recreational vehicles, boats, or any other vehicles for which driving behaviors can be analyzed. Vehicle 260 can include vehicle operation sensors 261 capable of detecting and recording various conditions at the vehicle and operational parameters of the vehicle. For example, sensors 261 can detect and store data corresponding to the vehicle's location (e.g., GPS coordinates), time, travel time, speed and direction, rates of acceleration or braking, gas mileage, and specific instances of sudden acceleration, braking, swerving, and distance traveled. Sensors 261 also can detect and store data received from the vehicle's 260 internal systems, such as impact to the body of the vehicle, air bag deployment, headlights usage, brake light operation, door opening and closing, door locking and unlocking, cruise control usage, hazard lights usage, windshield wiper usage, horn usage, turn signal usage, seat belt usage, phone and radio usage within the vehicle, autonomous driving system usage, maintenance performed on the vehicle, and other data collected by the vehicle's computer systems, including the vehicle on-board computing device (OBD).

Additional sensors 261 can detect and store the external driving conditions, for example, external temperature, rain, snow, light levels, and sun position for driver visibility. For example, external cameras and proximity sensors 261 can detect other nearby vehicles, vehicle spacing, traffic levels, road conditions, traffic obstructions, animals, cyclists, pedestrians, and other conditions that can relate to vehicle accidents and accident characteristics. Sensors 261 also can detect and store data relating to moving violations and the observance of traffic signals and signs by the vehicle 260. Additional sensors 261 can detect and store data relating to the maintenance of the vehicle 260, such as the engine status, oil level, engine coolant temperature, odometer reading, the level of fuel in the fuel tank, engine revolutions per minute (RPMs), software upgrades, and/or tire pressure.

Vehicles sensors 261 also can include cameras and/or proximity sensors capable of recording conditions inside or outside of the vehicle 260. For example, internal cameras can detect conditions such as the identity of the driver (e.g., using facial recognition software), the number of the occupants, the types of occupants (e.g. adults, children, teenagers, pets, etc.), and the seating/positioning of the occupants in the vehicles. Internal cameras also can detect potential sources of driver distraction within the vehicle, such as pets, phone usage, and unsecured objects in the vehicle. Sensors 261 also can be configured to collect data identifying a current driver from among a number of different possible drivers, for example, based on driver's seat and mirror positioning, driving times and routes, radio usage, etc. Sensors 261 also can be configured to collect data relating to a driver's movements or the condition of a driver. For example, vehicle 260 can include sensors that monitor a driver's movements, such as the driver's eye position and/or head position, etc. Additional sensors 261 can collect data regarding the physical or mental state of the driver, such as fatigue or intoxication. The condition of the driver can be determined through the movements of the driver or through other sensors, for example, sensors that detect the content of alcohol in the air or blood alcohol content of the driver, such as a breathalyzer.

Certain vehicle sensors 261 also can collect information regarding the vehicle's location, current and past driving routes, in order to classify the type of trip (e.g. work or school commute, shopping or recreational trip, unknown new route, etc.). In certain embodiments, sensors and/or cameras 261 can determine when and how often the vehicle 260 stays in a single lane or stray into other lanes. A global navigation satellite system (GNSS) such as Global Positioning System (GPS), locational sensors positioned inside the vehicle 260, and/or locational sensors or devices external to the vehicle 260 can be used to determine the route, lane position, road-type (e.g. highway, entrance/exit ramp, residential area, etc.) and other vehicle position/location data which can be used to analyze accidents and accident characteristics, generate driver safety ratings, generate one or more user or driver insights, generate one or more outputs, and the like.

The data collected by vehicle sensors 261 can be stored and analyzed within the respective vehicle 260, for example, in vehicle data analysis device 264, which can be integrated into or installed at the vehicle 260. In other cases, the data collected by vehicle sensors 261 can be transmitted to one or more external devices for analysis, such as a mobile device 250 or external servers 210. In some examples, the data may be transmitted to and stored by a third party computing system (such as external data computing device 740) and transmitted to other devices for analysis, as discussed more fully herein. The sensor data can be transmitted from vehicles 260 via a telematics device 263 or other network interface(s) to one or more remote computing devices, such as one or more mobile devices 250, determination server 210, and/or other external servers or systems (e.g., external data computing device 740).

Vehicle 260 can use telematics devices 263 to transmit data to and receive data from servers 210 and mobile devices 250. Telematics devices 263 can be computing devices containing many or all of the hardware/software components as a computing device described herein. In some cases, telematics devices 263 can receive vehicle sensor data, operation data, location data, and/or driving data from vehicle sensors 261, and can transmit the data to one or more external computer systems (e.g., determination server 210, other external data computing system, such as external data computing system 740, or the like) over a wireless transmission network 230. The telematics devices 263 also can store the type of their respective vehicle 260, for example, the make, model, trim (or sub-model), year, and/or engine specifications, as well as other information such as vehicle owner or driver information, insurance information, warranty information, and financing information for the vehicle 260.

Telematics devices 263 can receive data from vehicle sensors 261, and can transmit the data to a mobile device 250 or determination server 210. However, in other examples, one or more of the vehicle sensors 261 or other vehicle-based systems can be configured to receive and transmit data directly from or to other servers 210 or mobile device 250 without using a telematics device. For instance, telematics devices 263 can be configured to receive and transmit data from certain vehicle sensors 261 or systems, while other sensors or systems can be configured to directly receive and/or transmit data to servers 210 or mobile device 250 without using the telematics device 263. Thus, telematics devices 263 can be optional in certain embodiments.

The system 200 also can include one or more external servers, such as determination server 210, which can contain some or all of the hardware/software components as computing devices described herein. Determination server 210 can communicate with vehicle 260 and mobile devices 250 via one or more communication networks 230. The determination server 210 can include some or all of the components and/or functionality described with respect to FIG. 1. The server 210 can include one or more databases 212 configured to store data associated with a user, device, or the like, that can be used to evaluate risk. Further, the server 210 can include device usage analysis module 211 which can provide some or all of the operations and/or functionality described with respect to FIG. 1. The determination server 210 can include one or more databases 242 configured to store data associated with driving behaviors, performance data, operational data, and the like.

Figure 3:
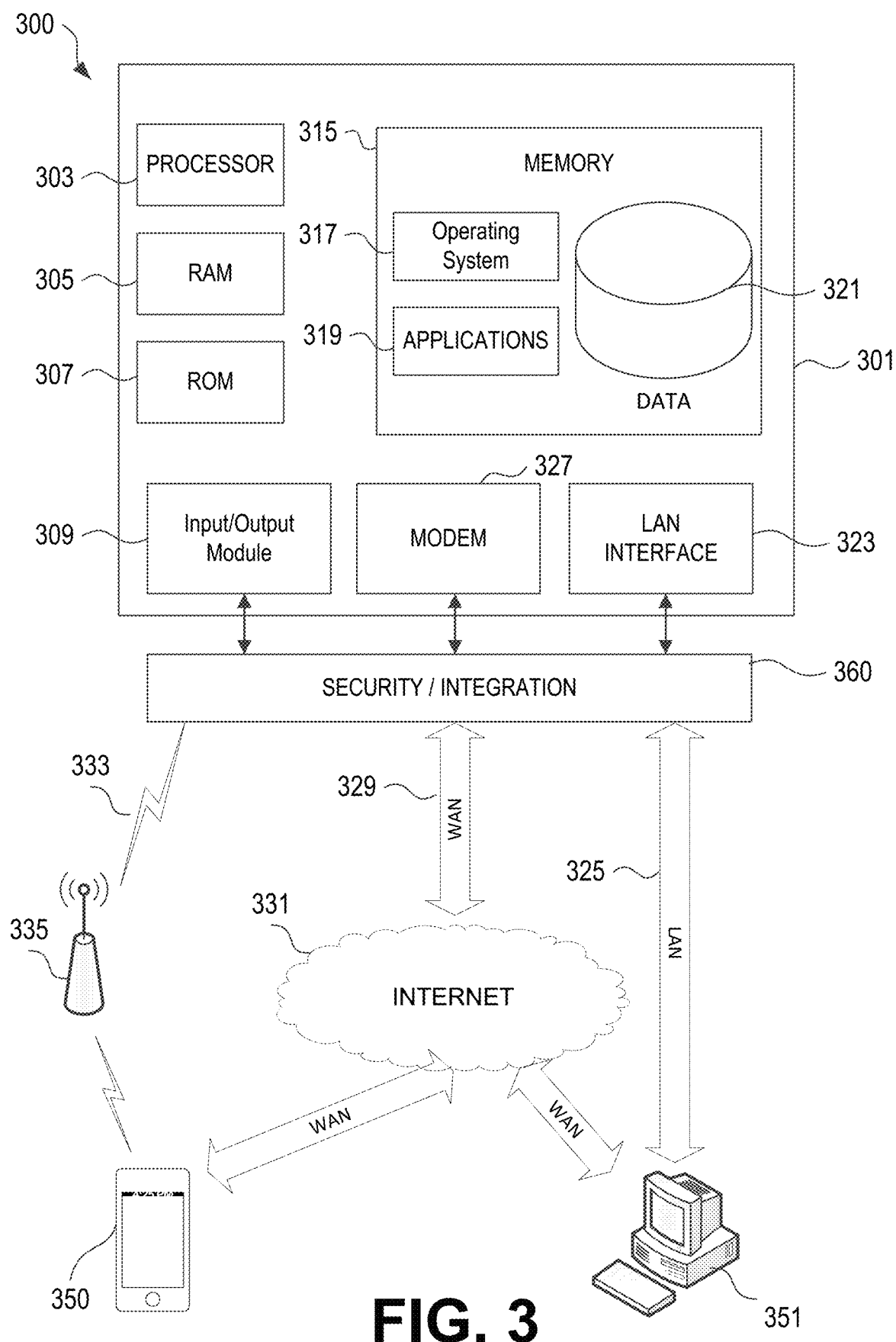
FIG. 3 illustrates a network environment and computing systems that can be used to implement aspects of the disclosure.

FIG. 3 illustrates a block diagram of a computing device (or system) 301 in a computer system 300 that can be used according to one or more illustrative embodiments of the disclosure. The device 301 can have a processor 303 for controlling overall operation of the device 301 and its associated components, including RAM 305, ROM 307, input/output module 309, and memory 315. The computing device 301, along with one or more additional devices (e.g., terminals 350 and 351, security and integration hardware 360) can correspond to any of multiple systems or devices, such as a mobile device, a vehicle-based computing system, a wearable device such as a fitness tracker, or a computer server, configured as described herein for capturing data, receiving requests for insights, offers or outputs, extracting and transmitting data, analyzing data, evaluating device usage, determining one or more outputs, insights or offers, generating one or more recommendations, generating one or more incentives, determining whether one or more recommendations have been implemented, and the like.

Input/Output (I/O) 309 can include a microphone, keypad, touch screen, and/or stylus through which a user of the computing device 301 can provide input, and can also include one or more of a speaker for providing audio output and a video display device for providing textual, audiovisual and/or graphical output. Software can be stored within memory 315 and/or storage to provide instructions to processor 303, allowing device 301 to perform various actions. For example, memory 315 can store software used by the device 301, such as an operating system 317, application programs 319, and an associated internal database 321. The various hardware memory units in memory 315 can include volatile and nonvolatile, removable and non-removable media implemented in any method or technology for storage of information such as computer readable instructions, data structures, program modules or other data. Certain devices/systems within the system can have minimum hardware requirements in order to support sufficient storage capacity, analysis capacity, network communication, etc. For instance, in some embodiments, one or more nonvolatile hardware memory units having a minimum size (e.g., at least 1 gigabyte (GB), 2 GB, 5 GB, etc.), and/or one or more volatile hardware memory units having a minimum size (e.g., 256 megabytes (MB), 512 MB, 1 GB, etc.) can be used in a device 301 (e.g., a mobile computing device 301, vehicle-based computing system 301, determination server 301, external server 301, etc.), in order to store and execute offer generation control applications, receive requests for offer generation, extract and transmit data, analyze data, generate offers or outputs, execute device usage and output determination software application, collect and analyze usage data, generate outputs, generate recommendations and/or incentives, and the like. Memory 315 also can include one or more physical persistent memory devices and/or one or more non-persistent memory devices. Memory 315 can include, but is not limited to, random access memory (RAM) 305, read only memory (ROM) 307, electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 303.

Processor 303 can include a single central processing unit (CPU), which can be a single-core or multi-core processor (e.g., dual-core, quad-core, etc.), or can include multiple CPUs. Processor(s) 303 can have various bit sizes (e.g., 16-bit, 32-bit, 64-bit, 96-bit, 128-bit, etc.) and various processor speeds (ranging from 100 MHz to 5 Ghz or faster). Processor(s) 303 and its associated components can allow the system 301 to execute a series of computer-readable instructions, for example, to execute a device usage and output determination software application that receives and processes usage data, generate one or more outputs, generates recommendations and/or incentives, receive a request for generation of an offer, extract and/or transmit data, analyze data using, for example, machine learning, generate one or more offers or outputs, and the like.

The computing device (e.g., a mobile computing device, a vehicle-based device, external server, etc.) can operate in a networked environment 300 supporting connections to one or more remote computers, such as terminals 350 and 351. The terminals 350 and 351 can be personal computers, servers (e.g., web servers, database servers), or mobile communication devices (e.g., mobile phones, portable computing devices, on-board vehicle-based computing systems, and the like), and can include some or all of the elements described above with respect to the computing device 301. The network connections depicted in FIG. 3 include a local area network (LAN) 325 and a wide area network (WAN) 329, and a wireless telecommunications network 333, but can also include other networks. When used in a LAN networking environment, the computing device 301 can be connected to the LAN 325 through a network interface or adapter 323. When used in a WAN networking environment, the device 301 can include a modem 327 or other means for establishing communications over the WAN 329, such as network 331 (e.g., the Internet). When used in a wireless telecommunications network 333, the device 301 can include one or more transceivers, digital signal processors, and additional circuitry and software for communicating with devices (e.g., mobile phones, portable computing devices, on-board vehicle-based computing systems, etc.) via one or more network devices 335 (e.g., base transceiver stations) in the wireless network 333.

Also illustrated in FIG. 3 is a security and integration layer 360, through which communications can be sent and managed between the device 301 (e.g., a user's personal mobile device, a vehicle-based system, a determination server or other external server, an offer generation computing platform, etc.) and the remote devices (350 and 351) and remote networks (325, 329, and 333). The security and integration layer 360 can comprise one or more separate computing devices, such as web servers, authentication servers, and/or various networking components (e.g., firewalls, routers, gateways, load balancers, etc.), having some or all of the elements described above with respect to the computing device 301. As an example, a security and integration layer 360 of a mobile computing device, vehicle-based device, or a server operated by an insurance provider, financial institution, governmental entity, or other organization, can comprise a set of web application servers configured to use secure protocols and to insulate the server 301 from external devices 350 and 351. In some cases, the security and integration layer 360 can correspond to a set of dedicated hardware and/or software operating at the same physical location and under the control of same entities as driving data analysis server 301. For example, security and integration layer 360 can correspond to one or more dedicated web servers and network hardware in an organizational datacenter or in a cloud infrastructure supporting a cloud-based driving data analysis system. In other examples, the security and integration layer 360 can correspond to separate hardware and software components which can be operated at a separate physical location and/or by a separate entity.

As discussed below, the data transferred to and from various devices in the computing system 300 can include secure and sensitive data, such as device usage data, application usage data, application type data, user movement or location data, user activity data, user internet browsing history, and the like. Therefore, it can be desirable to protect transmissions of such data by using secure network protocols and encryption, and also to protect the integrity of the data when stored on in a database or other storage in a mobile device, determination server, or offer generation computing platform and other computing devices in the system 300, by using the security and integration layer 360 to authenticate users and restrict access to unknown or unauthorized users. In various implementations, security and integration layer 360 can provide, for example, a file-based integration scheme or a service-based integration scheme for transmitting data between the various devices in a system 300. Data can be transmitted through the security and integration layer 360, using various network communication protocols. Secure data transmission protocols and/or encryption can be used in file transfers to protect to integrity of the driving data, for example, File Transfer Protocol (FTP), Secure File Transfer Protocol (SFTP), and/or Pretty Good Privacy (PGP) encryption. In other examples, one or more web services can be implemented within the various devices 301 in the system 300 and/or the security and integration layer 360. The web services can be accessed by authorized external devices and users to support input, extraction, and manipulation of the data (e.g., device usage data, location data, vehicle data, etc.) between the various devices 301 in the system 300. Web services built to support system 300 can be cross-domain and/or cross-platform, and can be built for enterprise use. Such web services can be developed in accordance with various web service standards, such as the Web Service Interoperability (WS-I) guidelines. In some examples, a movement data and/or driving data web service can be implemented in the security and integration layer 360 using the Secure Sockets Layer (SSL) or Transport Layer Security (TLS) protocol to provide secure connections between servers 301 and various clients 350 and 351 (e.g., mobile devices, data analysis servers, etc.). SSL or TLS can use HTTP or HTTPS to provide authentication and confidentiality. In other examples, such web services can be implemented using the WS-Security standard, which provides for secure SOAP messages using XML encryption. In still other examples, the security and integration layer 360 can include specialized hardware for providing secure web services. For example, secure network appliances in the security and integration layer 360 can include built-in features such as hardware-accelerated SSL and HTTPS, WS-Security, and firewalls. Such specialized hardware can be installed and configured in the security and integration layer 360 in front of the web servers, so that any external devices can communicate directly with the specialized hardware.

Although not shown in FIG. 3, various elements within memory 315 or other components in system 300, can include one or more caches, for example, CPU caches used by the processing unit 303, page caches used by the operating system 317, disk caches of a hard drive, and/or database caches used to cache content from database 321. For embodiments including a CPU cache, the CPU cache can be used by one or more processors in the processing unit 303 to reduce memory latency and access time. In such examples, a processor 303 can retrieve data from or write data to the CPU cache rather than reading/writing to memory 315, which can improve the speed of these operations. In some examples, a database cache can be created in which certain data from a database 321 (e.g., a device usage database, a vehicle data database, location database, etc.) is cached in a separate smaller database on an application server separate from the database server. For instance, in a multi-tiered application, a database cache on an application server can reduce data retrieval and data manipulation time by not needing to communicate over a network with a back-end database server. These types of caches and others can be included in various embodiments, and can provide potential advantages in certain implementations of retrieving device usage data, vehicle data, and individual data, such as faster response times and less dependence on network conditions when transmitting/receiving device usage and output determination software applications (or application updates), usage data, vehicle data, etc.

It will be appreciated that the network connections shown are illustrative and other means of establishing a communications link between the computers can be used. The existence of any of various network protocols such as TCP/IP, Ethernet, FTP, HTTP and the like, and of various wireless communication technologies such as GSM, CDMA, WiFi, and WiMAX, is presumed, and the various computer devices and system components described herein can be configured to communicate using any of these network protocols or technologies.

Additionally, one or more application programs 319 can be used by the various computing devices 301 within a device usage and output determination system 300 (e.g., device usage and output determination software applications, etc.), an offer generation control system 700 (e.g., offer generation computing platform 710, and the like) including computer executable instructions for receiving and storing device usage data, vehicle data, analyzing data, determining outputs, generating recommendations, generating incentives, receiving offer generation requests, extracting and transmitting data, analyzing data, generating user interfaces, generating offers or outputs, and performing other related functions as described herein.

A variety of devices and systems are described with respect to FIGS. 1-3. In many embodiments, data obtained and/or generated by any of these devices, as well as various devices described below, can be stored and/or obtained by a variety of third-party server systems as appropriate. For example, the location history of a mobile device can be stored locally using the mobile device and/or remotely using a third party server system, such as described more fully below. When transmitting (and/or obtaining) the location data, this data can be provided directly by the mobile device and/or the third-party server system as appropriate to the requirements of specific applications of embodiments of the invention. In other examples, data obtained by the mobile device can be aggregated and anonymized before it is shared with a third-party server system. The various aspects described herein of sharing, transmitting, analyzing, etc. user data, such as location data, wearable device data, wellness data, and the like, may be performed with appropriate permissions from users.

Figure 4A:
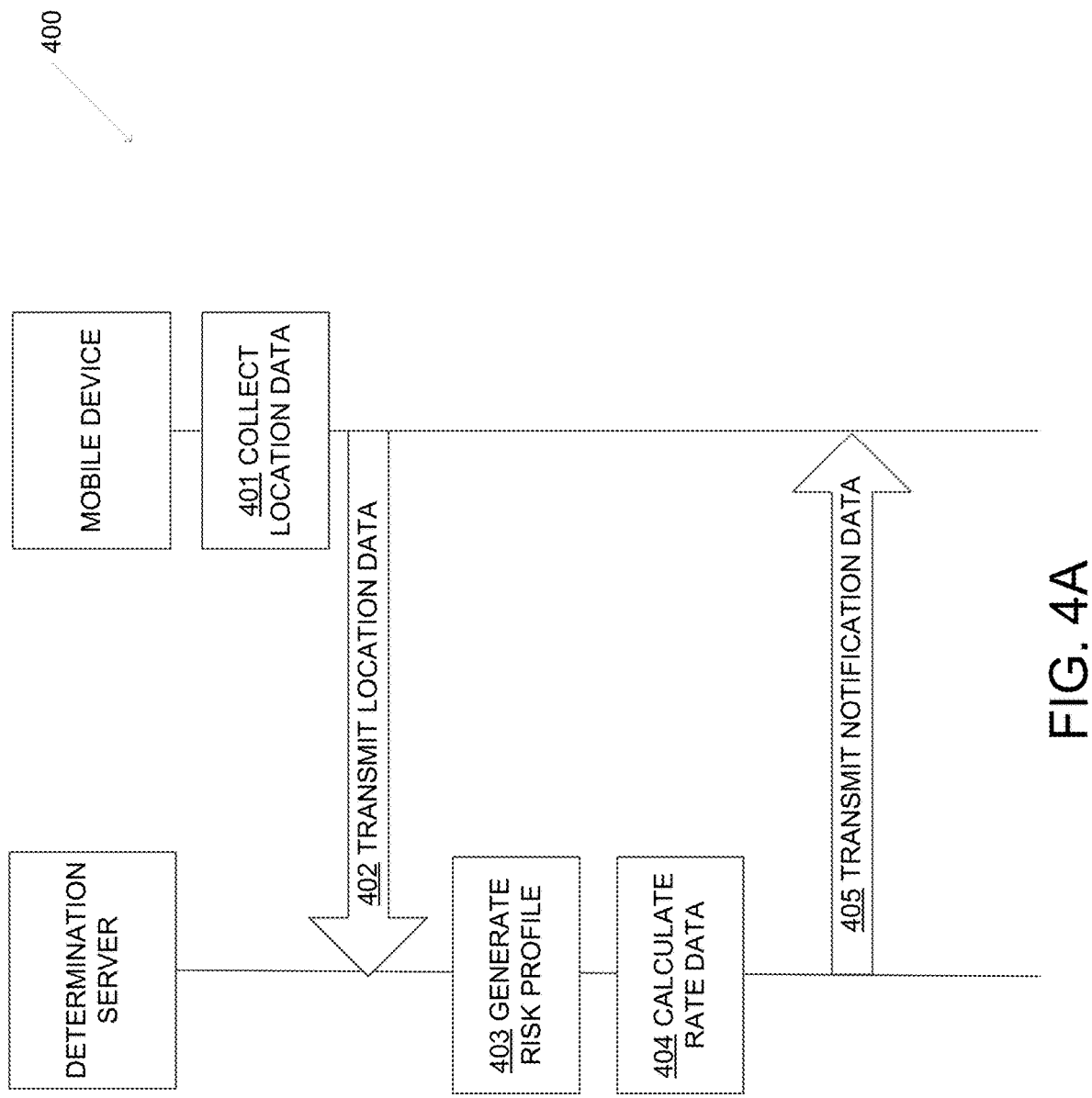
FIGS. 4A-B depict illustrative event sequences for evaluating device usage and generating an output according to one or more aspects described herein.
Figure 4B:
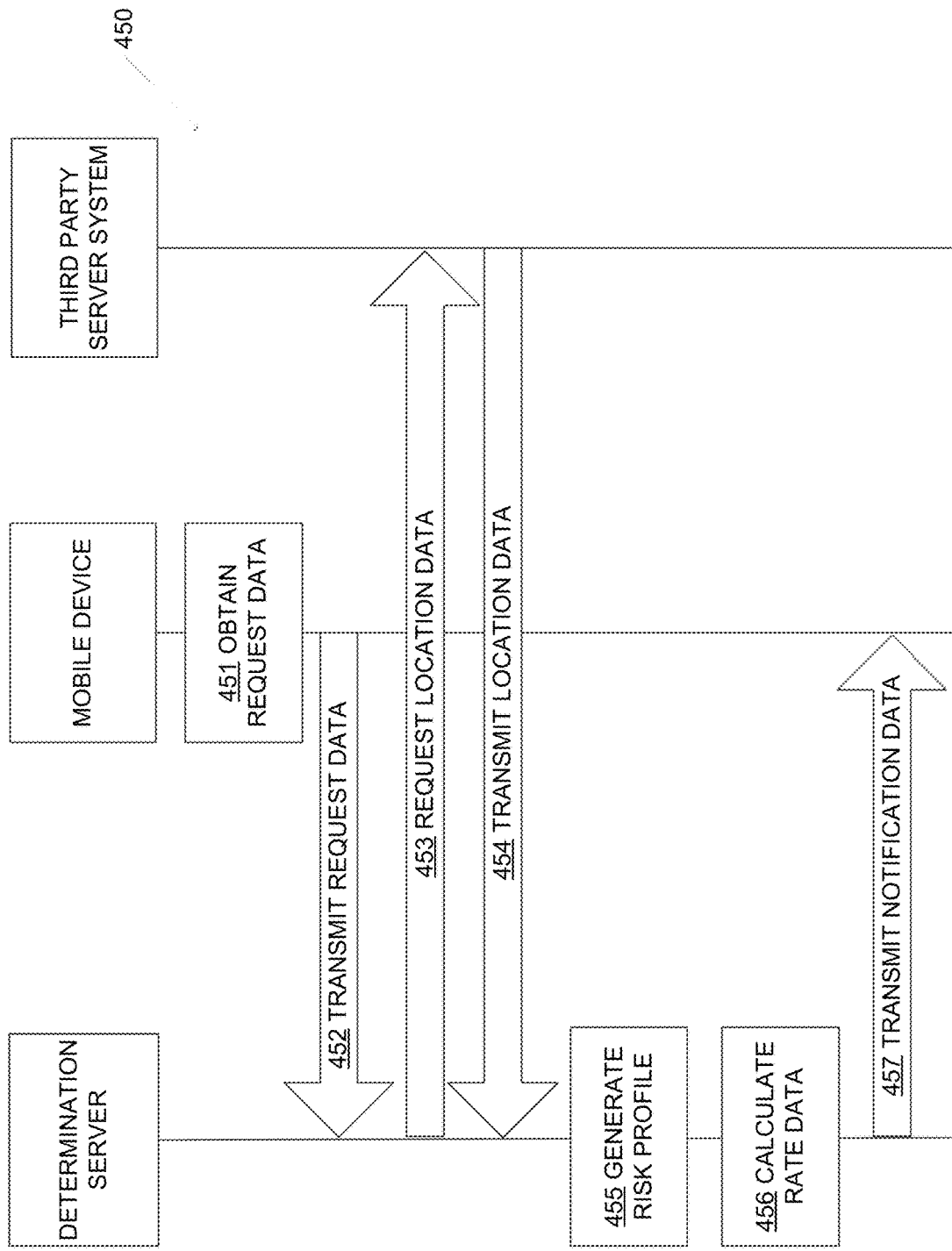

FIGS. 4A and 4B illustrate example event sequences for evaluating device usage and determining an output in accordance with one or more aspects described herein. The sequences illustrated are merely example sequences and various other events can be included, or events shown can be omitted, without departing from the invention.

With reference to FIG. 4A, in step 401, location data can be collected by a mobile device. As discussed herein, the raw sensor data can be directed to movement of the device and the like. The location data can include an amount of time a user spends within a predefined proximity of a designated or determined "home" location, "work" location, or the like. The location data can also include information related to a current location of the user. The current location information can be based on GPS data, geo-tagged location information associated with a captured image or the like, etc. Other data instance, data related to what applications are used, how often and/or for how long, and a type of application. In some examples, the data can be related to an amount of usage (e.g., hours, minutes, etc.) of use for each application within a predefined time period (e.g., one week, one month, or the like). In some examples, driving data or behaviors associated with the user can be used. Vehicle data, such as operational data, performance data, and the like, can be collected by one or more sensors within the mobile device. The received data can be processed to evaluate the data and/or identify one or more driving behaviors associated with the user. For instance, processing the data can determine whether at least a threshold number of hard braking occurrences have taken place within a predefined time period (e.g., one week, one month, etc.). In another example, the data can be processed to determine a typical rate of acceleration for a user, whether the user is able to maintain his or her lane while driving, and the like. In some arrangements, driving data from a plurality of connected vehicles may be captured and analyzed to "learn" from one use in order to "teach" another user. For instance, driving data may be analyzed using one or more machine learning techniques to analyze both structured and unstructured data to identify patterns, behaviors and the like, that may be used to generate recommendations, outputs, or insights for improved driving.

The data can be transmitted to the determination server in step 402. In step 403, a risk profile is generated. The risk profile can be generated based on any of the data related to the mobile device described herein. In a variety of embodiments, the risk profile includes a driver score describing one or more features of the user. In several embodiments, the risk profile is generated using the location data and a risk map. In some examples, a risk score or likelihood of damage associated with each factor being considered can be calculated. For instance, a score associated with a level of risk of potential damage to the vehicle can be determined for each of raw sensor data, usage data, location data, and/or application data. A risk score can be determined for data retrieved from one or more databases. The scores for each factor can then be summed to determine an overall score. The overall score can be compared to one or more premium thresholds to determine an appropriate premium or rate to insure the vehicle. Although the arrangement shown includes raw sensor data, usage data, location data and application data, more or fewer factors can be used without departing from the invention.

In step 404, rate data is calculated. In a variety of embodiments, the calculated rate data includes an insurance rate for a vehicle having travel patterns corresponding to those of the mobile device. The rate data can be further based on the risk profile. The rate data can also include a verification of data provided by the user. In this way, the location history of the mobile device can be used to verify information provided by a user and provide more accurate risk profiles and/or rates. The rate data can be for a particular term (e.g., six months, one year, etc.). In other examples, the rate can be a usage-based type of policy in which a user can purchase insurance and funds (or other credits) can be stored in an account. As the device is used (e.g., by actual use minutes, hours, or the like or per day) a balance of the account can be reduced by a predetermined amount.

In step 405, notification data can be transmitted to the mobile device. The notification data can include the rate data, the risk profile, and/or any other data of interest to the user. The notification data can be displayed to the user using the mobile device. In several embodiments, the notification data includes one or more incentives to implement the generated recommendation(s). For instance, an insurance incentive can include a reduced premium for a next term if one or more of the recommendations are implemented. In another example, an incentive can include a refund of a portion of a premium paid if one or more recommendations are implemented.

With reference to FIG. 4B, in step 451, a mobile device can obtain request data. In many embodiments, the request data includes a request for insurance for a vehicle or other offer. The request data can be transmitted to a determination server in step 452. The determination server can request location data describing the location history of the mobile device from a third party server system in step 453. In step 454, the location data for the mobile device can be transmitted by the third party server system to the determination server. In step 455, the determination server can generate a risk profile and, in step 456, calculate rate data. In step 457, notification data can be provided to the mobile device.

A user's mobile device can provide a variety of data about the user's mobility patterns in order to assess automotive risks, how the user is making choices, and their driving behavior. Mobile devices (and/or third party server systems which receive location data from the mobile devices) can map significant locations that the mobile device travels. This location data describing where and when the user is traveling to a variety of locations can be correlated with a risk map to build a risk profile. The risk profile provides important indicators about a user and driving behavior. These indicators may include: total miles driven during a time period (one month, three months, one year, etc.), the number of miles driven, type of roads used (highway, local, etc.), the time the user is driving (nighttime, daytime, etc.), the riskiness of particular locations traveled to and/or through, the locations commonly traveled to (work, home, bars, restaurants, stores, etc.), usage data of various applications, time stamps, location stamps (e.g. are applications being used with the phone was in use or in motion), and/or profile data (who are the customers communicating with (texting, emailing, snapchatting), etc.)

This data can be utilized to validate the information provided by the user (e.g. is the person sharing true information or giving wrong information), which may aid in detecting fraud or potential fraud. Additionally, the data can be analyzed to provide information for risk assessment and/or risk management to the users, such as information for parents about their teen drivers. The data can also be utilized for existing customers to verify current driving behaviors, patterns, and to find customers that meet a certain profile to target market them.

Figure 5:
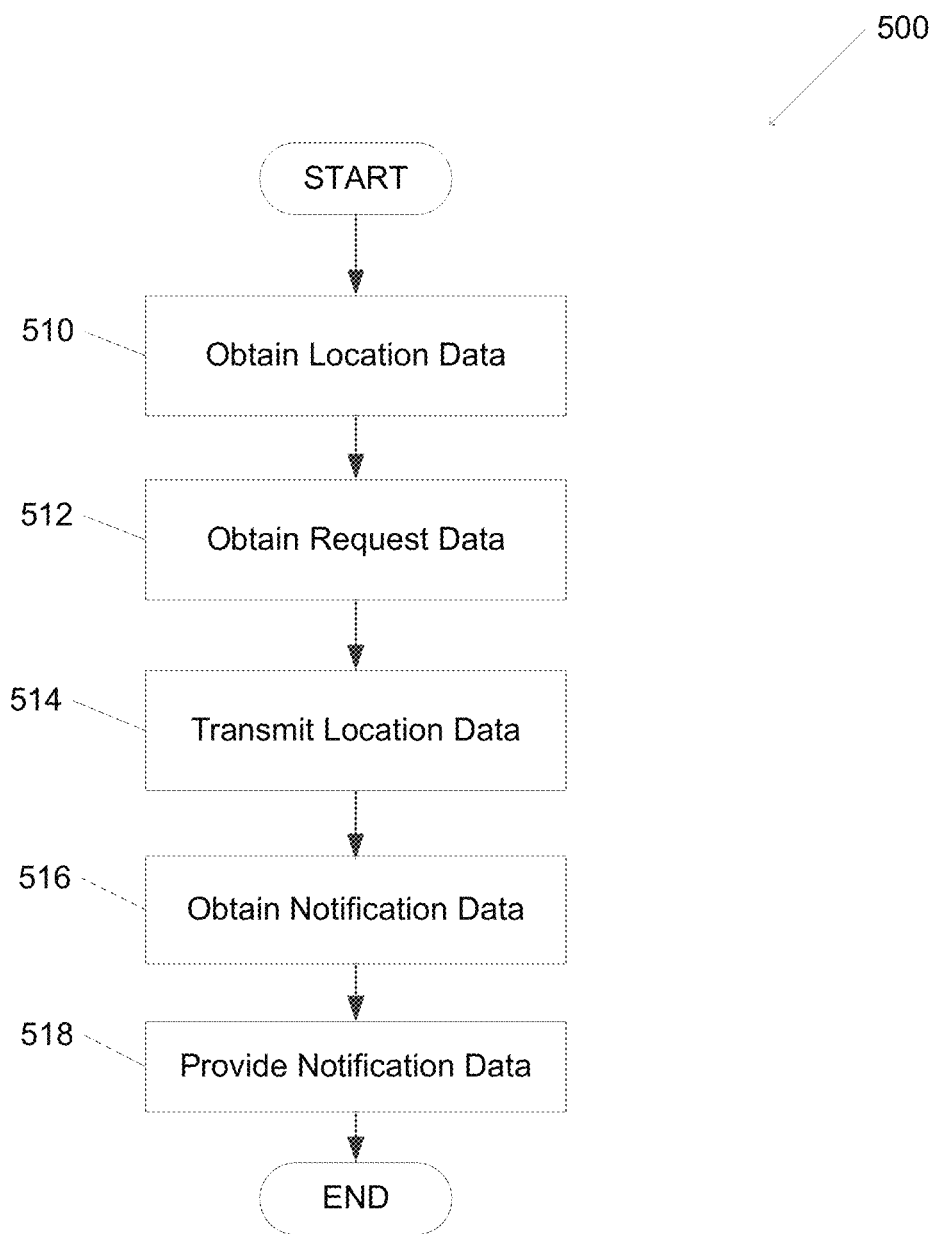
FIG. 5 is a flow chart illustrating a process for providing location data from a mobile device in accordance with an embodiment of the invention.

Turning now to FIG. 5, an example process for evaluating device usage to determine an output, such as an insurance premium, according to one or more aspects described herein. The process 500 includes obtaining (510) location data. As discussed herein, the location data can be received from a variety of sources. A variety of other data, such as amount of usage, type of usage, applications executing on the device, type of applications executing on the device, use of applications on the device at the time of driving (e.g. texting while driving) and the like, can also be obtained in addition to the location data. The data can be received from various sources, such as one or more sensors within the device, GPS systems within the device, usage monitors associated with the device, and the like. The location data can be based on GPS information obtained by the mobile device, from geo-tagged location information embedded in or associated with other data, images used by the mobile devices or applications run on the mobile device or the like captured by the mobile device, and the like.

Request data can be obtained (512). In many embodiments, the request data includes a request for the location history of a mobile device described using the location data after suitable permissions from the user are obtained. The location data can be transmitted (514). In many embodiments, notification data is obtained (516) and notification data is provided (518) utilizing any of a variety of processes describe herein.

Figure 6:
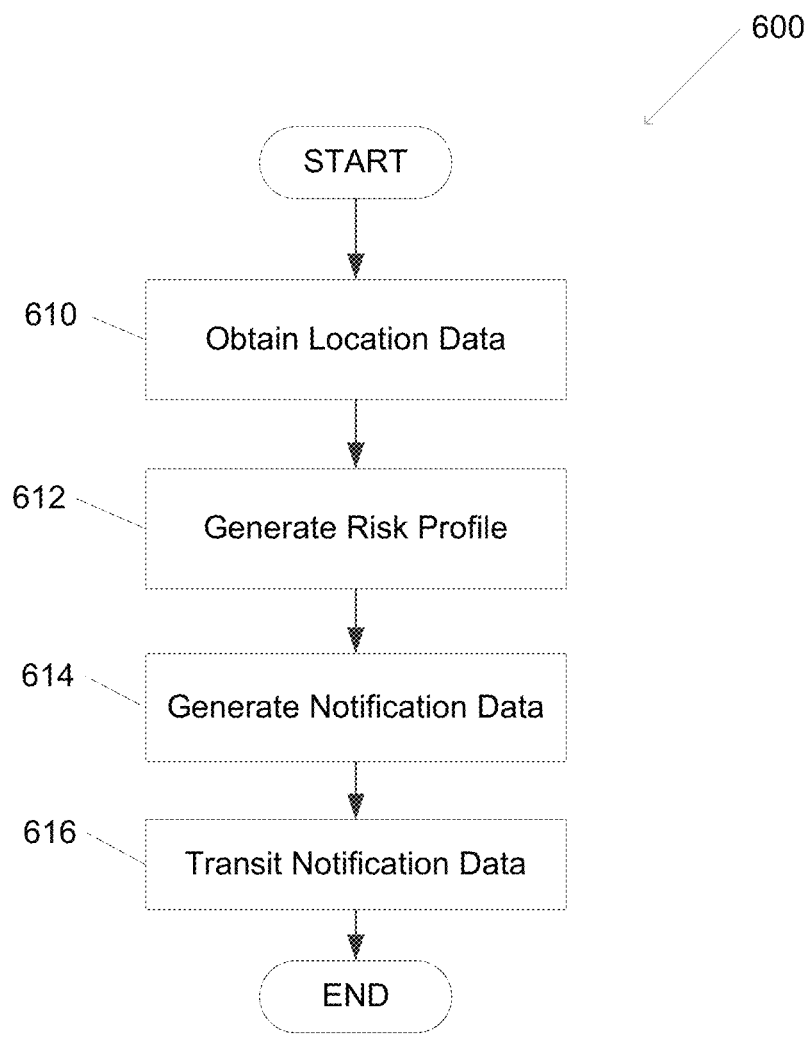
FIG. 6 is a flow chart illustrating a process for generating a risk profile in accordance with an embodiment of the invention.

Turning now to FIG. 6, an example process for generating a risk profile in accordance with an embodiment of the invention is shown. Location data can be obtained (610). In many embodiments, the location data describes the geographic location of a mobile device at one or more times as described herein. A risk profile can be generated (612). The risk profile can be generated utilizing any of the processes described herein. Additionally, a determination can be made as to whether automobile and/or driving data can be included in determining the risk profile. Notification data can be generated (614) and transmitted (616).

Notifications can be transmitted to a mobile device for display. The notification data can include information regarding the risk profile, insurance rates for a vehicle generated based on the risk profile, one or more incentives, and any other notifications which may be of interest to a user. The notifications can include one or more features or characteristics of an insurance policy associated with a vehicle having travel patterns corresponding to those of the mobile device.

As discussed herein, various examples for generating a risk profile and/or customizing an insurance policy and/or premium based on usage of a mobile device are described. In some examples, the insurance can cover theft, damage, and the like. The system can generate one or more levels of coverage depending on a desired level of protection. For instance, in arrangements in which the vehicle is only insured for theft, some types of data can be less relevant to determining the premium. Accordingly, the determination server can control an amount or type of data collected by the device and/or utilized in the determination of the risk profile. Accordingly, the determination server can control a type of amount of data received, processed, etc., thereby controlling the computing resources needed to process the data, determine one or more outputs, and the like.

Further, in some examples, a baseline cost can be established for a particular risk profile and the usage data can be analyzed to adjust the baseline cost. For instance, the system can generate a baseline level of risk associated with a particular area and/or travel pattern. This can form a baseline for cost associated with insuring a vehicle and can be associated with a baseline insurance premium. The various types of data described herein can then be analyzed to determine whether an adjustment to the baseline premium should be made based on an increased likelihood of damage (or an increase over a predetermined threshold amount for which the baseline value might not be adjusted). If the analysis of usage data (and other data as desired) indicates an increase in likelihood of damage over a certain threshold, the premium can be increased.

The usage data collected by the devices and systems described herein can be obtained with the permission of the user associated with the device and, in some examples, the user can be given the option to share an anonymized version of his or her data with one or more entities. In some embodiments, the usage data collected by the device can be aggregated or processed by the device itself, and the aggregated data can be shared with one or more entities.

In some examples, the system can detect multiple different users of a device and can determine travel patterns based on each user's usage of the device. For instance, a fingerprint, voice print, pattern of finger or thumb movement, or the like can be used to distinguish between different users of a device (e.g., a parent and child, siblings, husband and wife, etc.). Accordingly, usage data for each user can be evaluated to determine the travel profile associated with each user, which then can be used to determine a risk profiles for each individual user. In some arrangements, analyzing data to evaluate a user may include detecting multiple different users of a device to determine travel patterns based on each user's usage of the device.

Various aspects discussed above with respect to FIGS. 1-6 may be performed by or in conjunction with offer generation computing platform 710 described herein. Similarly, aspects discussed below with respect to FIGS. 7A-18 may be performed by or in conjunction with the devices described with respect to FIGS. 1-6 (e.g., determination server 110, determination server 210, vehicle 260, mobile device 250, or the like). Further a combination of devices described in FIGS. 1-18, as well as processes, functions and aspects described with respect to FIGS. 1-18 may be used without departing from the invention.

As discussed herein, vast amounts of user data are collected by, for instance, a mobile device, wearable device, or the like, of a user on a daily basis. For instance, information such as location data (e.g., GPS coordinates and corresponding time and date stamps, and the like), wellness data, activity data, social media data, internet browsing data, and the like, may be captured by one or more user computing devices. This information may be transmitted to one or more third party systems (e.g., web browser providers, application providers, wearable devices and systems, and the like) and stored with the permission of the user. Historically, this stored data was not viewable by the user or it was prohibitively difficult to obtain access to the user via the third party system. However, several third party systems have begun permitting users to view their data and enabling more efficient methods of accessing, viewing, downloading, and the like, the user data.

Accordingly, aspects described herein are directed to facilitating extraction and transmission of a user's data from the third party system to a system associated with a first entity from which the user has requested a generated offer or output. Accordingly, the user may facilitate transmission of the data from the third party system to the first entity system via his or her mobile device. By transmitting extracted data stored by the third party, greater amounts of data may be transmitted for analysis, previously captured data may be used to generate insights and offers rather than conventional arrangements in which a user must engage with an entity based on a non-user data based offer, and the like. The first entity system may then evaluate the data to generate one or more offers or outputs, generate and/or display insights into user behaviors, and the like. In some examples, machine learning may be used to generate one or more offers, outputs and/or insights.

In at least some arrangements, some or all of the aspects described herein may be performed in real-time or near real-time in order to facilitate quick output generation for a user. Further, aspects described herein with respect to capturing and storing user data are performed with the permission of the user.

These and other aspects will be described more fully herein.

Figure 7A:
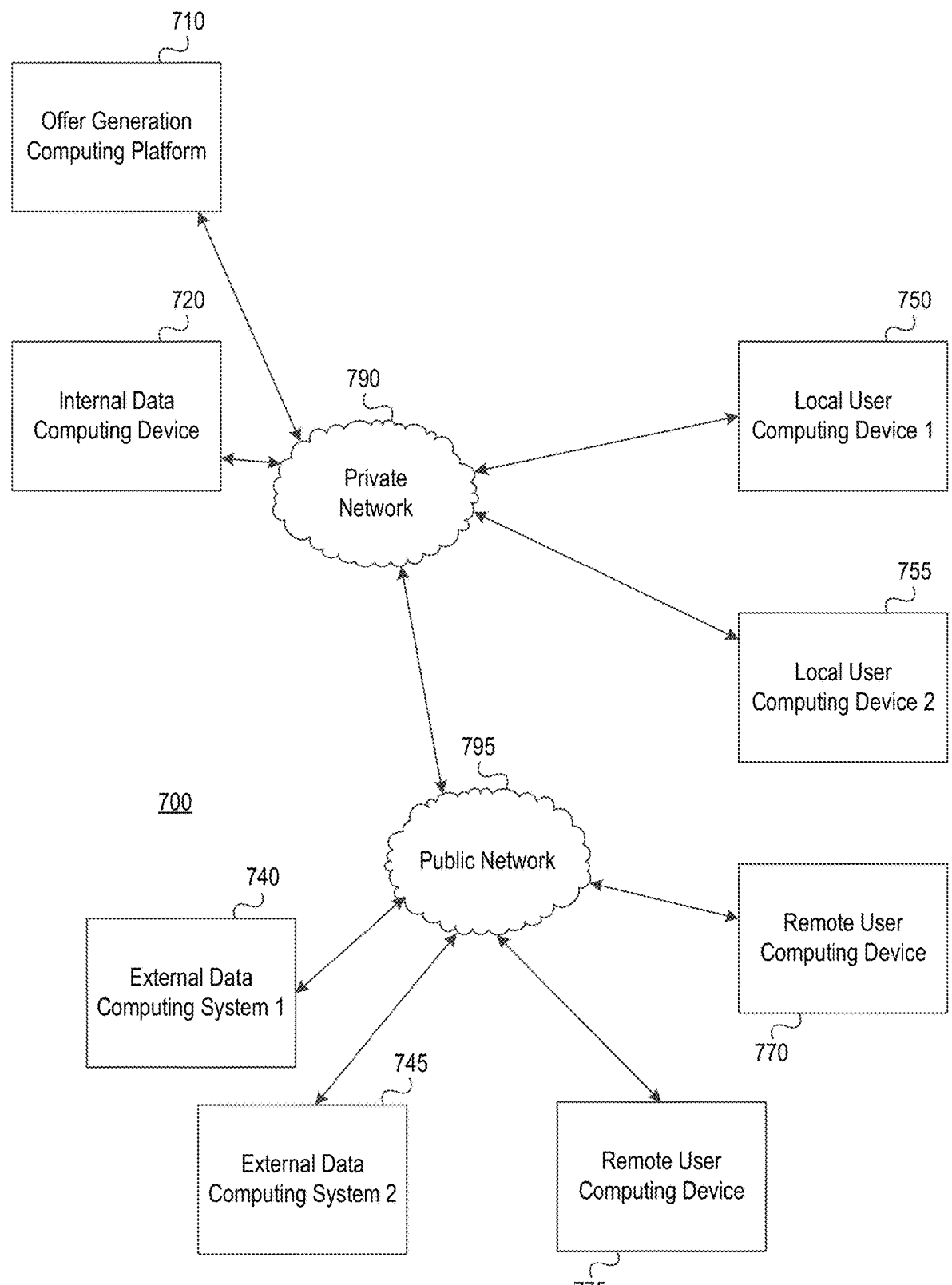
FIGS. 7A and 7B illustrate an illustrative computing environment for implementing offer generation control functions, according to one or more aspects described herein.
Figure 7B:
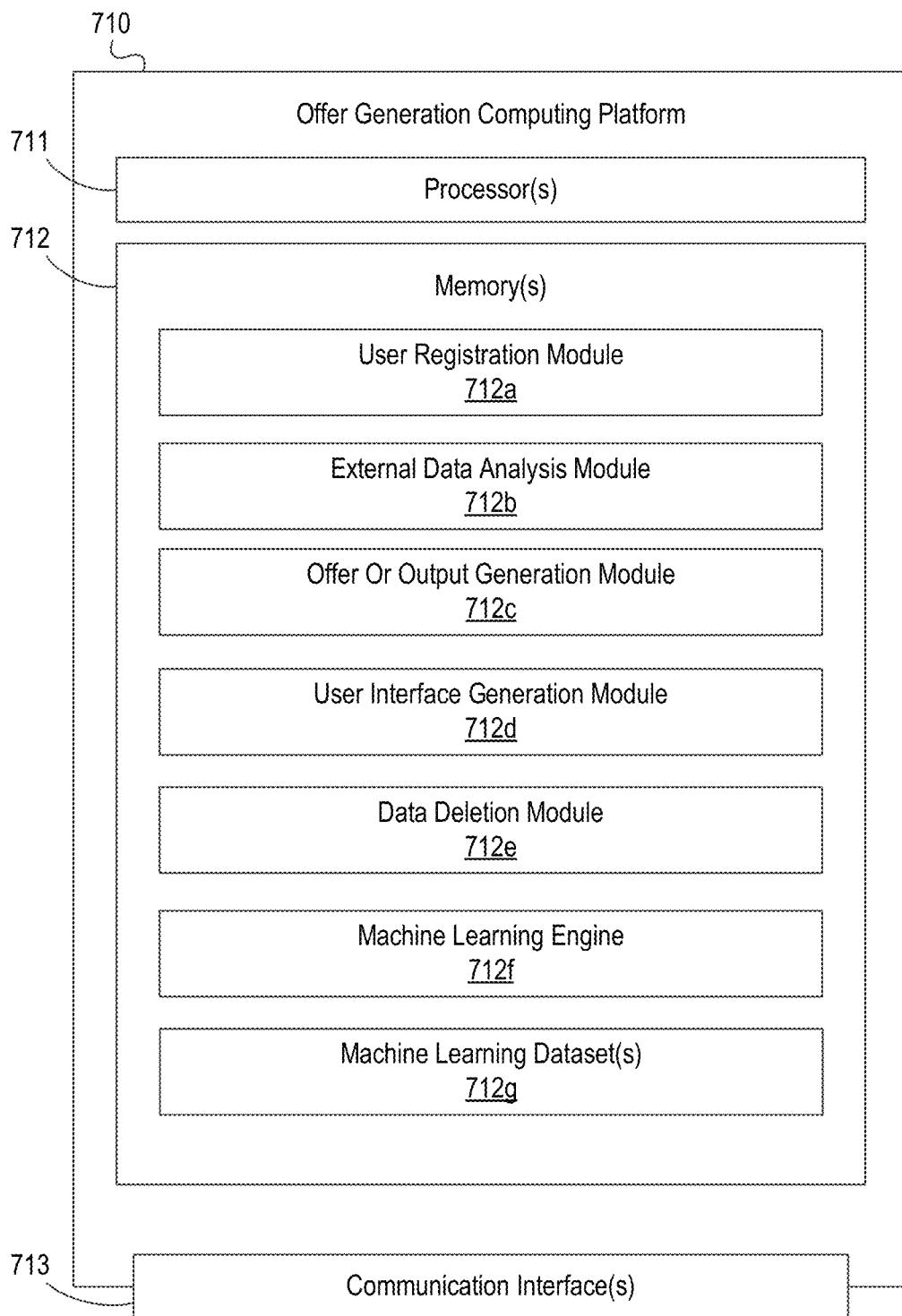

FIGS. 7A-7B depict an illustrative computing environment for implementing and using an offer generation control system in accordance with one or more aspects described herein. Referring to FIG. 7A, computing environment 700 may include one or more computing devices and/or other computing systems. For example, computing environment 700 may include an offer generation computing platform 710, an internal data computing device 720, a first local user computing device 750, a second local user computing device 755, a first external data computing system 740, a second external data computing system 745, a remote user computing device 770, and a remote user computing device 775. Further, computing environment 700 may include one or more of the devices described above with respect to FIGS. 1-6 and/or the devices described with respect to FIG. 7 may be used to perform one or more of the processes and/or functions described above with respect to FIGS. 1-6, as well as the arrangements described below.

Offer generation computing platform 710 may be configured to host and/or execute one or more modules including instructions for providing data analysis and offer or output generation functions. In some examples, offer generation computing platform 710 may be configured to receive a request for generation of an offer. In some examples, the request may include a request for an insurance quote (e.g., automobile insurance, life insurance, homeowner's or renter's insurance, or the like) and/or user insights, offers or outputs. In some examples, the request may be received from a user device (e.g., a mobile device of a user) associated with a user who is not currently a customer of the entity generating the quote or offer or is a current customer but is looking to obtain additional products or services.

In some examples, responsive to receiving the request, the offer generation computing platform 710 may transmit a request for registration information to a user. The request may include a request for name, contact information, login credentials, and the like. In some arrangements, registration information or other user information may be provided to the offer generation computing platform 710 prior to receiving the request. The offer generation computing platform 710 may receive registration response data from the user device (such as remote user computing device 770) and may process the data. In some examples, the offer generation computing platform 710 may transmit an application to the user device and may cause the application to execute on the user device.

In some examples, executing the application on the mobile device may cause the mobile device to establish a connection with one or more external data computing systems, such as external data computing system 1 740, external data computing system 2 745, or the like. User data associated with the user, such as significant location data (e.g., frequent routes, frequently visited locations, frequent drive times, or the like), activity data, internet browsing data, physical characteristics or traits, biometric data, or the like, that was previously captured by the user computing device (e.g., remote user computing device 770) and stored by the external computing system may then be identified and/or extracted by the external data computing system and transmitted to the user device. The user device may then transmit the data to the offer generation computing platform 710 where it may be analyzed.

In some arrangements, the offer generation computing platform 710 may analyze the data using clustering techniques, machine learning algorithms, and the like. In some examples, the data may be sorted into one or more tiers of data that may be used to pre-determine or pre-calculate a score or rating for the user (e.g., prior to the user becoming a customer of the entity implementing the offer generation computing platform 710, prior to making an offer for or the user accepting an offer for additional products or services if a current customer, or the like).

In some examples, additional data may be received from, for example, the mobile device of the user (e.g., remote user computing device). For instance, requests for image data may be generated by the offer generation computing platform 710 and transmitted to the mobile device. Images may be captured using an image capture device of the mobile device and transmitted to the offer generation computing platform 710 for analysis.

Additionally or alternatively, user physical (e.g., physical trait data) or biometric data may be captured by the mobile device of the user. Data such as steps taken in a predetermined time period (e.g., one day, one week, or the like), heart rate (e.g., resting heart rate, elevated heart rate, or the like), blood pressure, fitness or activity data, oxygen capacity, pulse, and the like may be captured by the mobile device and transmitted to the offer generation computing platform 710 for analysis. In some examples, some data (e.g., step data, activity data, and the like) may be captured by a wearable device (e.g., fitness tracking device) and transmitted to the offer generation computing platform 710 for analysis.

In some examples, data may be captured or received from a variety of sources, including third party or external data sources, storing user data related to financial transactions, purchase history, Internet browsing history, fitness tracker data (e.g., steps, distance, and the like), social media data, ride share application or other application usage data, and the like. The data may be received directly from the user or via a third party (as discussed more fully herein). The data may be captured, stored, processed, and the like, with the permission of the user.

In some arrangements, this data may be captured prior to the user registering with the system and/or may be stored by a third party. Accordingly, the user may provide this pre-stored data upon registration in order to obtain an offer that is accurately based on user data without requiring a period of data capture after the user has registered. Additionally or alternatively, this data may be captured after the user has registered, in response to a request for output, or the like, in order to obtain a current dataset. In some examples, this user data may be used in addition to or in lieu of traditional underwriting processes to generate, for example, a life insurance quote. Traditional underwriting processes may require a fitness or physical examination with a medical professional. The arrangements described herein may reduce or eliminate the need for the medical examination by providing data via a mobile device of a user or other available means. In some examples, the offer generation computing platform may connect to an external data computing device storing medical data of the user (e.g., results of blood tests, general physical health, prescription information, and the like) and may extract data associated with the user, as permitted by the user.

As discussed above, machine learning may be used to evaluate the data provided to determine a risk associated with a user (e.g., a mortality rate upon which an insurance rate may be based). In some examples, the data may be clustered to perform the analysis. In some arrangements, deep learning may be used to evaluate the data.

In some arrangements, the data may be formatted or otherwise modified from a format in which it was transmitted. In some examples, the data may be filtered and/or portions removed, deleted or otherwise not further analyzed based on a type of data, content, or the like. The offer generation computing platform 710 may generate one or more user interfaces for display on the user computing device. The user interfaces may display formatted data, requests for user input, offer generation outputs, and the like.

Internal data computing device 720 may have, store and/or include data associated with or obtained by an entity implementing the offer generation computing platform 710 and/or stored by the entity. In some examples, internal data computing device 720 may include data associated with customers, one or more insurance claims, accident histories and associated damages or costs, risk ratings associated with a road or road segment, pricing data, user information, user physical data provided (e.g., height, weight, age, and the like), and the like. In some examples, internal data computing device 720 may include multiple computing devices storing various different types of data. In other examples, internal data computing device 720 may store the various types of data. In still other examples, internal data computing device 720 may query databases in one or more other computing devices, systems, or the like, to obtain data that may be used in one or more processes described herein. In some examples, data retrieved from internal data computing device 720 may be used (e.g., in combination with externally obtained data) to generate one or more offers, insights, outputs, or the like.

External data computing system 740 and external data computing system 745 may have, store and/or include data from outside of or external to the entity. For instance, external data computing system 740 and/or external data computing system 745 may include systems associated with service providers, web browsers, applications and entities associated with wearable devices such as fitness trackers, and the like. In some examples, external data computing system 740 and/or external data computing system 745 may store data associated with a user, such as location data captured by, for example, a GPS system of a mobile device of a user, including latitude, longitude, time stamps, date stamps, and the like. External data computing system 740 and/or external data computing system 745 may also store additional types of data captured by a mobile device, wearable device, or the like, such as social medial data, wellness data, activity data, fitness data, step count data, biometric data (e.g., heart rate data, oxygen consumption data, and the like), and the like. The data may be collected via a mobile device of the user, wearable device of a user, vehicle of a user, and the like, such as remote user computing device 770, 775, and may be stored by the external data computing system 740 and/or 745. In some arrangements, external data computing system 740 and/or external data computing system 745 may store other user information, such as Internet browsing history, purchase history, financial transaction data (e.g., stored by a bank or financial institution), social media data, medical information or history, prescription information or history, actions or selections made by the user, identifying information, authentication information, and the like. In some examples, external data computing system 740 may be associated with an entity different from and entity implementing external data computing system 745 and/or different from the entity implementing the offer generation computing platform 710. In at least some arrangements, external data computing system 740 and/or external data computing system 745 may be a cloud-based data storage or computing system. Data retrieved from the external data computing system 740, 745 may be obtained with the appropriate permissions of the user.

Local user computing device 750 and local user computing device 755 may be computing devices associated with an entity implementing or operating the offer generation computing platform 710. For instance, local user computing device 750, 755 may be computing devices used to develop and/or modify one or more applications associated with extracting and/or transmitting data, generating user interfaces, generating or modifying machine learning algorithms, and the like. Local user computing device 750, 755 may also be used to modify parameters associated with offer generation computing platform 710.

Remote user computing device 770 and remote user computing device 775 may be computing devices not associated with the entity implementing or operating the offer generation computing platform 710 (e.g., owned by a customer, service provider, vendor, or the like, rather than the entity). Remote user computing device 770, 775 may be computing devices associated with a user requesting generation of an offer (e.g., a mobile device of a user, a vehicle of a user, a wearable device of a user, or the like). As discussed herein, remote user computing device 770, 775 may be used to download an application to facilitate data extraction, connect to one or more external data computing systems 740, 745 (e.g., initiate a communication session via a wireless connection), receive data from those systems, transmit data to the offer generation computing platform 710, receive and display user interfaces, and the like.

Local user computing device 750, 755, internal data computing system 720, external data computing system 740, external data computing system 745, remote user computing device 770, and remote user computing device 775 may be configured to communicate with and/or connect to one or more computing devices or systems shown in FIG. 7A. For instance, local user computing device 750, 755 and/or internal data computing device 720 may communicate with one or more computing systems or devices via network 790, while remote user computing device 770, remote user computing device 775, external data computing system 740, and/or external data computing system 745 may communicate with one or more computing systems or devices via network 795.

In one or more arrangements, internal data computing device 720, local user computing device 750, local user computing device 755, external data computing system 740, external data computing system 745, remote user mobile computing device 770, and/or remote user computing device 775 may be or include a computing device or combination of devices configured to perform the particular functions described herein. For example, internal data computing device 720, local user computing device 750, local user computing device 755, external data computing system 740, external data computing system 745, remote user mobile computing device 770, and/or remote user computing device 775 may, in some instances, be and/or include server computers, desktop computers, laptop computers, tablet computers, smart phones, or the like that may include one or more processors, memories, communication interfaces, storage devices, and/or other components. As noted above, and as illustrated in greater detail below, any and/or all of offer generation computing platform 710, internal data computing device 720, local user computing device 750, local user computing device 755, external data computing system 740, external data computing system 745, remote user computing device 770, and/or remote user computing device 775 may, in some instances, be or include special-purpose computing devices configured to perform specific functions.

Computing environment 700 also may include one or more computing platforms. For example, and as noted above, computing environment 700 may include offer generation computing platform 710. As illustrated in greater detail below, offer generation computing platform 710 may include one or more computing devices configured to perform one or more of the functions described herein. For example, offer generation computing platform 710 may have or include one or more computers (e.g., laptop computers, desktop computers, tablet computers, servers, server blades, or the like).

As mentioned above, computing environment 700 also may include one or more networks, which may interconnect one or more of offer generation computing platform 710, internal data computing device 720, local user computing device 750, local user computing device 755, external data computing system 740, external data computing system 745, remote user computing device 770, and/or remote user computing device 775. For example, computing environment 700 may include private network 790 and public network 795. Private network 790 and/or public network 795 may include one or more sub-networks (e.g., Local Area Networks (LANs), Wide Area Networks (WANs), or the like). Private network 790 may be associated with a particular organization (e.g., a corporation, financial institution, educational institution, governmental institution, or the like) and may interconnect one or more computing devices associated with the organization. For example, offer generation computing platform 710, internal data computing device 720, local user computing device 750, and/or local user computing device 755, may be associated with an organization (e.g., a financial institution), and private network 790 may be associated with and/or operated by the organization, and may include one or more networks (e.g., LANs, WANs, virtual private networks (VPNs), or the like) that interconnect offer generation computing platform 710, internal data computing device 720, local user computing device 750, and/or local user computing device 755, and one or more other computing devices and/or computer systems that are used by, operated by, and/or otherwise associated with the organization. Public network 795 may connect private network 790 and/or one or more computing devices connected thereto (e.g., offer generation computing platform 710, internal data computing device 720, local user computing device 750, local user computing device 755) with one or more networks and/or computing devices that are not associated with the organization. For example, external data computing system 740, external data computing system 745, remote user computing device 770, and/or remote user computing device 775 might not be associated with an organization that operates private network 790 (e.g., because external data computing system 740, external data computing system 745, remote user computing device 770 and remote user computing device 775 may be owned, operated, and/or serviced by one or more entities different from the organization that operates private network 790, such as one or more customers of the organization, public or government entities, and/or vendors of the organization, rather than being owned and/or operated by the organization itself or an employee or affiliate of the organization), and public network 795 may include one or more networks (e.g., the internet) that connect external data computing system 740, external data computing system 745, remote user computing device 770 and remote user computing device 775 to private network 790 and/or one or more computing devices connected thereto (e.g., offer generation computing platform 710, internal data computing device 720, local user computing device 750, and/or local user computing device 755).

Referring to FIG. 7B, offer generation computing platform 710 may include one or more processors 711, memory 712, and communication interface 713. A data bus may interconnect processor(s) 711, memory 712, and communication interface 713. Communication interface 713 may be a network interface configured to support communication between offer generation computing platform 710 and one or more networks (e.g., private network 790, public network 795, or the like). Memory 712 may include one or more program modules having instructions that when executed by processor(s) 711 cause offer generation computing platform 710 to perform one or more functions described herein and/or one or more databases that may store and/or otherwise maintain information which may be used by such program modules and/or processor(s) 711. In some instances, the one or more program modules and/or databases may be stored by and/or maintained in different memory units of offer generation computing platform 710 and/or by different computing devices that may form and/or otherwise make up offer generation computing platform 710. Further, one or more functions shown or described with respect to offer generation computing platform 710 may, in some examples, be performed by determination server 110, determination server 210, or any of the data analysis devices or servers described herein and configured to process data, generate outputs, offers, insights, or the like.

For example, memory 712 of offer generation computing platform 710 may have, store, and/or include a user registration module 712a. The user registration module 712a may store instructions and/or data that may cause or enable the offer generation computing platform 710 to receive information or a request from a user requesting generation of an offer, output, insights, or the like, registration with the offer generation computing platform 710, or the like. In some examples, a request to register may be received from a user computing device, such as remote user computing device 770, 775. In some examples, the user computing device may be a mobile device of the user. The user registration module 712a may receive the request and generate a request for user information. The user registration module 712a may transmit the request for user information to the device from which the request was received and may receive user information response data from the device. The user information response data may be used to generate a record of the user in the user registration module 712a. The record may include user information such as name, contact information, unique identifier associated with the user computing device, physical traits or characteristics (e.g., height, weight, age, and the like), and the like.

In some examples, the user request for registration may be received prior to a request to generate an offer (e.g., a user may register with a system 710 in a separate request from the request to generate an offer, output, insights, or the like). In other examples, a user may already be registered with a system (e.g., offer generation computing platform 710) based on previous interactions with the entity and may use login credentials from the previous registration to login and request the offer, output or insight generation. Additional registration or initiation information may be requested. In still other examples, the user may request an offer, output or insight and registration may occur.

In some examples, the user registration module 712a may transmit an application to the user computing device, such as remote user computing device 770, 775. The application may include one or more applications discussed above and/or other applications having the functionality described herein. The application may be executed on the remote user computing device 770, 775 and may cause the remote user computing device 770, 775 to establish a connection with one or more external data computing systems 740, 745, as well as offer generation computing platform 710. Data may be received by the remote user computing device and transmitted to the offer generation computing platform 710.

In some examples, the application may execute to control an image capture device of the remote user computing device 770, 775 in order to capture one or more images of a user requesting an offer or registration. In some arrangements, executing the application may include identifying, extracting and/or retrieving data from the remote user computing device 770, 775, such as step count data, fitness data, activity data, and the like. In some examples, the application may execute to prompt the user to perform one or more functions with the remote user computing device 770, 775 in order to capture particular data or types of data.

Offer generation computing platform 710 may further have, store and/or include an external data analysis module 712b. External data analysis module 712b may store instructions and/or data that may cause or enable the offer generation computing platform 710 to receive external data (e.g., data extracted from one or more of external data computing system 740, 745, transmitted to the remote user computing device 770, 775 and transmitted from the remote user computing device 770, 775 to the offer generation computing platform 710). The external data analysis module 712b may process the data (e.g., format data, or the like). In some examples, the data may be received in hypertext markup language (HTML) format, PDF format, JavaScript Object Notation (JSON) format, Keyhole Markup Language (KML) format, or the like. The data may be analyzed in the format in which it is received or may be further formatted, converted, or the like, prior to processing.

In some examples, the data may be analyzed using clustering techniques, machine learning algorithms, or the like. In some examples, the received data may be sorted into one or more tiers. For instance, the data may be sorted or categorized into four tiers. Although four tiers are used in this example, more or fewer tiers may be used without departing from the invention. In some examples, a first tier may include aggregated data related to number of miles traveled by the user (e.g., based on data from the mobile device of the user), number of trips taken, and other general contours. A second tier may include a slightly more granular level of categorization and may include general destination and/or origin information, routes, or the like. A third tier may be slightly more granular than the second tier and may include types of route segments, amount of time driving during the day, amount of time driving during the night, speed data, high risk driving, low risk driving, and the like. The fourth tier may include the most granular level of data and may include driving behavior data such as hard braking, swerving, acceleration, speed data, and the like.

The data may be sorted into tiers and may be further analyzed to determine a likely level of risk associated with the user. In some examples, data in one or more tiers may be weighted more heavily than data in another tier. Accordingly, the system may generate a score or rating associated with the user. The score or rating may, in some examples, be based on the external data received from the third party and gathered prior to the user becoming a customer of the entity generating the output (e.g., implementing the offer generation computing platform 710).

External data analysis module 712b may further store instructions and/or data that may cause or enable the offer generation computing platform 710 to analyze other types of data from external sources, as well as data from internal sources, from the remote user computing device 770, 775, and the like. For instance, data may be received from additional external sources, such as physical activity data, medical history data, prescription data, purchase history, financial transactions, social media data, and the like. Data, such as step count data, activity data, fitness data, and the like, may be received from the remote user computing device 770, 775 (e.g., mobile device of the user, fitness tracker, or the like). Data, such as physical trait data, such as heart rate, blood pressure, and the like, may also be received from remote user computing device 770, 775, and/or one or more external sources. This data may be analyzed to evaluate health of a user to determine a risk associated with a user (e.g., a mortality rate). This information may then be used to generate one or more outputs or offers. The received and analyzed data may be received and analyzed with permission of the user.

In some examples, external data analysis module 712b may filter the received data to remove data elements, types of data, and the like. For instance, data of a certain format (e.g., photos in JPEG format) may be removed from further processing and, in some examples, deleted prior to analysis of the data. Additionally or alternatively, content within data received may be analyzed to determine whether the data should be removed, obscured, deleted, or the like. For example, image, photo and/or video data may be analyzing using object recognition, optical character recognition, or the like, to identify content within the images and a determination may be made as to whether the content should be included in the data analysis. Accordingly, identification of particular objects within the image data may cause the data to be further analyzed to generate and output, insight, or the like, while identification of other objects may cause the image data to be removed from further processing and/or deleted. These processes may be performed with permission of the user and in compliance with any associated regulations, such as general data protection regulation (GDPR), one or more consumer privacy acts, or the like. Accordingly, image data that cannot be shared per one or more regulations, laws, or the like, may be removed from further processing.

In some examples, the data may be received from the various sources in different formats. In some examples, the formats may be structured data formats and/or unstructured data formats (e.g., based on a type of data being received). In some examples, the data may be segmented and anonymized. For instance, personally identifiable information (PII) may be segmented and/or anonymized as desired or needed. Other data that may be considered sensitive but not PII may be segmented and/or anonymized as desired.

In some examples, data may be stored in a most efficient format for manipulation. For instance, a relational database management system may be used to store data, such as structured data, to enable ease of search, manipulation, analysis, and the like. Non-structured data sets may be stored, for instance, large streaming files, image data, and the like, may also be stored for analysis in, in some arrangements, a non-relational database.

In examples in which location data is received (e.g., from a user computing device directly, from a third party system, or the like) the data may be contained in a large historical data file having location attributes including latitude, longitude, and the like. In some examples, clustering processes may be executed on the data file to identify frequently visited locations. Additionally or alternatively, map matching techniques may be used to map a location to a road way, trail way, bike path, or the like. In some examples, matching techniques may be used to match public transport datasets (including, e.g., route information, schedule information, and the like) to location data in order to identify occurrences of multi-modal transport.

In some arrangements, location date contained in a received file may include various inaccuracies, irrelevant data, and the like. For instance, in some examples in which data is received from a third party source, the data received may include location data for all devices associated with a particular user account. Accordingly, if a user has a smartphone and a tablet and both devices are associated or execute an application associated with the account, location data may be captured from both devices, although the user might only be physically present at a location of one of the devices. Accordingly, the data may be filtered using time series relationships to identify datasets at a user's particular physical or geographic location, rather than just the location of a user device. For instance, in some examples, the location data may be filtered to favor data from the smartphone as it is more likely to be with the user than a tablet. In another example, time and date data associated with location entries may be compared with other user to data (e.g., wearable device data, social media data, or the like) to determine a likelihood that the user is at a same physical location as that particular device.

Offer generation computing platform 710 may further have, store and/or include an offer or output generation module 712c. Offer or output generation module 712c may receive analyzed data, scores or other ratings associated with the user (e.g., from external data analysis module 712b) and may generate one or more outputs or offers. For instance, based on the rating generated from the external data received, and/or analysis of other data, the offer or output generation module 712c may generate an offer for a user, one or more user insights, and the like. The offer may include an insurance premium, one or more discounts, one or more incentives, user insights such driving behaviors, frequently visited locations, recommendations for conserving resources or saving money, and the like. In some examples, the offer may include an indication that it is generated based on external data associated with the user and collected via a third party. The offer may include an option for the user to provide additional data to the offer generation computing platform 710 (and/or the entity implementing the offer generation computing platform 710) after the user has become a customer of the entity, directly from the mobile device or other sensors of the user (e.g., vehicle sensors, telematics device, or the like), or the like. Accordingly, the entity may make an initial determination of risk associated with the user based on data collected via a third party or data provided by the user (e.g., data pre-captured by a mobile device of the user, fitness tracker, or the like) and that the user has provided to the entity and generate an offer and/or insights based on that data, but may revise or modify that initial determination of risk after the user has become a customer and the entity has directly collected data (e.g., independent of the third party) from the user or user device(s). The entity (e.g., offer generation computing platform 710) may then make further offer, output or insight determinations based on that data.

Offer generation computing platform 710 may further have, store and/or include a user interface generation module 712d. The user interface generation module 712d may store instruction and/or data that may cause or enable the offer generation computing platform 710 to generate one or more user interfaces, transmit the one or more user interfaces to the user computing device (e.g., remote user computing device 770, 775), and/or cause the one or more user interfaces to display on the user computing device. In some examples, a user interface may be generated to display a portion of the received external data and/or a first generated insight. The portion of the received external data may be processed and may be formatted for display to the user to provide insights into user driving behaviors, significant locations, recommendations, or the like. In some examples, the user interface may be transmitted to the user and may include a request for user input. The request for user input may include a request for a user to indicate that he or she would like the offer generation computing platform 710 to continue to process the user data collected by the third party and provided by the user or to discontinue processing the data. If the user requests to continue processing, the system may analyze additional data, generate additional user interfaces, or the like.

If the user input indicates the user does not want to continue processing the data, the data deletion module 712e may delete the user data from the offer generation computing platform 710. For instance, data deletion module 712e may store instructions and/or data that may cause or enable the offer generation computing platform 710 to delete (e.g., permanently remove) the user data collected by the third party and provided to the entity by the user via the remote user computing device 770, 775. In some examples, data deletion module 712e may further store instructions and/or data that may cause or enable the offer generation computing platform 710 to automatically delete user data upon expiration of a predetermined time period (e.g., one month, three months, or the like). Accordingly, data may be received from a plurality of sources and may be stored, analyzed, or the like. However, upon expiration of the time period, the data may be automatically deleted. In some examples, the generated insights or offers may be saved but the underlying data may be deleted.

In some arrangements, data may be deleted at a request of a user. For instance, a user may request automatic deletion after a triggering event (e.g., after insights or digital holograms are generated, after a predetermined time) or may request on-demand deletion of data. In some examples, this user request for deletion may be received after the portion of the data is processed and the user is prompted to continue and/or at any time during the processing of data, after processing data, after processing insights, after generating a digital hologram, or the like. Accordingly, a user may request deletion of one or more types of data, of particular data, of data sets, or the like, at any time during or after the process of capturing, analyzing and providing generated insights or displays of data.

In some examples, a user may select types of data for deletion or to not be used for further processing. For instance, a user may select certain types of data to be shared, analyzed, or the like. In some examples, the type of data may be based on content of the data (e.g., location data, spending data, photo data, social media data, or the like). In other examples, the type of data to be shared or not shared may be based on a format of the data (e.g., don't share photos in JPEG format, or the like).

In some examples, a user may view data being downloaded for transmission and analysis prior to transmitting it for analysis. Accordingly, the user may view the data and select particular data elements, data types or the like, to share or not share for further analysis. In some arrangements, data may be shared for analysis but portions of the data may be obscured or anonymized, as desired by the user. Accordingly, the user may control the data being shared for analysis and offer or output generation.

User interface generation module 112d may further generate user interfaces prompting a user to provide user input (e.g., create a new archive, provide user identifying information, capture particular types of data, or the like). In some examples, the user interfaces may include instructions to a user to perform one or more functions (e.g., using one or more devices or systems, such as an image capture device of the remote user computing device 770, 775). The generated user interfaces may further include insights generated, offers or outputs generated, and the like. Some examples of user interfaces that may be generated are discussed more fully herein and, in particular, with respect to FIGS. 17A-17T, as well as other example user interface figures. User interfaces including additional or alternative data may be generated without departing from the invention.

User interface generation module 112d may further generate one or more user interfaces displaying physical characteristic data, fitness or activity data, and the like. In some examples, user interface generation module 112d may generate one or more user interfaces requesting user input, such as height, weight, and the like, and/or prompting the user to perform an action (e.g., place finger on pulse sensor to detect heart rate, walk on treadmill for 10 minutes with mobile device, or the like).

Offer generation computing platform 710 may further have, store and/or include a machine learning engine 712f and machine learning datasets 712g. Machine learning engine 712f and machine learning datasets 712g may store instructions and/or data that cause or enable offer generation computing platform 710 to evaluate data, such as data received from the user (e.g., data captured by a mobile device of a user, a wearable device of a user, a vehicle of a user, or the like (e.g., remote user computing device 770, 775), and collected and/or stored by a third party (e.g., extracted from external data computing system 740, external data computing system 745, or the like), data from one or more other sources, such as internal data computing device 720, and the like, and generate one or more insights, offers and/or outputs, such as a user score or rating, a cost for insurance, an insurance discount, driving patterns or behaviors, a mortality rate and associated risk or cost, or the like. The machine learning datasets 712g may be generated based on analyzed data (e.g., data from previously received offer requests, historical data, and the like), raw data, and/or received from one or more outside sources. In some examples, training data may be received from one or more users and used to generate machine learning datasets and update and/or validate the machine learning datasets.

The machine learning engine 712f may receive data and, using one or more machine learning algorithms, may generate one or more machine learning datasets 712g. Various machine learning algorithms may be used without departing from the invention, such as supervised learning algorithms, unsupervised learning algorithms, regression algorithms (e.g., linear regression, logistic regression, and the like), instance based algorithms (e.g., learning vector quantization, locally weighted learning, and the like), regularization algorithms (e.g., ridge regression, least-angle regression, and the like), decision tree algorithms, Bayesian algorithms, clustering algorithms, artificial neural network algorithms, and the like. Additional or alternative machine learning algorithms may be used without departing from the invention. In some examples, the machine learning engine 712f may analyze data to identify patterns of activity, sequences of activity, and the like, to generate one or more machine learning datasets 712g.

In some arrangements, different types of machine learning algorithms may be used to analyze different types of data. This may improve the ability of aspects described herein to be scaled to accommodate users that may number into the millions or even billions. For instance, supervised learning may be used to evaluate unstructured datasets while free form text data may be evaluated using another, different type of machine learning algorithm that permits more automatic processing and sorting or classifying of data.

The machine learning datasets 712g may include machine learning data linking one or more user characteristics or user data set characteristics (e.g., identified from the third party data provided by the user prior to the user becoming a customer of the entity or prior to obtaining the requested additional product or service (e.g., prior to the entity directly accessing and/or collecting the data of the user)) to a score or rating, risk level, insurance premium tier, or the like. In some examples, the machine learning data may link one or more fitness or health factors (e.g., blood pressure, resting heart rate, step count data, medical history, prescription history, or the like) to a fitness level, which may then be used to evaluate or determine risk, generate an output, such as an insurance rate or premium, or the like.

In some examples, data may be annotated using various labels. For instance, incoming data may be used as training data or for validation of existing machine learning datasets and the data may be annotated or labeled in order to be added to one or more buckets of data. Intelligent labels and annotations may be used to efficiently identify and classify data, compare data, and the like.

The machine learning datasets 712g may be updated and/or validated based on later-received data. For instance, as additional data collected from subsequent offer requests may be used to validate and/or update the machine learning datasets 712g based on the newly received information. Accordingly, the system may continuously refine determinations, outputs, and the like.

FIGS. 8A-8F illustrate one example event sequence for performing offer generation control functions in accordance with one or more aspects described herein. The sequence illustrated in FIGS. 8A-8F is merely one example sequence and various other events may be included, or events shown may be omitted, without departing from the invention.

Figure 8A:
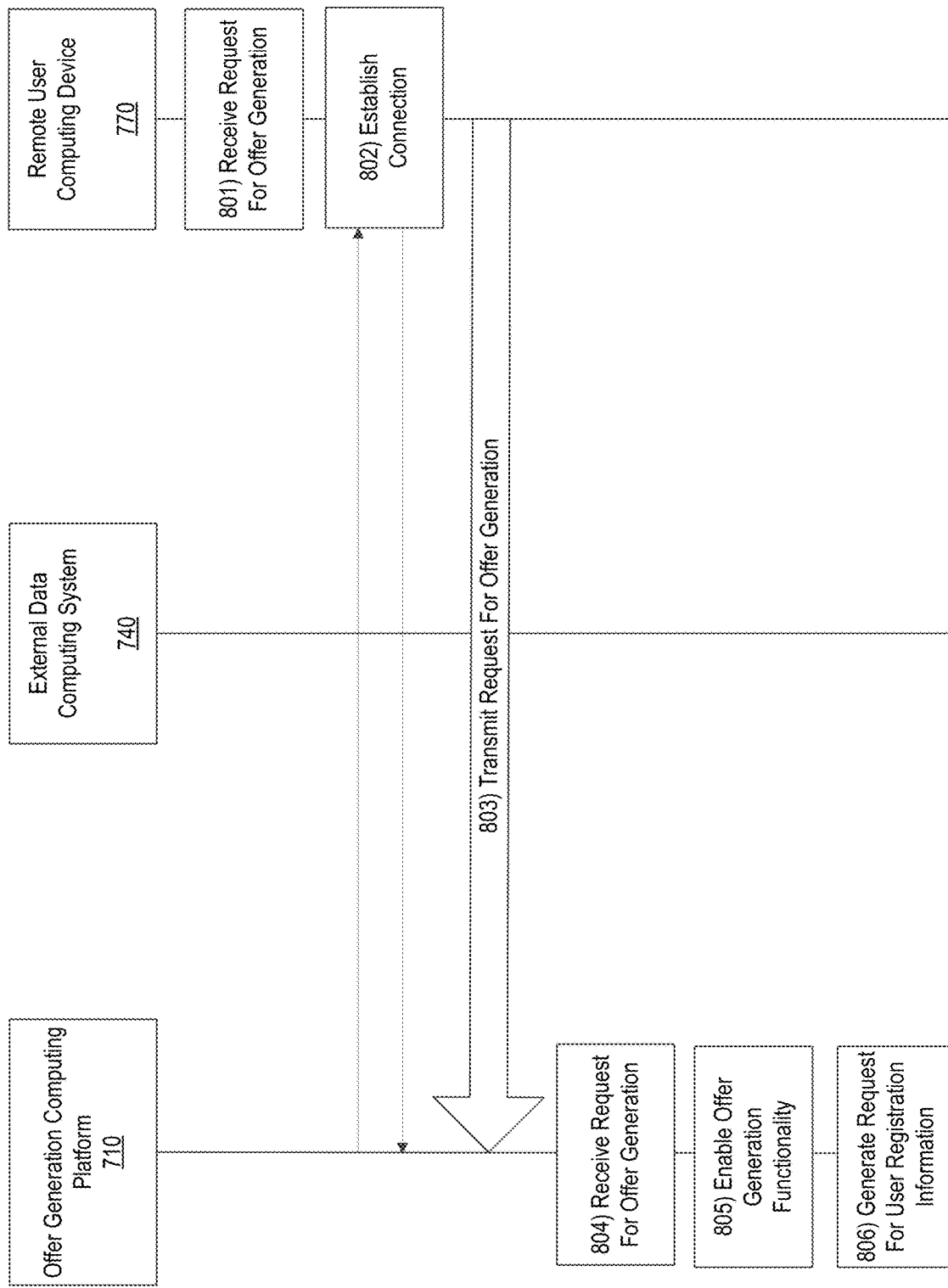
FIGS. 8A-8F depict an illustrative event sequence for performing offer and insight generation functions, according to one or more aspects described herein.

With reference to FIG. 8A, in step 801, a request for offer generation may be received by, for instance, remote user computing device 770. In some examples, the remote user computing device 770 may be a mobile device of a user. In some arrangements, the request for offer generation may include, for instance, a request for an insurance quote. The request for offer generation may be made by the user prior to the user becoming a customer of an entity implementing the offer generation computing platform 710.

At step 802, a connection may be established between the remote user computing device 770 and the offer generation computing platform 710. For instance, a first wireless connection may be established between the remote user computing device 770 and the offer generation computing platform 710. Upon establishing the first wireless connection, a communication session may be initiated between the offer generation computing platform 710 and the remote user computing device 770.

At step 803, the request for offer generation may be transmitted from the remote user computing device 770 to the offer generation computing platform 710. For instance, the request for offer generation may be transmitted during the communication session initiated upon establishing the first wireless connection. At step 804, the request for offer generation may be received by the offer generation computing platform 710.

At step 805, offer generation functionality may be enabled by the offer generation computing platform. For instance, one or more offer generation functions that may have been disabled may be enabled, activated and/or initiated in response to receiving the request for offer generation.

At step 806, the request for offer generation may be processed and a request for user registration information may be generated. The request for user registration information may include a request for user information such as name, contact information, mobile device number, service or product requested, and the like.

Figure 8B:
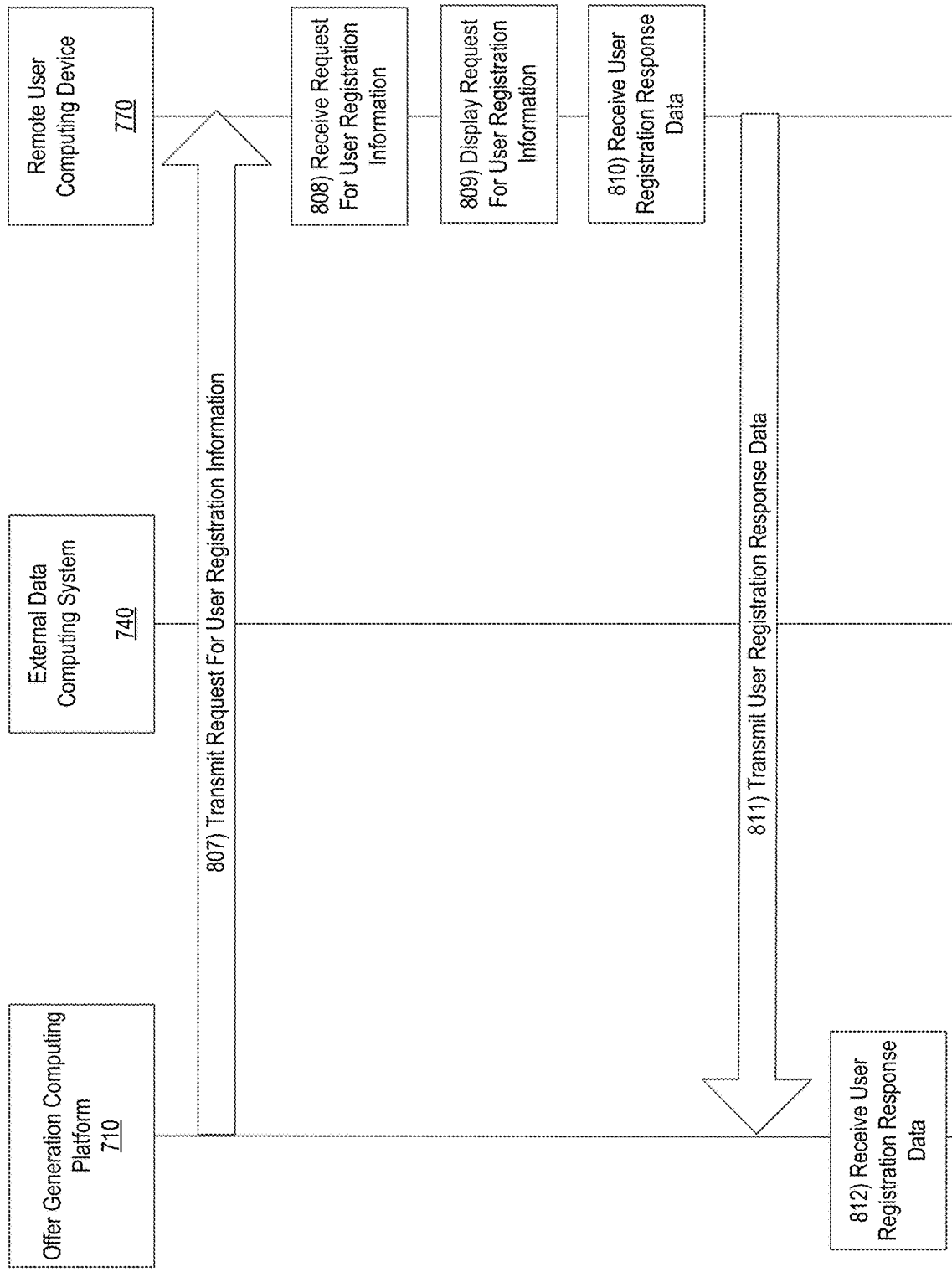

With reference to FIG. 8B, at step 807, the request for user registration information may be transmitted from the offer generation computing platform 710 to the remote user computing device 770. For instance, the request for user registration information may be transmitted during the communication session initiated upon establishing the first wireless connection.

At step 808, the request for user registration information may be received by the remote user computing device 770 and, at step 809, the request for user registration information may be displayed on a display of the remote user computing device 770.

At step 810, user registration response data may be received by the remote user computing device 770. For instance, a user may input, via one or more input devices of the remote user computing device 770, the requested user registration information and user registration response data may be generated.

At step 811, the user registration response data may be transmitted from the remote user computing device 770 to the offer generation computing platform 710. For instance, the user registration response data may be transmitted during the communication session initiated upon establishing the first wireless connection.

At step 812, the user registration response data may be received by the offer generation computing platform 710.

Figure 8C:
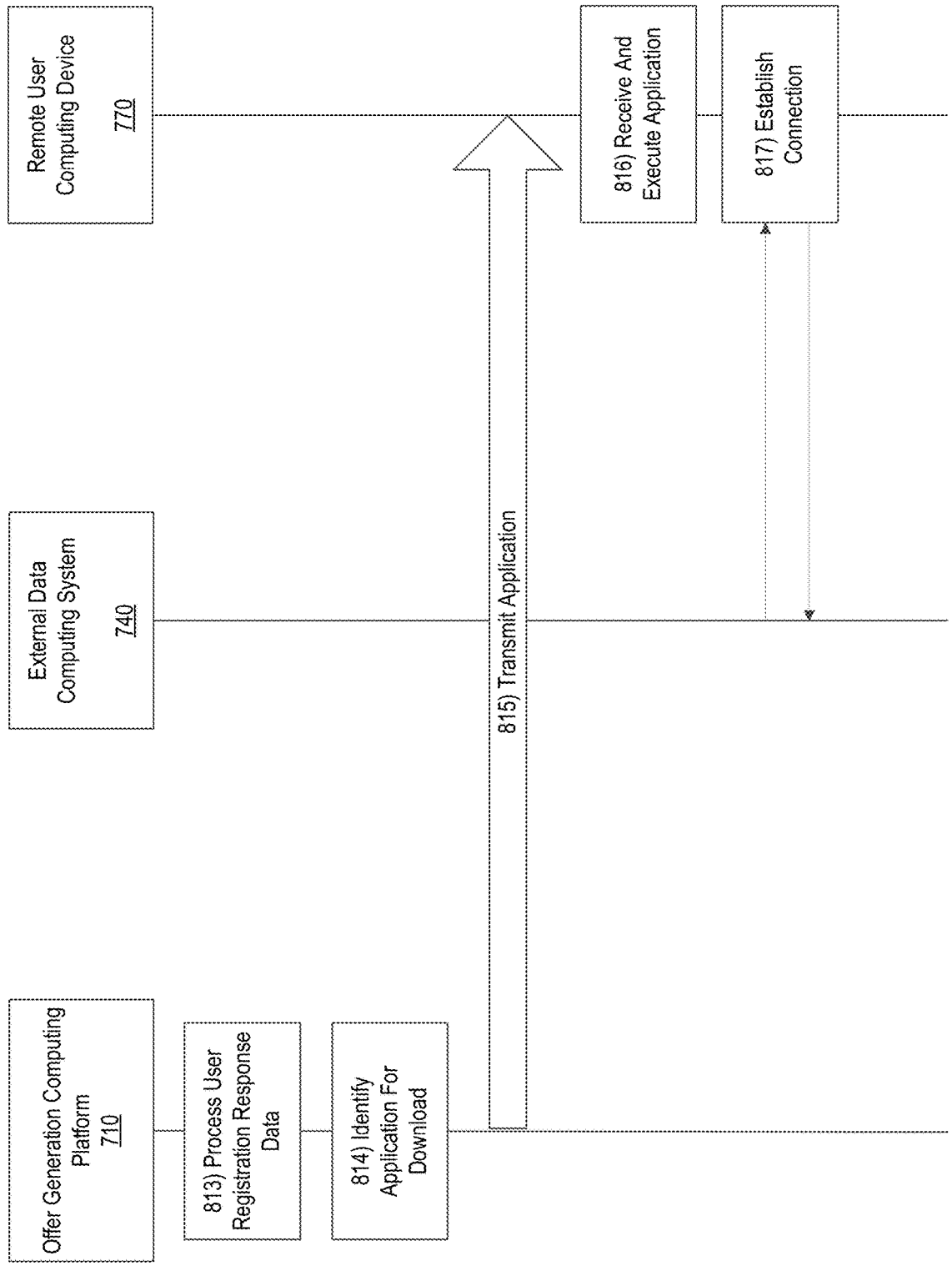

With reference to FIG. 8C, at step 813, the user registration response data may be processed by the offer generation computing platform 710. For instance, a user record may be generated and the received user registration response data may be stored in the record.

At step 814, an application may be identified by the offer generation computing platform 710. For instance, a data extraction and transmission application may be identified by the offer generation computing platform. In some examples, the application may be configured to establish a connection between a remote user computing device 770 and one or more external data computing systems, such as external data computing system 740, external data computing system 745, or the like. The application may then target data associated with the user and collected and/or stored by the external data computing system 740, 745.

At step 815, the application may be transmitted to the remote user computing device 770 for download. The transmission described in step 815, and various other transmissions (e.g., of user data between devices, of recommendations, outputs or insights, or the like) maybe performed over a secure communication channel. At step 816, the identified application may be received by the remote user computing device 770 and executed by the remote user computing device 770.

As indicated above, executing the application may cause the remote user computing device to establish a connection with an external data computing system. Accordingly, at step 817, a connection may be established between the remote user computing device 770 and external data computing system 740. For instance, a second wireless connection may be established between the remote user computing device 770 and the external data computing system 740. Upon establishing the second wireless connection, a communication session may be initiated between the external data computing system 740 and the remote user computing device 770.

Figure 8D:
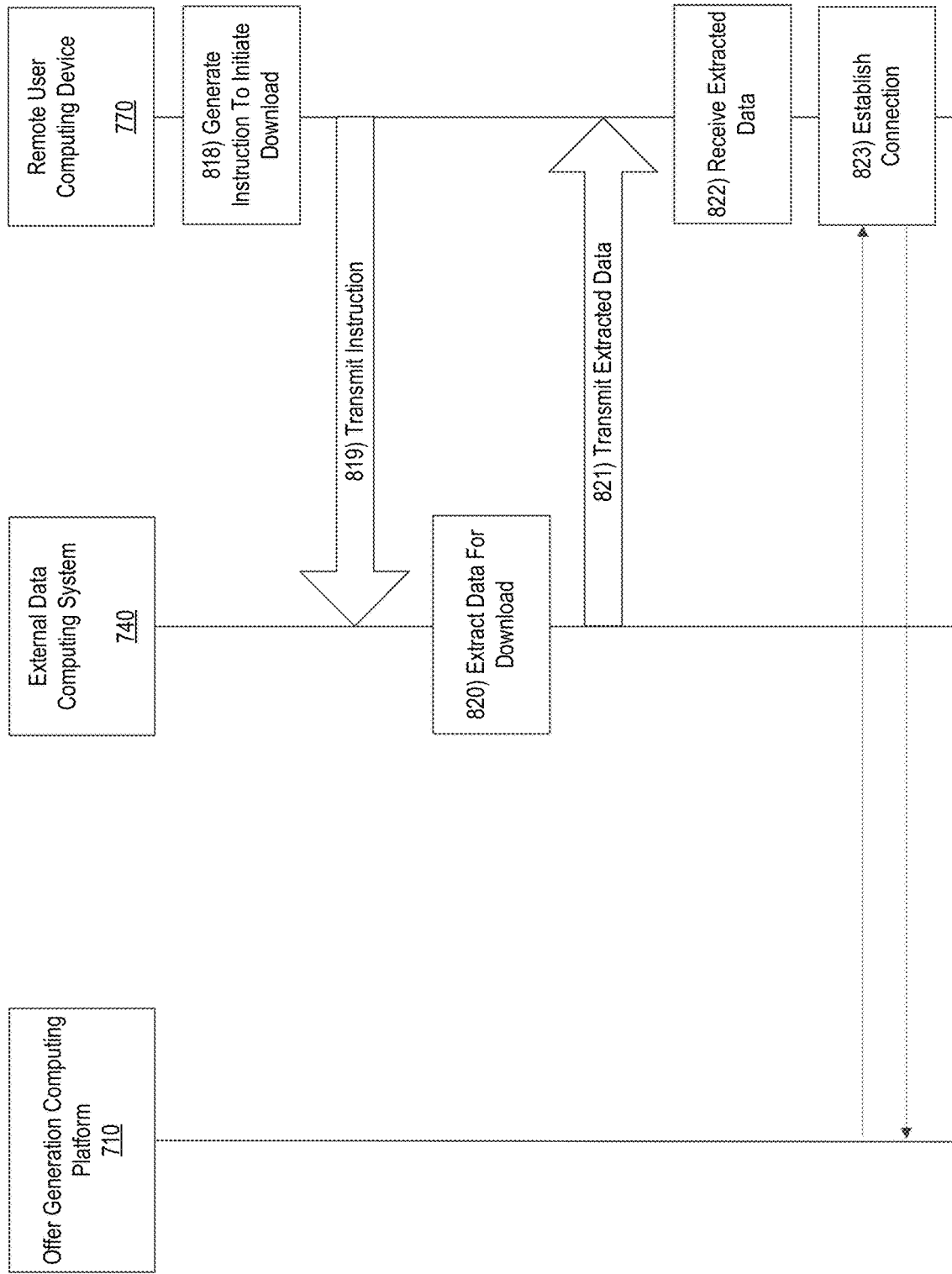

With reference to FIG. 8D, at step 818, an instruction to initiate download of the user's data stored by the external data computing system 740 may be generated. In some examples, the instruction may be generated by the application executing on the remote user computing device 770. For instance, the application may direct the mobile device, via a universal resource locator (URL) associated with the user's data, to the desired data. In some examples, the data may include location data of the user (e.g., collected via GNSS or global positioning system (GPS) on the mobile device of the user. The instruction may then be transmitted to the external data computing system 740 in step 819.

At step 820, the targeted data may be extracted and, at step 821, the extracted data may be transmitted or downloaded to the remote user computing device 770. The extracted data may include data in one or more file formats, as discussed above. In some examples, data may be encrypted to preserve the format of the data.

At step 822, the extracted data may be received by the remote user computing device 770. At step 823, a connection may be established between the remote user computing device 770 and the offer generation computing platform 710. For instance, a third wireless connection may be established between the remote user computing device 770 and the offer generation computing platform 710. Upon establishing the third wireless connection, a communication session may be initiated between the offer generation computing platform 710 and the remote user computing device 770. In some examples, the first wireless connection and associated communication session may be maintained. In those examples, step 823 may be omitted.

Figure 8E:
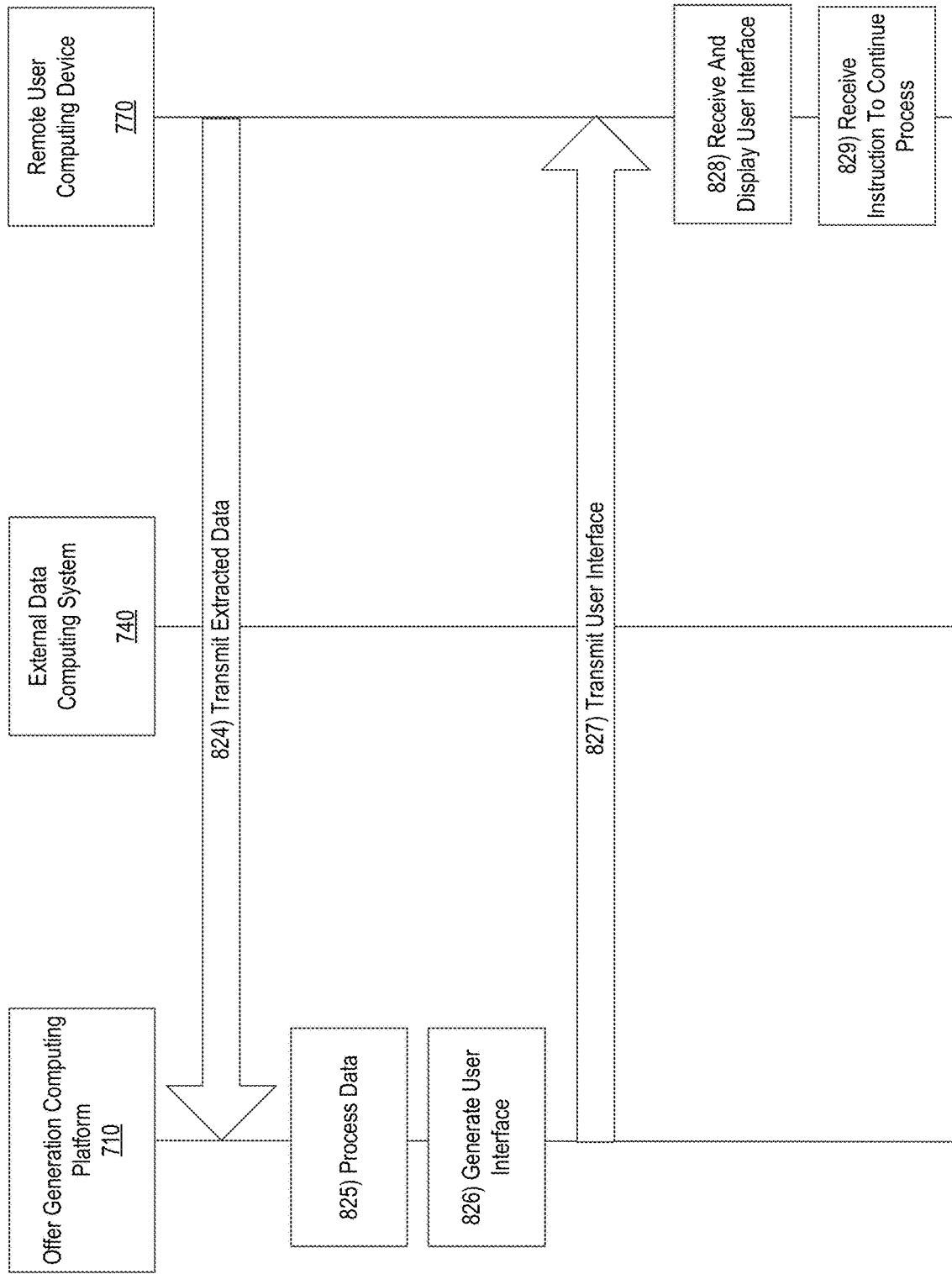

With reference to FIG. 8E, the extracted data may be transmitted from the remote user computing device 770 to the offer generation computing platform 710. The extracted data may include raw data and/or aggregated data (e.g., data from a plurality of users, plurality of devices, or the like). At step 825, the data may be received by the offer generation computing platform 710 and processed. For instance, as discussed herein, a portion of the received data may be processed and/or formatted for display to the user. In some examples, the portion of the data displayed to the user may include a request for user instructions to continue processing data or discontinue processing data. In some arrangements, processing the data may include filtering data based on format, content, or the like. For instance, as discussed herein, types of data (e.g., based on format, such as JPEG data), may be removed from further processing and/or deleted. In some examples, content of data may be evaluated (e.g., using optical character recognition, object recognition, or the like) to determine whether data or portions of data should be removed, deleted, or the like.

In some examples, a user may identify, for instance, at registration, types of data, data content, data elements, or the like to be shared or not shared. Accordingly, when data is extracted, the user preferences may be executed and only data identified by the user for sharing and analysis may be transmitted for processing. In some examples, the user may view the downloaded data (e.g., at step 822 when extracted data is received) and may make determinations at that point of what data should be shared for further processing. In some arrangements, a user may select one or more data types, data format, or the like for sharing. Additionally or alternatively, a user may select to obscure portions of the data prior to transmission for further processing. Thus, the user may view the data in a secure environment to understand what is being shared and choose to share or not share particular data or types of data as desired.

For example, a user may select to blur any facial images appearing in image data being transmitted for analysis. Thus, the user may select to share image data (e.g., based on, for example, format) but, when viewing the data, may select an option to blur facial images. The system may then, using, for instance, object recognition, identify facial images in the data and obscure the facial images. In some examples, this process may be performed by the application executing on the remote user computing device 770.

In some arrangements, the system may implement or use identity-based encryption to control one or more (or each) element of a user's dataset and who may access each element of the dataset. Identity-based encryption may be a type of public-key encryption in which the public key of the user includes unique information about the identity of the user. Use of identity-based encryption may enable control over each element of a dataset, while providing the ability to encode additional information (such as, for example, an expiration date) into the identifier.

The above example is merely one example of user control elements that may be executed to provide the user with control over data being shared, analyzed and the like. Various other control elements may be used without departing from the invention.

Although aspects discussed herein are directed to transmitting the data to the offer generation computing platform 710 for processing (e.g., as a separate device), in some examples, the offer generation computing platform 710, and/or one or more functions performed by the offer generation computing platform 710, may be part of (or performed by) the remote user computing device 770 and, thus, may process the data at the remote user computing device 770.

At step 826, a user interface may be generated. For instance, a user interface including the portion of the data processed and formatted and/or a request for instructions may be generated. At step 827, the generated user interface may be transmitted to the remote user computing device 770. At step 828, the user interface may be received by the remote user computing device 770 and displayed on the display of the remote user computing device 770.

At step 829, instructions regarding whether to continue processing data may be received by the remote user computing device 770.

Figure 8F:
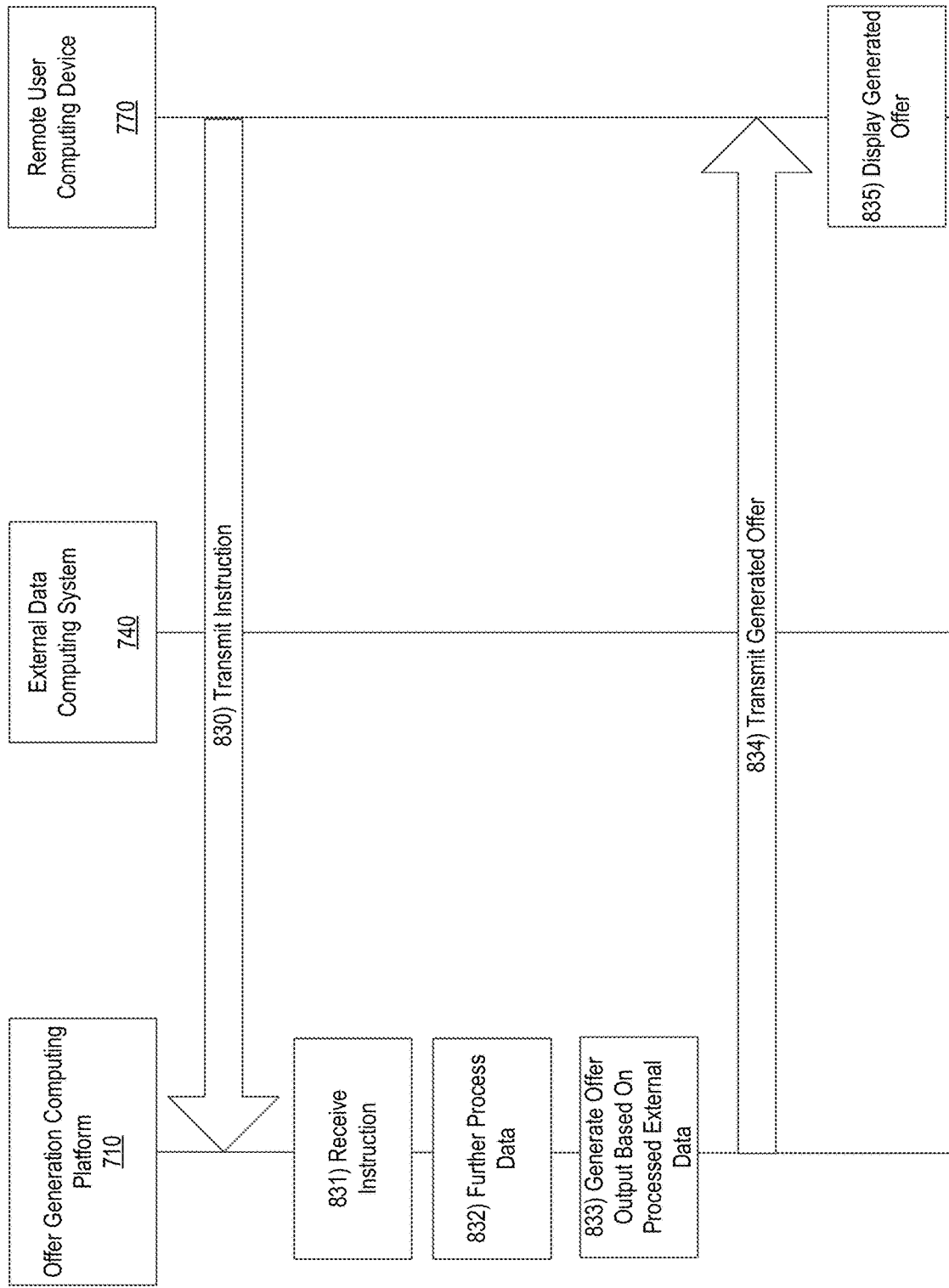

With reference to FIG. 8F, at step 830, an instruction to continue processing data may be transmitted from the remote user computing device 770 to the offer generation computing platform 710. At step 831, the instruction may be received and executed.

At step 832, the data may be further processed and/or additional data may be processed. For instance, clustering processes, one or more machine learning algorithms, or the like, may be used to process the data. In some examples, processing the data may include categorizing the data into one or more tiers or categories, as discussed more fully above. In some examples, the tiers may have increasing granularity in the type of data categorized in each tier.

At step 833, an output may be generated. For instance, an offer, such as an insurance quote including a premium or other cost, user insights, or the like, may be generated based on the processed data. Accordingly, in at least some examples, an insurance quote or other offer or insight may be generated based on data provided by the user, rather than data collected by the entity providing the quote. For instance, the user may generate data by going about his or her daily life. Data associated with user behaviors, activities, and the like, may be collected via one or more sensors arranged in, for instance, a mobile device of the user, a vehicle of a user, a wearable device of a user, or the like. This data may also include location data based on GPS within the device. This data may be stored not only by the device but may be captured by other entities monitoring the user's device, such as web browser providers, and the like. The data may be captured by the third party with the permission of the user. This data may then be extracted from the third party system and provide to the insurance provider (e.g., entity implementing the offer generation computing platform 710) for use in evaluating risk associated with the user. Accordingly, the user is able to provide his or her own data, collected by another entity, to provide the insurance provider with a snapshot of the user's behaviors which may be a strong indicator of risk associated with the user. The data provides insight into risk associated with the user prior to the user becoming a customer or otherwise engaging with the insurance provider, thereby improving accuracy of quotes provided.

At step 834, the generated offer may be transmitted from the offer generation computing platform 710 to the remote user computing device 770. At step 835, the generated offer may be displayed on a display of the remote user computing device 770.

In some examples, the processes described above with respect to FIGS. 8A-8F may be performed in real-time or near real-time. Accordingly, a user may request a quote, download an application, extract and transfer data and receive the quote based on processed data within a matter of minutes or even seconds. Further, one or more aspects described above with respect to FIGS. 8A-8F may be performed by one or more devices other than those discussed with respect to FIGS. 8A-8F, such as devices described above with respect to at least FIGS. 1-4B.

Figure 9:
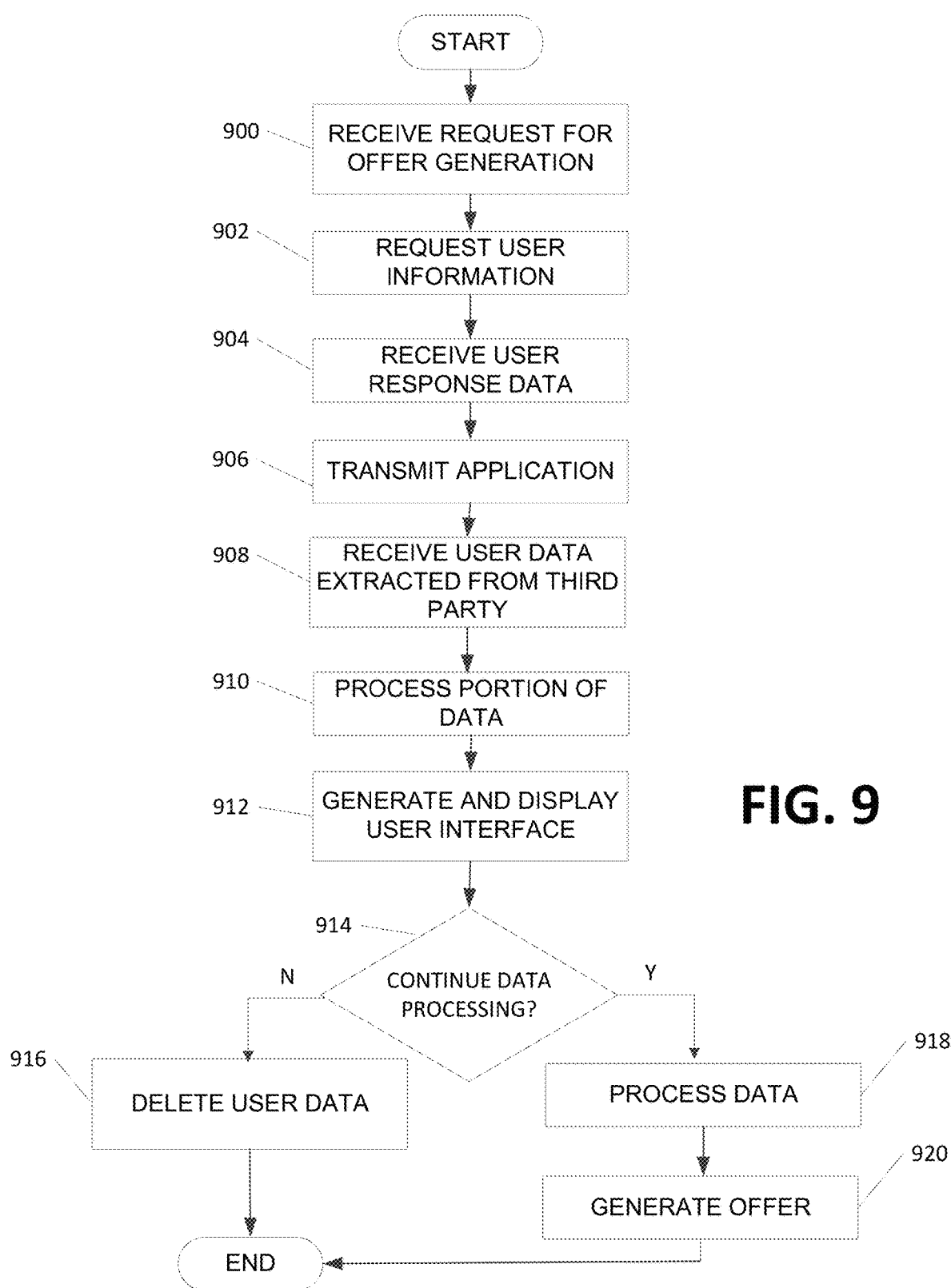
FIG. 9 illustrates one example flow chart illustrating an example method of offer generation control functions, according to one or more aspects described herein.

FIG. 9 illustrates one example process for generating an offer based on third party data according to one or more aspects described herein. The steps described with respect to FIG. 9 may be performed by one or more of the various devices and/or systems described herein, such as the offer generation computing platform 710, determination server 110, determination server 210, mobile device 250, vehicle 260, remote user computing device 770, and the like. In some examples, one or more of the processes or steps described may be performed in real-time or near real-time and the capture, transmission, use, and the like of user data may be performed with user permission.

In step 900, a request for offer generation may be received. As discussed herein, the request may be received from a remote user computing device 770, such as a mobile device of a user.

At step 902, a request for user registration information may be generated and transmitted to the user device (e.g., the remote user computing device 770). At step 904, user registration response data may be received from the remote user computing device 770.

At step 906, an application may be transmitted from the offer generation computing platform to the remote user computing device 770 for download. The application may then execute on the remote user computing device causing the remote user computing device 770 to establish a connection and initiate a communication session with a third party data storage system, such as external data computing system 740, 745, extract user data, such as user location data, from the external data computing system 740, 745, and transmit the data to the remote user computing device 770. In some examples, initiating the communication session, identifying the user data, extracting the data and/or transmitting the data may be performed automatically and without additional user input.

At step 908, the data received by the remote user computing device 770 from the external data computing system 770 may be transmitted from the remote user computing device 770 to the offer generation computing platform 710. In some examples, this data transmission may be performed automatically and without additional user input.

At step 910, a portion of the data may be processed. For instance, a portion of the received data may be formatted and/or processed to provide user insights into one or more behaviors. At step 912, a user interface may be generated and transmitted to the remote user computing device 770 for display. In some examples, the user interface may include the processed data and/or one or more user insights.

In some arrangements, the user interface may also include a request for user input instructing the system to continue processing data or discontinue processing data. At step 914, a determination may be made as to whether received user input included instructions to continue processing the data. If not, processing of the received data may be discontinued and data received by the offer generation computing platform and associated with the user may be deleted at step 916.

If, at step 914, user input includes instructions to continue processing the data, the data may be processed at step 918, as discussed herein. At step 920, the processed data may be used to generate one or more offers or other outputs. For instance, the processed data may be used to generate an insurance quote.

In some arrangements, in order to provide an insurance offer or quote, the user may need to provide information about themselves, their vehicle(s), and the like, which can be time consuming, inefficient and inaccurate when performed manually in conventional systems. Further, in order to tailor an offer to a user, detailed information about the user's driving behaviors, which can be derived from their location history may be required or desirable. This information may be difficult or impossible for a user to provide accurately. Accordingly, arrangements described herein provide a platform for providing user input including personal information in the form of a photographic identification and vehicle information in the form of a machine-readable or scannable code. Responsive to receiving this data, location data for the user may be automatically obtained based on the identity information and vehicle information. Such arrangements may reduce the amount of user input required to obtain an insurance offer by using a mobile device to obtain the relevant data through minimal user interaction. The location data may then be automatically obtained without further user interaction.

FIGS. 10A-10K illustrate another example event sequence for performing offer/insight generation control functions in accordance with one or more aspects described herein. The sequence illustrated in FIGS. 10A-10K is merely one example sequence and various other events may be included, or events shown may be omitted, without departing from the invention.

Figure 10A:
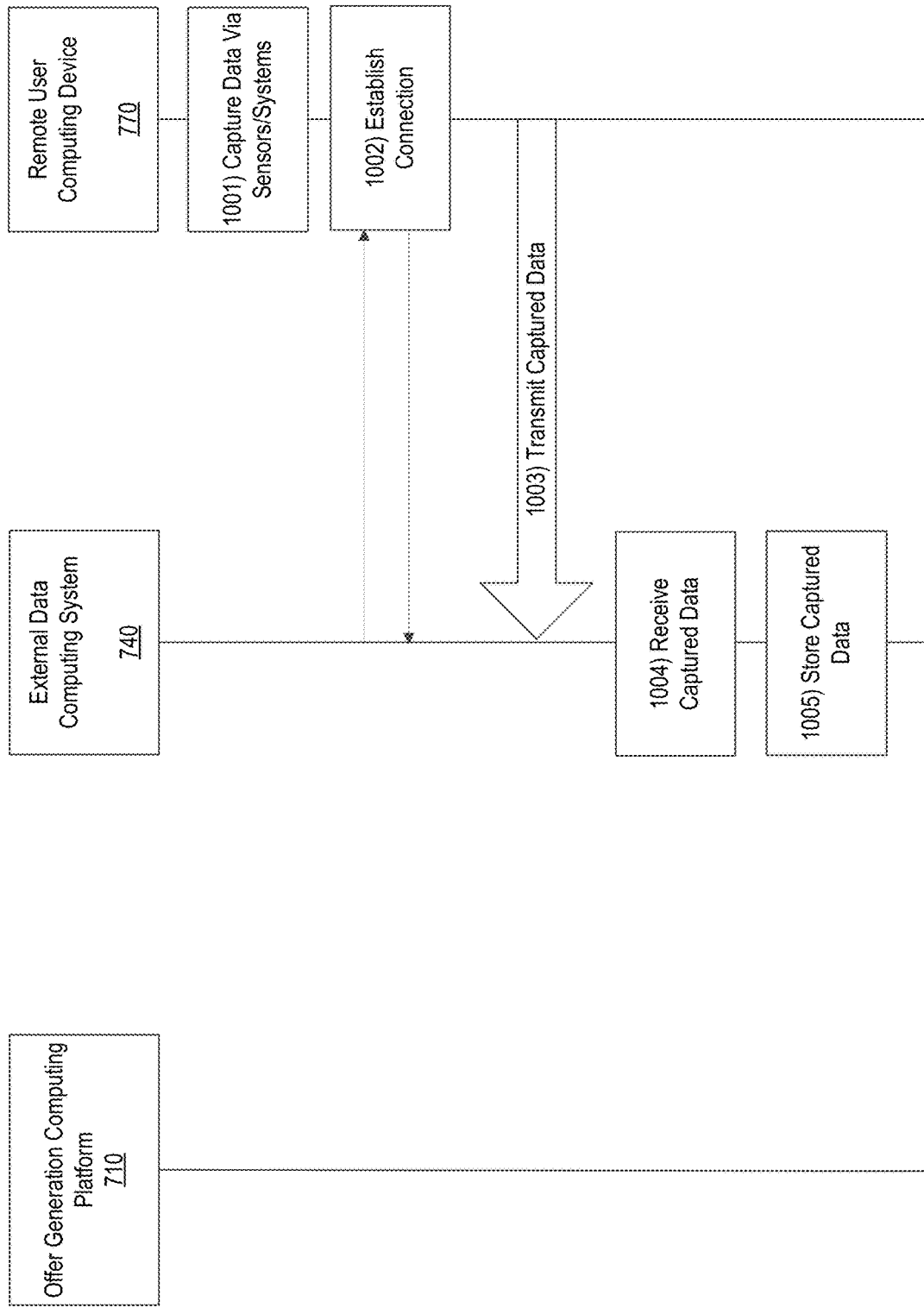

With reference to FIG. 10A, at step 1001, data may be captured by a remote user computing device 770. For instance, data such as location data (e.g., GPS data including latitude and longitude, time stamp, date stamp, and the like) captured via a mobile device of a user (e.g., remote user computing device 770) may be captured. The location data may be captured throughout a user's regular routine (e.g., driving, walking, at work, at home, and the like) Additionally or alternatively, other types of data may be captured via the remote user computing device 770. For instance, social media data, wellness data, activity data, application usage data, and the like, may be captured. In some examples, remote user computing device 770 may be a wearable device such as a fitness tracker, a vehicle, or the like. Data from that device may be captured. Although only one remote user computing device 770 is shown, more remote user computing devices may be used to capture data and/or the additional devices may be a same type of device or a different type of device without departing from the invention.

As discussed herein, data may be captured via sensors within or associated with the remote user computing device 770. For instance, GPS sensors, accelerometers, gyroscopes, and the like, may be used to captured data. Additionally or alternatively, various other types of sensors may be used to capture data without departing from the invention.

At step 1002, a connection may be established between the remote user computing device 770 and the external data computing system 740. For instance, a first wireless connection may be established between the remote user computing device 770 and the external data computing system 740. Upon establishing the first wireless connection, a communication session may be initiated between the external data computing system 740 and the remote user computing device 770.

At step 1003, the captured data may be transmitted from the remote user computing device 770 to the external data computing system 740. For instance, the captured data may be transmitted during the communication session initiated upon establishing the first wireless connection. In some examples, the captured data may be transmitted in real-time as the data is captured. In other examples, the captured data may be transmitted on a periodic or aperiodic basis, according to a predetermined schedule, or the like. In some examples, captured data from a period of time (e.g., one week, one month, six months, 1 year, or the like) may be captured prior to additional functions described herein being performed.

At step 1004, the external data computing system 740 may receive the captured data and, at step 1005, the external data computing system 740 may store the captured data. As discussed herein, the external data computing system 740 may be a third party system (e.g., associated with a party different from the user associated with the remote user computing device 770 and the entity associated with the offer generation computing platform 710). In some examples, the external data computing system 740 may receive and store the captured data with the necessary permissions received from the user and the third party may use the captured and stored data for additional third party uses unrelated to the processes described herein. This stored data may then later be accessed by the user (e.g., the user associated with the device from which the data was captured) for personal use, transmission to other entities, or the like.

Figure 10B:
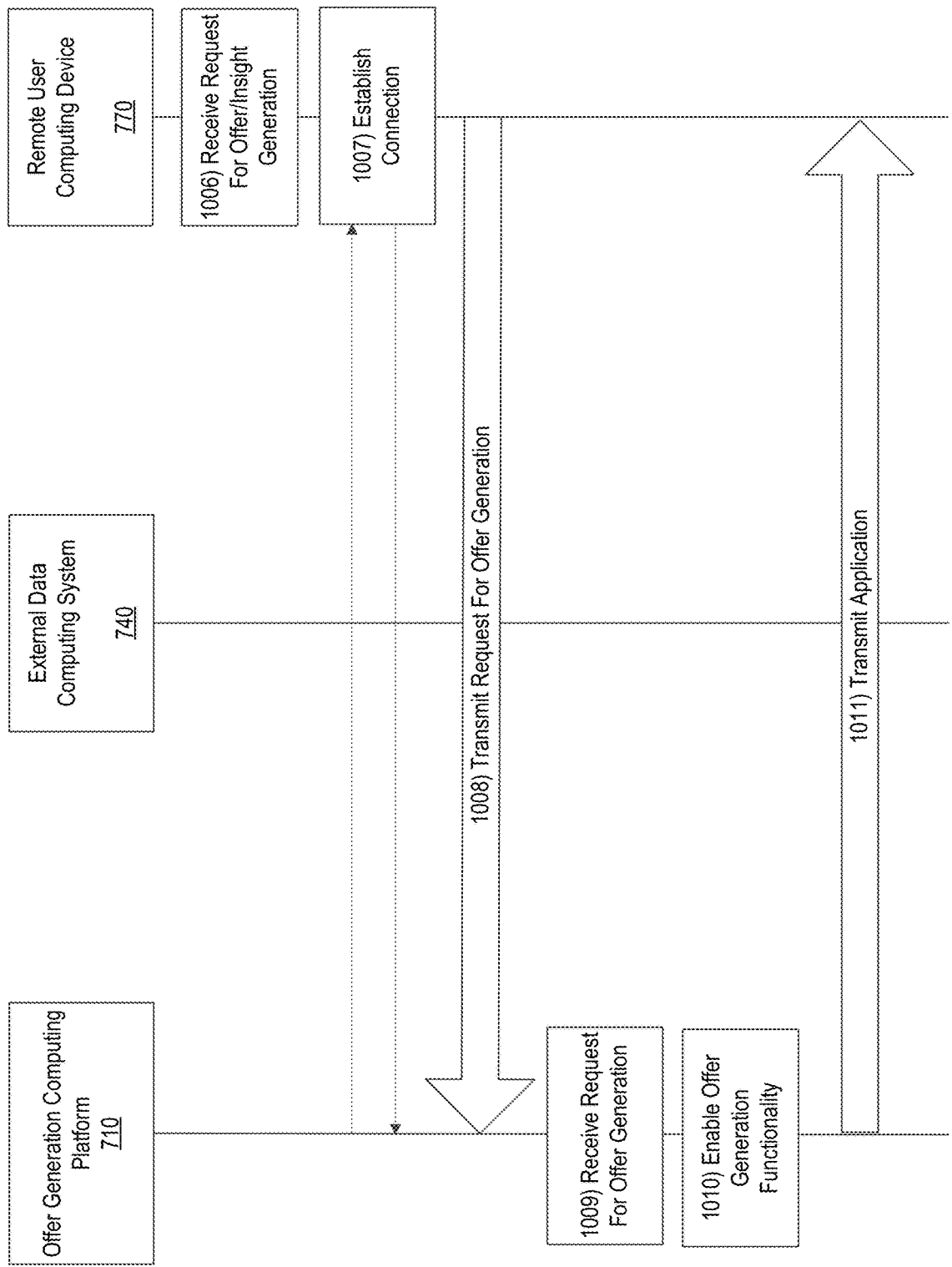

With reference to FIG. 10B, at step 1006, a request for offer/insight generation may be received. For instance, a user may input a request into remote user computing device 770. In some examples, the request may be input into an application executing on the remote user computing device 770 and provided by the offer generation computing platform 710.

At step 1007, a connection may be established between the remote user computing device 770 and the offer generation computing platform 710. For instance, a second wireless connection may be established between the remote user computing device 770 and the offer generation computing platform 710. Upon establishing the second wireless connection, a communication session may be initiated between the offer generation computing platform 710 and the remote user computing device 770.

At step 1008, the request for offer generation may be transmitted from the remote user computing device 770 to the offer generation computing platform 710. For instance, the request for offer generation may be transmitted during the communication session initiated upon establishing the second wireless connection.

At step 1009, the request for offer/insight generation may be received by the offer generation computing platform 710. At step 1010, offer generation functionality may be enabled by the offer generation computing platform 710. For instance, functionality that was previously disabled may be enabled, activated or initiated in response to receiving the request for offer/insight generation. In some examples, enabling offer generation functionality may include identifying an application for transmission to a user device (e.g., remote user computing device 770).

At step 1011, an application may be transmitted from the offer generation computing platform 710 to the remote user computing device 770. The application may be an application to facilitate communication between one or more systems, identify data for extraction, and the like. Although the arrangement of FIG. 10B includes the application being transmitted after the request for offer is received, in some examples, the application may be transmitted to the remote user computing device 770 prior to the request for offer generation being received by either the remote user computing device 770 or the offer generation computing platform 710.

Figure 10C:
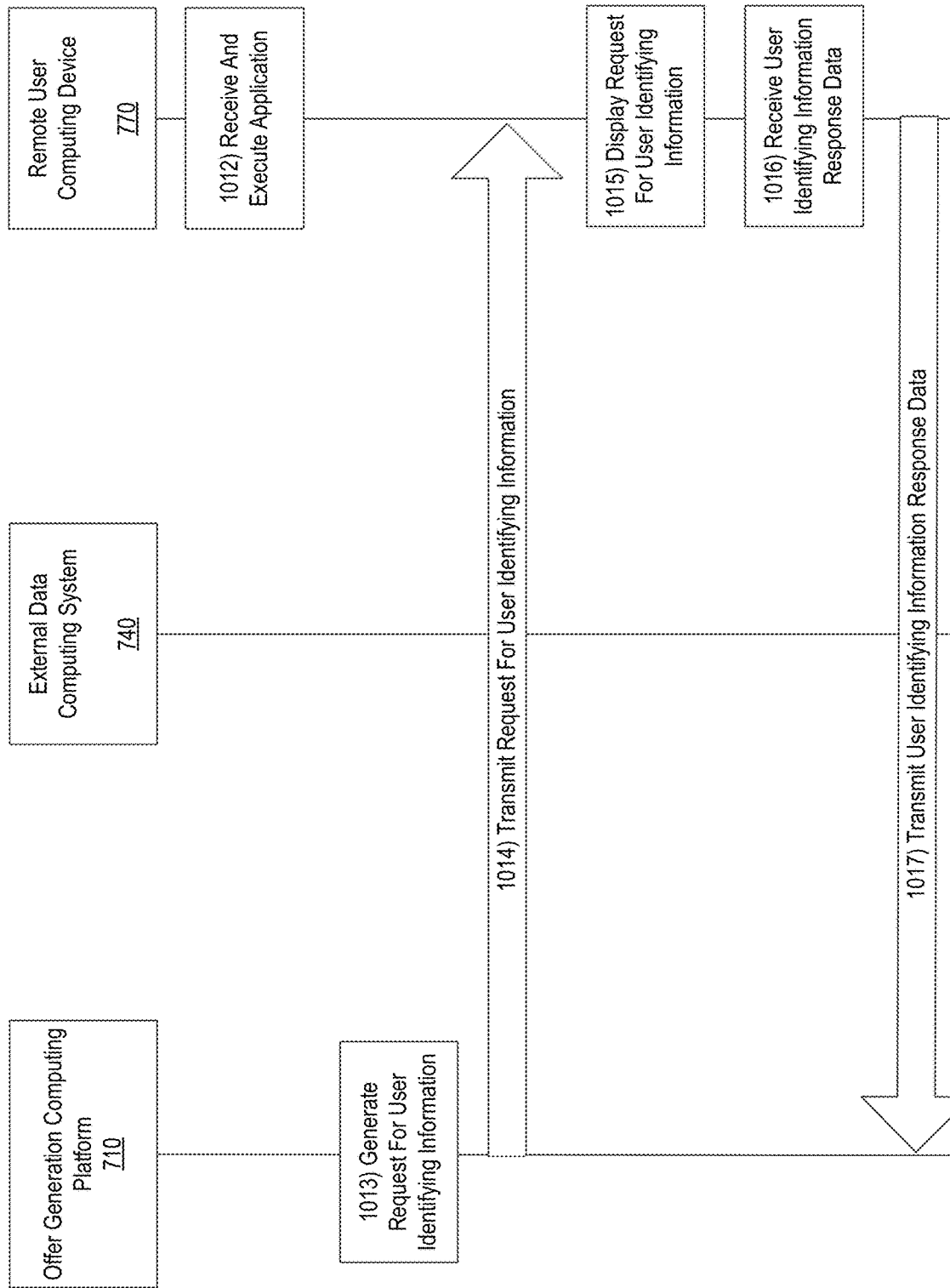

With reference to FIG. 10C, at step 1012, the transmitted application may be received by the remote user computing device 770 and executed by the remote user computing device 770. In some examples, executing the application may include enabling functionality associated with the remote user computing device 770 (e.g., data capture functions, data transmission functions, and the like).

At step 1013, a request for user identifying information may be generated by the offer generation computing platform 710. In some examples, the request for user identifying information may include a request for an image of a photographic identification of a user, such as a driver's license or passport, a scan of a machine readable or scannable code from the photographic identification, and the like. In some examples, the request for user identifying information may include a user interface including instructions for capturing an image of a front face of the photographic identification, rear face of the photographic identification, scanning a machine readable code (e.g., quick response (QR) code, bar code, or the like), or the like.

At step 1014, the generated request for user identifying information may be transmitted from the offer generation computing platform 710 to the remote user computing device 770. For instance, the request may be transmitted during the communication session initiated upon establishing the second wireless connection.

At step 1015, the request for user identifying information may be received and displayed by the remote user computing device 770 (e.g., on a display of the device 770).

At step 1016, user identifying information response data may be received and/or captured by the remote user computing device 770. For instance, a user may capture an image of one or more sides of a photographic identification, scan a machine readable code, and the like, using an image capture device of the remote user computing device 770. The captured images may constitute user identifying information response data and, at step 1017, may be transmitted from the remote user computing device 770 to the offer generation computing platform 710. In some examples, the user identifying information response data may be transmitted during the communication session establishing upon initiating the second wireless connection.

With reference to FIG. 10D, at step 2018, the user identifying information response data may be received by the offer generation computing platform 710 and, at step 1019, the user identifying information response data may be processed by the offer generation computing platform 710. For instance, the user identifying information response data may be stored by the offer generation computing platform 710.

At step 1020, a request for a self-captured photograph or image may be generated by the offer generation computing platform 710. For instance, a user interface including a request and/or instruction to self-capture an image of the user requesting the offer/insights may be generated. At step 1021, the generated request for the self-captured photograph or image may be transmitted from the offer generation computing platform 710 to the remote user computing device 770. In some examples, the request may be transmitted during the communication session initiated upon establishing the second wireless connection.

At step 1021, the generated request for the self-captured photograph or image may be transmitted from the offer generation computing platform 710 to the remote user computing device 770. In some examples, the generated request may be transmitted during the communication session initiated upon establishing the second wireless connection.

At step 1022, the request for a self-captured photograph or image may be received by the remote user computing device 770 and displayed by the remote user computing device 770 (e.g., on a display of device 770).

Figure 10E:
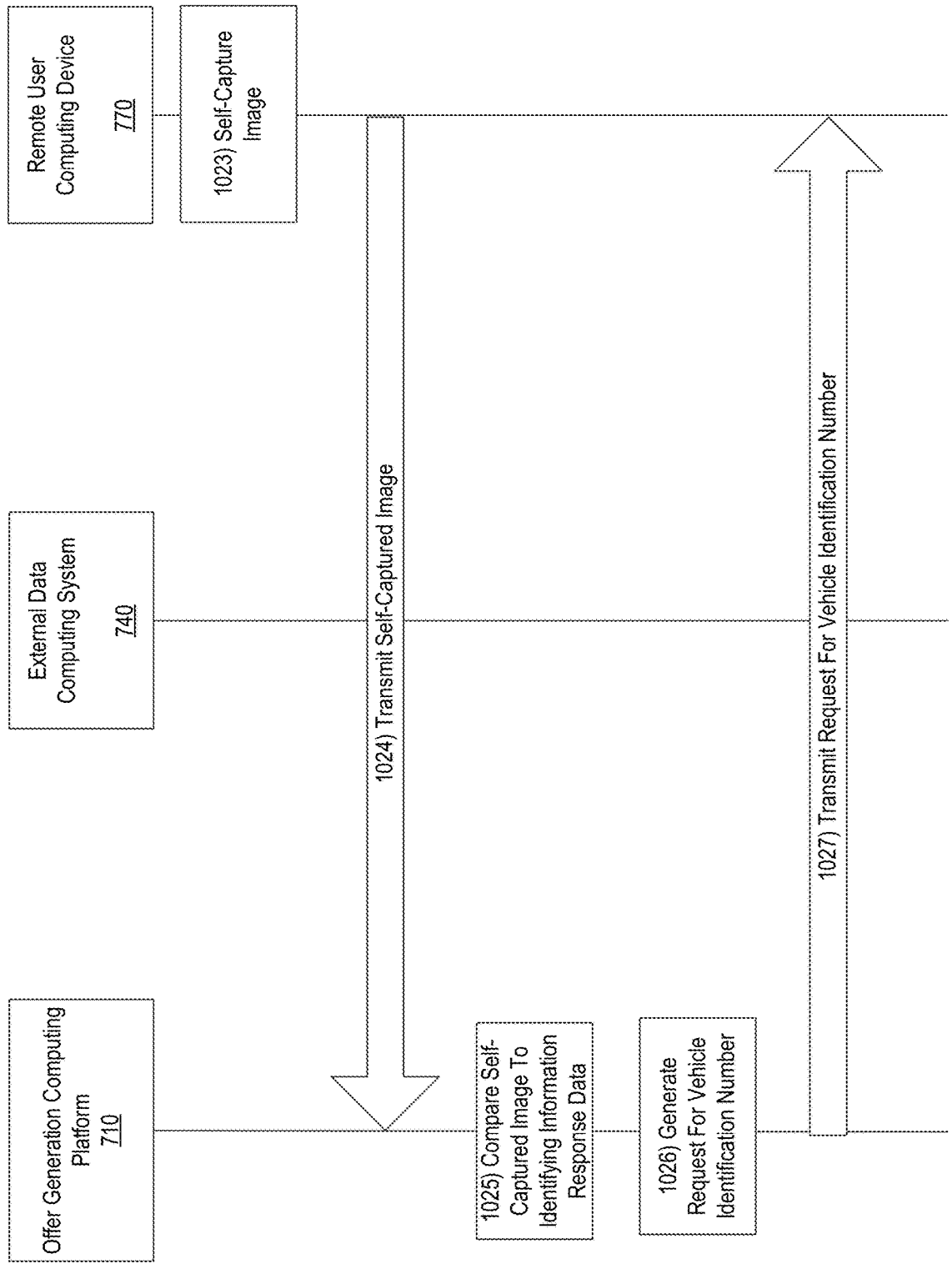

With reference to FIG. 10E, at step 1023, a self-captured image of the user may be captured, e.g., by the image capture device of the remote user computing device 770. At step 1024, the self-captured image of the user may be transmitted from the remote user computing device 770 to the offer generation computing platform 710. In some examples, the self-captured image of the user may be transmitted during the communication session initiated upon establishing the second wireless connection.

At step 1025, the self-captured image may be received by the offer generation computing platform 710 and may be compared to image data from the user identifying information response data. For instance, facial recognition, optical character recognition, other image processing techniques, and the like, may be used to identify and/or isolate an image of a user in the user identifying information response data. That isolated image of the user may be compared to the self-captured image of the user (e.g., using facial recognition, machine learning algorithms, image processing, and the like) to determine whether the images match (e.g., whether the user who captured the self-captured image is the person pictured in the photographic identification captured as part of the user identifying information response data). This process may be performed to ensure the user requesting the offer or insights is authenticated and the request is not fraudulent.

If the images do not match, a notification may be generated and transmitted to the remote user computing device 770 indicating that the request for offer generation is denied, requesting additional information, or the like.

At step 1026, if the images match (e.g., the user is authenticated) a request for a vehicle identification number associated with a vehicle of the user may be generated. In some examples, the request may include a user interface including the request for the vehicle identification number, and/or instructions to capture the vehicle identification number using, for example, the image capture device of the remote user computing device 770. In some examples, the instructions may include an instruction to scan a machine readable code on the vehicle that may include the vehicle identification number, as well as additional information associated with the vehicle (e.g., make, model, color, trim, or the like).

At step 1027, the generated request for vehicle identification number may be transmitted from the offer generation computing platform 710 to the remote user computing device 770. In some examples, the generated request may be transmitted during the communication session initiated upon establishing the second wireless connection.

Figure 10F:
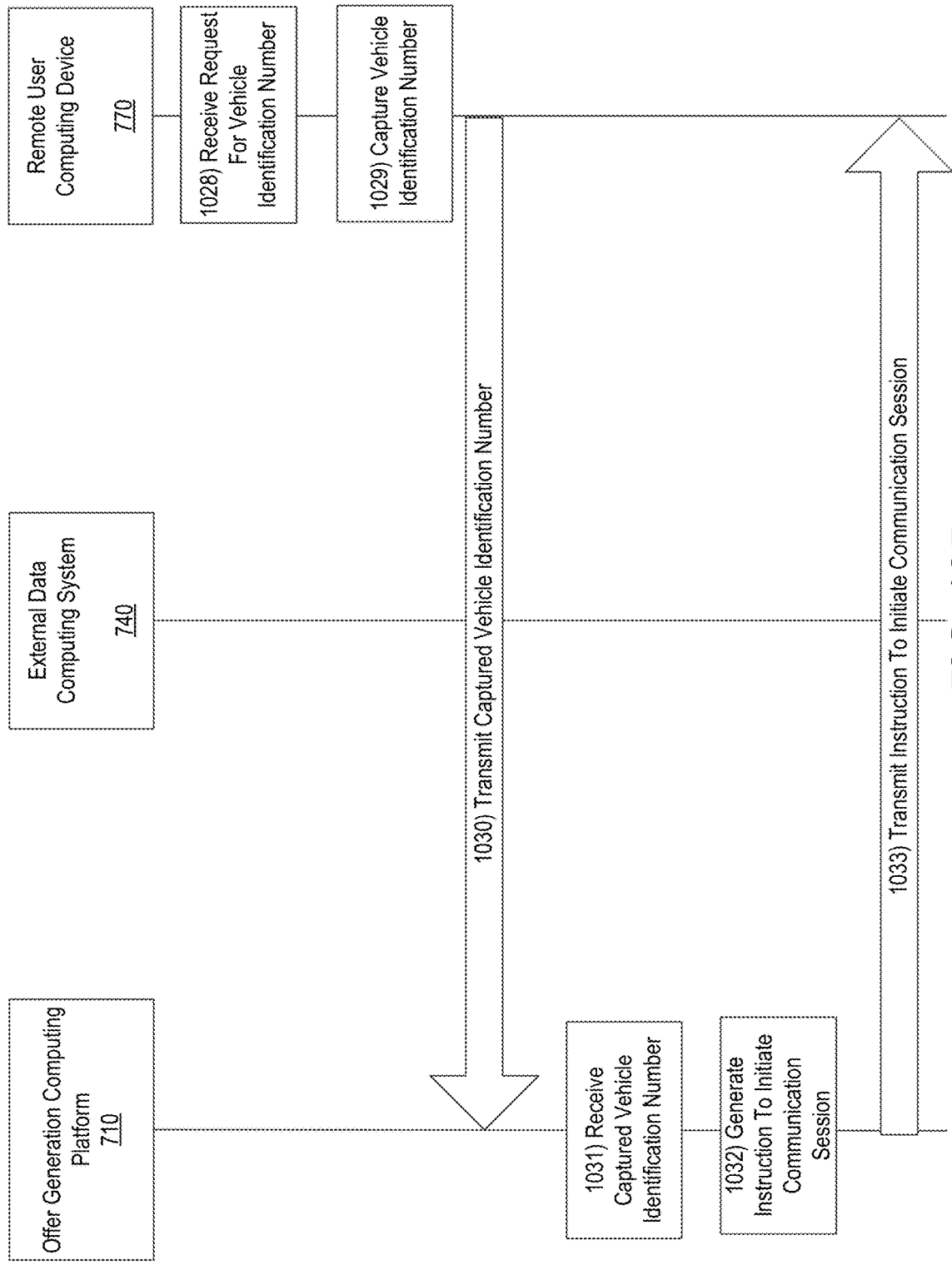

With reference to FIG. 10F, at step 1028, the request for vehicle identification number may be received by the remote user computing device 770 and displayed by the device (e.g., on a display of the device 770). At step 1029, the vehicle identification number may be captured. In some examples, the vehicle identification number may be captured by scanning a machine readable code on the vehicle, the machine readable code including the vehicle identification number and/or other data. Additionally or alternatively, the vehicle identification number may be manually input or an image of the vehicle identification number may be captured (e.g., via an image capture device of the remote user computing device 770) and optical character recognition may be used to identify the vehicle identification number from the image.

At step 1030, the captured vehicle identification number may be transmitted from the remote user computing device 770 to the offer generation computing platform 710. In some examples, the captured vehicle identification number may be transmitted during the communication session initiated upon establishing the second wireless connection.

At step 1031, the captured vehicle identification number may be received by the offer generation computing platform 710.

At step 1032, an instruction to initiate a communication session between the remote user computing device 770 and another system, such as external data computing device 740, may be generated. In some examples, the instruction may include instructions that, when executed, automatically cause initiation of the communication session, establish a connection, or the like.

At step 1033, the generated instruction may be transmitted from the offer generation computing platform 710 to the remote user computing device 770. In some examples, the generated instruction may be transmitted during the communication session initiated upon establishing the second wireless connection.

Figure 10G:
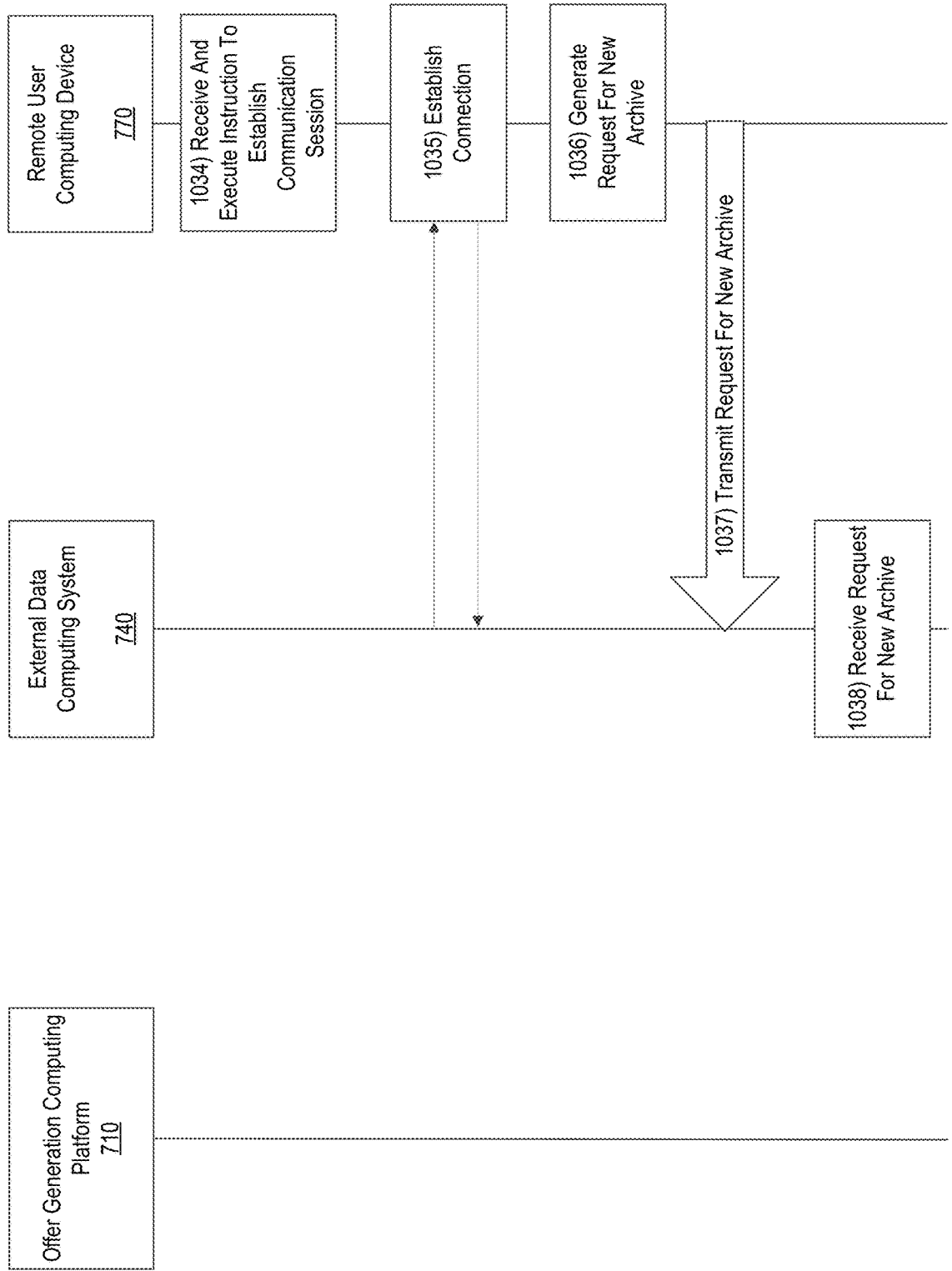

With reference to FIG. 10G, at step 1034, the generated instruction may be received by the remote user computing device 770 and executed to initiate the communication session. At step 1035, in response to execution of the instruction, a connection may be established between the remote user computing device 770 and external data computing system 740. For instance, a third wireless connection may be established between the remote user computing device 770 and the external data computing system 740. Upon establishing the third wireless connection, a communication session may be initiated between the external data computing system 740 and the remote user computing device 770.

At step 1036, a request for a new archive or dataset may be generated by, for example, the remote user computing device 770. The new archive or dataset may include user data captured by the remote user computing device 770 and stored by the external data computing system 740. At step 1037, the request for the new archive or dataset may be transmitted from the remote user computing device 770 to the external data computing system 740. For example, the request to generate the new archive or dataset may be transmitted during the communication session initiated upon establishing the third wireless connection.

At step 1038, the request for the new archive or dataset may be received by the external data computing system 740.

Figure 10H:
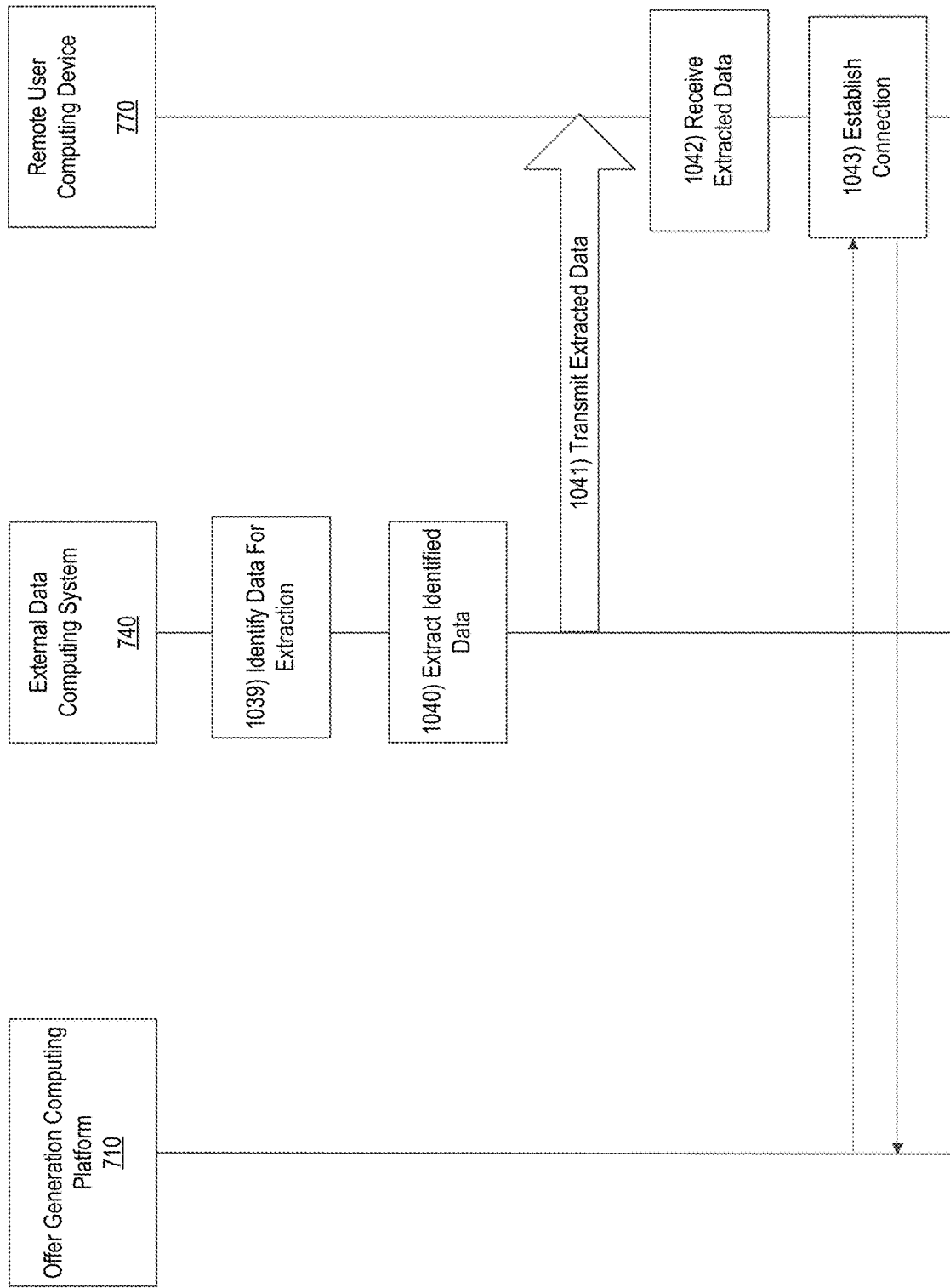

With reference to FIG. 10H, at step 1039, data for extraction may be identified. For example, the request for a new archive or dataset may include additional information identifying a user, identifying types of data for extraction, identifying a time period of data for extraction, identifying a format for the extracted data, information identifying the remote user computing device that captured the data, and the like. Accordingly, the external data computing system 740 may identify the appropriate data for extraction based on, for example, data provided with the request for the new archive. In some examples, a time and/or data stamp may be used as a key value to synch data being extracted. At step 1040, the identified data may be extracted.

At step 1041, the extracted data may be transmitted from the external data computing system 740 to the remote user computing device 770. In some examples, the extracted data may be transmitted during the communication session initiated upon establishing the third wireless connection.

At step 1042, the extracted data may be received by the remote user computing device 770. At step 1043, a connection may be established between the remote user computing device 770 and the offer generation computing platform 710. For instance, a fourth wireless connection may be established between the remote user computing device 770 and the offer generation computing platform 710. Upon establishing the fourth wireless connection, a communication session may be initiated between the offer generation computing platform 710 and the remote user computing device 770.

With reference to FIG. 10I, at step 1044, the extracted data may be transmitted from the remote user computing device 770 to the offer generation computing platform 710. In some examples, the extracted data may be transmitted during the communication session initiated upon establishing the fourth wireless connection.

Although aspects described herein provide the extracted data being transmitted from the external data computing system 740 to the remote user computing device 770 and then to the offer generation computing platform 710, in some examples, the data may be transmitted directly from the external data computing system 740 to the offer generation computing platform 710 with first being transmitted to the remote user computing device 770. Further, in some arrangements, portions of the data process described herein may be performed by the remote user computing device 770 while portions may be performed by the offer generation computing platform 710 (e.g., parallel processing may occur).

At step 1045, the extracted data may be received by the offer generation computing platform 710. In some examples, the extracted data may be tagged together with the received photographic identification data, self-captured image data, vehicle identification number data, and the like, using the time and/or date stamp as a key value. At step 1046, the extracted data may be processed to generate one or more offers or insights (e.g., similar to other arrangements described herein). For example, the extracted data may be analyzed (e.g., using machine learning as discussed herein, by grouping the data into tiers as discussed, or the like) to identify frequent trips or routes, time spent driving after dark, time spent driving on highways vs. side roads, locations frequently visited, and the like. In some examples, the generated offers and/or insights may be generated based on the received external data as well as internal data retrieved from an internal data computing device 720.

In some examples, additional insights may be generated with respect to wellness, user activity, and the like. For instance, based on data from, for example, a wearable fitness tracker, one or more insights directed to active time, types of activity, and the like may be generated.

Additionally or alternatively, one or more offers may be generated for the user. For instance, based on the extracted data, vehicle identification number and/or additional information, an insurance rate or quote may be generated for the user. For instance, the extracted vehicle identification number may be used as input in a query to retrieve additional details or data associated with the vehicle (e.g., accident history, make, model, specifications, trim, features, and the like). As discussed herein, aspects described with respect to FIGS. 10A-10I may be performed in real-time or near real-time in order to retrieve user data and generate insights in a fast, efficient manner (e.g., in less than 5 minutes, less than 2 minutes, less than 1 minute, or the like).

As step 1047, a user interface may be generated including the generated insights and/or offer. In some examples, the user interface may include options for displaying the generated insights and/or offer in different ways (e.g., map view, list view, graph view, or the like).

At step 1048, the generated user interface(s) may be transmitted from the offer generation computing platform 710 to the remote user computing device 770. In some examples, the generated user interface(s) including the generated insights and/or offer may be transmitted during the communication session initiated upon establishing the fourth wireless connection.

Figure 10J:
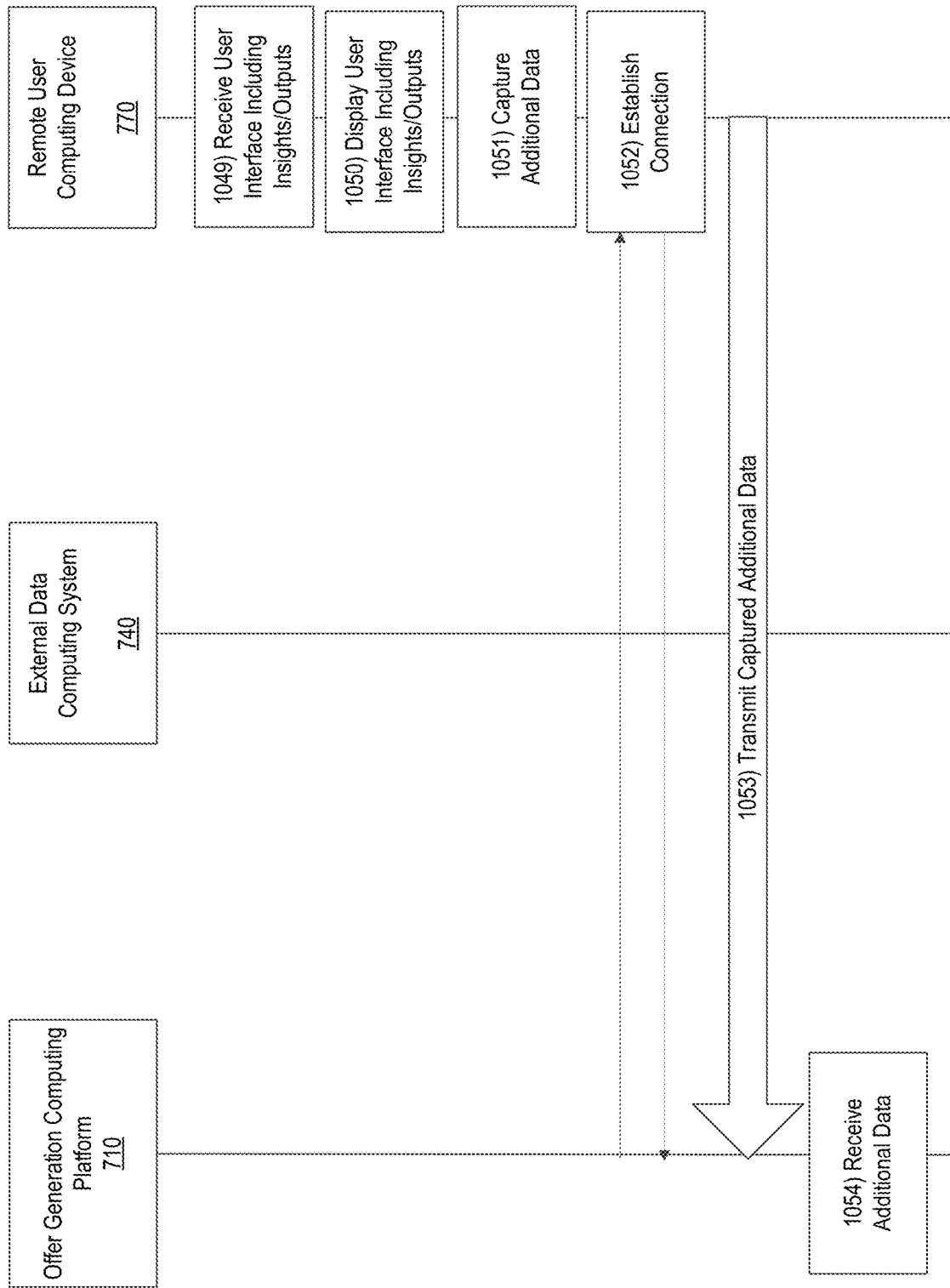

With reference to FIG. 10J, at step 1049, the transmitted user interface(s) including the generated insights and/or offer may be received by the remote user computing device 770 and, at step 1050, the generated user interface(s) may be displayed by the remote user computing device 770 (e.g., on a display of the remote user computing device 770). In some examples, the established wireless connected may be terminated after transmitting the user interfaces.

At step 1051, additional data may be captured by the remote user computing device 770. For instance, in some examples, after a user has accepted a generated offer (e.g., an offer displayed at step 1050), the user may agree to provide additional data captured by the remote user computing device 770 to the offer generation computing platform 710 to generate additional insights, updated offers, and the like. Accordingly, the remote user computing device 770 may capture additional data over a period of time (e.g., one week, one month, 3 months, 6 months, or the like). In some examples, the data may be stored by the remote user computing device 770. Additionally or alternatively, the data may be transmitted to the offer generation computing platform 710 in real-time or on a periodic basis (e.g., each day, each hour, or the like).

At step 1052, a connection may be established between the remote user computing device 770 and the offer generation computing platform 710. For instance, a fifth wireless connection may be established between the remote user computing device 770 and the offer generation computing platform 710. Upon establishing the fifth wireless connection, a communication session may be initiated between the offer generation computing platform 710 and the remote user computing device 770.

At step 1053, the captured additional data may be transmitted from the remote user computing device 770 to the offer generation computing platform 710. In some examples, the captured additional data may be transmitted during the communication session initiated upon establishing the fifth wireless connection.

At step 1054, the captured additional data may be received by the offer generation computing platform 710.

Figure 10K:
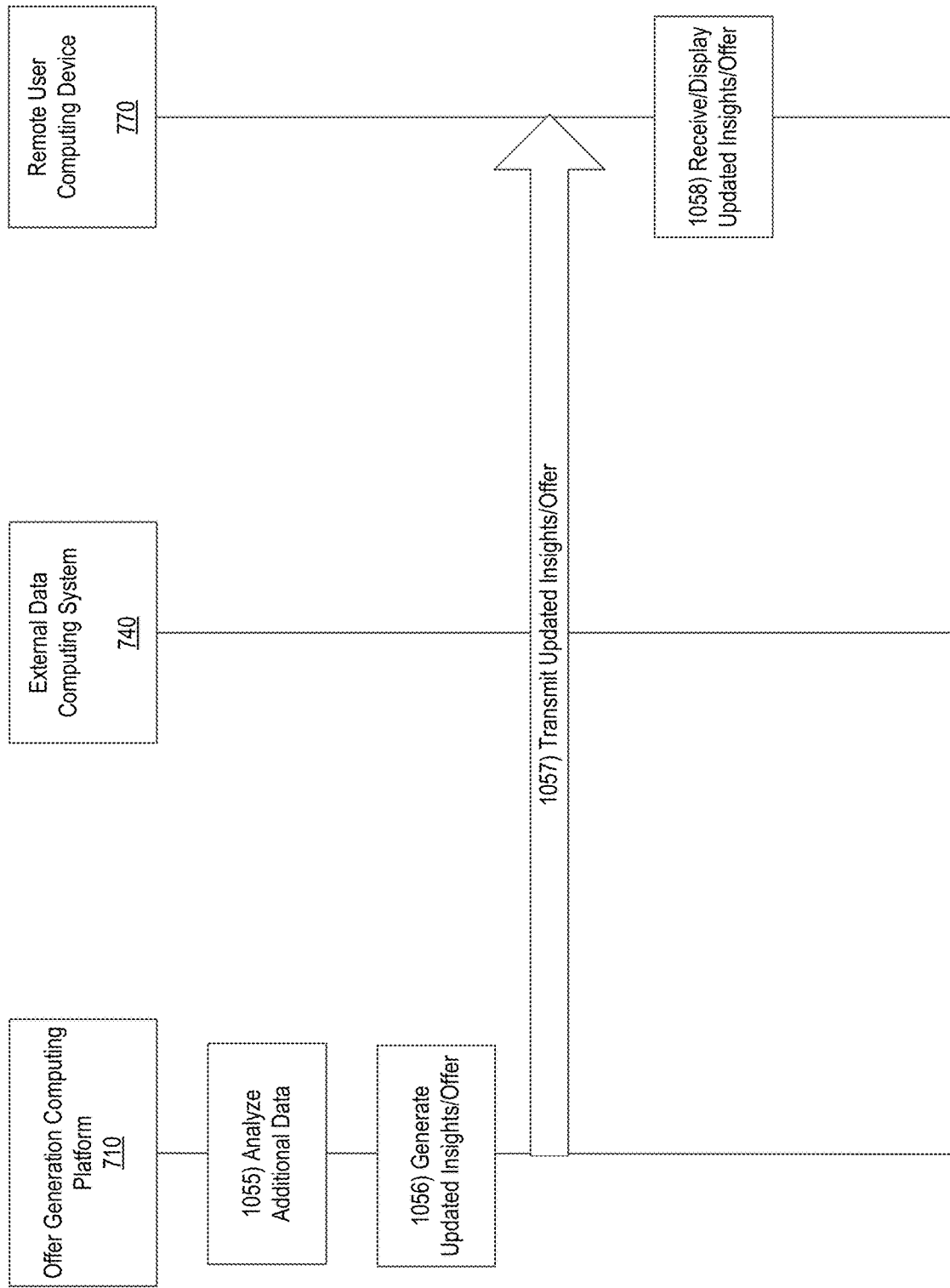

With reference to FIG. 10K, at step 1055, the received additional data may be analyzed. For instance, machine learning may be used to further analyze the received additional data. At step 1056, updated insights and/or offers or outputs may be generated (e.g., based on the analyzed additional data). In some examples, generated updated insights and/or offers may include generating user interfaces including the updated insights or offers.

At step 1057, the updated insights and/or offers may be transmitted to the remote user computing device 770. At step 1058, the updated insights and/or offers may be received by the remote user computing device 770 and displayed by the device 770.

As also discussed herein, in some aspects, in order to obtain location data that may be used to generate one or more insights related to a user's behavior, it may be necessary or desirable to verify an identity of the user (e.g., the user is who they say they are) and obtain location data from an external computing system, such as a cloud network. Accordingly, in some aspects, the user identity may be verified and then location data associated with the verified user identity may be obtained to generate one or more insights. These arrangements may reduce an amount of user input required and may ensure accuracy of location data for a user. The location data can be obtained automatically without needing user interaction other than data for identity verification.

Figure 11:
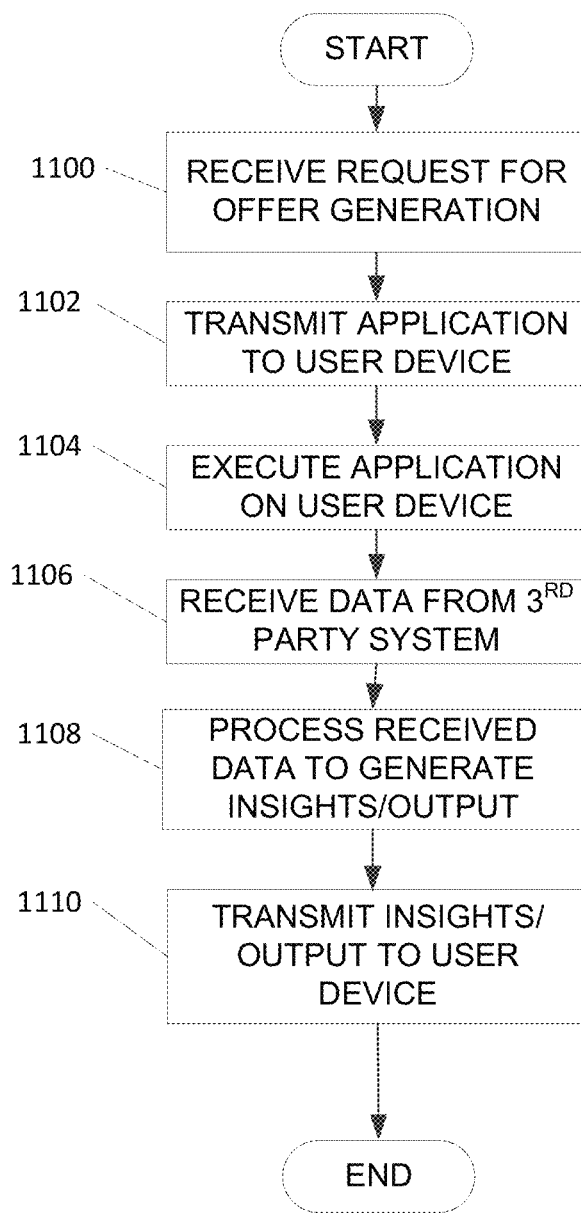
FIG. 11 illustrates one example flow chart illustrating another example method of offer and/or insight generation functions, according to one or more aspects described herein.

FIG. 11 illustrates another example process for generating an offer based on data captured by a user device and stored by a third party system according to one or more aspects described herein. The steps described with respect to FIG. 11 may be performed by one or more of the various devices and/or systems described herein, such as the offer generation computing platform 710, determination server 110, determination server 210, and the like. In some examples, one or more of the processes or steps described may be performed in real-time and the capture, transmission, use, and the like of user data is performed with user permissions.

At step 1100, a request for offer generation may be received. For instance, a user may input a request for an offer into a user computing device, such as a mobile device, (e.g., remote user computing device 770, remote user computing device 775, or the like) and the request may be transmitted to, for instance, the offer generation computing platform 710.

At step 1102, an application may be transmitted to the user computing device requesting the offer (e.g., remote user computing device 770). For instance, the offer generation computing platform 710 may transmit an application to the user computing device (e.g., remote user computing device 770) via a wireless connection establishing a communication session between the devices.

At step 1104, the transmitted application may be executed on the remote user computing device 770. Executing the application may enable functionality of the remote user computing device 770 that, in some examples, might not have been enabled prior to execution of the application. Additionally or alternatively, executing the application may automatically cause one or more connections to be establishing, communication sessions to be initiated, user interfaces to be displayed, and the like.

Executing the application may include establishing a communication session with an external data computing device, such as external data computing system 740, external data computing system 745, or the like. The external data computing system 740 may be a cloud-based computing and/or storage environment that may, for example, store data captured by the remote user computing device 770 (e.g., data generated and stored prior to the request for output is received). Accordingly, at step 1106, data from the external data computing system 740 may be extracted and received by, for example, the offer generation computing platform 710. In some examples, the data may first be transmitted from the external data computing system 740 to the remote user computing device 770, which may then transmit the data to the offer generation computing platform 710. In other examples, the data may be transmitted directly from the external data computing system 740 to the offer generation computing platform 710.

In some arrangements, the data may include location data including one or more location entries having longitude and latitude coordinates, time stamp, date stamp, and the like. In some examples, the location data may correspond to location data captured via the remote user computing device 770 (e.g., a GNSS or global positioning system of the remote user computing device 770). The location data may correspond to a plurality of locations to which the user associated with the remote user computing device 770 travelled (e.g., as the associated user goes about his or her day, for instance, in a car or other vehicle, while walking, a home location, a work location, and the like). In some examples, the location data may include location entries corresponding to one or more locations of the remote user computing device 770 at which location data was recorded or captured. For instance, as a user performs routine functions while carrying a mobile device with him or her, the mobile device (e.g., remote user computing device 770) may capture or record GNSS or GPS data corresponding to the various locations to which the mobile device travelled, at which location information was detected, or the like. This captured data may then be used to generate insights into user behaviors, verify validity of a user or user-provided data, and the like.

Additionally or alternatively, the data may include data captured by a wearable device, such as a fitness tracker (e.g., remote user computing device 770), a vehicle of a user, social media history of a user, web browsing history of a user, purchase history of a user, and the like. This data may be captured and/or stored by the external data computing system 740 with permission of the user and may, in some examples, be extracted and transmitted for further processing and/or analysis.

At step 1108, the extracted data may be analyzed and/or processed to generate one or more insights and/or offers. In some examples, insights may include aggregated data providing information to a user (e.g., aggregated data to indicate user behaviors, habits, routines, or the like). For example, generated insights may include insights based on location entries and/or location data, such as total miles driven in a time period, total time spent driving or in a vehicle for a time period, time spent driving after dark in a time period, time spent driving in precipitation for a time period, frequently visited locations, frequent routes, a home location, a work location, and the like. In another example, generated insights may include insights based on wearable device data such as amount of active time, number of steps per day, amount of intense activity, types of activity, and the like. In yet another example, generated insights may include insights based on browsing history, purchase history, or the like, such as frequently visited websites, frequent categories of purchase, and the like.

In some examples, an offer may be generated based on the processed data. For instance, an offer may include an insurance rate or premium and may be based on the processed data, as well as additional information provided by the user (e.g., vehicle identification number, driver information, and the like) as discussed herein. In some examples, generating the insights and/or offer may include generating one or more user interfaces.

At step 1110, the generated insights and/or offer (and/or user interface(s)) may be transmitted to the remote user computing device 770 and caused to display on the remote user computing device 770.

Figure 12:
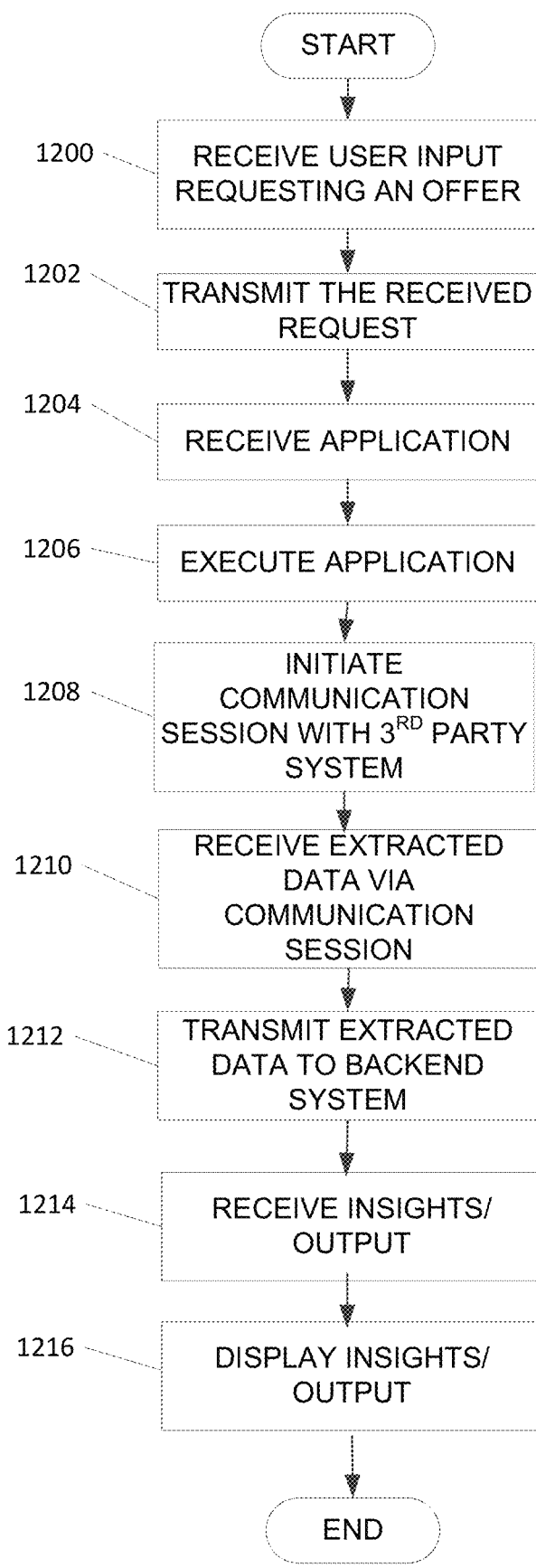
FIG. 12 illustrates one example flow chart illustrating another example method of offer and/or insight generation functions, according to one or more aspects described herein.

FIG. 12 illustrates another example process for generating an offer and/or insights based on data captured by a user device and stored by a third party system according to one or more aspects described herein. The steps described with respect to FIG. 12 may be performed by one or more of the various devices and/or systems described herein, such as offer generation computing device 710, determination server 110, determination server 210, remote user computing device 770, mobile device 250, vehicle 260, and the like. In some examples, one or more of the processes or steps described may be performed in real-time or near real-time and the capture, transmission, use, and the like of user data is performed with user permissions.

At step 1200, user input requesting generation of an offer may be received. For instance, a remote user computing device 770 may receive user input requesting generation of an offer. This request may, in some examples, initiate or activate offer/insight generation functions.

At step 1202, the request for the offer may be transmitted to, for example, offer generation computing platform 710. At step 1204, an application may be received by the remote user computing device 770 from, for example, the offer generation computing platform 710.

At step 1206, the application may be executed by the remote user computing device 770. For instance, the remote user computing device 770 may execute the application to enable functionality of the remote user computing device 770, automatically perform one or more functions, and the like.

At step 1208, the remote user computing device 770 may initiate a communication session with another device or system, such as external data computing system 740. In some examples, the communication session may be automatically initiated upon executing the application.

At step 1210, user data stored by the external data computing system 740 may be extracted and received by the remote user computing device 770. For instance, data captured by the remote user computing device 770 (and/or other remote user computing devices 775) that was previously captured and stored by the external data computing system 740 may be extracted and received by the remote user computing device 770.

At step 1212, the received, extracted data may be transmitted to, for example, offer generation computing platform 710, for processing and analysis. In some examples, other devices, such as determination server 110, determination server 210, or the like, may process the data. Further, in some examples, a portion of the data may be processed by the remote user computing device 770 while another portion of the data may be processed by another device (e.g., offer generation computing platform 710, determination server 110, determination server 210, or the like).

At step 1214, generated insights and/or outputs or offer may be received by the remote user computing device 770. In some examples, the generated insights and/or outputs or offers may include user interfaces generated to include the insights and/or outputs or offers, present the insights and/or outputs or offers in different formats, or the like.

At step 1216, the received insights and/or outputs or offers may be displayed on a display of the remote user computing device 770.

Figure 13:
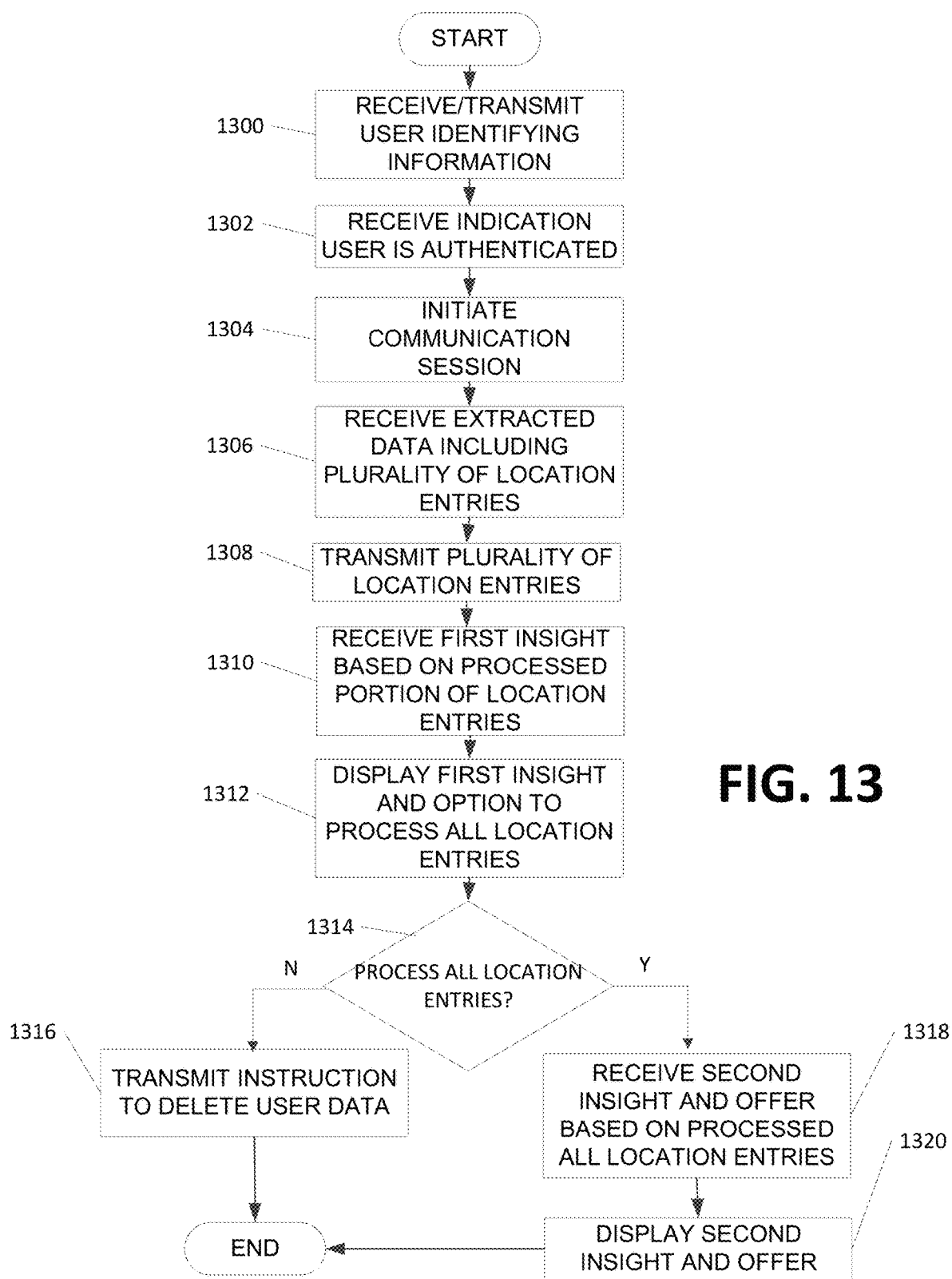
FIG. 13 illustrates one example flow chart illustrating yet another example method of offer and/or insight generation functions, according to one or more aspects described herein.

FIG. 13 illustrates another example process for generating an offer and/or insights based on data captured by a user device and stored by a third party system according to one or more aspects described herein. The steps described with respect to FIG. 13 may be performed by one or more of the various devices and/or systems described herein, such as offer generation computing device 710, determination server 110, determination server 210, remote user computing device 770, mobile device 250, vehicle 260, and the like. In some examples, one or more of the processes or steps described may be performed in real-time or near real-time and the capture, transmission, use, and the like of user data is performed with user permissions.

At step 1300, user identifying information may be received by, for example, remote user computing device 770. In some examples, the user identifying information may include a self-captured photograph of the user captured using, for example, an image capture device of the remote user computing device 770. The user identifying information may be transmitted for a first computing system, such as offer generation computing platform 710, for comparison with pre-stored user identifying information. For instance, the self-captured photograph of the user may be compared to an image of a photographic identification of the user that was captured and/or stored prior to the user transmitting the user identifying data. In some examples, facial recognition techniques may be used to compare the images to determine whether the images match (e.g., the user is authenticated). If the images do not match, a notification may be transmitted to the user. If the images do match, the user may be authenticated and an indication that the user is authenticated may be generated by the offer generation computing platform 710 and transmitted to the remote user computing device 770.

At step 1302, the remote user computing device 770 may receive the indication that the user is authenticated. Responsive to receiving the indication that the user is authenticated, the remote user computing device 770 may initiate a communication session with a second computing system, such as external data computing system 740 in step 1304. The communication session may be initiated after establishing a wireless connection between the remote user computing device 770 and the external data computing system 740.

At step 1306, the remote user computing device 770 may receive extracted data from the external data computing system 740. For instance, user data associated with various locations at which location information (e.g., GPS data, time stamps, and the like) was captured by the remote user computing device and was stored by the external data computing system 740 may be extracted and received by the remote user computing device 770 from the external data computing system 740. The data may include a plurality of location entries corresponding to locations of the remote user computing device 770 in, for example, a predetermined time period. In some examples, the location entries may include longitude and latitude coordinates of locations, time stamps, date stamps, and the like.

In step 1308, the received plurality of location entries may be transmitted to the offer generation computing platform 710 for processing and analysis. In step 1310, based on processing a portion of the location entries (e.g., fewer than all location entries in the plurality of location entries), a first insight generated by the offer generation computing platform 710 may be received by the remote user computing device 770. The first insight may include insight into user driving habits or behaviors, locations frequently visited, and the like. The insight may be transmitted from the offer generation computing platform 710 to the remote user computing device 770 with or part of a user interface. In some examples, the user interface may include an option to process all location entries (e.g., to process a remainder of the location entries not previously processed or analyzed).

At step 1312, the remote user computing device 770 may display the first insight and/or the option to process all location entries. At step 1314, a determination may be made as to whether user input selecting the option to process all location entries was received.

If, at step 1314, the user option to process all location entries was not received (or a request to discontinue processing was received), at step 1316, an instruction to delete user data including all location entries may be generated by the remote user computing device 770 and transmitted to the offer generation computing platform 710.

If, at step 1314, the option to process all location entries is received, the selection may be transmitted to the offer generation computing platform 710 and additional insights and/or offers may be generated based on processing all of the location entries.

At step 1318, at least a second insight and/or an offer may be received by the remote user computing device 770. The at least a second insight and/or an offer may be generated by the offer generation computing platform 710 based on processing all of the location entries and may be transmitted to the remote user computing device 770.

At step 1320, the received at least a second insight and/or offer may be displayed by the remote user computing device 770. In some examples, the offer may include an offer for an insurance premium, discount, or the like, generated based on the analyzed user data.

Figure 14:
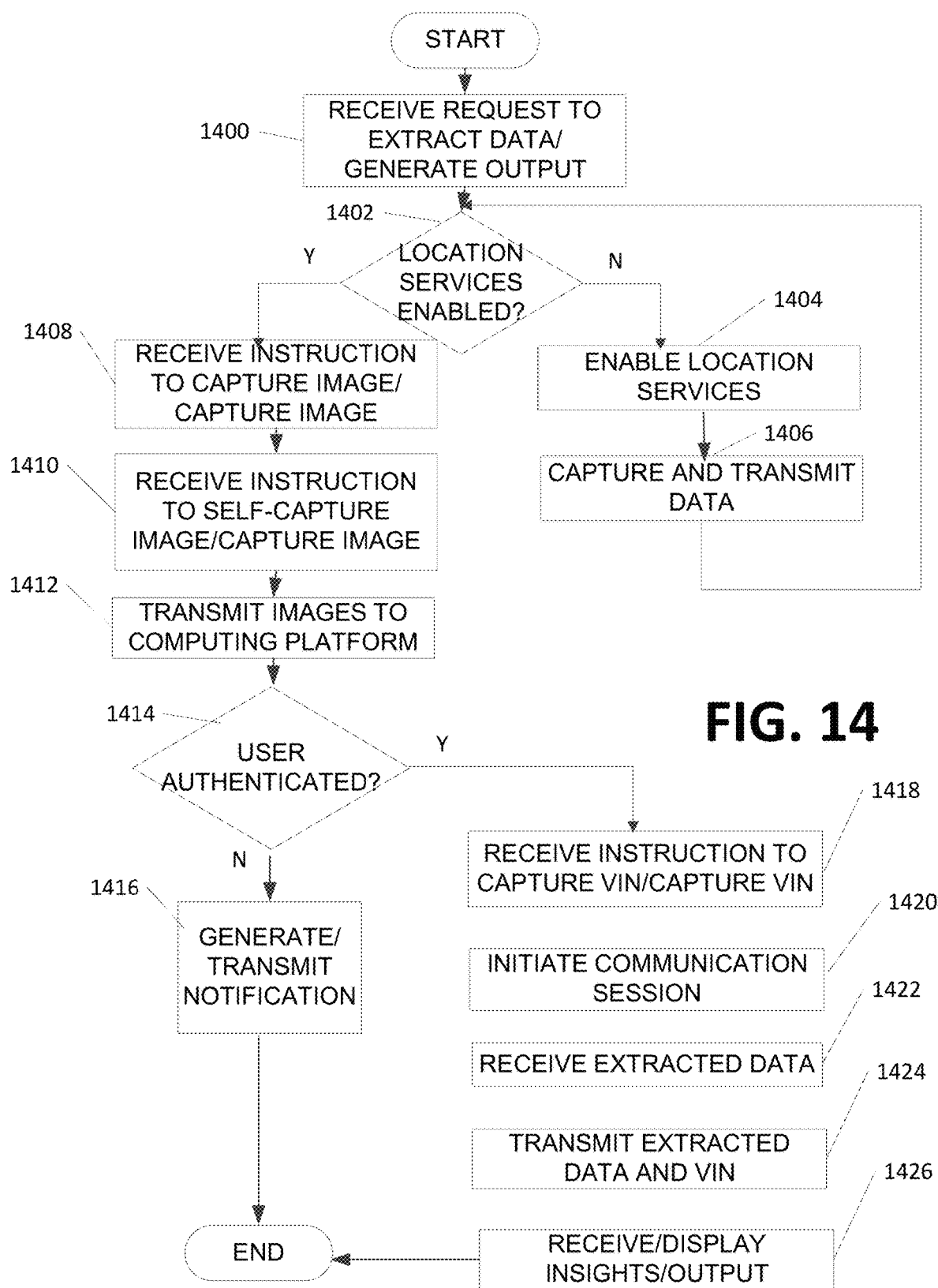
FIG. 14 illustrates one example flow chart illustrating still another example method of offer and/or insight generation function according to one or more aspects described herein.

FIG. 14 illustrates another example process for generating an offer and/or insights based on data captured by a user device and stored by a third party system according to one or more aspects described herein. The steps described with respect to FIG. 14 may be performed by one or more of the various devices and/or systems described herein, such as offer generation computing device 710, determination server 110, determination server 210, remote user computing device 770, mobile device 250, vehicle 260, and the like. In some examples, one or more of the processes or steps described may be performed in real-time or near real-time and the capture, transmission, use, and the like of user data is performed with user permissions.

At step 1400, a request to extract data and/or generate an output may be received. For instance, user input may be received by a user computing device, such as remote user computing device 770, requesting initiation of a process to generate insights and/or an offer or other output based on extracted data. In some examples, extracting data may include extracting location data from a third party source, from a mobile device of the user, or the like.

At step 1402, a determination may be made as to whether location services on the remote user computing device 770 are enabled. For instance, the remote user computing device 770 may determine whether location services of the remote user computing device (e.g., location detection services, GPS, or the like) are enabled on the device. If not, location services may be enabled in step 1404. After enabling the location services, location data may be captured by the remote user computing device 770 (e.g., over a time period) and transmitted to, for example, external data computing device 740 for storage in step 1406. The process may then return to step 1404.

If, at step 1402, location services are enabled, at step 1408, an instruction to capture an image of a photographic identification of a user may be received. The instruction may include an instruction to capture, in some examples, both sides of the photographic identification. Additionally or alternatively, the instruction may include an instruction to capture a side of the photographic identification including an image of the user and an instruction to scan a machine readable code, such as a QR code, bar code, or the like, to capture additional data. In some arrangements, the image(s) may be captured using an image capture device of the remote user computing device 770.

At step 1410, an instruction to self-capture an image of the user may be received. For instance, an instruction for the user to self-capture an image using the image capture device of the remote user computing device 770 may be received. The user may self-capture the image using the image capture device.

At step 1412, the captured images may be transmitted to, for example, offer generation computing platform 710. For instance, the self-captured image of the user and the image(s) of the photographic identification may be transmitted to from the remote user computing device 770 to the offer generation computing platform 710. In some examples, the images may be transmitted together to the offer generation computing platform 710. In other examples, the images may be transmitted separately, at different times, or the like.

At step 1414, a determination may be made as to whether a user is authenticated (e.g., whether an indication that a user is authenticated has been received). For example, the offer generation computing platform 710 may compare the image of the user from the photographic identification and the self-captured image and, using facial recognition or other techniques, may determine whether the images match. This step is performed to ensure that the user is not making fraudulent request for information and/or to ensure privacy of the user's data.

If the images do not match, the user might not be authenticated at step 1414 and, at step 1416, a notification indicating that the images did not match may be generated and transmitted to the remote user computing device 770.

If, at step 1414, the images do match, the user may be authenticated and an instruction to capture a vehicle identification number (VIN) may be received at step 1418. The instruction may include an instruction to capture an image of the VIN, scan a machine readable code including the VIN, or the like. Also at step 1418, the VIN may be captured.

At step 1420, a communication session may be initiated between the remote user computing device 770 and a third party system, such as external data computing system 740. The communication session may be initiated upon establishing a wireless connection between the remote user computing device 770 and the external data computing system 740.

At step 1422, user data may be extracted from the external data computing system 740 and may be received by the remote user computing device 770. At step 1424, the extracted data and VIN may be transmitted from the remote user computing device 770 to the offer generation computing platform 710. The offer generation computing platform 710 may then analyze the data to generate one or more user insights, offers, or other outputs. In some examples, machine learning may be used to generate the insights, outputs or offers, as discussed herein. Generating the insights, offers, and/or outputs may include generating one or more user interfaces for presenting the insights, offers and/or outputs. Example user interfaces are discussed more fully herein.

At step 1426, the generated insights, offers and/outputs may be received by the remote user computing device 770 and displayed on a display of the device 770.

Figure 15:
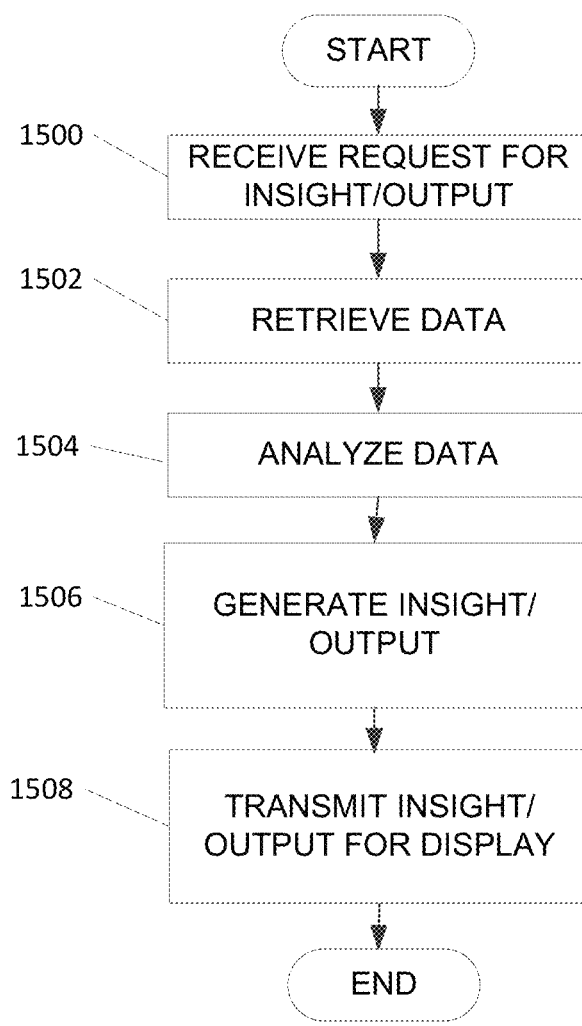
FIG. 15 illustrates one example flow chart illustrating yet another example method of offer and/or insight generation functions according to one or more aspects described herein.

FIG. 15 illustrates another example process for generating an offer and/or insights based on data captured by a user device according to one or more aspects described herein. The steps described with respect to FIG. 15 may be performed by one or more of the various devices and/or systems described herein, such as offer generation computing device 710, determination server 110, determination server 210, remote user computing device 770, mobile device 250, vehicle 260, and the like. In some examples, one or more of the processes or steps described may be performed in real-time or near real-time and the capture, transmission, use, and the like of user data is performed with user permissions.

At step 1500, a request for generation of insights, offers and/or outputs may be received. In some examples, the request may be received from a mobile device of a user, such as remote user computing device 770.

At step 1502, user data may be retrieved. In some examples, retrieving user data may include receiving data stored in a third party system, as discussed herein. Additionally or alternatively, the data may be retrieved directly from one or more user computing devices. For instance, data may be received directly from a mobile device of a user (e.g., remote user computing device 770) and/or a wearable device of a user (e.g., remote user computing device 775). Data may be retrieved from more devices and/or other types of devices without departing from the invention. In some examples, the data may be data that was previously captured by the devices 770, 775 and stored either on the devices 770, 775 or stored by another device (e.g., external data computing system 740). In some examples, the data may be transmitted directly from remote user computing device 770 and/or remote user computing device 775 to the offer generation computing platform 710 (e.g., the data may be either stored on one or more of devices 770, 775 and transmitted to computing platform 710 or transmitted as the data is captured).

At step 1504, the received data may be analyzed by the offer generation computing platform 710. For instance, the data may be analyzed (e.g., using machine learning) to evaluate the data, identify patterns within the data, and the like).

At step 1506, one or more insights, offers and/or outputs may be generated. For instance, based on the analyzed data, one or more insights, offers, and/or outputs may be generated for a user.

At step 1508, the generated one or more insights, offers, and/or outputs may be transmitted to, for example, remote user computing device 770, for display on the device 770.

Figure 16:
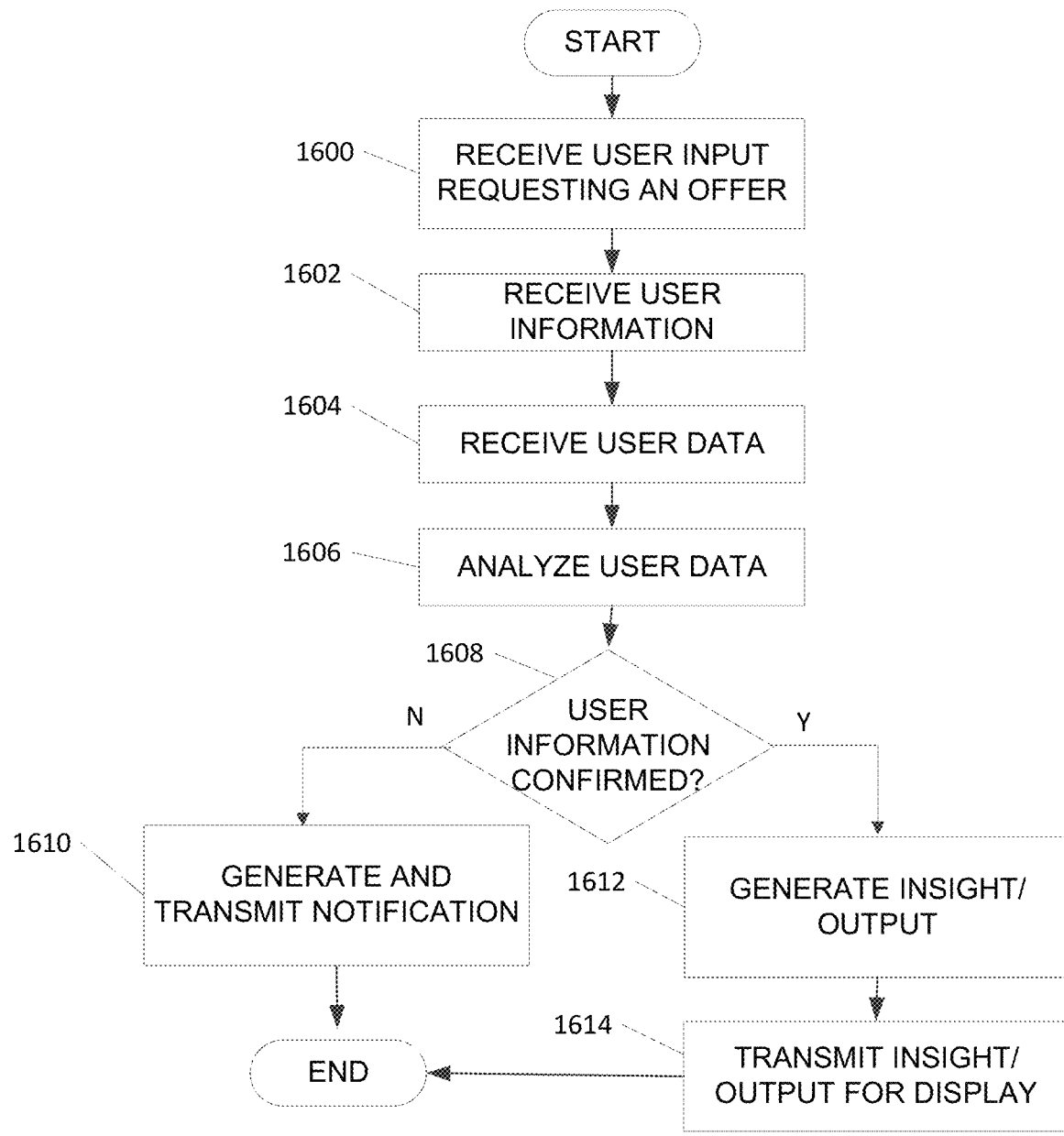
FIG. 16 illustrates one example flow chart illustrating another example method of verifying validity of user information and generating offer and/or insight generation functions according to one or more aspects described herein.

FIG. 16 illustrates another example process for generating an offer and/or insights based on data captured by a user device and stored by a third party system according to one or more aspects described herein. The steps described with respect to FIG. 16 may be performed by one or more of the various devices and/or systems described herein, such as offer generation computing device 710, determination server 110, determination server 210, remote user computing device 770, mobile device 250, vehicle 260, and the like. In some examples, one or more of the processes or steps described may be performed in real-time or near real-time and the capture, transmission, use, and the like of user data is performed with user permissions.

At step 1600, a request to generate an insight, offer and/or output may be received by, for instance, offer generation computing platform 710. At step 1602, user information associated with the request may be received. In some examples, user information may include user identifying information received as discussed herein with respect to other figures and associated processes. Additionally or alternatively, the received user information may include user name, contact information, address information, vehicle information, and the like.

At step 1604, user data may be received. For instance, the user data may be received from a third party system, such as external data computing system 740, (e.g., via the remote user computing device 770 or directly), and/or from remote user computing device 770 accordingly to arrangements described herein.

At step 1606, the user data may be analyzed. For instance, the user data may be compared to user information provided by the user to confirm accuracy of the user information provided by the user. For example, the received user data may include location data (as discussed here) that may indicate a home address or location of a user (e.g., based on time and frequency of location entries including a particular location. For example, if a user is frequently at a particular address or location overnight, that address or location is likely the user's home location). That location may be compared to location or address information provided by a user to confirm accuracy of the user's address (e.g., to identify potentially fraudulent activity).

At step 1608, based on the analyzed data, a determination may be made as to whether the received user information is confirmed. If not, a notification may be generated indicating the discrepancy and transmitted to remote user computing device 770 at step 1610.

If, at step 1608, the user information is confirmed, the received user data may be further processed and/or analyzed (e.g., as discussed more fully herein) to generate one or more insights, offers and/or outputs at step 1612. At step 1614, the generated one or more insights, offers and/or outputs may be transmitted to remote user computing device 770 and displayed by the device.

Figure 17B:
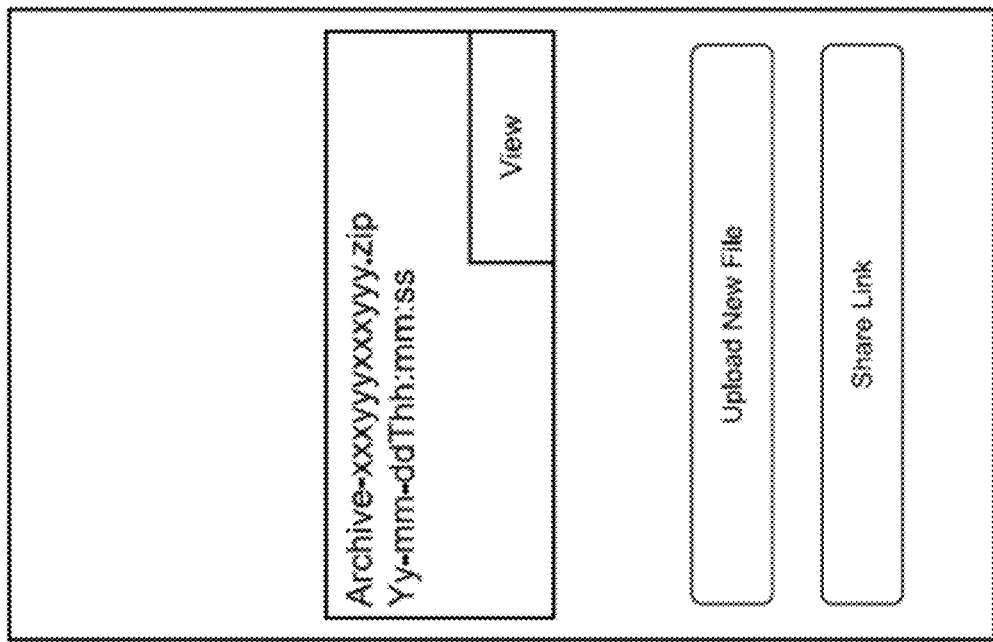
FIGS. 17A-17T illustrate example user interfaces that may be generated and displayed to capture user information, extract user data and/or generate and display insights, offers and/or outputs according to one or more aspects described herein.
Figure 17A:
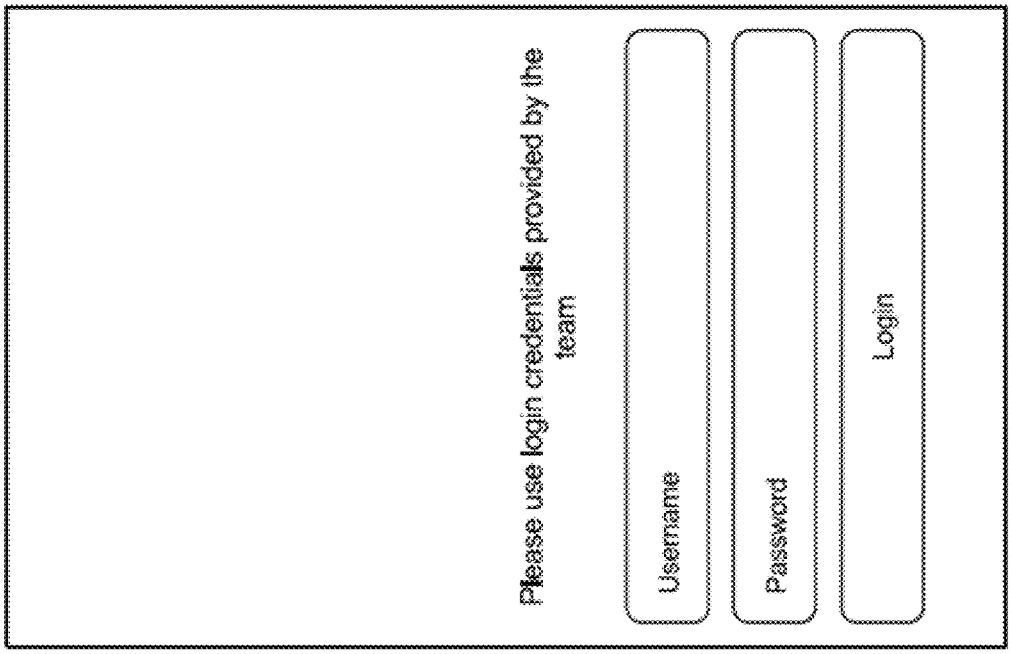
Figure 17D:
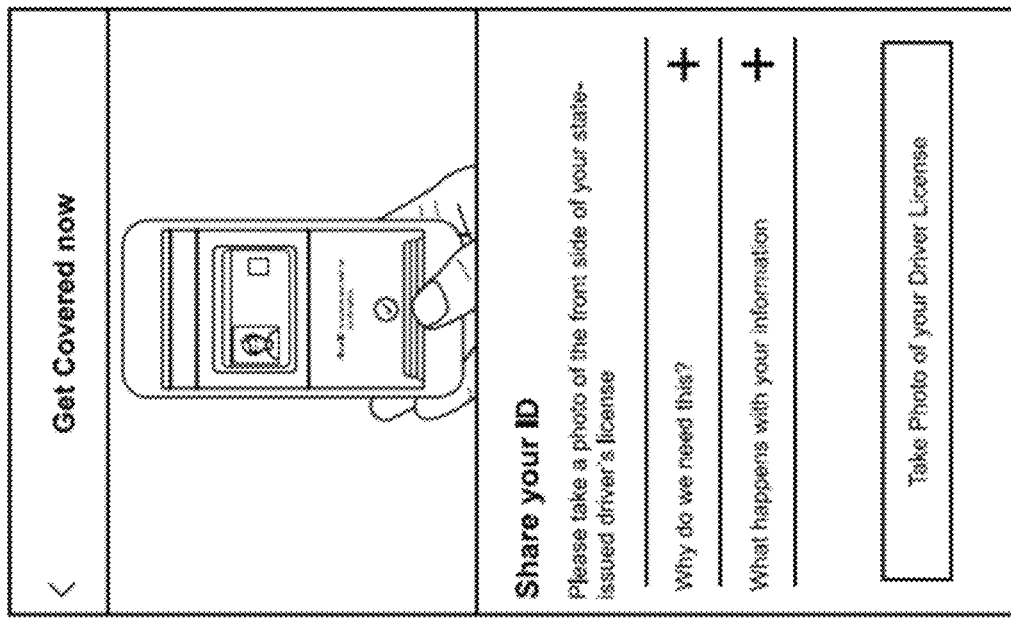
Figure 17C:
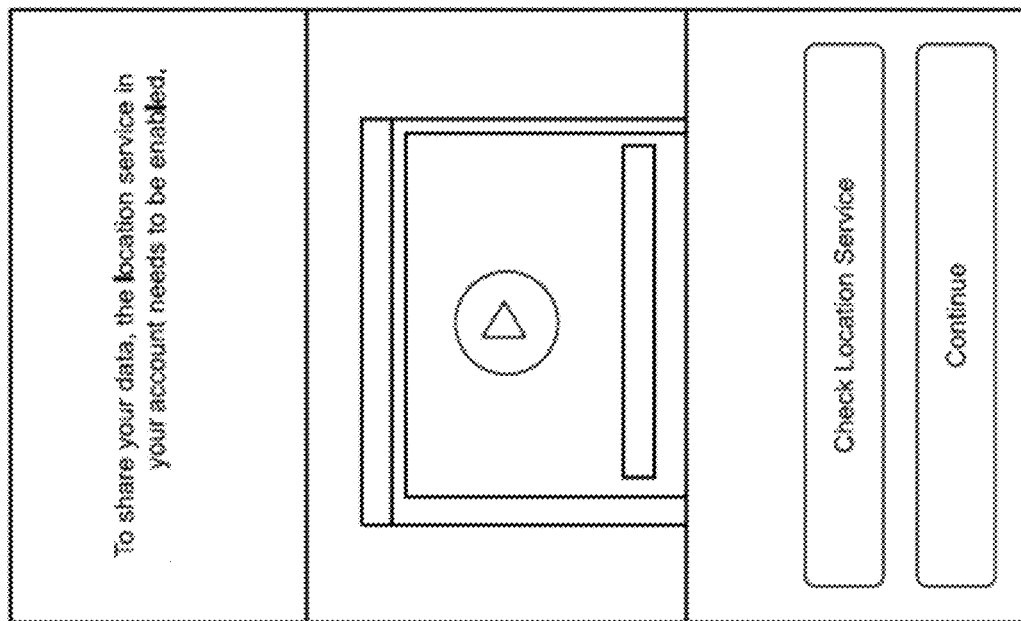
Figure 17H:
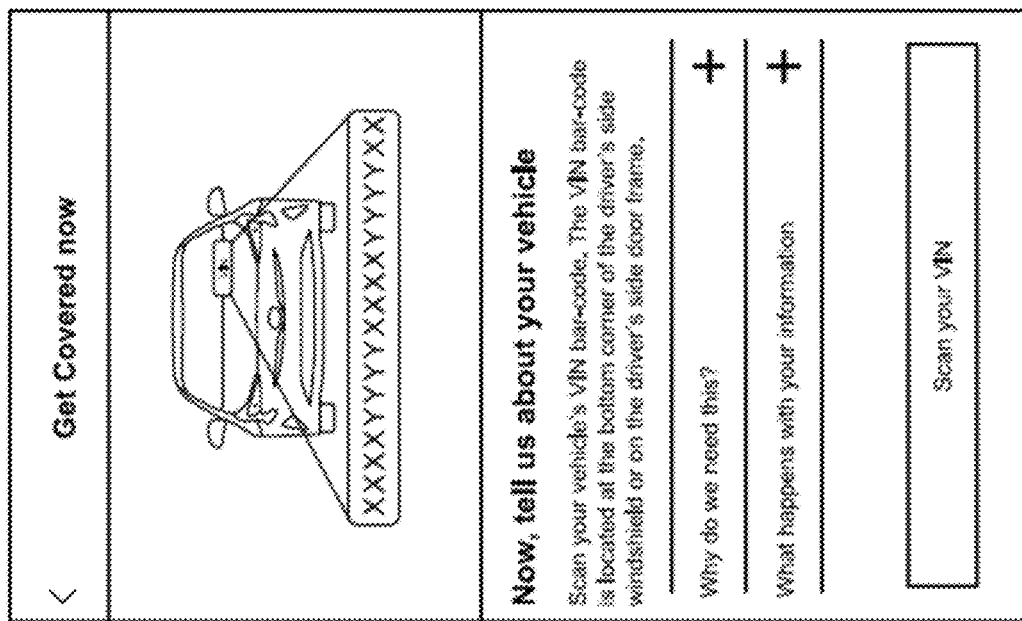
Figure 17G:
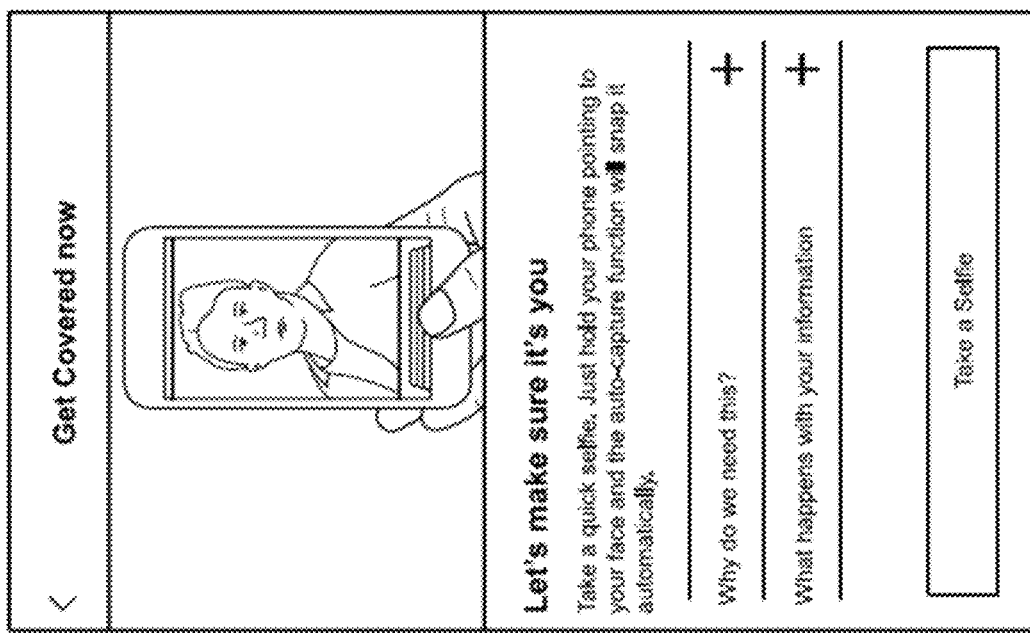
Figure 17J:
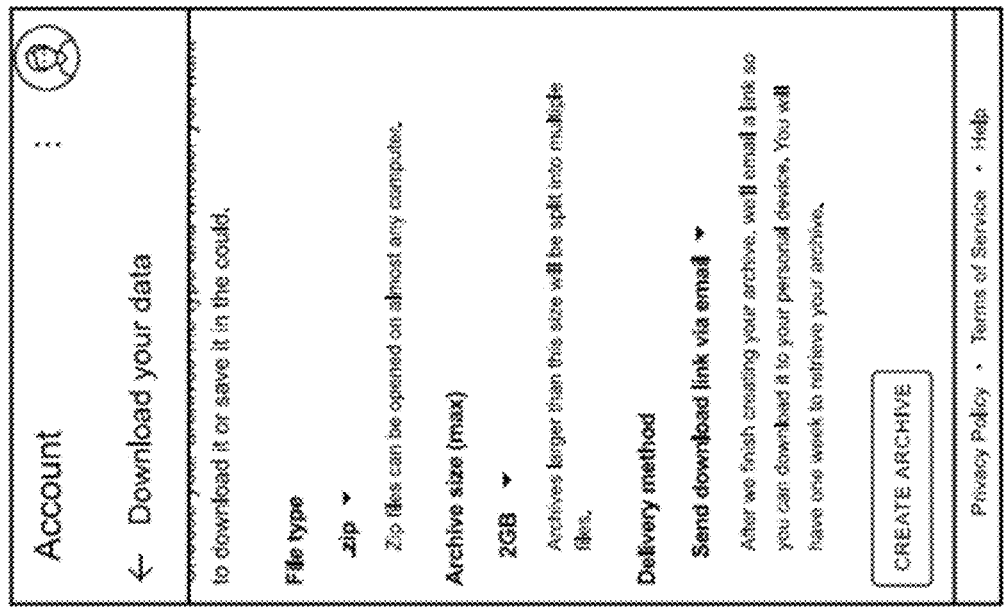
Figure 17I:
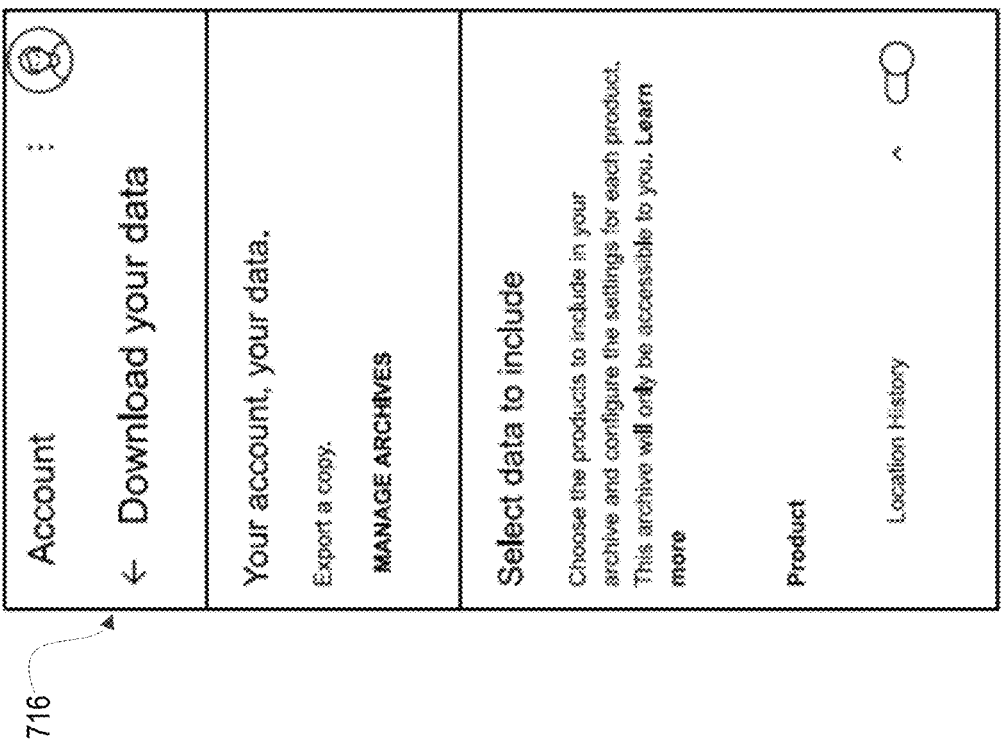
Figure 17L:
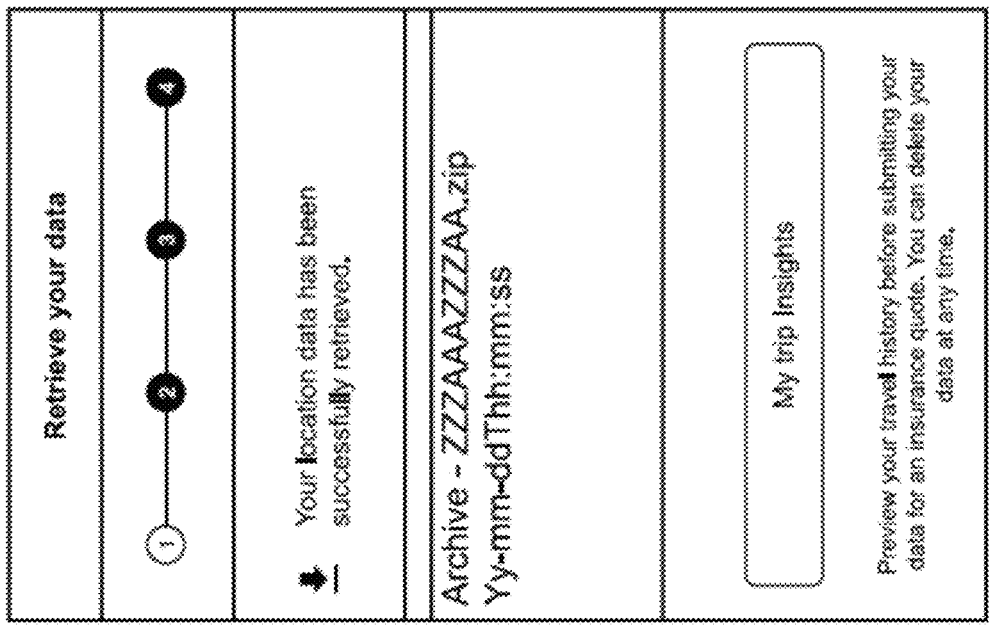
Figure 17K:
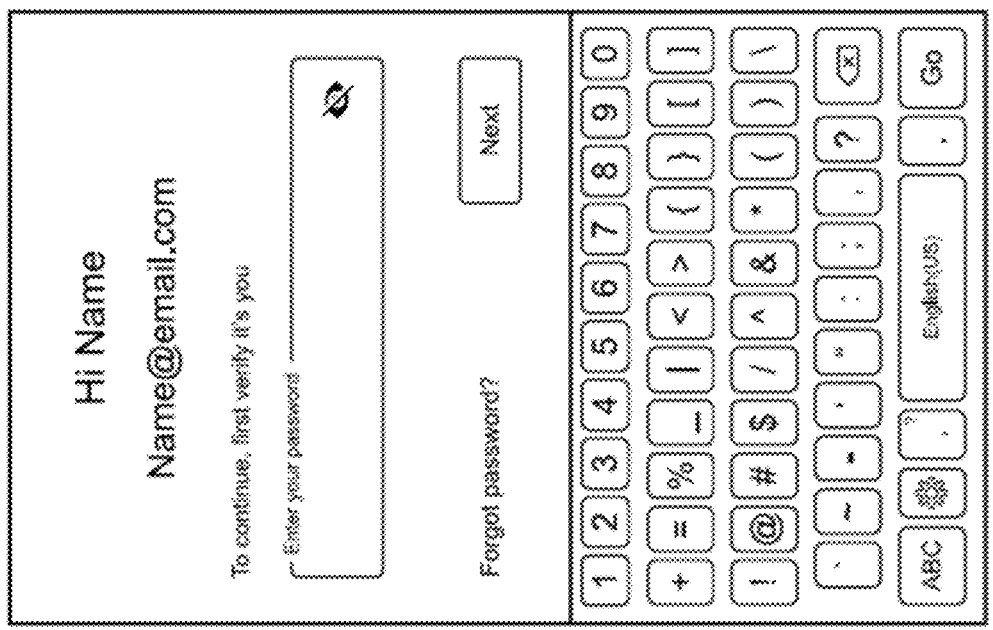
Figure 17N:
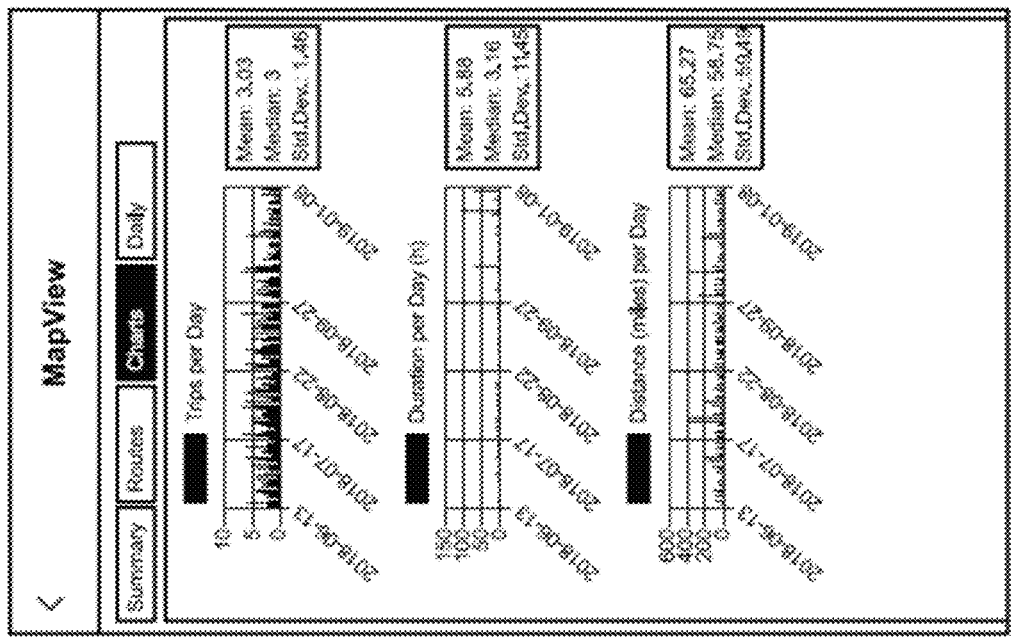
Figure 17M:
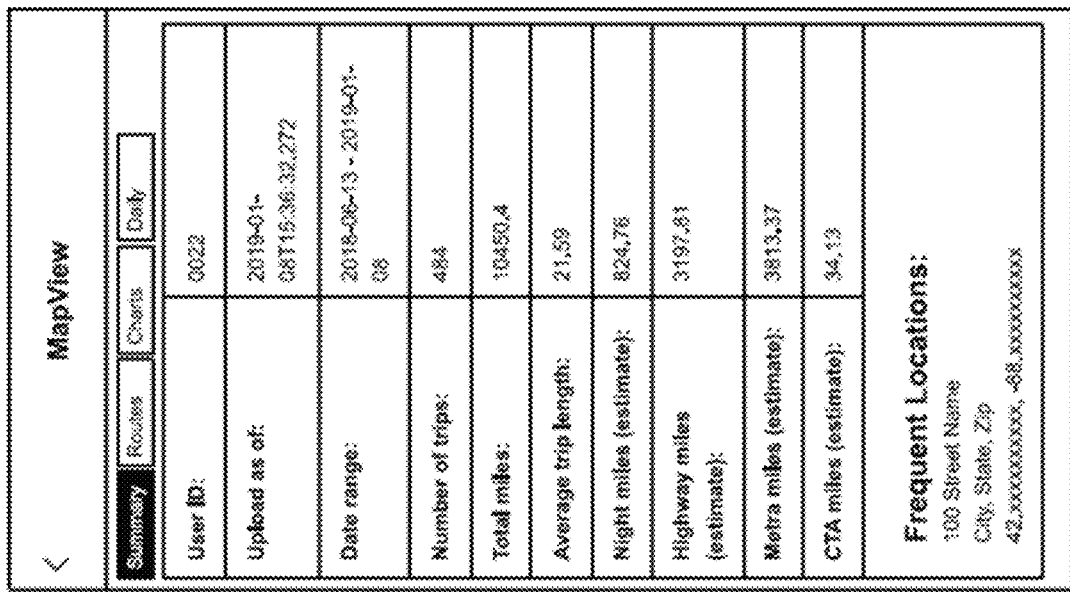
Figure 17P:
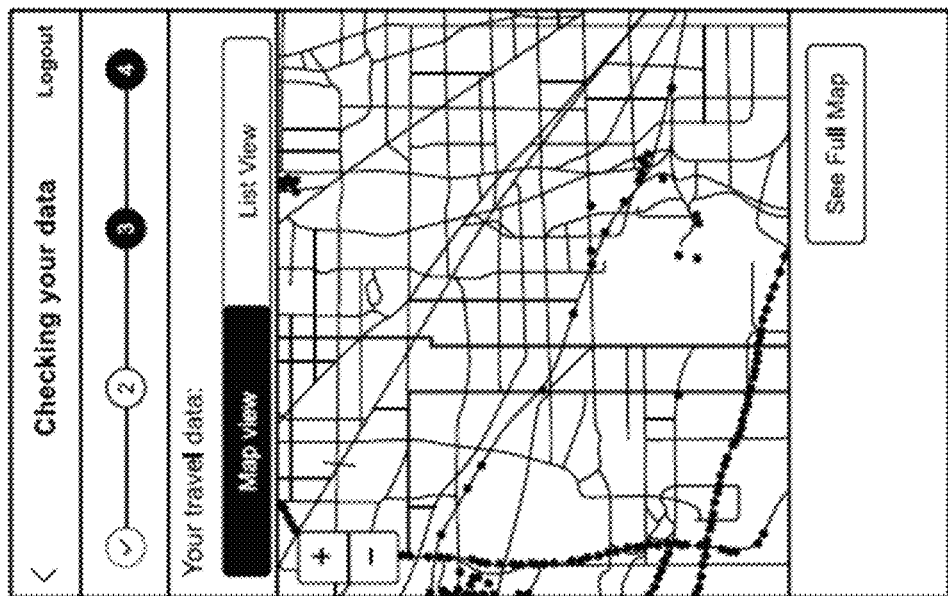
Figure 17O:
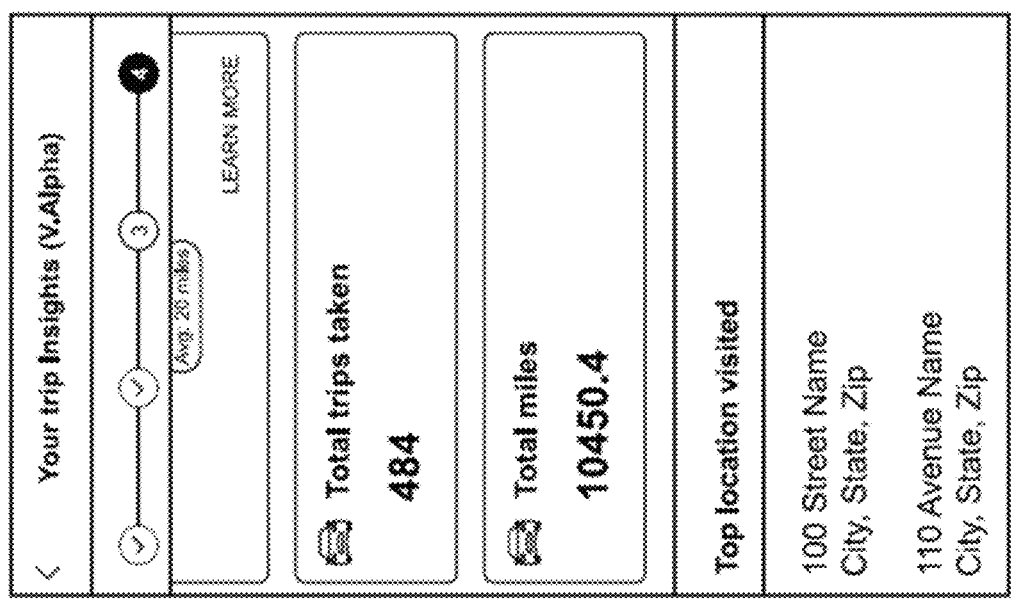
Figure 17R:
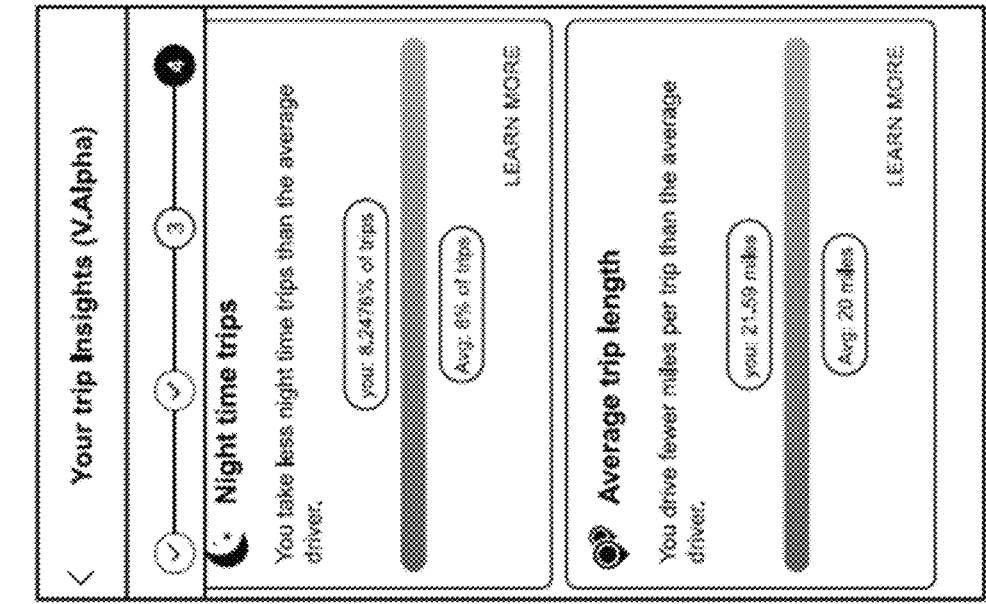
Figure 17Q:
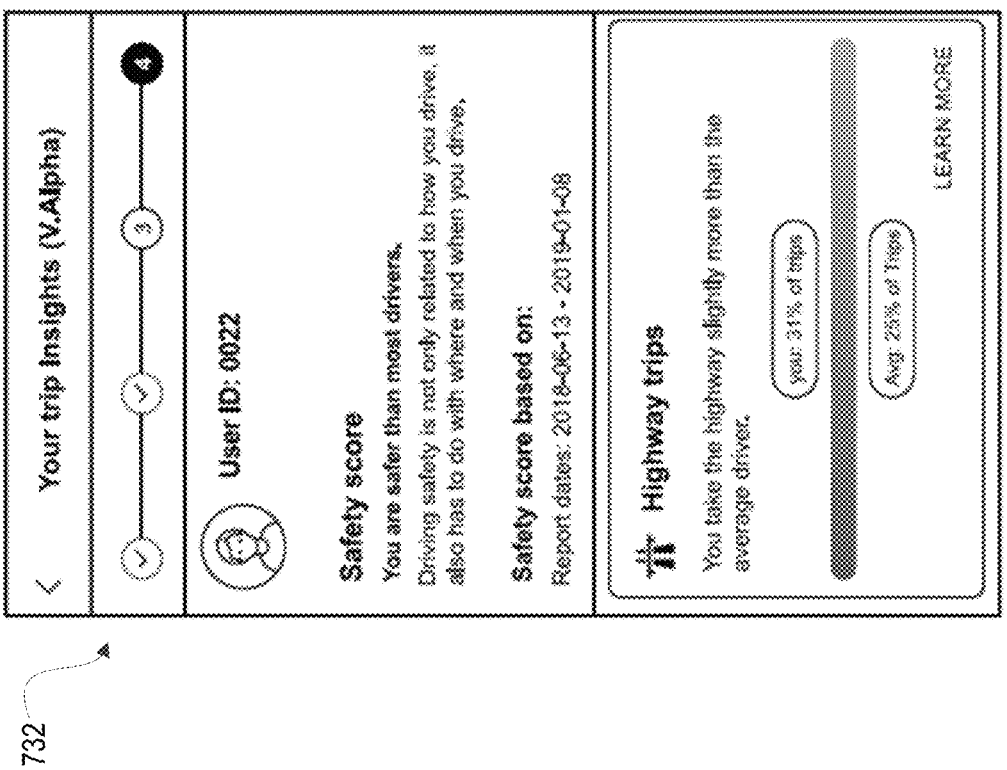
Figure 17T:
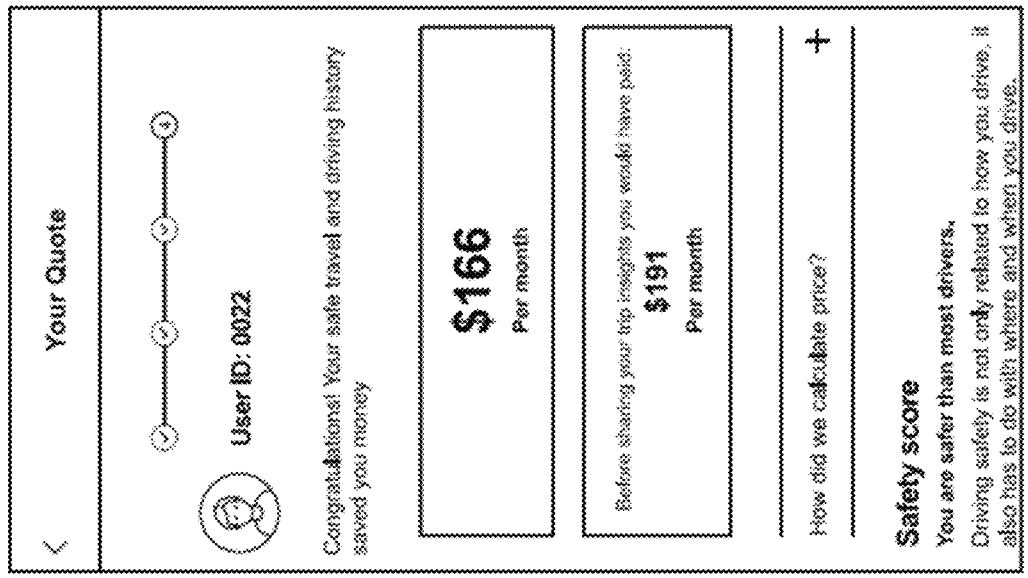

FIGS. 17A-17T illustrate some example user interfaces that may be generated by one or more devices described herein (e.g., offer generation computing platform 710, determination server 110, determination server 210, or the like). The user interfaces shown are merely some example interfaces and additional interfaces and/or interfaces including additional or alternative information may be generated without departing from the invention.

FIG. 17A illustrates one example login interface 1700 that may be generated and displayed to a user (e.g., on a display of a user mobile device such as remote user computing device 770). For instance, upon downloading or otherwise receiving the application, the application may be executed by the remote user computing device 770. Execution of the application may include causing display of the user interface 1700 shown in FIG. 17A. It may include field in which a user may input login credentials. The login credentials may be newly created login credentials generated upon requesting an insight or offer, may be login credentials created for another system (e.g., to access online data associated with the entity from which the insight and/or offer is being requested), may be login credentials for another system that are linked to the arrangements described herein, are login credentials created upon registration, or the like.

After inputting the login credentials, the user may select login option and may be prompted with the interface 1702 shown in FIG. 17B. For instance, the user may be provided with an option to view a previously generated dataset (e.g., a dataset extracted from a third party system, such as external data computing system 740) if a dataset has been previously generated. An option to share a link to the previously generated dataset may also be provided. An option to upload a new file (e.g., extract data from the third party system and generate a new dataset) may also be provided.

With reference to FIG. 17C, upon logging into the application or system, in some examples, a user may be prompted to confirm that location services on the mobile device are enabled. Accordingly, user interface 1704 may be displayed as shown in FIG. 17C that includes an option to confirm that location services are enabled. In some examples, this may include evaluating the device to ensure that location services are enabled, as well as evaluating one or more applications executing on the device, such as an application enabling communication with, data transmission to, and the like, the third party associated with the external data computing system 740 (e.g., that location services are enabled and the user has provided permission for the third party system to access the location or other data).

In examples in which additional types of data are captured, retrieved, or the like, the interface 1704 may include additional options to confirm that other services are enabled (e.g., fitness tracking, or the like).

If a user would like to confirm that location services are enabled, the user may select the available option and the remote user computing device 770 may evaluate a status of the services. If they are not enabled, a user interface displaying options to enable, provide any additional permissions, and the like, may be displayed. If a user does not wish to confirm that location services are enabled, the user may select continue option.

FIG. 17D illustrates one example user interface 1706 including instruction to capture a photographic identification of a user. The user interface may include frequently asked questions (e.g., how does this work, what happens to my information, or the like) that, when selected, may cause additional user interfaces to be displayed. When the user is ready to begin the process, he or she may select an option to capture the photographic identification. Selection of this option may cause the image capture device of remote user computing device 770 to be enabled or activated. For instance, as shown in the image of user interface 1706, a first or front side of the photographic identification including an image of the user identified may be captured (e.g., an image of the side may be captured).

With reference to FIG. 17E, in some examples, a second or rear side of the photographic image, or data thereon, may also be captured. For instance, as shown in user interface 1708, a user may capture an image of a rear or second side of the identification or may scan a machine readable code located on the photographic identification. Similar to interface 1706, frequently asked questions may also be presented in user interface 1708. In some examples, after the images are captured and/or data is scanned, the system may cause the image capture device of the remote user computing device 770 to be disabled or deactivated.

After receiving the image(s) and/or scanned data of the photographic identification, the system may display user data extracted from the images and/or scanned data. For instance, optical character recognition, image processing techniques and/or other methods of data extraction may be used extract data from the image(s) and/or scanned data and the extracted data may be displayed for confirmation of accuracy, as shown in the user interface 1710 of FIG. 17F. The data may include the user's name, address, date of birth, unique photographic identification number, issue date of the photographic identification, expiration date of the photographic identification, or the like. In some examples, if one or more errors or inaccuracies are identified, the user interface may include an option to enter the data manually.

FIG. 17G includes a user interface 1712 providing instructions to self-capture an image of the user. This image data may be compared to previously captured and/or pre-stored image data (e.g., from the photographic identification of the user) to confirm an identity of a user and/or authenticate the user. Upon selection of an option to self-capture an image (e.g., "take a selfie"), the image capture device of the remote user computing device 770 may be enabled or activated. In examples in which multiple image capture devices are available, a front facing camera or image capture device may be enabled in response to selection of the option to self-capture the image.

After capturing the image, the image capture device may be disabled or deactivated and the images may be evaluated as discussed herein to confirm an identity/authenticate a user.

FIG. 17H includes a user interface 1714 including instructions to capture information about a vehicle (e.g., a vehicle associated with an offer being generated), such as a vehicle identification number. The instructions may include a location of the vehicle identification number on the vehicle. In some examples, an image of the vehicle identification number may be captured and/or a machine readable code may be scanned to capture the vehicle identification number. Upon selection of the option to capture the vehicle identification number, an image capture device of the remote user computing device 770 may be enabled or activated and the user may capture the requested data.

FIG. 17I includes a user interface 1716 that displays available that that may be extracted and transmitted for analysis in order to generate insights, offers, and the like. For instance, after capturing the desired user and vehicle data, the system may establish a communication session with a third party system, such as external data computing system 740. Various types of data may be stored by the external data computing system 740 (e.g., with user permissions, such as location data, application usage data, activity data, and the like). In some examples user interface 1716 may be configured to display only particular types of data that are available for extraction, are going to be used in the analysis, or the like (e.g., "location data" in user interface 1716). For instance, a third party system may include options for a user to download, extract, transmit, or the like, a plurality of different types of data or data captured via various devices, sensors, or the like. However, the user interface 1716 may be configured to only display types of data or categories of data that may be used in the analysis to generate insights, offers, and the like. Accordingly, the user might not be permitted to download data that will not be used to generate these outputs via this application, user interface, system or the like. Rather, a user may have to access another system, application or the like, to access the additional data. This may aid in ensuring privacy of a user's data by only extracting and/or transmitting data that will be used in the analysis.

FIG. 17J includes user interface 1718 that may include one or more options to configure the data being extracted. For instance, a user may select a format for the data, a delivery method, and the like. In some examples, default options may be provided. Selection of "create archive" option may initiate the process to extract user data from the third party system.

For instance, initiating the process may include prompting a user to input login credentials associated with access to the third party system or application. For instance, a user may have registered with the third party system (e.g., established an email address, document sharing account, or the like, provided permission for the system to access data, and the like). Accordingly, upon initiation of the process to extract data from the third party system, the user may be prompted to input authenticating credentials associated with the third party system (that may, in some examples, be different from the credentials to login described in FIG. 17A). Accordingly, user interface 1720 shown in FIG. 17K includes fields to input user login credentials. The user interface shown in FIG. 17K may be generated by the offer generation computing platform 710 or by the third party entity.

Upon successful login, a new dataset or archive may be created by downloading or extracting the selected data. FIG. 17L includes user interface 1722 that illustrates successful retrieval of the user's data from the third party system. In at least some examples, to generate the requested one or more insights, offers, and/or outputs, the downloaded or extracted data may be transmitted to, for instance, offer generation computing platform 710 or other device configured to perform the functions described herein. Accordingly, the user may select an option to generate or obtain insights, offers, outputs or the like, from interface 1722. Selection of the option may cause the remote user computing device 770 to transmit the downloaded or extracted data (e.g., the dataset obtained from the third party system, such as external data computing system 740) to, for example offer generation computing platform 710. Causing transmission may, in some examples, including initiating a communication session between the devices by establishing a wireless connection.

FIGS. 17M and 17N include user interfaces 1724 and 1726, respectively, which illustrate some example insight data that may be generated based on the user data. For instance, data associated with total number of miles driven, frequently visited locations, trips per day, duration of trips, and the like, may be provided.

FIG. 17O provides additional insight data in interface 1728. FIG. 17P includes an interface 1730 illustrating insight data in a map view (e.g., highlighting particular routes, marking particular locations, and the like). Similar or the same data may also be displayed in a list view.

FIGS. 17Q and 17R include interfaces 1732 and 1734, respectively, that provide additional examples of user interfaces that may be displayed by, for example, remote user computing device 770. For instance, a safety score indicating a level of safe driving may be displayed as shown in interface 1732. Further, insights such as average trip length, night time trips, or the like may be displayed, as shown in interface 1734.

Figure 17S:
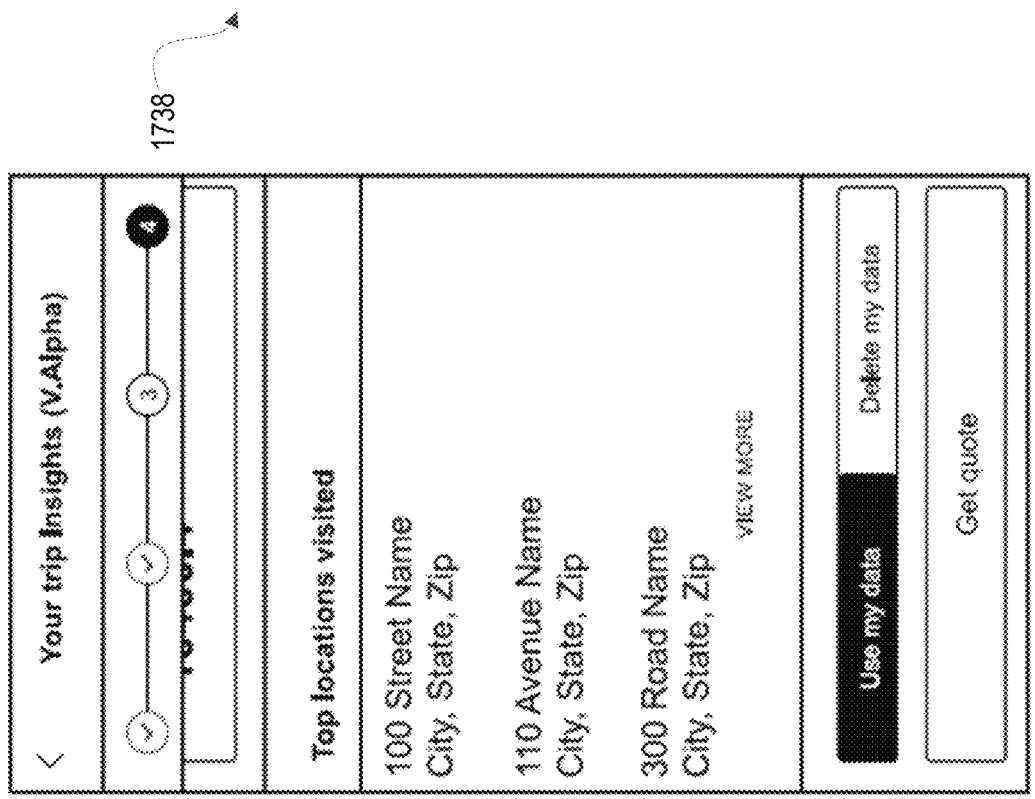

FIG. 17S illustrates one example user interface 1736 that can be used when processing a portion of user data as discussed herein. For instance, in arrangements in which a portion of data is processed and an insight is provided along with an option to process all data, an interface such as interface 1736 may be used to provide the initial insights, an option to the user to process the remaining data, delete the user data, generate an offer, and the like. Accordingly, the initial insights generated may include, for example, as shown in interface 1736, top locations visited. The interface 1736 then includes additional options to process the remaining data (e.g., "use my data"), delete user data (e.g., "delete my data"), and generate an offer (e.g., "get quote"). Selection of the option to process all data may cause the system to process the data, generate additional insights, and the like. Selection of delete user data option may cause the system to not process any additional data and to delete any data transmitted thereto for processing. Selection of generate an offer option may cause the system to process data and generate an offer (e.g., in lieu or of in addition to additional generating further insights).

FIG. 17T illustrates one example user interface 1738 that includes a generated offer. For instance, a user may request an offer for an insurance quote, such as car insurance. Accordingly, the system may generate one or more insurance rates, premiums, or the like, based on the received data and may display the generated premium, rate, or other offer in a user interface such as interface 1738. Accordingly, the use of previously captured user data may enable the system to generate an accurate premium, rate, or other offer that is customized to the user's behaviors, patterns, and the like, at a time of initial quote (e.g., before the user has accepted an offer of insurance or become a customer). After becoming a customer, a user may continue to capture data and provide it to the entity for analysis and further refining of the premium, rate, or the like (e.g., based on driving data, location data, and/or other data provided with permission of the user). However, the arrangements described herein provide for accuracy in initial offer generation based on previously captured data, rather than making an initial determination based on conventional factors and subsequently capturing the data to provide a customized rate or premium.

In some examples, the interface 1738 may also include an indication of a discount given for sharing user data. For instance, as shown in FIG. 17T, an offer generated without using the analyzed user data may also be displayed, thus illustrating the savings to the user by sharing previously captured user data.

The various arrangements described herein can be used together or in combination with other arrangements. For instance, aspects described with respect to one figure may be used in combination with aspects described with respect to another figure, without departing from the invention.

As discussed herein, aspects described are directed to a system, apparatus, method, computer-readable instructions, or the like, directed to facilitating extraction of user data from a third party system and analyzing the data to generate one or more offers, outputs and/or insights. Aspects described herein permit an entity to generate an accurate offer for a user prior to the user becoming a customer of the entity by evaluating risk associated with the user based on the user data retrieved from the third party. For instance, similar to a way a credit score is pre-calculated based on user data prior to a user becoming a customer of a particular entity (e.g., when applying for a loan, credit card, or the like), the arrangements described herein provide a unique system for extracting user data, including, for example, location data associated with locations significant to the user (e.g., frequently visited destinations such as work, school, etc.) and evaluating the data to determine risk associated with a user to generate, for example, an insurance quote. The insurance quote (e.g., car insurance, life insurance, homeowner's insurance, renters insurance, or the like) generated maybe more accurate than an insurance quote generated based on conventional factors because it is based on data particular to a user. Further, it enables the entity to provide the most accurate quote prior to the user becoming a customer, rather than after the user has become a customer and the entity has directly collected user data.

In some examples, the location data captured by the mobile device of the user and stored by the third party entity may be based on GPS data associated with the mobile device. In other examples, the location data may be based on cellular network triangulation. In some arrangements, if a user has location services disabled on his or her device, the device may periodically ping one or more cellular towers to perform a triangulation function to identify a location, comply with emergency procedures requirements, or the like. This and other data may be passively collected or gathered by the mobile device (e.g., by applications executing in a background on the mobile device of the user) after the user has provided suitable permissions.

In some examples, the amount of data available for a particular user may be based on privacy settings set by the user (e.g., on the mobile device of the user). Additionally or alternatively, the amount of data available may be based on how intensely a user engages with the mobile device. For instance, if a user frequently leaves his or her device at home or work while travelling to other locations, less data may be available for the user. Alternatively, if the user always carries his or her phone, there may be more data available for evaluation.

The data collected may be stored, in some examples, by third party systems. For instance, the data may be stored on one or more devices or in a cloud-based storage arrangement associated with the third party. In some examples, the user may be able to access (e.g., view, extract, download, or the like) the data via the third party system. The user may then use this data (e.g., user data collected via the mobile device) as he or she desires. Accordingly, the user may provide access to the data to one or more other entities for use, as discussed more fully herein.

Accordingly, an entity may receive the user data from the third party entity (e.g., via the user) and may evaluate the data to determine a risk associated with the user. For instance, the user may download the user data from the third party system to his or her mobile device and then upload the extracted data to a first entity system, such as offer generation computing platform 710. The extracted data may include raw data and/or aggregated data. The system may evaluate how often a user travels, a number of miles, whether travel is performed during daylight or at night, whether a user is in a car, on public transportation, walking, on a bicycle, and the like. In some examples, the data may be sorted or categorized into tiers to aid in evaluating the data and risk associated with the user.

In some examples, the data may be aggregated with other user data, such as social media data, data collected by a wearable device such as a fitness tracker, wellness or activity data captured by the mobile device, internet browsing history data, and the like.

In some examples, the data evaluated may be used to determine risk associated with a user for providing an insurance quote, such as an auto insurance quote, life insurance quote, or the like. In some examples, other types of data may also be used, such as video data (e.g., from an unmanned aerial vehicle) of a property in order to provide a quote for homeowners insurance. In some examples, other data such as image data of a user's driver's license, or the like, may also be used in evaluating the user.

Aspects described herein may also be used to detect fraudulent or other unauthorized activity. For instance, as discussed herein, data may be categorized into tiers. A first tier may include an aggregate number of miles driven, number of trips, and the like. A second tier may include data associated with information reported by the user and may be used to verify the information. For instance, if a user is claiming that a vehicle is garaged at a certain location, the extracted location data may be used to confirm this and/or identify potential instances of fraud. In some examples, a third tier of data may include types of routes and/or road segments travelled by the user. For instance, an amount of traffic, daytime driving vs. nighttime driving, and the like, may be captured in the third tier. In some examples, a fourth tier may include driving behavior data, safe driving indications, and the like, such as instances of hard braking, swerving, obeying posted speed limits, and the like.

In another example, as discussed more fully above, the data received and analyzed may be used to confirm a home address of a user. For instance, a user may provide user information, including an address, during a registration process, offer or insight request process, or the like. The system may evaluate the extracted data to identify a location at which the mobile device of the user (e.g., the device with which the location data was captured) is located overnight (e.g., based on time stamps) on a regular basis (e.g., greater than a threshold number of days in a week, month, or the like). The location identified by the system may be compared to the address/location information provided by the user to confirm that the user provided an accurate address and/or that the request is not fraudulent.

This information can be used to not only detect fraud but also to confirm that the user is providing correct information. For instance, a user may register a vehicle in one location but, based on the extracted data, a second location may be more appropriate for registering the vehicle. Accordingly, a notice may be generated and transmitted to the user recommending registration of the vehicle at the second location.

In another example, a user may have moved but not updated his or her driver's license address. Accordingly, the system may compare a home location identified based on analysis of the received data to address data extracted from the user's photographic identification. If a discrepancy exists, a notification may be generated and transmitted to the user.

In another example, the extracted data may be used to evaluate whether a user provided expected number of miles driven is accurate.

In another example, the data may be used to evaluate whether a user is complying with one or more requirements. For instance, if a teenager is not permitted to drive after a certain time of day, the system may evaluate driving and/or location data of the teenager to determine whether he or she is complying with the requirement.

The analyzed data may further provide insights into user behaviors that may indicate a risk level associate with the user. For instance, the data may indicate patterns including how often a user device (and associated user) is located at a home location. If a user is frequently at the home location based on the extracted data, this may indicate a reduced risk level associated with the user because, for instance, a risk of break-in at a home is reduced when people are present.

The extracted data may also aid in predicting user behaviors, such as when a user travels, how often a user is at a home location or work location, and the like. This information may impact risk associated with a user, as well as premium and/or rate pricing.

The arrangements described herein provide for vast amounts of data to be processed and used to generate offers, insights, and the like, for customers in order to improve accuracy. Although several aspects discussed herein are directed to evaluating user data prior to the user becoming a customer of the entity, similar arrangements may be performed with respect to existing customers to obtain additional data and improve accuracy.

In some examples, a rating or score associated with one user may impact a rating or score associated with another user. For instance, ratings or scores associated with different members of a household may impact scores or ratings for other members of the household. Further, additional data captured from other household members may increase accuracy of data analysis and/or predictions made based on the data.

As discussed herein, data may be downloaded in one or more formats, such as HTML, KML, JSON, or the like. In some examples, the data may be formatted or converted to a different format prior to processing. In some examples, data in a first format may be used as a first pass filter to identify data for further evaluation. The data may then be processed in another format, converted, downloaded in another format, or the like.

Example arrangements implementing aspects discussed herein are provided below. The examples may be implementing using any of the devices described herein. Further, the examples provided below are merely some example arrangements are not intended to limit the scope of the invention. Additional example arrangements may be implemented without departing from the invention.

In some examples, a user may request an offer, such as an offer or quote for insurance, such as car insurance, life insurance, homeowner's insurance, and the like. In conventional arrangements, obtaining a quote can take time and may require a user to interact with an agent or other person. Accordingly, it would be advantageous to provide a system for providing an insurance quote that limits interaction with an agent and is able to generate a quote very quickly (e.g., in less than a minute, less than 2 minutes, or the like).

Further, in many conventional systems, a quote is provided based on conventional factors. For instance, with respect to auto insurance, a quote may be provided based on a driving history, age, location, and the like, of the user. However, generating a quote based on these factors does not allow for evaluation of the user or user's behaviors, or other unique characteristics of the user. In some examples, an initial insurance quote may be provided based on conventional factors and, after accepting a policy based on the quote, the user may permit the insurance provider to capture or otherwise receive data from the user (e.g., driving data, activity data, and the like) that may be used to further refine a premium or rate provided to the user (e.g., generate a discount, adjust a premium, or the like).

However, arrangements described herein provide for a user to provide pre-generated data to the insurance provider in order to generate a more customized initial quote in a fast, efficient manner by extracting user data stored by a third party and providing it to the insurance provider during the quoting process.

For example, user mobile device data may be captured as a user performs regular activities. The mobile device data may include location data (e.g., based on GPS data). The location data may, as it is collected or at predetermined intervals, be transmitted to a third party where the data may be stored.

Accordingly, a user may input a request for an insurance quote from an insurance provider into the mobile device. In some examples, the request may be input into an application provided by the insurance provider and executing on the mobile device. The application may prompt the user to capture data from a photographic identification, such as a driver's license. In some examples, the user may capture an image of a front of the driver's license and scan a machine readable code on a back of the driver's license. That data may be transmitted to the insurance provider where data may be extracted from the image and/or scanned machine readable code.

In some examples, the application may then prompt the user to capture a selfie. Accordingly, parallel processing of data may occur. For example, as the insurance provider system (e.g., offer generation computing platform 710) is processing the driver's license data (e.g., extracting data, and the like), the mobile device (e.g., remote user computing device 770) is processing data associated with additional instructions, displaying additional user interfaces, enabling devices such as a camera, and the like. This parallel and/or background processing may speed up the process and reduce the time needed to generate the quote.

The selfie image may be captured and transmitted to the insurance provider for comparison to an image from the driver's license. This information may be used to confirm that the user for which the quote is being prepared (e.g., the user on the driver's license) is the user making the request (e.g., the user in the selfie). Accordingly, fraudulent requests may be avoided and user privacy may be maintained.

In some examples, a voice sample or recording of the user may be captured and used to verify an identity of a user, as well. The voice sample or recording may be captured via the mobile device and compared to pre-stored data by the insurance provider system to authenticate the user.

After confirming that the selfie image matches the image in the driver's license, a prompt to capture a vehicle identification number of a vehicle associated with the insurance quote may be provided. The user may scan the vehicle identification number from the vehicle and transmit the data to the insurance provider for additional processing.

As the vehicle identification number is being processed by the insurance provider system (e.g., offer generation computing platform 710), additional processing may occur at the mobile device (e.g., remote user computing device 770). For instance, the mobile device may establish a communication session with a third party system. In some examples, this may include the insurance provider application directing the mobile device to execute an application of the third party. The user may login to the third party system, identify data for extraction and/or download (e.g., identify, for example, location data) and may download the data to generate a new dataset or archive. Accordingly, the data extraction process may be performed while background processing of, for example, vehicle identification number data, is occurring. Again, this may increase efficiency and reduce time to obtain the quote.

The mobile device may transmit the generated dataset or archive to the insurance provider system for analysis. As discussed herein, the data may be analyzed (e.g., using machine learning, by sorting data into tiers, by aggregating data with other insurance provider data, and the like) and one or more insights and/or offers may be generated. For instance, one or more insights directed to user patterns or behaviors may be generated. In addition, a quote for, for example, auto insurance may be provided as an offer to the user. The insights and/or offer may be transmitted to the mobile device and displayed to the user. In some examples, generating the offer may include generating a second offer based on, for example, only traditional or conventional factors (e.g., without the user data) and displaying the offer to the user may include displaying the second offer as well (e.g., simultaneously) to indicate potential savings to the user.

If the user accepts the quote and obtains the associated policy, the user may select to continue to provide data to the insurance provider system (e.g., from one or more devices, such as a mobile device, wearable device, vehicle or the like). The data may be provided directly from the device (e.g., without extracting the data from the third party system) or via the arrangements described above with respect to extracting data from the third party system. That additional data may be used to further refine a risk determined for the user, a premium or rate for the user, and the like.

Accordingly, as discussed herein, the arrangements described provide for quick, efficient generation of insights and/or offers, such as insurance rate quotes. The arrangements include parallel or simultaneous processing of data at a local location and a remote location to increase the speed in which insights and/or offers are generated. Accordingly, a user may experience an efficient and fast quote generation process while receiving insights and quotes that are customized or tailored to the user and the user's behaviors.

As discussed above, although various aspects discussed herein are directed to use of the arrangements described in generating outputs related to automobile insurance, aspects described herein may also be used to generate one or more outputs related to, for example, life insurance, homeowner's insurance, as well as non-insurance related insights, such as purchase recommendations, lifestyle recommendations, driving recommendations, and the like.

For example, conventional processes for obtaining life insurance may take days or even weeks and may be a multi-step process. One part of the process may include underwriting which is a process of assessing a user's mortality risk and putting them into a class upon which a rate or premium may be generated. Traditional underwriting is performed with a complex application process, a medical examination by a medical professional, fluid draws and analysis, and the like.

However, with the vast amounts of user data available today, and with the capabilities of today's mobile devices to capture different types of data using one or more sensors on the mobile device, as discussed herein, the underwriting process can be substantially streamlined and, in some cases, an examination by a medical professional might not be required. Instead, consumers may provide direct access to their data from their mobile devices, such as step count data, heart rate data, location data, financial transaction data, data from electronic health records, and the like. This information may be used to predict a consumer's underwriting class based on predictors of health conditions impacting mortality, risk, and the like. Various aspects of these arrangements are discussed more fully herein.

In some examples, in order to provide customized insurance offers or quotes to a user, detailed information about the user's health (e.g., biometric data, medical history, medication, or the like) may be required or desirable to generate an accurate quote (e.g. based on permissions provided by the user). Providing this information manually may be time consuming, inaccurate and inefficient. Accordingly, upon receiving the request for an insurance offer or quote, a software application may be executed on a computing device, such as a mobile computing device of the user. The application may obtain health data associated with the user from various sources (e.g., the mobile device and associated sensors, external sources, and the like), to provide an output to display to the user. The output may include an offer or quote and/or general information about the user, user's health, or the like. Such arrangements enable relevant and accurate data to be obtained without user input or interaction. Accordingly, the amount of user input needed to obtain the customized insurance offer or quote and/or provide information about the user's health may be significantly reduced FIGS. 18A-18K illustrate one example event sequence for performing offer generation control functions in accordance with one or more aspects described herein. The sequence illustrated in FIGS. 18A-18K is merely one example sequence and various other events may be included, or events shown may be omitted, without departing from the invention.

With reference to FIG. 18A, at step 1801, data may be captured by a remote user computing device 770. For instance, data such as location data (e.g., GPS data including latitude and longitude, time stamp, date stamp, and the like) captured via a mobile device of a user (e.g., remote user computing device 770) may be captured. The location data may be captured throughout a user's regular routine (e.g., driving, walking, at work, at home, and the like) Additionally or alternatively, other types of data may be captured via the remote user computing device 770. For instance, social media data, wellness data, activity data, step count data, physical trait data (e.g., blood pressure, heart rate, or the like), application usage data, and the like, may be captured. In some examples, remote user computing device 770 may be a mobile device of a user, such as a smartphone, tablet, or the like. In some examples, remote user computing device 770 may store some or all of the captured data.

As discussed herein, data may be captured via sensors within or associated with the remote user computing device 770. For instance, GPS sensors, accelerometers, gyroscopes, pedometers, oxygen sensors, pulse sensors, and the like, may be used to captured data. Additionally or alternatively, various other types of sensors may be used to capture data without departing from the invention.

At step 1802, a connection may be established between the remote user computing device 770 and the external data computing system 740. For instance, a first wireless connection may be established between the remote user computing device 770 and the external data computing system 740. Upon establishing the first wireless connection, a communication session may be initiated between the external data computing system 740 and the remote user computing device 770.

At step 1803, the captured data may be transmitted from the remote user computing device 770 to the external data computing system 740. For instance, the captured data may be transmitted during the communication session initiated upon establishing the first wireless connection. In some examples, the captured data may be transmitted in real-time as the data is captured. In other examples, the captured data may be transmitted on a periodic or aperiodic basis, according to a predetermined schedule, or the like. In some examples, captured data from a period of time (e.g., one week, one month, six months, 1 year, or the like) may be captured prior to additional functions described herein being performed.

At step 1804, the external data computing system 740 may receive the captured data and, at step 1805, the external data computing system 740 may store the captured data. As discussed herein, the external data computing system 740 may be a third party system (e.g., associated with a party different from the user associated with the remote user computing device 770 and the entity associated with the offer generation computing platform 710). In some examples, the external data computing system 740 may receive and store the captured data with the necessary permissions received from the user and the third party may use the captured and stored data for additional third party uses unrelated to the processes described herein. This stored data may then later be accessed by the user (e.g., the user associated with the device from which the data was captured) for personal use, transmission to other entities, or the like.

Figure 18B:
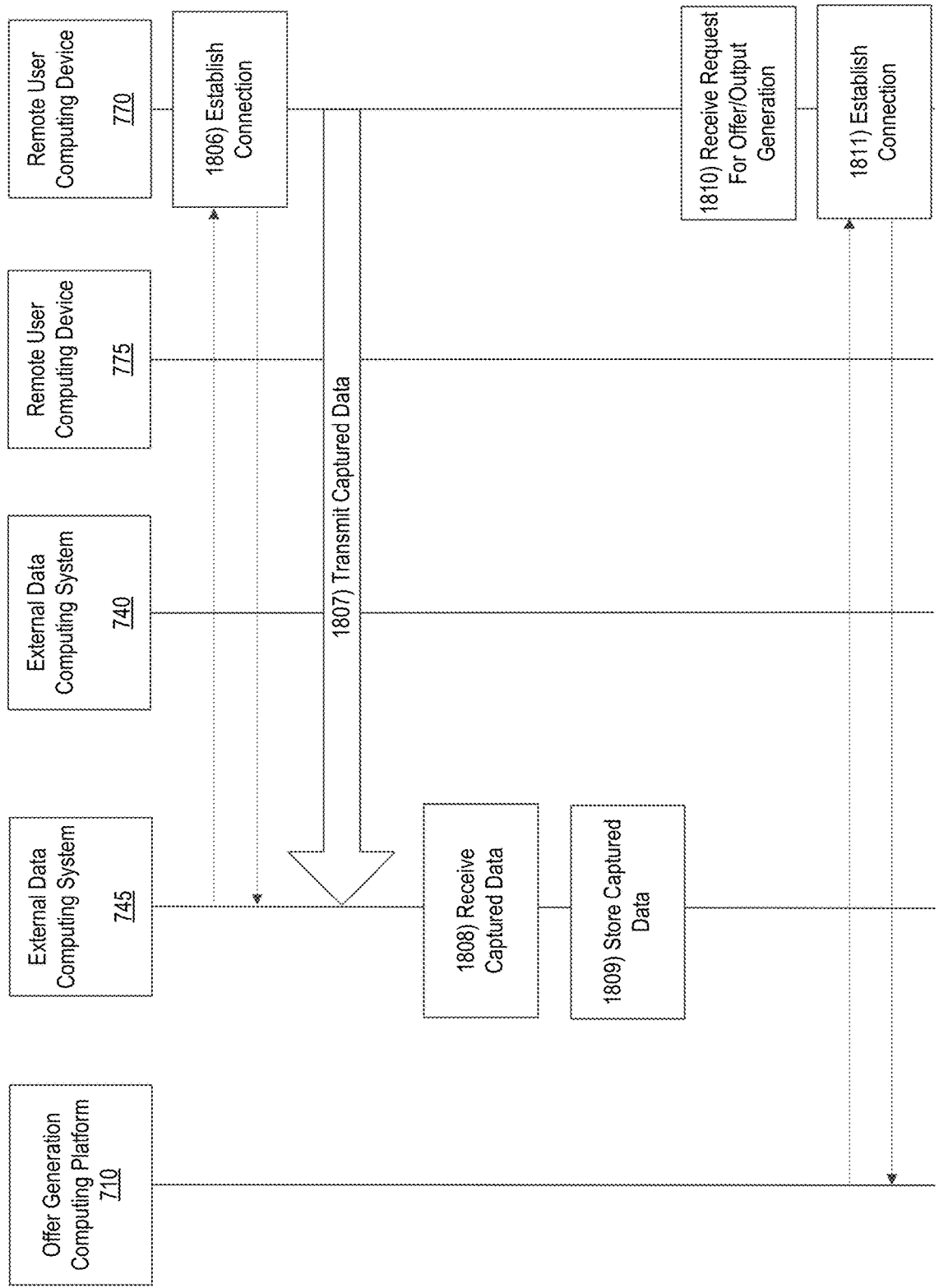

With reference to FIG. 18B, some or all of the captured data may be transmitted to a second, different external data computing device, such as external data computing system 745. Accordingly, at step 1806, a connection may be established between the remote user computing device 770 and the external data computing system 745. For instance, a second wireless connection may be established between the remote user computing device 770 and the external data computing system 745. Upon establishing the second wireless connection, a communication session may be initiated between the external data computing system 745 and the remote user computing device 770.

At step 1807, the captured data may be transmitted from the remote user computing device 770 to the external data computing system 745. For instance, the captured data may be transmitted during the communication session initiated upon establishing the second wireless connection. In some examples, the captured data may be transmitted in real-time as the data is captured. In other examples, the captured data may be transmitted on a periodic or aperiodic basis, according to a predetermined schedule, or the like. In some examples, captured data from a period of time (e.g., one week, one month, six months, 1 year, or the like) may be captured prior to additional functions described herein being performed.

At step 1808, the external data computing system 745 may receive the captured data and, at step 1809, the external data computing system 745 may store the captured data. As discussed herein, the external data computing system 745 may be a third party system (e.g., associated with a party different from the user associated with the remote user computing device 770 and the entity associated with the offer generation computing platform 710). In some examples, the external data computing system 745 may receive and store the captured data with the necessary permissions received from the user and the third party may use the captured and stored data for additional third party uses unrelated to the processes described herein. This stored data may then later be accessed by the user (e.g., the user associated with the device from which the data was captured) for personal use, transmission to other entities, or the like.

In some arrangements, all data may be transmitted to a single external data computing system, rather than to multiple systems. However, multiple external data computing systems or devices may be accessed to obtain user data, as will be discussed more fully herein.

Additionally or alternatively, although the arrangements discussed above with respect to steps 1801-1809 are directed to capturing data from a mobile device of a user, various other types of data may be captured and transmitted to the external data computing systems for storage and/or data may be provided by the user (e.g., rather than captured via one or more sensors) and may be transmitted for storage.

At step 1810, a request for offer/output generation may be received. For instance, a user may input a request into remote user computing device 770. In some examples (e.g., if the user is already a customer of the entity implementing the offer generation computing platform 710), the request may be input into an application executing on the remote user computing device 770 and provided by the offer generation computing platform 710. In some examples, the request for offer/output may be received after the data is captured and pre-stored, as discussed with respect to steps 1801-1809.

At step 1811, a connection may be established between the remote user computing device 770 and the offer generation computing platform 710. For instance, a third wireless connection may be established between the remote user computing device 770 and the offer generation computing platform 710. Upon establishing the third wireless connection, a communication session may be initiated between the offer generation computing platform 710 and the remote user computing device 770.

Figure 18C:
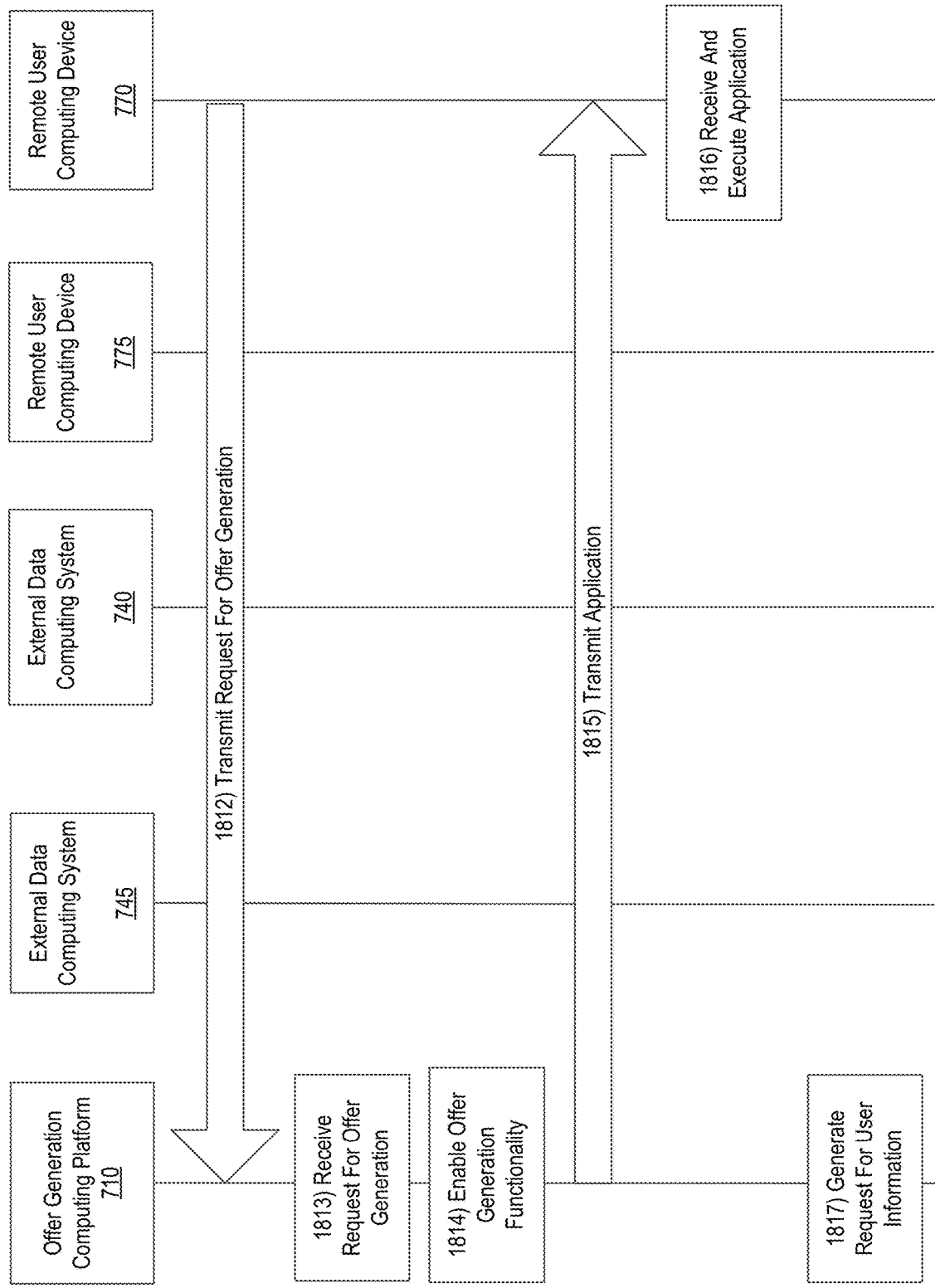

With reference to FIG. 18C, at step 1812, the request for offer generation may be transmitted from the remote user computing device 770 to the offer generation computing platform 710. For instance, the request for offer generation may be transmitted during the communication session initiated upon establishing the third wireless connection.

At step 1813, the request for offer/output generation may be received by the offer generation computing platform 710. At step 1814, offer generation functionality may be enabled by the offer generation computing platform 710. For instance, functionality that was previously disabled may be enabled, activated or initiated in response to receiving the request for offer/output generation. In some examples, enabling offer generation functionality may include identifying an application for transmission to a user device (e.g., remote user computing device 770).

At step 1815, an application may be transmitted from the offer generation computing platform 710 to the remote user computing device 770. The application may be an application to facilitate communication between one or more systems, identify data for extraction, and the like. Although the arrangement of FIG. 18C includes the application being transmitted after the request for offer is received, in some examples, the application may be transmitted to the remote user computing device 770 prior to the request for offer generation being received by either the remote user computing device 770 or the offer generation computing platform 710.

At step 1816, the transmitted application may be received by the remote user computing device 770 and executed by the remote user computing device 770. In some examples, executing the application may include enabling functionality associated with the remote user computing device 770 (e.g., data capture functions, data transmission functions, activating one or more sensors, and the like).

At step 1817, a request for user information may be generated by the offer generation computing platform 710. In some examples, the request for user information may include a request for an image of a user. In some examples, the request for user information may include a user interface including instructions for capturing one or more images of the user, one or more angles for image capture, and the like. In some arrangements, the application executing on remote user computing device 770 may control an image capture device of the remote user computing device 770 in order to capture the desired images. In some examples, the request for user information may further include request for user physical characteristics, such as height, weight, body mass index (which may, alternatively, be calculated by the remote user computing device 770 and/or the offer generation computing platform 710), and the like. In some examples, additional demographic information may be requested, such as age, race, ethnicity, tobacco use, and the like. This data may be used to generate an underwriting output without, in at least some examples, requiring additional underwriting including a medical or other physical examination.

With reference to FIG. 18D, at step 1818, the generated request for user information may be transmitted from the offer generation computing platform 710 to the remote user computing device 770. For instance, the request may be transmitted during the communication session initiated upon establishing the third wireless connection.

At step 1819, the request for user information may be received and displayed by the remote user computing device 770 (e.g., on a display of the device 770).

At step 1820, user information response data may be received and/or captured by the remote user computing device 770. For instance, a user may capture one or more images of himself or herself (e.g., via the image capture device of remote user computing device 770). Additionally or alternatively, the user may input (e.g., via one or more user interfaces generated and transmitted with the request) the requested physical characteristic data, demographic data, and the like. The captured images, physical characteristic data, demographic data, and the like, may constitute user information response data and, at step 1821, may be transmitted from the remote user computing device 770 to the offer generation computing platform 710. In some examples, the user information response data may be transmitted during the communication session establishing upon initiating the third wireless connection.

Figure 18E:
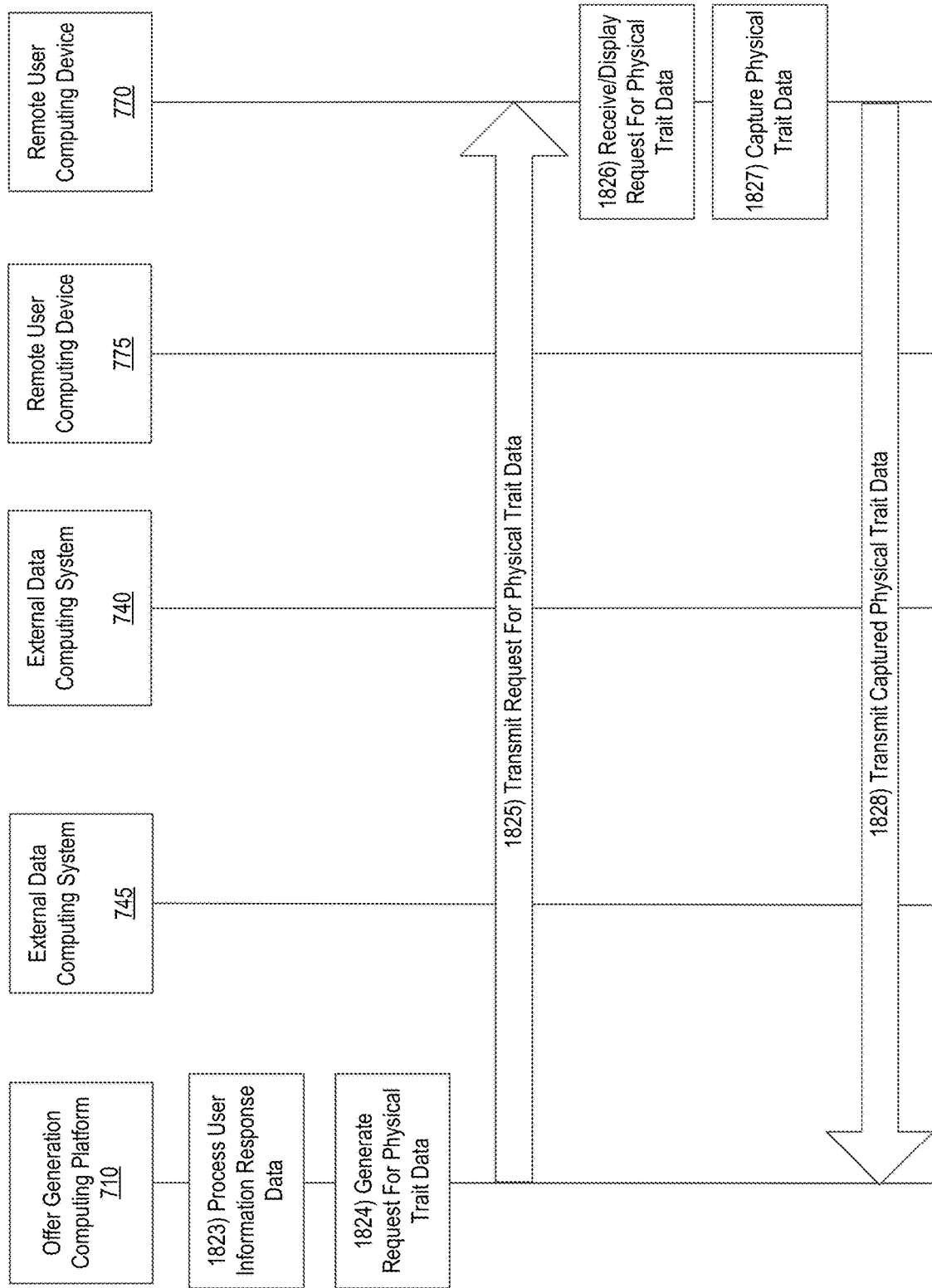

At step 1822, the user information response data may be received by the offer generation computing platform 710 and, with reference to FIG. 18E, at step 1823, the user information response data may be processed by the offer generation computing platform 710. For instance, the user information response data may be stored in an event record generated for the user by the offer generation computing platform 710.

At step 1824, a request for physical trait data may be generated. In some examples, the request for physical trait data may include a request for the user to capture data such as a current and/or resting heart rate, blood pressure, oxygen consumption, fitness level, or the like, captured via one or more sensors on or associated with the remote user computing device 770. In some examples, the request for physical trait data may include a request for a user to execute or perform a function using or with the remote user computing device 770. For instance, the request for physical trait data may include a request for the user to walk on a treadmill for a predefined time period or distance (e.g., 10 minutes, 1 mile, or the like) with the remote user computing device 770 and then provide a heart rate, oxygen level, or the like.

At step 1825, the generated request for the physical trait data may be transmitted from the offer generation computing platform 710 to the remote user computing device 770. In some examples, the generated request may be transmitted during the communication session initiated upon establishing the third wireless connection.

At step 1826, the request for physical trait data may be received by the remote user computing device 770 and displayed by the remote user computing device 770 (e.g., on a display of device 770).

At step 1827, physical trait data may be captured using one or more sensors of the remote user computing device 770. For instance, one or more sensors may be used to capture movement data, heart rate data, pulse data, blood pressure data, oxygen data, and the like. Additional data, such as time, distance, location, and the like, may be captured along with the physical trait data and used to validate the data, confirm instructions were executed, and the like.

At step 1828, captured physical trait data may be transmitted from the remote user computing device 770 to the offer generation computing platform 710. In some examples, the captured physical trait data may be transmitted during the communication session initiated upon establishing the third wireless connection.

Figure 18F:
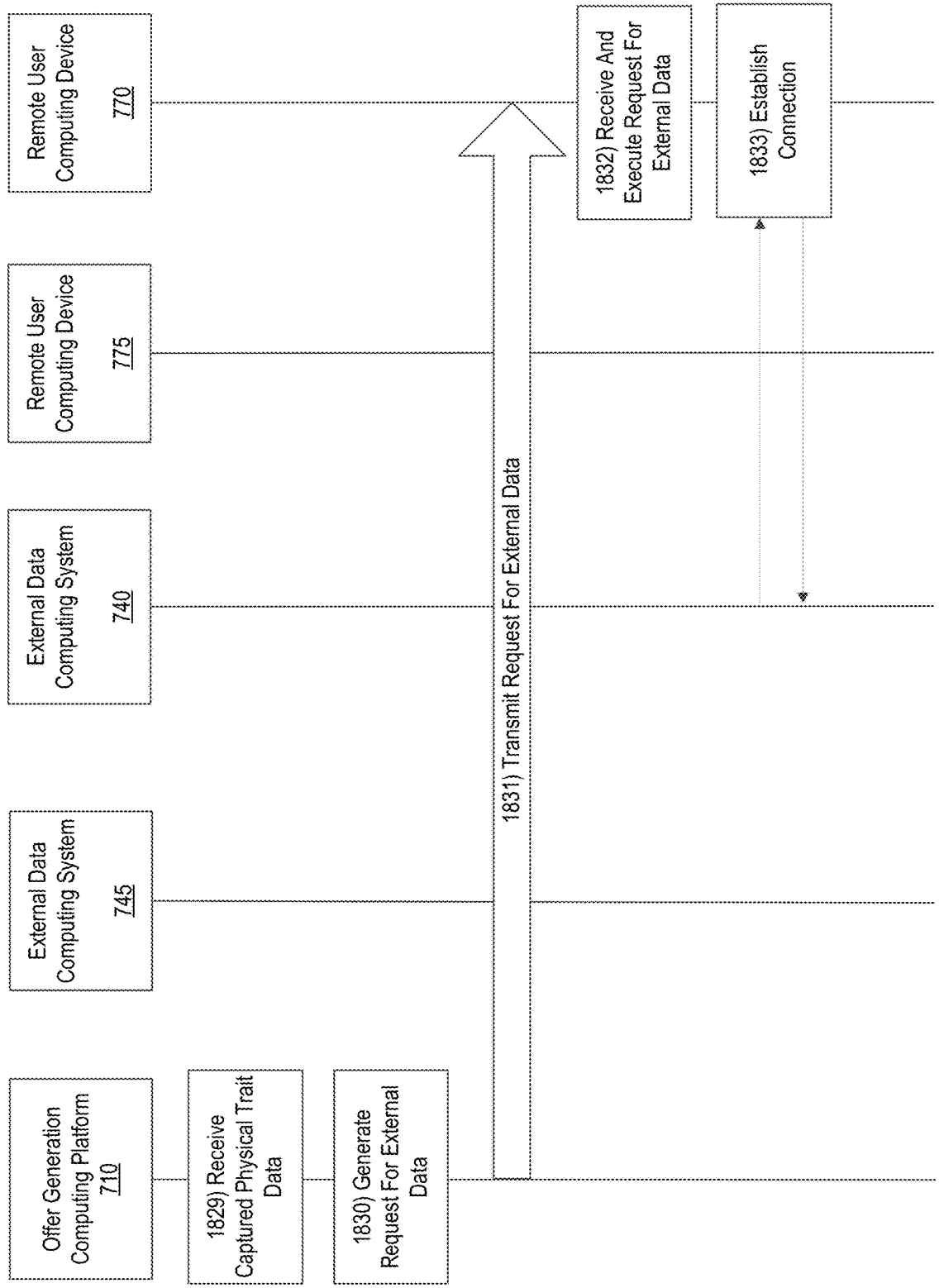

With reference to FIG. 18F, at step 1829, the captured physical trait data may be received by the offer generation computing platform 710. At step 1830, a request for external data may be generated. For instance, a request for previously stored activity, location, fitness, or the like, data may be generated. Additionally or alternatively, a request for user health or medical data or medical history data, prescription or prescription history data, and the like, may be generated.

At step 1831, the request for external data may be transmitted from the offer generation computing platform 710 to the remote user computing device 770. In some examples, the request for external data may include instructions or commands to initiate a communication session with one or more external computing devices or system to extract the data. In some examples, the communication sessions may be facilitated via the application executing on the remote user computing device 770 and provided by the offer generation computing platform 710.

At step 1832, the request for external data may be received any executed by the remote user computing device 770. At step 1833, a connection may be established between the remote user computing device 770 and external data computing system 740. For instance, a fourth wireless connection may be established between the remote user computing device 770 and the external data computing system 740. Upon establishing the fourth wireless connection, a communication session may be initiated between the external data computing system 740 and the remote user computing device 770.

Figure 18G:
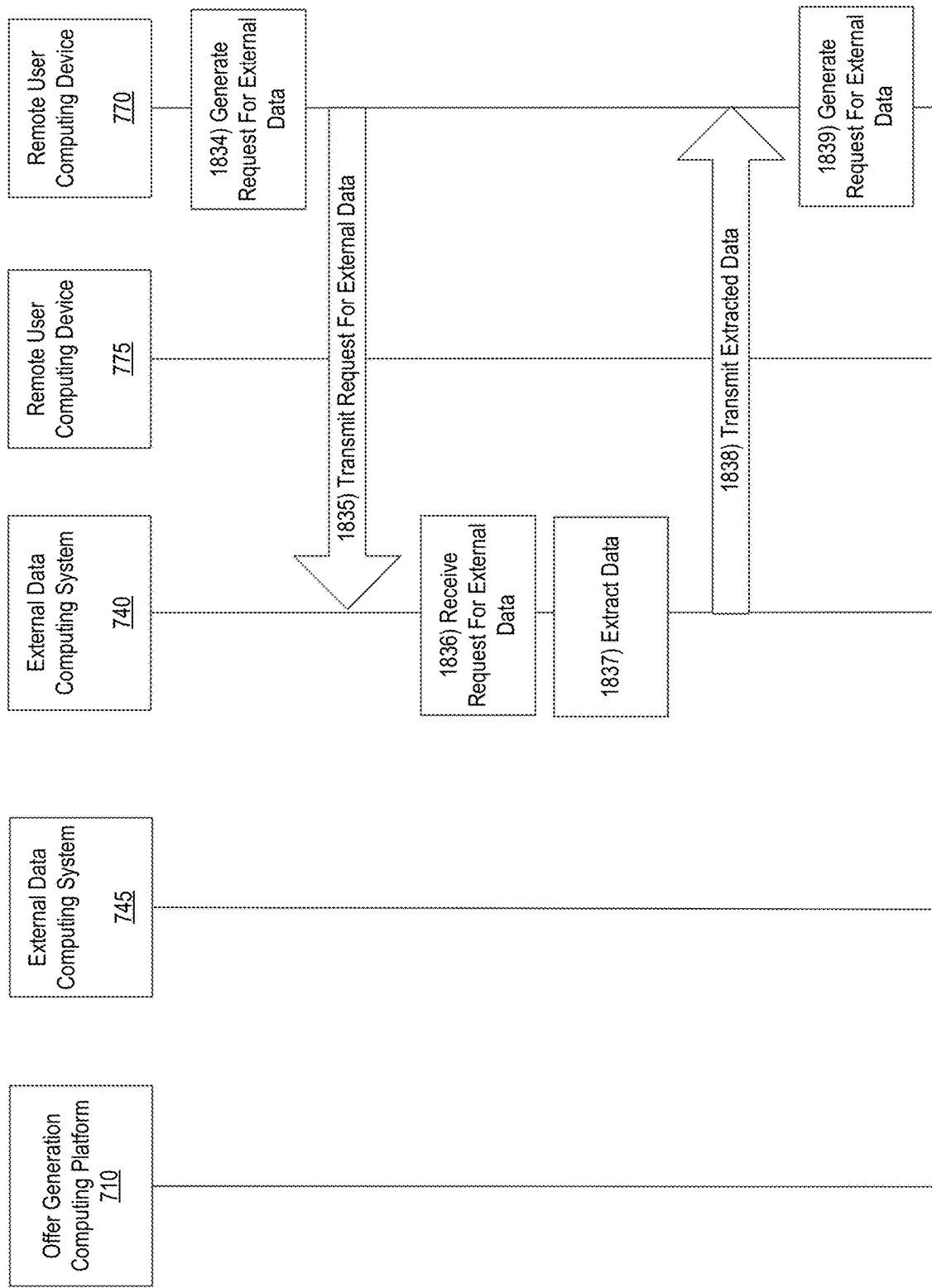

With reference to FIG. 18G, at step 1834, a request for external data may be generated by the remote user computing device 770. In some examples, the request may include information identifying the user, types of data, time period or date range of desired data, and the like. At step 1835, the request for external data may be transmitted from the remote user computing device to the external data computing system 740. In some examples, the request may be transmitted during the communication session initiated upon establishing the fourth wireless connection.

At step 1836, the request for external data may be received by the external data computing system 740. At step 1837, the request may be executed and the identified data may be extracted. At step 1838, the extracted data may be transmitted from the external data computing system 740 to the remote user computing device 770.

At step 1839, a request for additional external data may be generated. For instance, a request for external data stored in a second, different external data system may be generated. In some examples, the request may identify a user associated with the desired data, types of data, time period or date range of data, and the like.

Figure 18H:
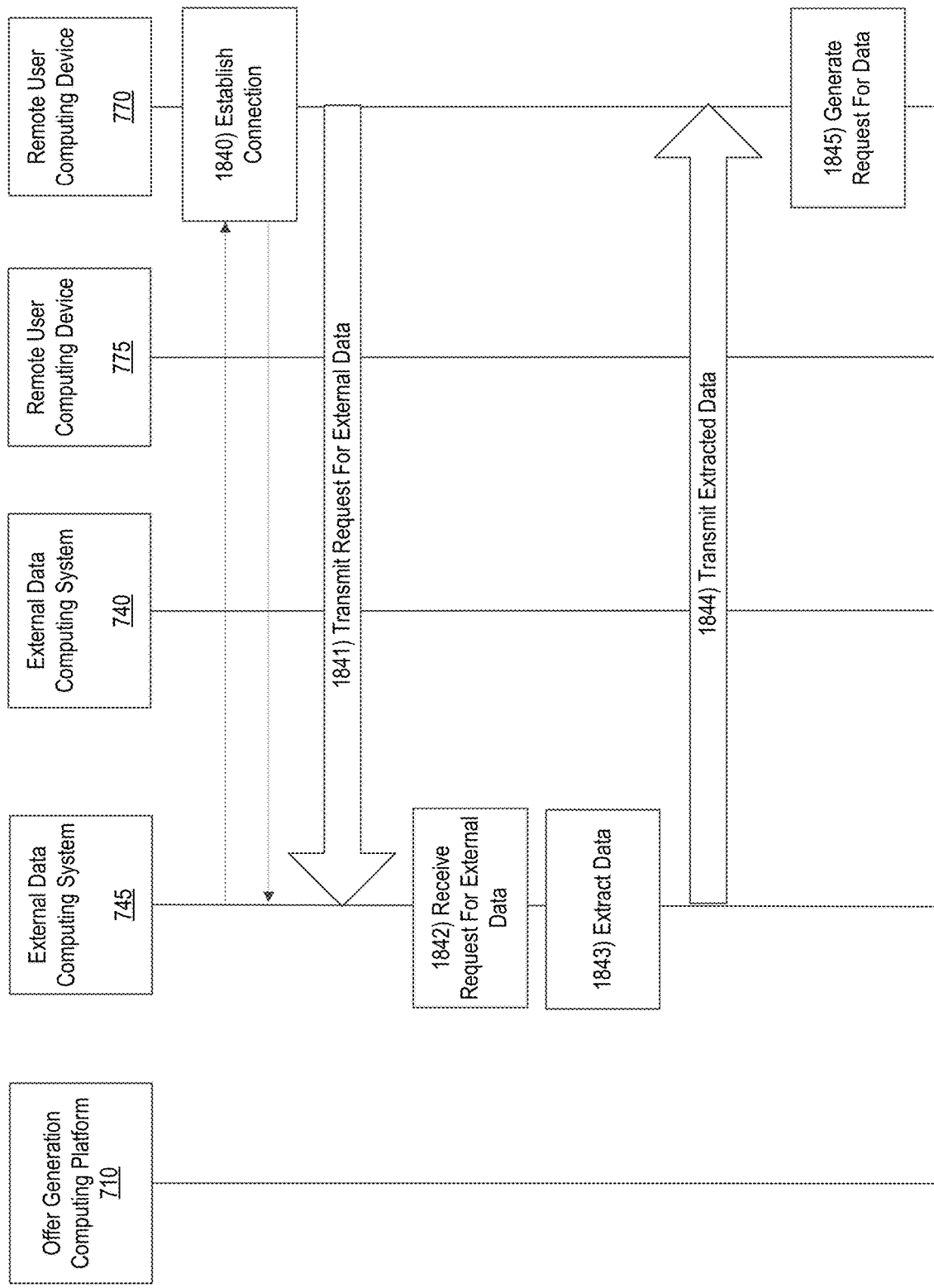

With reference to FIG. 18H, at step 1840, a connection may be established between the remote user computing device 770 and external data computing system 745. For instance, a fifth wireless connection may be established between the remote user computing device 770 and the external data computing system 745. Upon establishing the fifth wireless connection, a communication session may be initiated between the external data computing system 745 and the remote user computing device 770.

At step 1841, the request for external data may be transmitted from the remote user computing device 770 to the external data computing system 745. In some examples, the request may be transmitted during the communication session initiated upon establishing the fifth wireless connection.

At step 1842, the request for external data may be received by the external data computing system 745. At step 1843, the request may be executed and the identified data may be extracted. At step 1844, the extracted data may be transmitted from the external data computing system 745 to the remote user computing device 770.

At step 1845, a request for additional data may be generated by the remote user computing device 770. For instance, a request for data captured by a second, different remote user computing device, such as remote user computing device 775 may be generated. In some examples, remote user computing device 775 may be a wearable device such as a fitness tracker, smart watch, or the like. In some examples, the request for data may include a request for step count and/or other activity data.

Figure 18I:
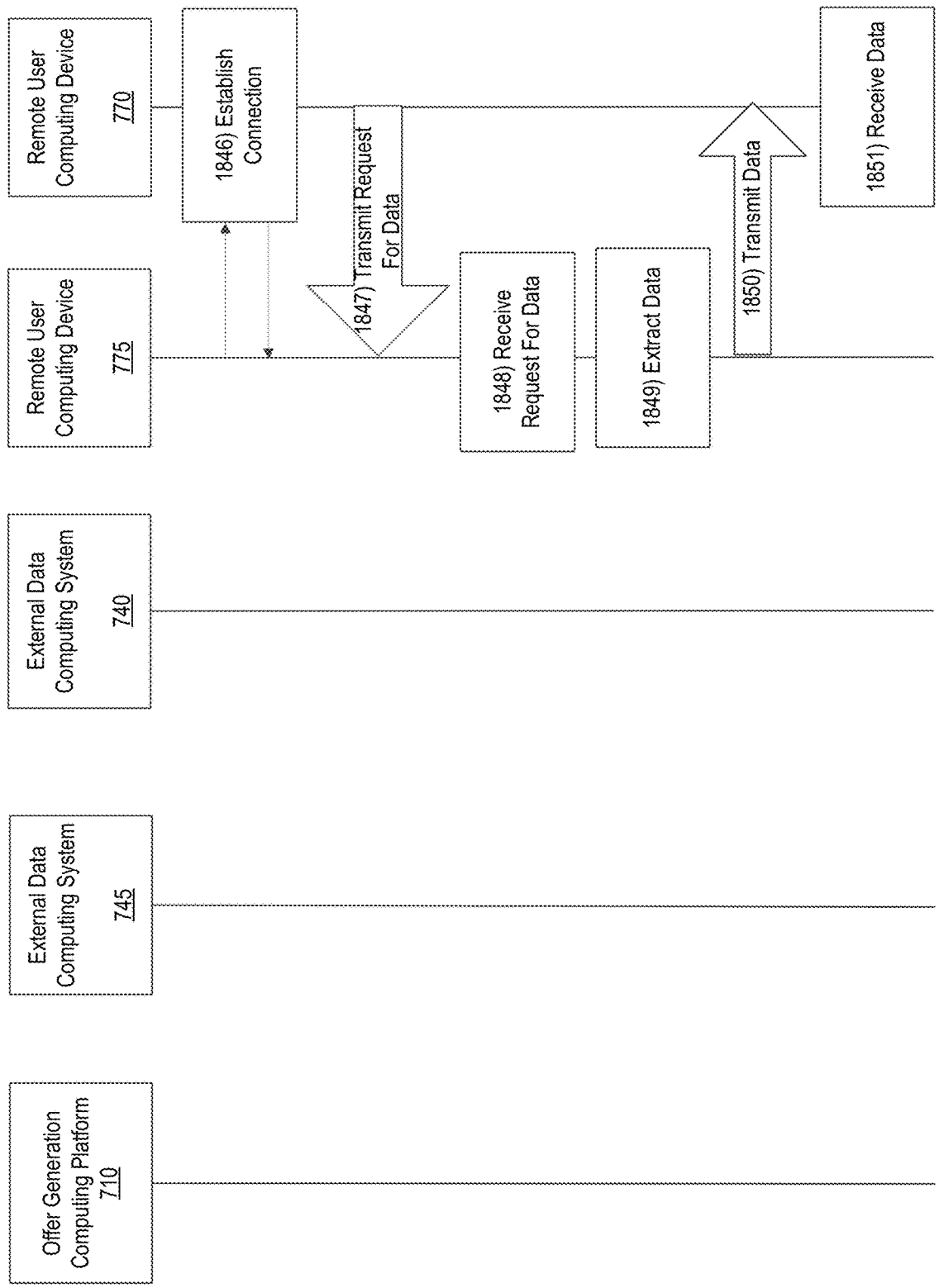

With reference to FIG. 18I, at step 1846, a connection may be established between the remote user computing device 770 and remote user computing device 775. For instance, a sixth wireless connection may be established between the remote user computing device 770 and remote user computing device 775. Upon establishing the sixth wireless connection, a communication session may be initiated between the remote user computing device 775 and the remote user computing device 770.

At step 1847, the request for data may be transmitted from the remote user computing device 770 to the remote user computing device 775. In some examples, the request may be transmitted during the communication session initiated upon establishing the sixth wireless connection.

At step 1848, the request for data may be received by the remote user computing device 775. At step 1849, the request may be executed and the identified data may be extracted. At step 1850, the extracted data may be transmitted from the remote user computing device 775 to the remote user computing device 770.

At step 1851, the data may be received by the remote user computing device 770.

With reference to FIG. 18J, at step 1852, a connection may be established between the remote user computing device 770 and the offer generation computing platform 710. For instance, a seventh wireless connection may be established between the remote user computing device 770 and offer generation computing platform 710. Upon establishing the seventh wireless connection, a communication session may be initiated between the offer generation computing platform 710 and the remote user computing device 770.

Although aspects described herein provide the data being transmitted from the various sources to the remote user computing device 770 and then to the offer generation computing platform 710, in some examples, the data may be transmitted directly from the source to the offer generation computing platform 710 without first being transmitted to the remote user computing device 770. Further, in some arrangements, portions of the data process described herein may be performed by the remote user computing device 770 while portions may be performed by the offer generation computing platform 710 (e.g., parallel processing may occur).

At step 1853, the data extracted and received by the remote user computing device 770 from the one or more sources (e.g., external data computing system 740, external data computing system 745, remote user computing device 775, and the like) may be transmitted to the offer generation computing platform 710. In some examples, the data from the one or more sources may be transmitted during the communication session initiated upon establishing the seventh wireless connection.

At step 1854, the offer generation computing platform 710 may receive the data from the one or more sources. At step 1855, the received data may be processed. For instance, the data received from the one or more sources, as well as any physical trait data received, and/or any user information response data received may be analyzed. In some examples, as discussed herein, machine learning (e.g., one or more machine learning techniques including one or more clustering techniques) may be used to analyze the data, determine risk associated with a user, mortality rates, fitness level, overall health, and the like.

At step 1856, one or more offers or outputs may be generated based on the analyzed data. For instance, based on the analyzed data and determined overall health, mortality rate, risk, and the like, an offer for, for example, life insurance may be generated. In some examples, unlike conventional arrangements, the offer for life insurance may be generated without requiring traditional underwriting (e.g., a medical or physical examination, blood tests, and the like). Instead, the data received from the user, the one or more sources, and the like, may be used to performed an accelerated underwriting function to generate the offer for life insurance. In some examples, a threshold level of risk may be required to be eligible for the accelerated underwriting. For instance, in some examples, if the determined risk or mortality rate associated with a user is high, the user may be required to complete traditional underwriting. However, if the risk or mortality rate is below a threshold, the accelerated underwriting process described herein may be sufficient to generate the offer and, in some examples, bind the user.

As discussed herein, aspects described with respect to FIGS. 18A-18K may be performed in real-time or near real-time in order to retrieve user data and generate outputs in a fast, efficient manner.

Figure 18K:
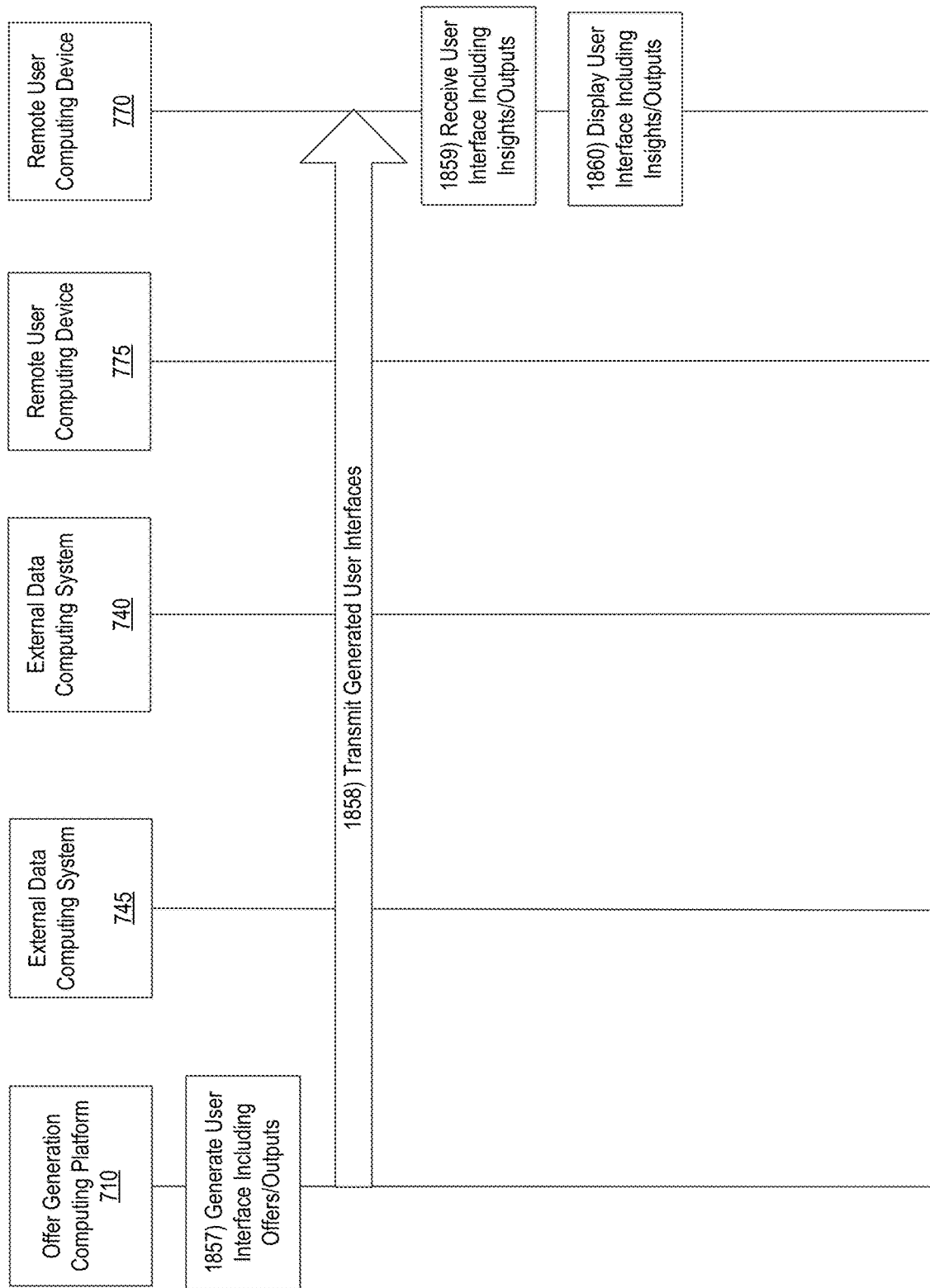

With reference to FIG. 18K, at step 1857, one or more user interfaces including the generated offer or output may be generated. In some examples, the user interfaces may include one or more selectable options available to the user and/or an option to bind the user (e.g., purchase the offered policy, accept the offer, or the like).

At step 1858, the generated user interface(s) may be transmitted from the offer generation computing platform 710 to the remote user computing device 770. In some examples, the generated user interface(s) including the generated outputs and/or offer may be transmitted during the communication session initiated upon establishing the seventh wireless connection.

At step 1859, the transmitted user interface(s) including the generated outputs and/or offer may be received by the remote user computing device 770 and, at step 1860, the generated user interface(s) may be displayed by the remote user computing device 770 (e.g., on a display of the remote user computing device 770). In some examples, the established wireless connected may be terminated after transmitting the user interfaces.

Figure 19:
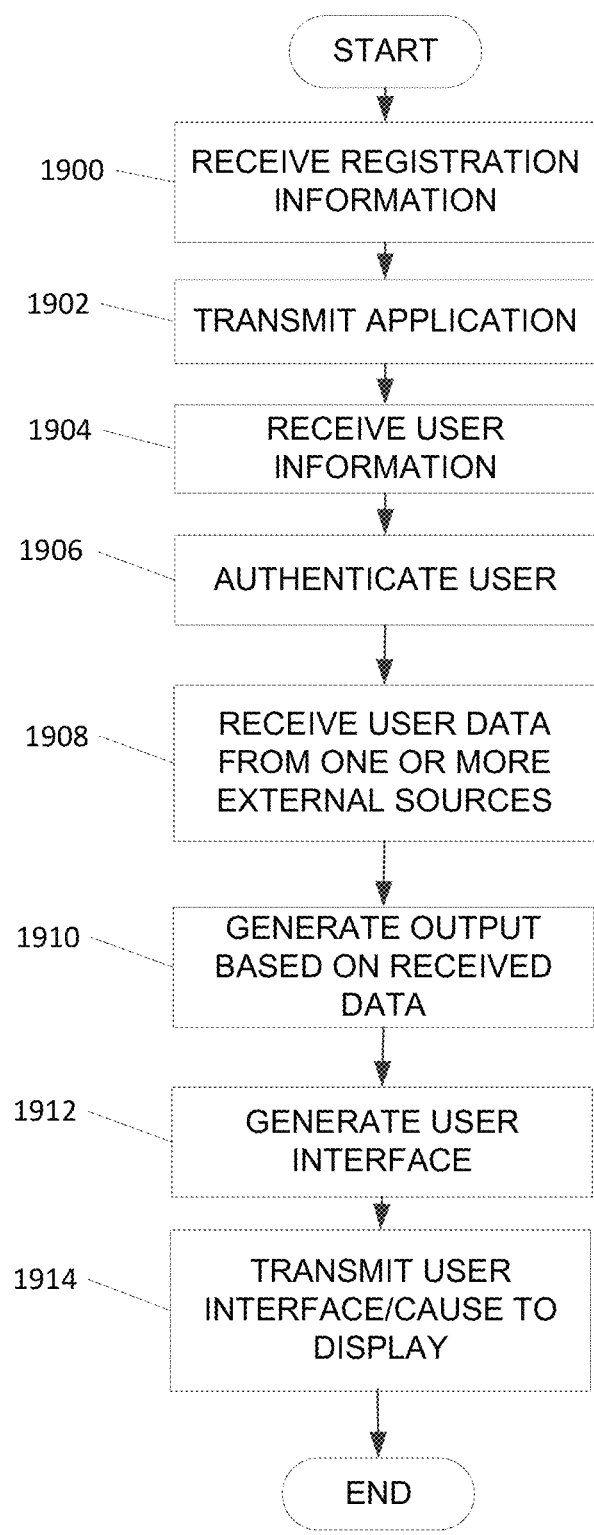
FIG. 19 illustrates one example flow chart for performing offer generating functions according to one or more aspects described herein.

FIG. 19 illustrates one example method of generating an offer or output according to one or more aspects described herein. The steps described with respect to FIG. 19 may be performed by one or more of the various devices and/or systems described herein, such as the offer generation computing platform 710, determination server 110, determination server 210, and the like. In some examples, one or more of the processes or steps described may be performed in real-time and the capture, transmission, use, and the like of user data is performed with user permissions. Further, the steps provided in FIG. 19 may be performed in the order shown, or in another order, without departing from the invention.

At step 1900, registration information may be received from, for instance, a mobile device of a user (e.g., remote user computing device 770). In some examples, the registration information may include a request for an offer or output, user identifying information such as name, contact information, and the like.

At step 1902, an application may be transmitted from the offer generation computing platform 710 to the remote user computing device 770. The application may be executed by the remote user computing device 770 to facilitate capture and transmission of data used to generate the offer or output.

At step 1904, user information may be received. In some examples, the user information may include captured image data, and the like. In some examples, the user information may include physical data of the user, such as height, weight and the like. In some arrangements, the user information may include demographic information, such as age, race, and the like. In some examples, the user information may include physical trait data, such as a heart rate, blood pressure, pulse, and the like.

At step 1906, the user may be authenticated. For instance, the received user information may be compared to pre-stored or publicly accessible information. For example, as discussed more fully herein, the user may be prompted to capture an image of a photographic identification, as well as a self-captured image, and image recognition data may be used to determine whether the user in the photographic identification is the same user as the user in the self-captured image.

At step 1908, user data may be received from one or more external sources. For instance, the remote user computing device 770 may communicate with one or more external sources, such as external data computing system 740, external data computing system 745, remote user computing device 775, and the like to obtain externally stored data. For example, the remote user computing device 770 may receive user data that was previously captured by, for example, the remote user computing device 770, and is stored by an external, third party source (e.g., with permission of the user). In some arrangements, the remote user computing device 770 may receive previously stored medical information of the user, prescription information of the user, and the like (e.g., with permission of the user). In some examples, the remote user computing device 770 may receive data captured by a fitness tracker or other wearable device, such as step count data. The data may be transmitted from the remote user computing device 770 to the offer generation computing platform.

At step 1910, the offer generation computing platform may process the data received from one or more sources to generate an output or offer. For instance, the data may be analyzed (e.g., using machine learning, deep learning, data clusters, and the like) to determine mortality rate of the user, risk associated with the user, and the like. This information may then be used to generate an insurance premium or offer, such as a life insurance premium or offer. Accordingly, the offer or output may be generated based on pre-captured data (e.g., data captured prior to the user requesting the offer) which may enable generation of an output without requiring traditional underwriting and accurately determining risk associated with a user without requiring a period of time in which data is collected and analyzed.

At step 1912, a user interface may be generate including the generated offer or output. At step 1914, the user interface may be transmitted to the remote user computing device 770 and displayed on a display of remote user computing device 770.

Figure 20:
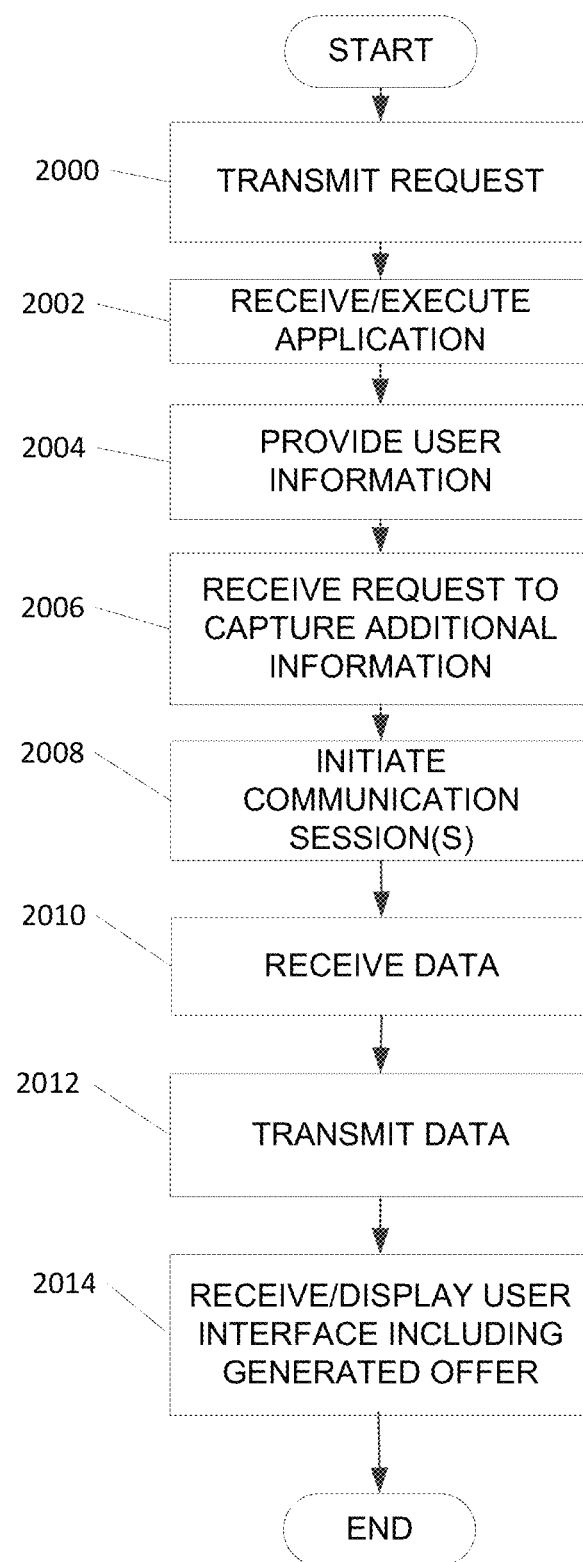
FIG. 20 illustrates another example flow chart for performing offer generating functions according to one or more aspects described herein.

FIG. 20 illustrates another example method of performing offer generation functions according to one or more aspects described herein. The steps described with respect to FIG. 20 may be performed by one or more of the various devices and/or systems described herein, such as the offer generation computing platform 710, determination server 110, determination server 210, and the like. In some examples, one or more of the processes or steps described may be performed in real-time and the capture, transmission, use, and the like of user data is performed with user permissions. Further, the steps provided in FIG. 20 may be performed in the order shown, or in another order, without departing from the invention At step 2000, a request to generate an offer or output may be transmitted from a mobile device of a user, such as remote user computing device 770, to an offer generation computing platform 710. The request may include user information such as name, contact information, and the like.

At step 2002, an application transmitted by the offer generation computing platform 710 may be received by the remote user computing device 770 and executed by the remote user computing device. In some examples, executing the application may include initiating a communication session with one or more external data sources (e.g., external data computing system 740, external data computing system 745, and the like) and identifying and receiving data from the one or more sources.

At step 2004, user information may be received by the remote user computing device 770 and transmitted to the offer generation computing platform 710. In some examples, the user information may include height, weight, and the like.

At step 2006, a request to capture additional information may be received. For instance, the offer generation computing platform 710 may transmit an instruction to capture additional data. For example, the instruction may include a request to capture data such as heart rate, blood pressure, and the like. The data may be captured via one or more sensors in or associated with the remote user computing device 770. In some examples, the request for additional information may include instructions to perform one or more activities with the remote user computing device 770 and capture data. For example, the instruction may include a request to climb a flight of stairs, walk a predefined distance or time, and the like. The activity may then be performed with the remote user computing device 770 and the remote user computing device 770 may capture data such as location or GPS data, accelerometer data, gyroscope data, and the like. This data may be transmitted to the offer generation computing platform 710 for analysis.

At step 2008, one or more communication sessions may be initiated with one or more external data sources. For instance, as described above, the remote user computing device 770 may initiate a communication session with external data computing system 740, external data computing system 745, remote user computing device 775, or the like.

At step 2010, data may be received from the one or more external data sources. At step 2012, the received data may be transmitted from the remote user computing device 770 to the offer generation computing platform 710.

At step 2014, a generated offer may be received by the remote user computing device 770 and displayed on a display of the remote user computing device.

Figure 21:

FIG. 21 illustrates one example user interface 2100 that may be generated and transmitted to the mobile device of a user for display. Interface 2100 includes instructions for capturing one or more physical traits of the user. In some examples, the listed physical traits may include selectable links that will cause display of one or more additional user interfaces having additional instructions, and the like.

Figure 22:
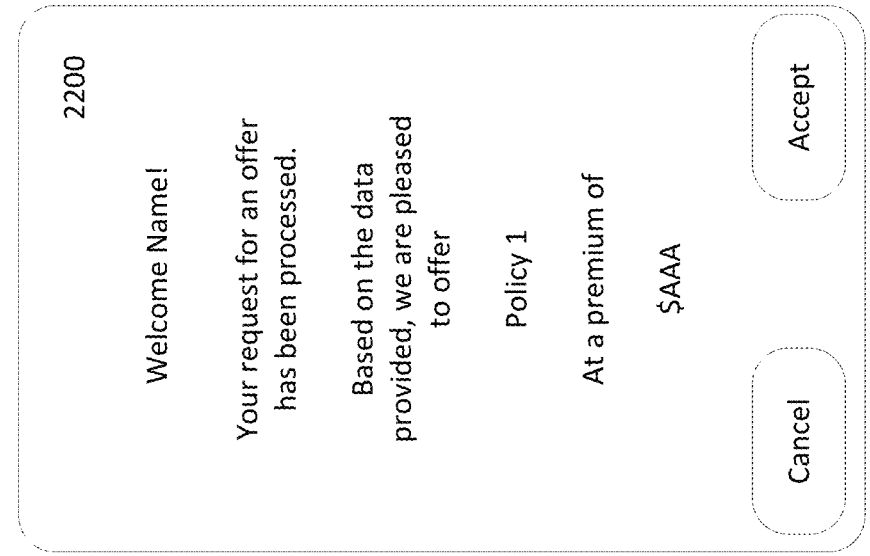
FIGS. 21 and 22 illustrate example user interfaces that may be generated and displayed according to one or more aspects described herein.

FIG. 22 illustrates another example user interface 2200 that may be generated and transmitted to the mobile device of the user. Interface 2200 includes an indication that the user data has been processed and includes a display of a generated offer or output for the user. If the user desires to accept the offer, the user may select "accept" option. Alternatively, the user may select to decline the offer by selecting "cancel."

As discussed above, although various aspects discussed herein are directed to use of the arrangements described in generating outputs related to automobile insurance, aspects described herein may also be used to generate one or more outputs related to, for example, life insurance.

For instance, aspects described herein may be used to generate an offer for life insurance (e.g., a premium, rate, or the like), without requiring the user to undergo traditional underwriting, including a medical or physical examination by medical personnel, or the like. Instead, the offer may be generated based on data captured by a mobile device of the user (e.g., via one or more sensors in the mobile device), and/or pre-stored data associated with the user, medical and/or prescription history data, and the like.

For example, in some arrangements, data may be captured by the mobile device, for example, in real-time or near real-time. For instance, an instruction may be transmitted to the mobile device to display a user interface requesting one or more types of physical trait data. For instance, the user interface may include a request for a resting heart rate of a user, a request for a user to capture one or more images, a pulse rate, an oxygen level, and the like. This data may be captured via one or more sensors in the mobile device.

In some arrangements, the user interface may include a request to perform one or more activities with the mobile device. For instance, the user interface may include a request to climb a flight of stairs, walk 1 mile at a user's best pace, walk for 10 minutes, or the like. In other examples, the request may include walking on a treadmill at a predetermined grade (e.g., 3%, 5% or the like) for a predetermined time (e.g., 3 minutes, 4 minutes, 5 minutes, or the like). In another example, the user may be requested to cycle for a predetermined time (e.g., 3 minutes, 5 minutes, and the like) at different resistance levels. In still other examples, the user may be requested to step up 2 stairs for a predetermined time, perform a predetermined number of squats in a predetermined time period, or the like.

Performance of the activity may be confirmed via sensor data (e.g., accelerometer data, gyroscope data, GPS data, and the like). Further, in some examples, the user may be requested to provide additional data before, during and/or after performance of the activity. For instance, the user may be requested to capture a heart rate before performing the activity, during the activity and after the activity. This data may then be used to evaluate fitness of the user which may impact mortality and risk ratings.

Additionally or alternatively, the mobile device may retrieve pre-stored user data from one or more third party devices or systems. For instance, location, activity, and other data that is captured by the mobile device on a day-to-day basis may be stored by a third party entity. The mobile device may execute an application configured to initiate a communication session with one or more of the third party devices or systems, identify and extract user data, and transmit the user data for further processing. Accordingly, a user is able to access his or her own data and provide that data (e.g., pre-stored data) to an entity evaluating risk and/or generating the output or offer. This provides for more data to be captured and analyzed, thereby improving the accuracy of mortality and risk evaluations of the user. In addition, it improves efficiency because a greater volume of data is provided up front for analysis, which enables the user to receive the offer far more quickly than if traditional underwriting was involved.

Additionally or alternatively, the pre-stored user data retrieved from the one or more third party systems or devices may include electronic medical records of the user and/or prescription records. The user may retrieve this data and provide it to the entity for further processing (e.g., with appropriate permissions for processing). Accordingly, by providing current and/or historical medical and/or prescription data, mortality and risk can be more accurately evaluated.

In some examples, the user may obtain data from one or more additional devices. For instance, if a user wears a fitness tracker or other wearable device, step count and/or other activity data from the device may be retrieved by the mobile device and transmitted to the entity for evaluation.

As discussed herein, user data may be captured, transmitted, processed, and the like with the appropriate permissions of the user and/or in accordance with one or more regulatory requirements. In addition, a user may limit the amount and/or type of data provided to the entity for evaluation. For instance, the user may provide current physical trait data but may elect to provide little or no current prescription data. Various other filtering arrangements may be used without departing from the invention.

In some examples, location data of a user may be retrieved and used to evaluate health. For example, if GPS or other location data indicates a user is at a gym 5 days per week, this data may be included in determining mortality and/or risk and generating an appropriate output or offer. In some examples, the location data may be aggregated with fitness and/or step count data to confirm that the user is working out while at the gym.

In some examples, additional data may also be retrieved and aggregated to perform the analysis. For instance, social media data, financial transaction data, and the like, may be retrieved (e.g., with permission of the user) and aggregated with one or more other types of data to provide a more robust picture of a user's health and wellness. For instance, various types of purchase may indicate a better or worse health condition of the user and this information may be considered when determining risk.

Accordingly, in some example arrangements, the user may directly provide some data (e.g., physical trait data, pre-stored data, and the like), while the entity processing the data may retrieve other user data directly from one or more third party entities (e.g., electronic health record stored, financial institutions, and the like) with permission of the user but, in at least some examples, without user input.

Although various aspects described herein are directed to generating an insurance premium or output, various other types of insights may be generated. For instance, machine learning may be used to evaluate the data and generate one or more recommendations for improved health of the user (e.g., walk more steps each day/week, take a break from work, or the like). In some examples, the insights, in addition to improving the health of the user, may also be associated with a savings (e.g., a lower premium, a discount, or the like). This information may also be generated and conveyed to the user (e.g., via one or more user interfaces).

As discussed herein, the data may be received in one or more different formats (e.g., JSON, XML, and the like). In some examples, the data may be reformatted to one format (e.g., all data may be formatted to a single desired format) and the data may be aggregated and processed in that format.

In some examples, the data received by the entity processing the data (e.g., via the offer generation computing platform) may store the data in a single, secure data store. The data may then be analyzed to map the data to conditions that predict mortality and/or an underwriting class. For instance, in some examples, step count, location and heart rate may be used to predict fitness level, which is correlated to mortality.

In another example, longitudinal health data from, for example, electronic health records, may be used to predict mortality trends over time.

In yet another example, financial transaction data may be used to predict diet patterns (e.g., charges at fast food restaurants, types of grocery stores at which the user is shopping, and the like).

In still another example, financial transaction and location data may be used to determine health habits. For instance, if GPS data indicates the user is at or near a gym 3 days per week, and financial transaction data shows the user paid for a gym membership, the user is likely exercising while at the gym on those days, which can predict fitness level which is correlated to mortality.

In yet another example, prescription drug history (e.g., as collected from medical health records with permission of the user) can be used to predict current medical conditions, which may impact mortality and/or risk.

Accordingly, as discussed herein, an output or offer may be generated based on various different types of data from various different sources. For instance, some data may be input or collected directly from the user (e.g., physical trait data), while other data may be captured via a mobile device from one or more third party systems or devices, while still other data may be received directly from the third party system or device.

For instance, some aspects of the arrangements described herein enable a user to provide his or her own data (e.g., pre-stored data captured by a mobile device or via user input). In some examples, the pre-stored data may be stored by a third party system or device or may be stored on the mobile device.

Additionally or alternatively, some aspects evaluate body composition of the user. In some arrangements, body composition may be determined from, for example, a height and weight of a user (e.g., body mass index may be determined), from one or more images of the user (e.g., determined waist-hip ratio, body fat percentage, and the like). In some examples, features such as waist-hip ration and/or body fat percentage may be determined using the mobile device (e.g., via one or more sensors, image capture devices, and the like).

Additional user data may also be captured via the mobile device, such as whether a user is a smoker (e.g., based on sensor data, facial analytics, or the like), blood pressure, diabetes, lung disease, and the like, may be determined using one or more sensors associated with a mobile device. In some examples, blood pressure and/or heart rate may be measured my measuring the wave form velocity of the blood flow in a user's finger using the image capture device of the mobile device. Additionally or alternatively, body mass index may be measured using user inputs of height and weight in combination with images of the user. In some examples, images may be captured and machine learning may be used to extract body measurements of the user from the images.

As discussed herein, the arrangements described provide efficient, accurate ways to evaluate health, wellness, risk and mortality of a user in order to generate one or more outputs or offers without, in at least some examples, requiring a physical examination of the user by a medical professional.

FIGS. 23A-23H illustrate another example event sequence for performing offer generation control functions in accordance with one or more aspects described herein. The sequence illustrated in FIGS. 23A-23H is merely one example sequence and various other events may be included, or events shown may be omitted, without departing from the invention.

Figure 23A:
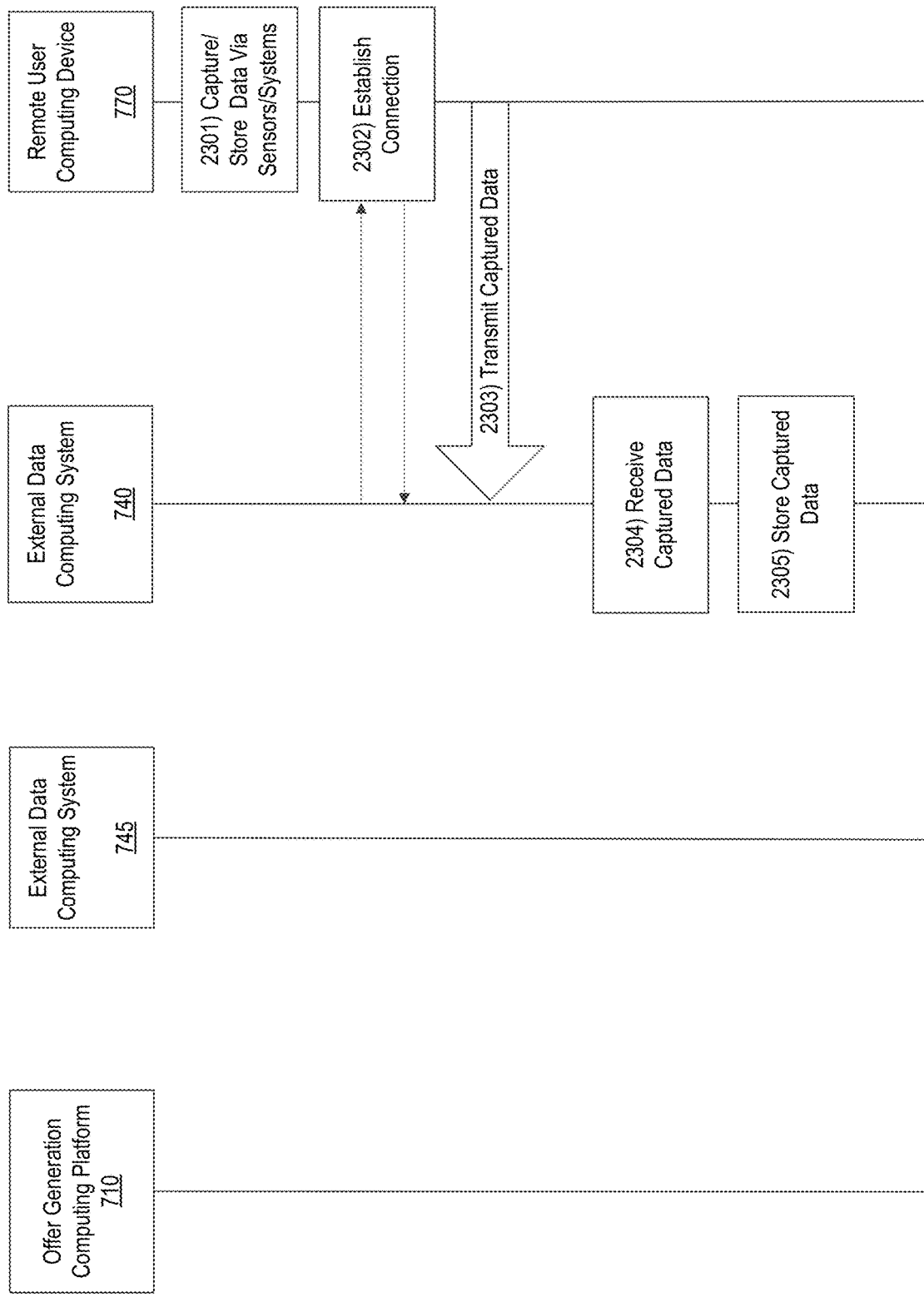

With reference to FIG. 23A, at step 2301, data may be captured by a remote user computing device 770. For instance, data such as location data (e.g., GPS data including latitude and longitude, time stamp, date stamp, and the like) captured via a mobile device of a user (e.g., remote user computing device 770) may be captured. The location data may be captured throughout a user's regular routine (e.g., driving, walking, at work, at home, and the like) Additionally or alternatively, other types of data may be captured via the remote user computing device 770. For instance, social media data, wellness data, activity data, step count data, physical trait data (e.g., blood pressure, heart rate, or the like), application usage data, and the like, may be captured. In some examples, remote user computing device 770 may be a mobile device of a user, such as a smartphone, tablet, or the like. In some examples, remote user computing device 770 may store some or all of the captured data. In some examples, remote user computing device 770 may include a wearable device such as a fitness tracker or other device.

As discussed herein, data may be captured via sensors within or associated with the remote user computing device 770. For instance, GPS sensors, accelerometers, gyroscopes, pedometers, oxygen sensors, pulse sensors, and the like, may be used to captured data. Additionally or alternatively, various other types of sensors may be used to capture data without departing from the invention.

At step 2302, a connection may be established between the remote user computing device 770 and the external data computing system 740. For instance, a first wireless connection may be established between the remote user computing device 770 and the external data computing system 740. Upon establishing the first wireless connection, a communication session may be initiated between the external data computing system 740 and the remote user computing device 770.

At step 2303, the captured data may be transmitted from the remote user computing device 770 to the external data computing system 740. For instance, the captured data may be transmitted during the communication session initiated upon establishing the first wireless connection. In some examples, the captured data may be transmitted in real-time as the data is captured. In other examples, the captured data may be transmitted on a periodic or aperiodic basis, according to a predetermined schedule, or the like. In some examples, captured data from a period of time (e.g., one week, one month, six months, 1 year, or the like) may be captured prior to additional functions described herein being performed.

At step 2304, the external data computing system 740 may receive the captured data and, at step 2305, the external data computing system 740 may store the captured data. As discussed herein, the external data computing system 740 may be a third party system (e.g., associated with a party different from the user associated with the remote user computing device 770 and the entity associated with the offer generation computing platform 710). In some examples, the external data computing system 740 may receive and store the captured data with the necessary permissions received from the user and the third party may use the captured and stored data for additional third party uses unrelated to the processes described herein. This stored data may then later be accessed by the user (e.g., the user associated with the device from which the data was captured) for personal use, transmission to other entities, or the like.

Figure 23B:
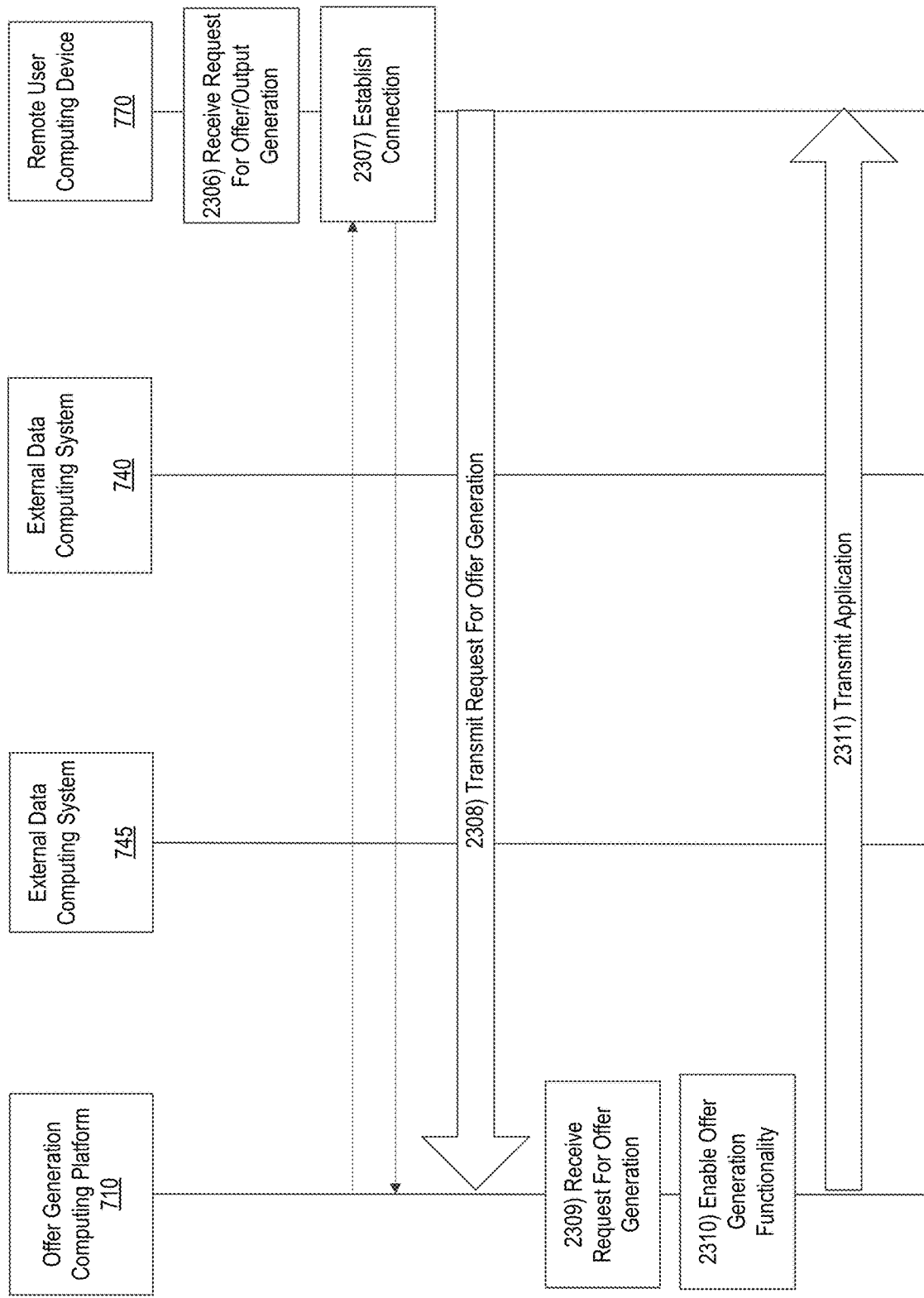

With reference to FIG. 23B, as step 2306, a request for offer/output generation may be received. For instance, a user may input a request into remote user computing device 770. In some examples (e.g., if the user is already a customer of the entity implementing the offer generation computing platform 710), the request may be input into an application executing on the remote user computing device 770 and provided by the offer generation computing platform 710. In some examples, the request for offer/output may be received after the data is captured and pre-stored, as discussed with respect to steps 2301-2305.

At step 2307, a connection may be established between the remote user computing device 770 and the offer generation computing platform 710. For instance, a second wireless connection may be established between the remote user computing device 770 and the offer generation computing platform 710. Upon establishing the second wireless connection, a communication session may be initiated between the offer generation computing platform 710 and the remote user computing device 770.

At step 2308, the request for offer generation may be transmitted from the remote user computing device 770 to the offer generation computing platform 710. For instance, the request for offer generation may be transmitted during the communication session initiated upon establishing the second wireless connection.

At step 2309, the request for offer/output generation may be received by the offer generation computing platform 710. At step 2310, offer generation functionality may be enabled by the offer generation computing platform 710. For instance, functionality that was previously disabled may be enabled, activated or initiated in response to receiving the request for offer/output generation. In some examples, enabling offer generation functionality may include identifying an application for transmission to a user device (e.g., remote user computing device 770).

At step 2311, an application may be transmitted from the offer generation computing platform 710 to the remote user computing device 770. The application may be an application to facilitate communication between one or more systems, identify data for extraction, and the like. Although the arrangement described includes the application being transmitted after the request for offer is received, in some examples, the application may be transmitted to the remote user computing device 770 prior to the request for offer generation being received by either the remote user computing device 770 or the offer generation computing platform 710.

Figure 23C:
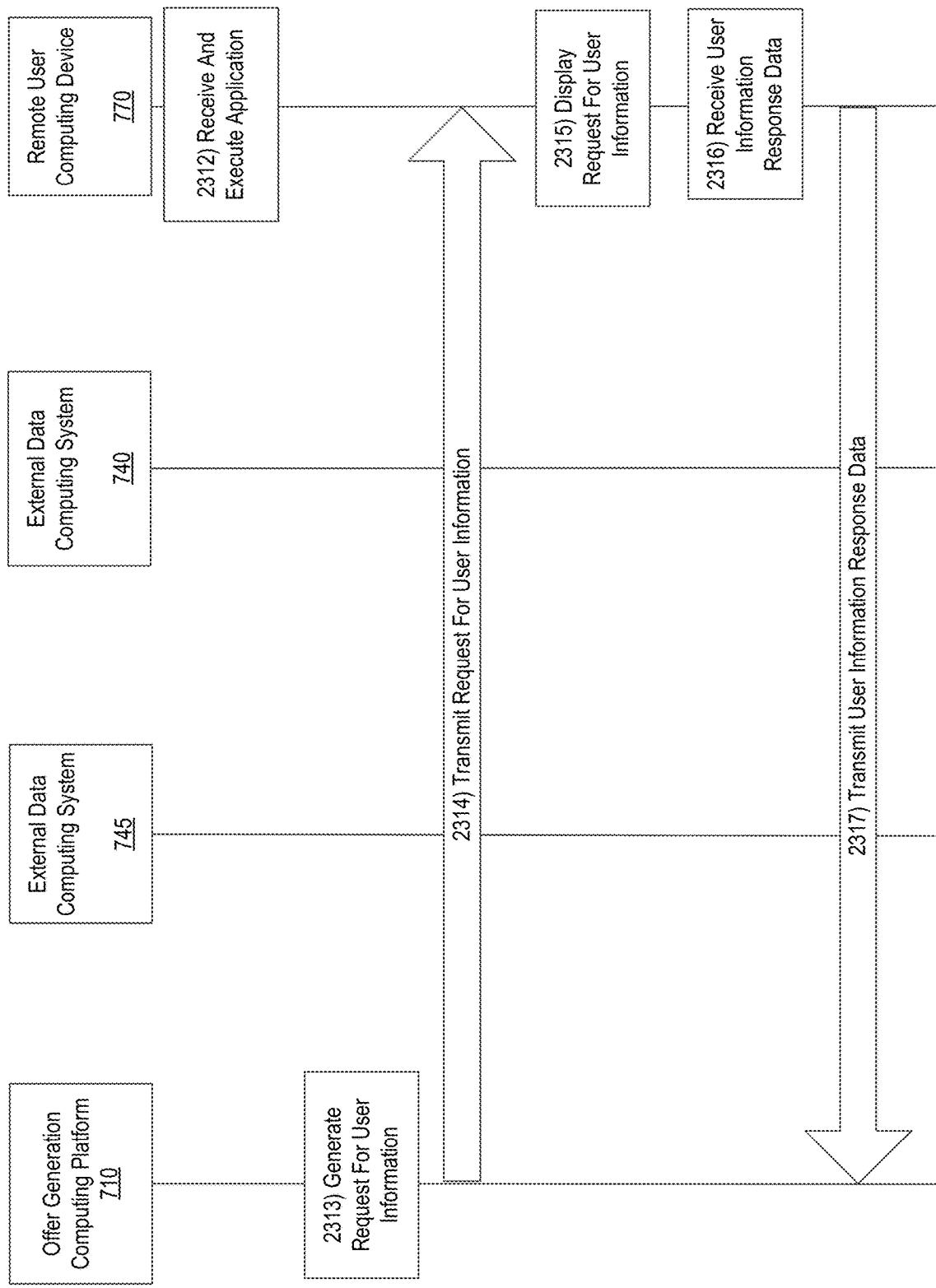

With reference to FIG. 23C, at step 2312, the transmitted application may be received by the remote user computing device 770 and executed by the remote user computing device 770. In some examples, executing the application may include enabling functionality associated with the remote user computing device 770 (e.g., data capture functions, data transmission functions, activating one or more sensors, and the like).

At step 2313, a request for user information may be generated by the offer generation computing platform 710. Similar to other arrangements discussed herein, the request may include a request for user identifying information, image data, and the like.

At step 2314, the generated request for user information may be transmitted from the offer generation computing platform 710 to the remote user computing device 770. For instance, the request may be transmitted during the communication session initiated upon establishing the second wireless connection.

At step 2315, the request for user information may be received and displayed by the remote user computing device 770 (e.g., on a display of the device 770) and, similar to other arrangements discussed herein, at step 2316, user information response data may be received and transmitted to the offer generation computing platform 710 at step 2317.

Figure 23D:
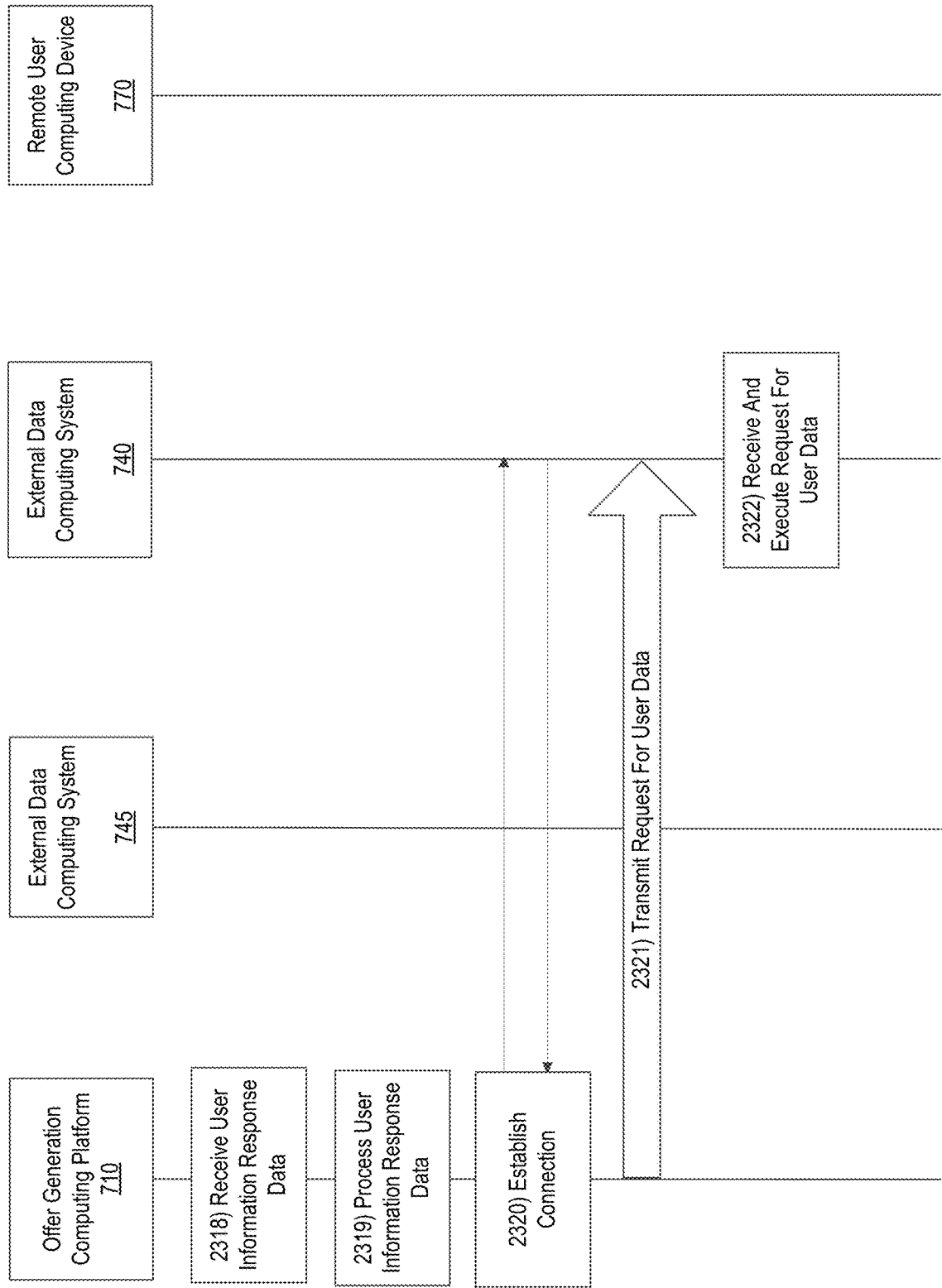

With reference to FIG. 23D, at step 2318, the user information response data may be received, and, at step 2319, may be processed, similar to other arrangements discussed herein.

At step 2320, a connection may be established between the offer generation computing platform 710 and external data computing system 740. For instance, a third wireless connection may be established between the offer generation computing platform 710 and the external data computing system 740. Upon establishing the third wireless connection, a communication session may be initiated between the offer generation computing platform 710 and the external data computing system 740.

At step 2321, the request for user data may be transmitted from the offer generation computing platform 710 to the external data computing system 740. For instance, the request for user data may be transmitted during the communication session initiated upon establishing the third wireless connection. In some examples, the request for user data may include selection of one or more options for types of data, categories of data, or the like, that the user would like to have evaluated via the offer generation computing platform 710. For instance, a user may select one or more types of data, categories of data, or the like, that may be captured and analyzed. The request for user data may include identification of the desired types of data, categories of data, or the like.

At step 2322, the request for user data may be received by the external data computing system 740 and may be executed. For instance, executing the request may include extracting the identified or requested data.

Figure 23E:
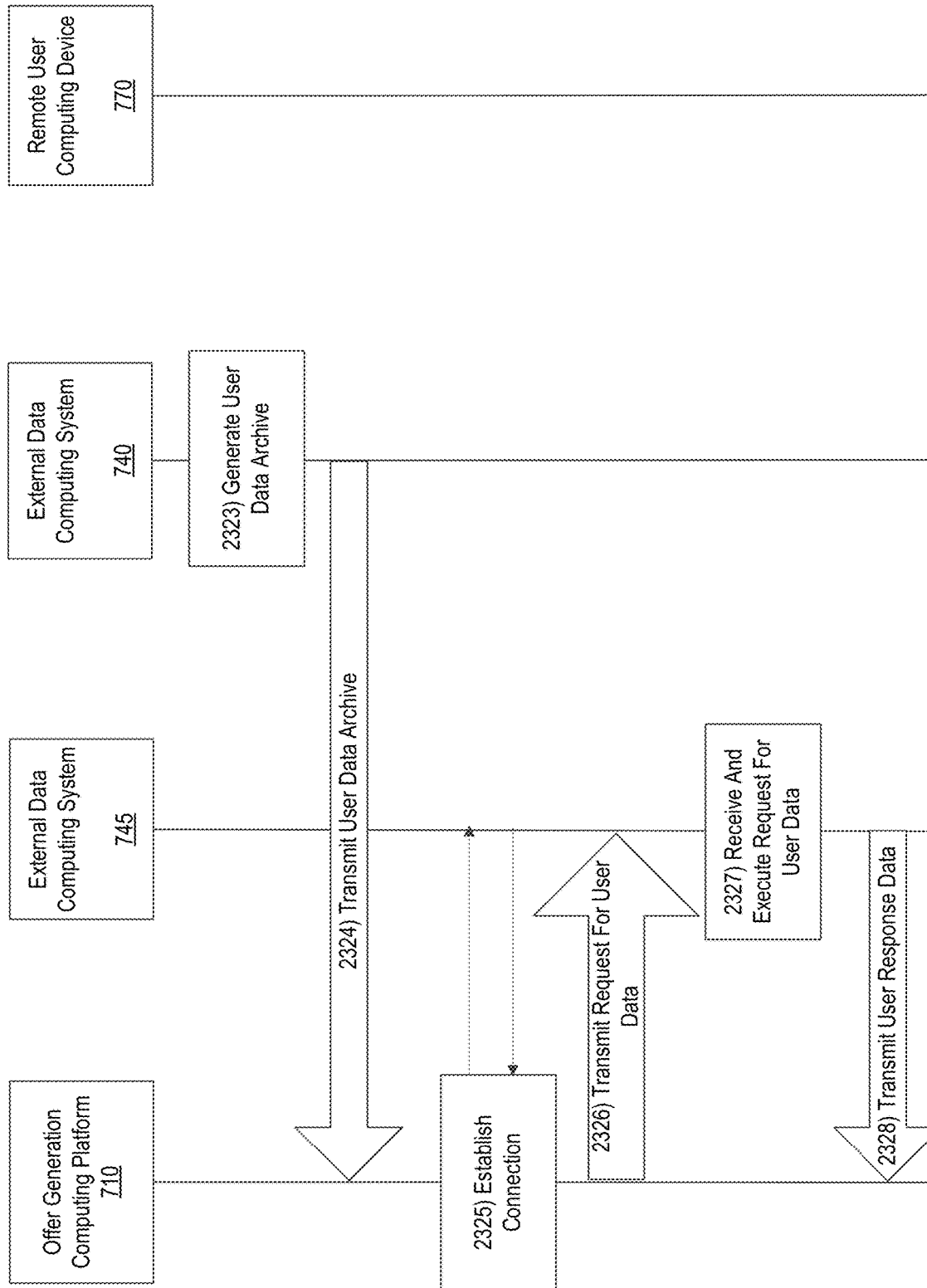

With reference to FIG. 23E, at step 2323, a user data archive may be generated. For instance, an archive containing the requested or identified user data may be generated and, at step 2324, may be transmitted to the offer generation computing platform 710.

At step 2325, a connection may be established between the offer generation computing platform 710 and the external data computing system 745. For instance, a fourth wireless connection may be established between the the offer generation computing platform 710 and the external data computing system 745. Upon establishing the fourth wireless connection, a communication session may be initiated between the offer generation computing platform 710 and the external data computing system 745.

At step 2326, the request for user data may be transmitted from the offer generation computing platform 710 to the external data computing system 745. For instance, the request for user data may include a request for user data different from data previously requested from external data computing system 740 (e.g., a different type or category of data) and may be transmitted during the communication session initiated upon establishing the fourth wireless connection.

At step 2327, the request for user data may be received and executed. For instance, the request for user data may include a request for financial transaction data, social media data, or the like. In some examples, the request may be to obtain data from a third party device storing the data.

At step 2328, generated user response data may be transmitted to the offer generation computing platform 710.

With reference to FIG. 23F, at step 2329, the user archive data and user response data may be received by the offer generation computing platform 710. At step 2330, the received user archive data and user response data may be processed and/or analyzed. In some examples, processing the data may include using machine learning to identify patterns or sequences within the data. The machine learning may then be used to generate one or more outputs, such as an offer, incentive, insight, or the like. For example, data may be received from multiple sources (e.g., external data computing systems 740, 745, remote user computing device 770, and the like) and may be analyzed to generate one or more insights related to the user. The insight may include predictions about products or services that may be desirable to the user, analysis of user history to provide recommendations regarding conserving resources, spending less, or the like, recommendations regarding mobility (e.g., own vs. lease a vehicle, purchase or lease a vehicle vs. relying on public transportation or ride share, or the like). In some examples, the data may be captured across multiple categories, such as location data, health and wellness data, financial data, social data, and the like. This data may be aggregated and analyzed to generate one or more outputs or insights.

At step 2331, one or more machine learning datasets may be updated and/or validated based on the received data.

At step 2332, a data hologram and user insights may be generated. In some examples, a user's data hologram may include identification of sources of different types of data (e.g., sources of financial data (e.g., particular bank, particular credit card, or the like), sources of location data (e.g., movement of the mobile device captured via GPS, ride share application data, or the like), sources of health and wellness data (e.g., fitness tracker data, mobile device health and wellness data, and the like), sources of social data (e.g., social media sites, and the like). The data hologram may further provide selectable options to obtain insights related to each category or type of data (e.g., selectable options for health, financial, location, or the like). Selection of an option may provide additional details related to data captured within that category (e.g., amount spent on dining out, miles travelled in a vehicle, miles travelled in public transportation, average number of daily active minutes, and the like). Additionally or alternatively, selection of the option may prompt display of one or more insights.

At step 2333, one or more user interfaces may be generated including the data hologram and/or generated insights. For instance, one or more user interfaces may be generated including selectable options as discussed above, insights, and the like.

Figure 23G:
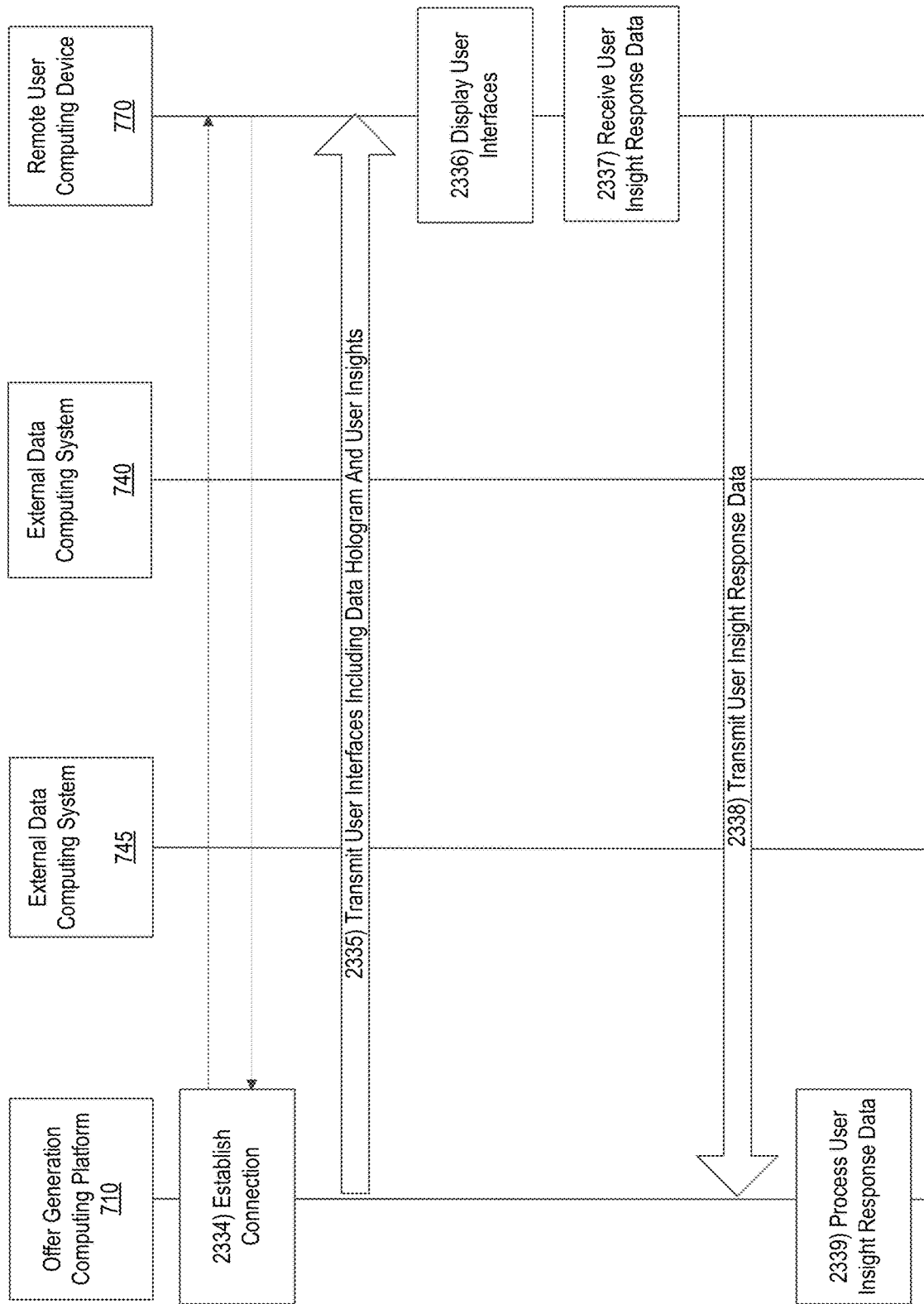

With reference to FIG. 23G, at step 2334, a connection may be established between the remote user computing device 770 and the offer generation computing platform 710. For instance, a fifth wireless connection may be established between the remote user computing device 770 and the offer generation computing platform 710. Upon establishing the fifth wireless connection, a communication session may be initiated between the offer generation computing platform 710 and the remote user computing device 770.

At step 2335, the generated user interfaces including the data hologram and one or more insights may be transmitted from the offer generation computing platform 710 to the remote user computing device 770. For instance, the generated user interfaces may be transmitted during the communication session initiated upon establishing the fifth wireless connection.

At step 2336, the user interfaces may be received by the remote user computing device 770 and displayed on a display of the remote user computing device 770. As discussed above, the user interfaces may include selectable options, and the like.

At step 2337, user insight response data may be received by the remote user computing device 770. For instance, in response to one or more insights or offers displayed on the device 770, user input may be received and user insight response data may be generated based on the received user input. In some examples, the user input may include selection of an option to display additional information. Additionally or alternatively, user input may include acceptance or selection of an offer. For instance, an offer or incentive related to the generated insights may be provided to the user. The user may accept or select an offer via user input and user insight response data may be generated.

At step 2338, the user insight response data may be transmitted to the offer generation computing platform 710. At step 2339, the user insight response data may be processed. For instance, if the user insight response data includes acceptance of an offer, the offer may then be processed (e.g., funds transferred, agreements executed, and the like).

Figure 23H:
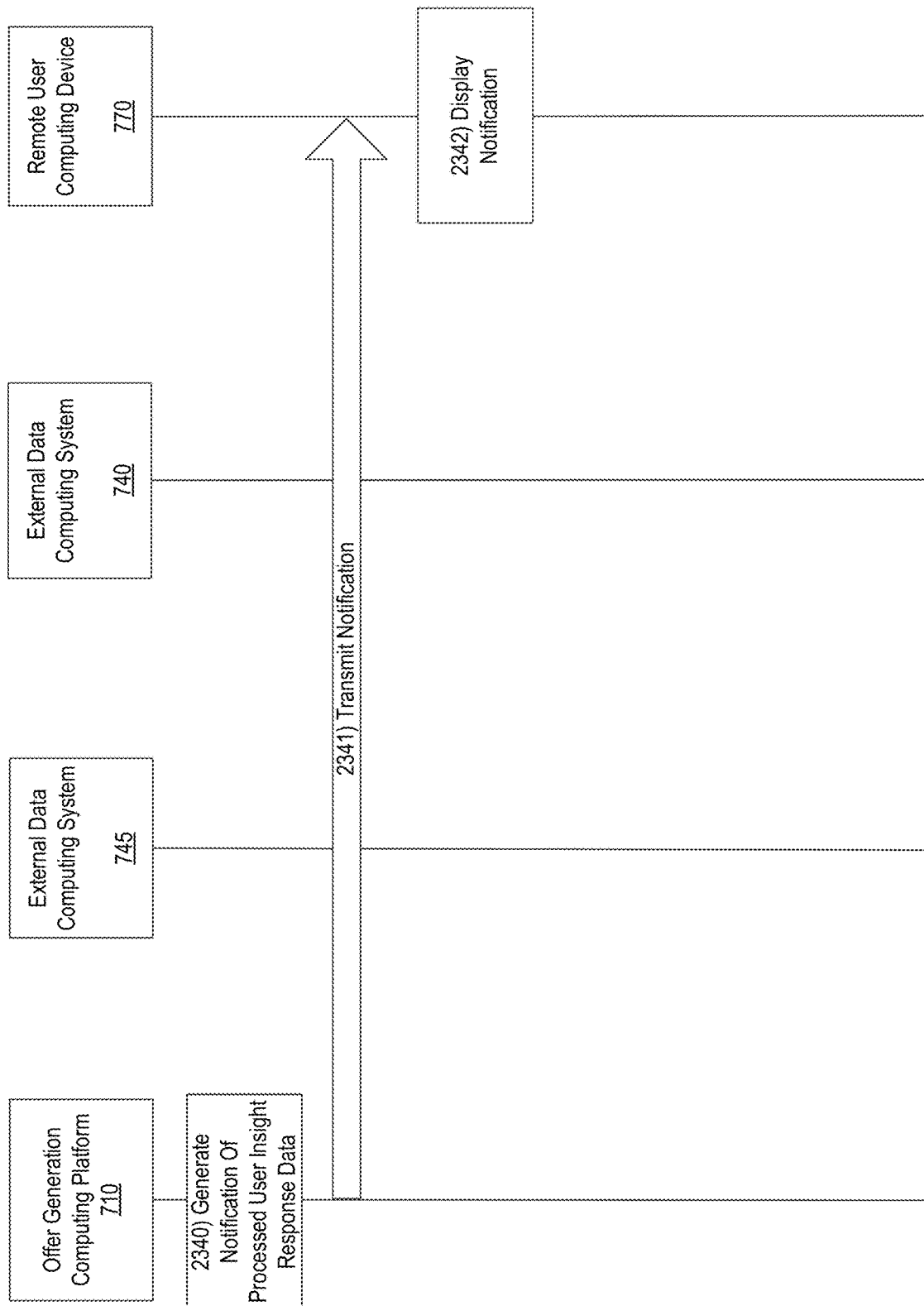

With reference to FIG. 23H, at step 2340, a notification of the processed user insight response data may be generated. For instance, the notification may include confirmation of acceptance of an offer, or the like. At step 2341, the notification may be transmitted to the remote user computing device 770. At step 2342, the notification may be displayed on a display of the remote user computing device.

Figure 24:
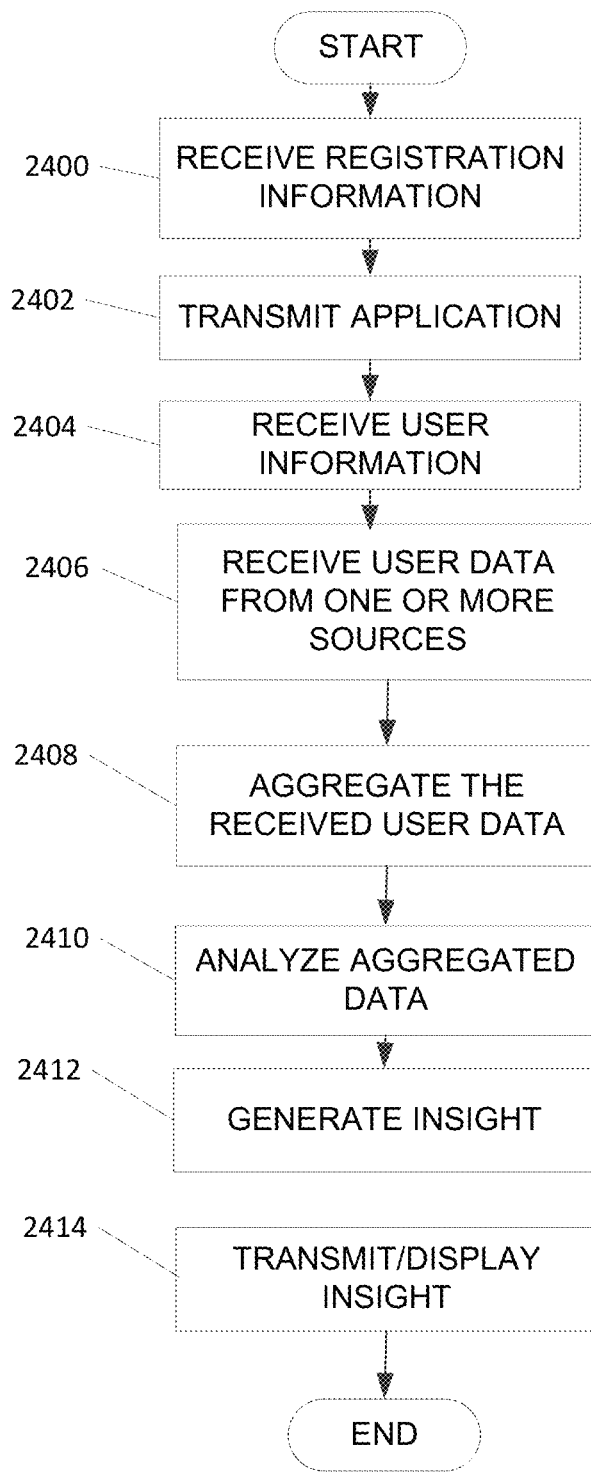
FIG. 24 illustrates another example flow chart for performing offer generation functions according to one or more aspects described herein.

FIG. 24 illustrates one example method of generating an offer or output according to one or more aspects described herein. The steps described with respect to FIG. 24 may be performed by one or more of the various devices and/or systems described herein, such as the offer generation computing platform 710, determination server 110, determination server 210, and the like. In some examples, one or more of the processes or steps described may be performed in real-time and the capture, transmission, use, and the like of user data is performed with user permissions. Further, the steps provided in FIG. 24 may be performed in the order shown, or in another order, without departing from the invention.

At step 2400, registration information may be received from, for instance, a mobile device of a user (e.g., remote user computing device 770). In some examples, the registration information may include a request for an offer or output, user identifying information such as name, contact information, and the like.

At step 2402, an application may be transmitted from the offer generation computing platform 710 to the remote user computing device 770. The application may be executed by the remote user computing device 770 to facilitate capture and transmission of data used to generate the offer or output.

At step 2404, user information may be received. Similar to other arrangements discussed herein, user information may include identification information, image data, demographic data, physical data, and the like.

At step 2406, user data may be received from one or more sources. For instance, similar to other arrangements discussed herein, data may be received from one or more external data sources, from the remote user computing device, such as a mobile device, smart watch, fitness tracker, or the like. In some examples, the data may include one or more of location data, purchase history data, financial transaction data, browser history data, fitness data, health or wellness data, and the like.

At step 2408, the received user data may be aggregated. For instance, data received from different sources may be formatted and/or aggregated for each of analysis.

At step 2410, the aggregated data may be analyzed. For instance, machine learning may be used to analyze the aggregated data to generate one or more outputs including offers, insights, and the like. At step 2412, one or more offers, insights, or other outputs may be generated. At step 2414, the generated outputs may be transmitted and displayed on a device, such as a mobile device of the user.

Figure 25:
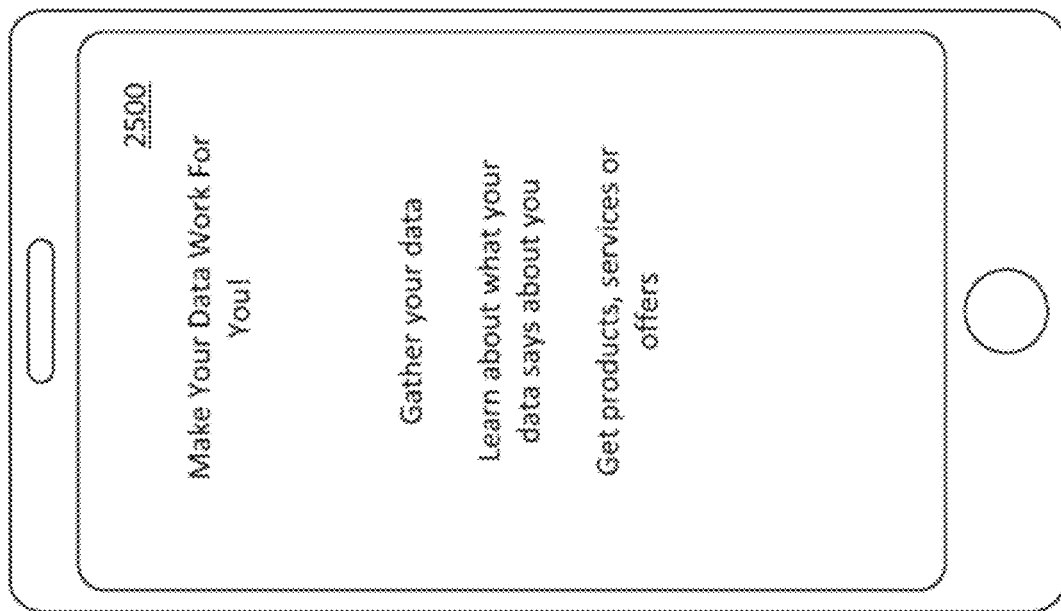

FIG. 25 illustrates one example user interface that may be generated by the offer generation computing platform 710. User interface 2500 includes one or more options available for selection and related to user data. For instance, a user may gather data (e.g., download data, upload data, generate an archive, or the like), learn about data insights (e.g., view data or portions of data, view summaries of data, and the like), and/or view products, services or offers (e.g., recommendations, incentives, and the like). A user may select one or more options and be prompted with one or more additional user interfaces, as discussed more fully herein (e.g., download data, view insights, and the like).

Figure 26:
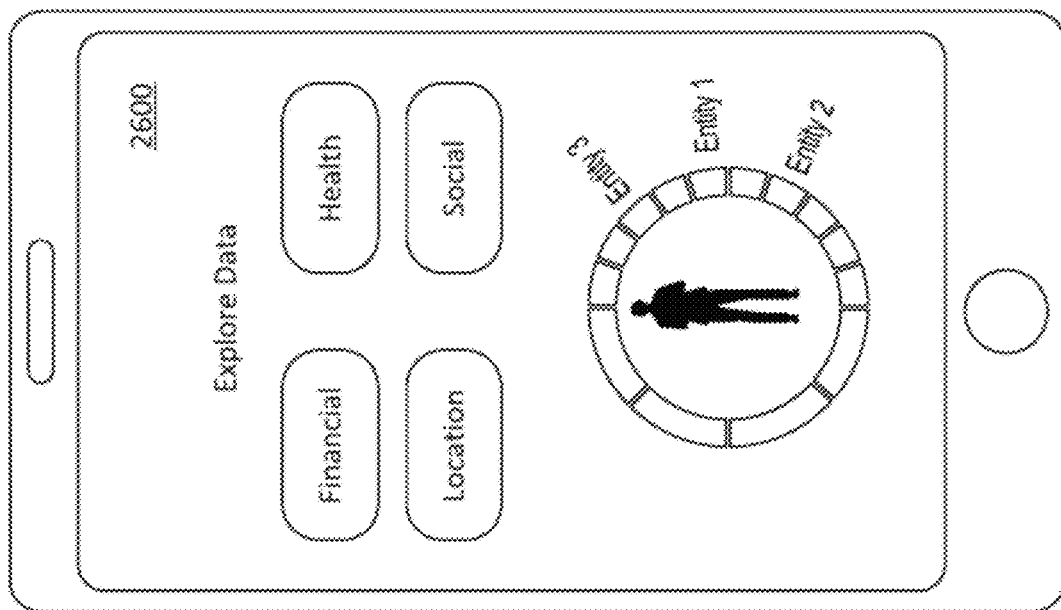
FIGS. 25-34 illustrate example user interfaces that may be generated and displayed in association with one or more processes or functions described herein.

FIG. 26 illustrates one example user interface 2600 showing types or categories of data available to explore. This arrangement may include the user's data hologram and may provide options to view data related to location, finances, health or fitness, social or social media, and the like. Although four options are provided, more or fewer options may be provided without departing from the invention.

Figure 27:
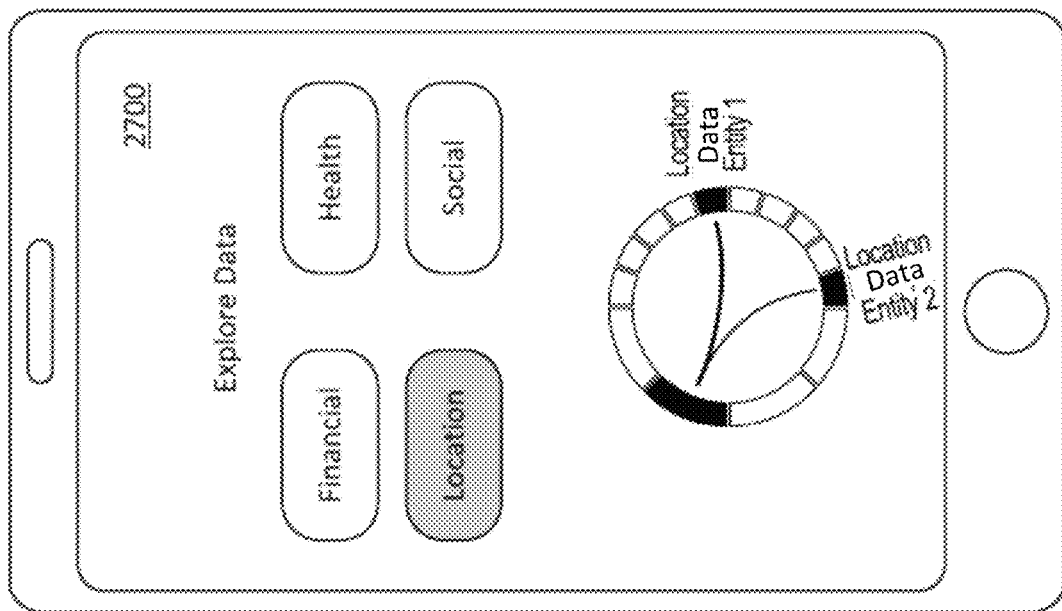

FIG. 27 illustrates one example user interface 2700 illustrating additional information related to location data. As shown, the data hologram provides additional information related to the source(s) of data collected in the location data category. Location data may be captured from a mobile device of a user (and, in some examples, stored by a third party), ride share application, and the like. The sources of the data may be identified on the user interface 2700.

Figure 28:
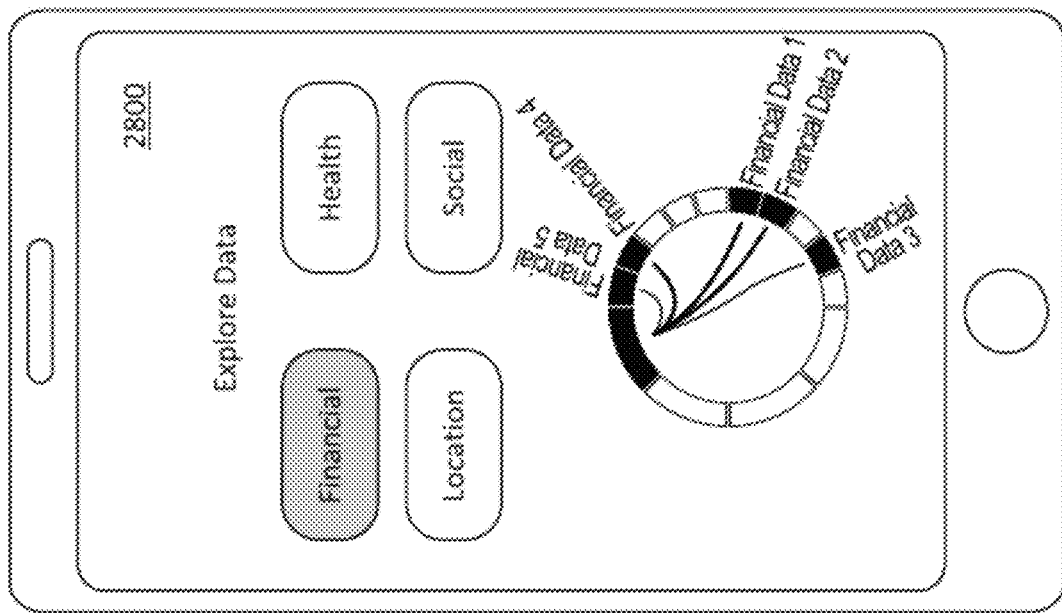

FIG. 28 illustrates one example user interface 2800 illustrating additional information related to financial data. As shown, the data hologram provides additional information related to the source(s) of data collected in the financial category. For instance, the sources may include a particular bank or financial institution associated with one or more credit or debit cards of the user, a mobile payment application, or the like.

Figure 29:
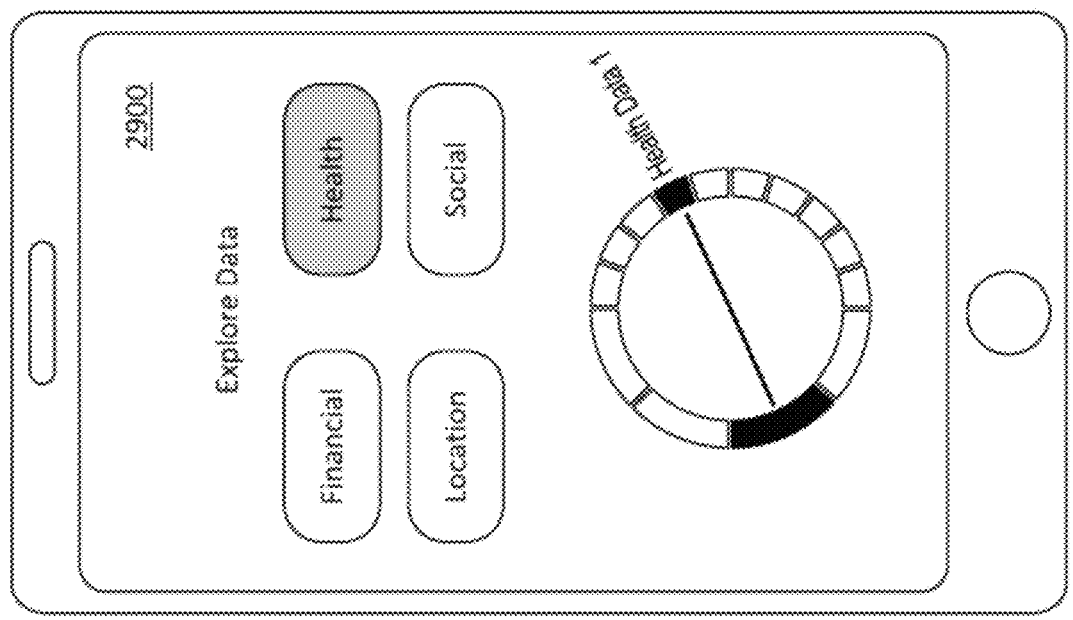

FIG. 29 illustrates one example user interface 2900 illustrating additional information related to health data. As shown, the data hologram may provide additional information related to source(s) of data collected in the health category. For instance, the source(s) of data may include a fitness tracker or other wearable device, health and wellness tracking application executing on a mobile device of a user, and the like. As discussed herein, the data used to generate the presented information may be obtained, analyzed, and the like, with her permissions and data being shared may be selected by the user (e.g., a user may share some times of data and not others, or the like).

Figure 30:
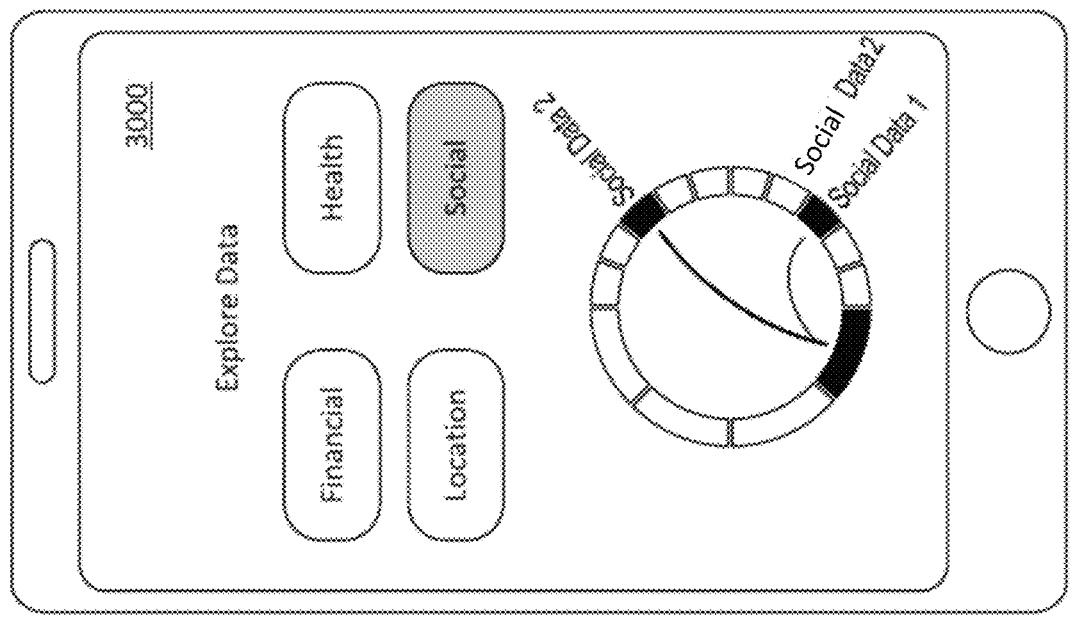

FIG. 30 illustrates one example user interface 3000 illustrating additional information related to social data. As shown, the data hologram may include additional information related to the source(s) of data collected in the social category. For instance, the source(s) of data may include one or more social media sites.

Figure 31:
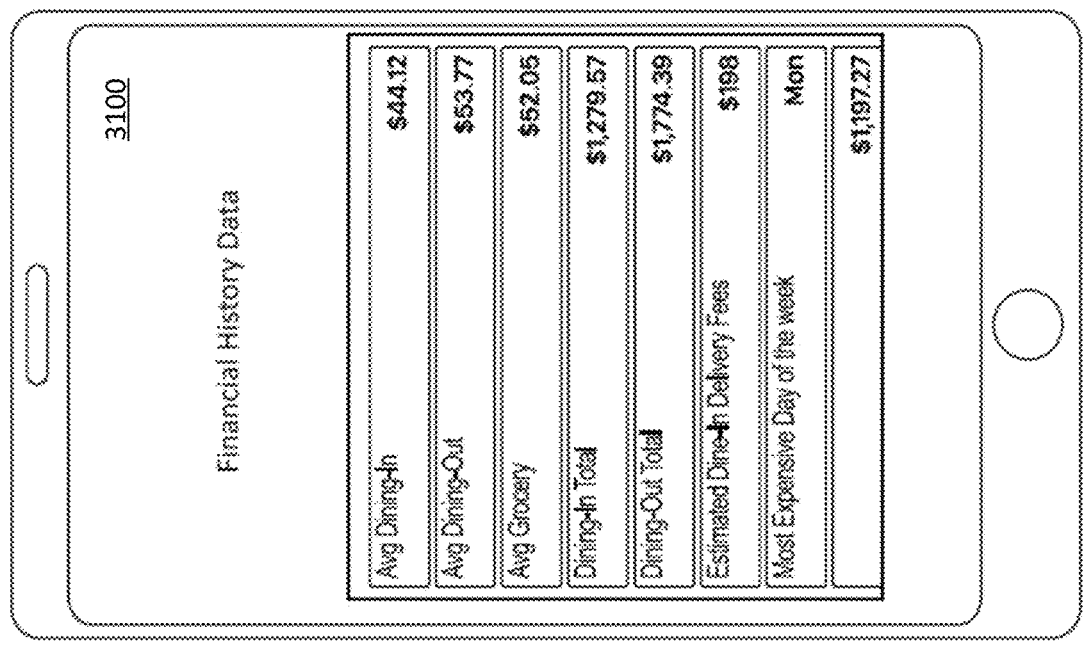

FIG. 31 illustrates one example user interface 3100 providing data summary information in a selected category. For instance, if a user selects a category, summary data may be provided. FIG. 31 illustrates financial summary data and provides data related to amounts spent on dining in, dining out, subscription services, groceries, average spent on dining in or out, food delivery fees, days of the week on which the most is spent, and the like.

Figure 32:
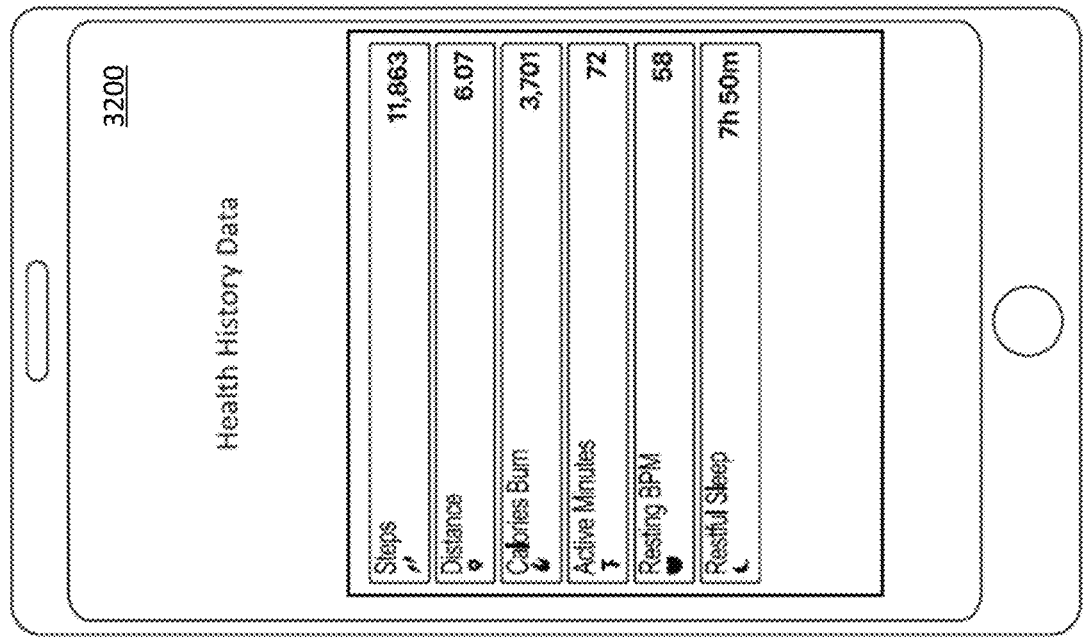

FIG. 32 illustrates one example user interface 3200 providing data summary information in a selected category. For instance, FIG. 32 may provide health summary history data related to steps, distance, calories burned, active minutes, heart rate (resting or other), restful sleep, and the like.

In some examples, data summary information may be presented for a particular time period (e.g., previous week, month, three months, or the like) or for a customized time period.

Figure 33:
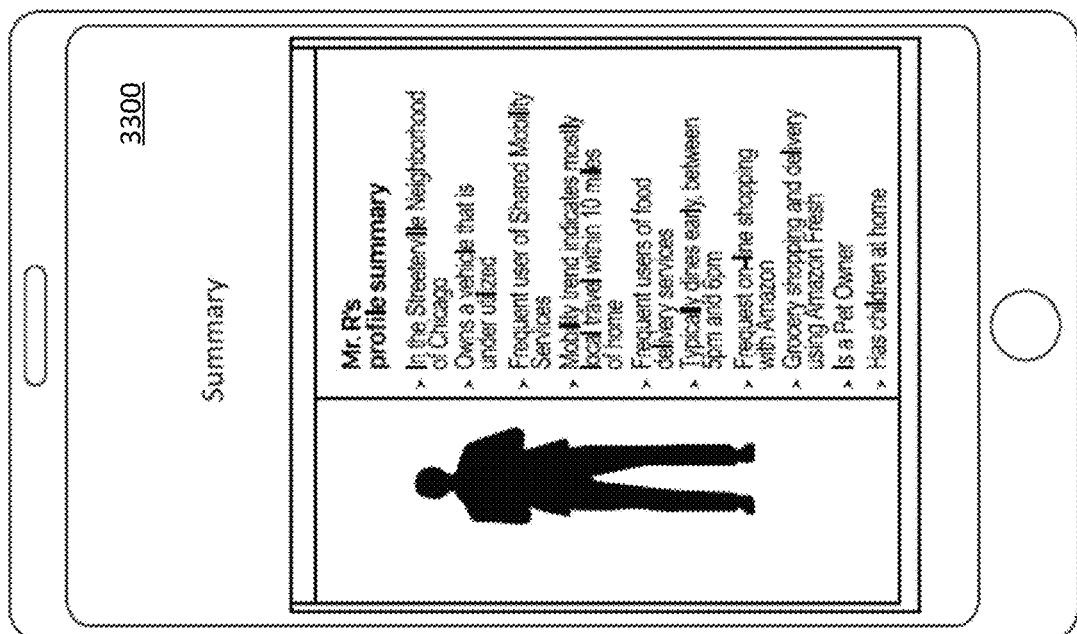

FIG. 33 illustrates one example user interface 3300 providing overall summary insight information related to a user. For instance, based on analysis of data across all categories, one or more insights may be generated about the user. Some example insights are shown in FIG. 33, however, more or fewer insights may be provided without departing from the invention.

Figure 34:
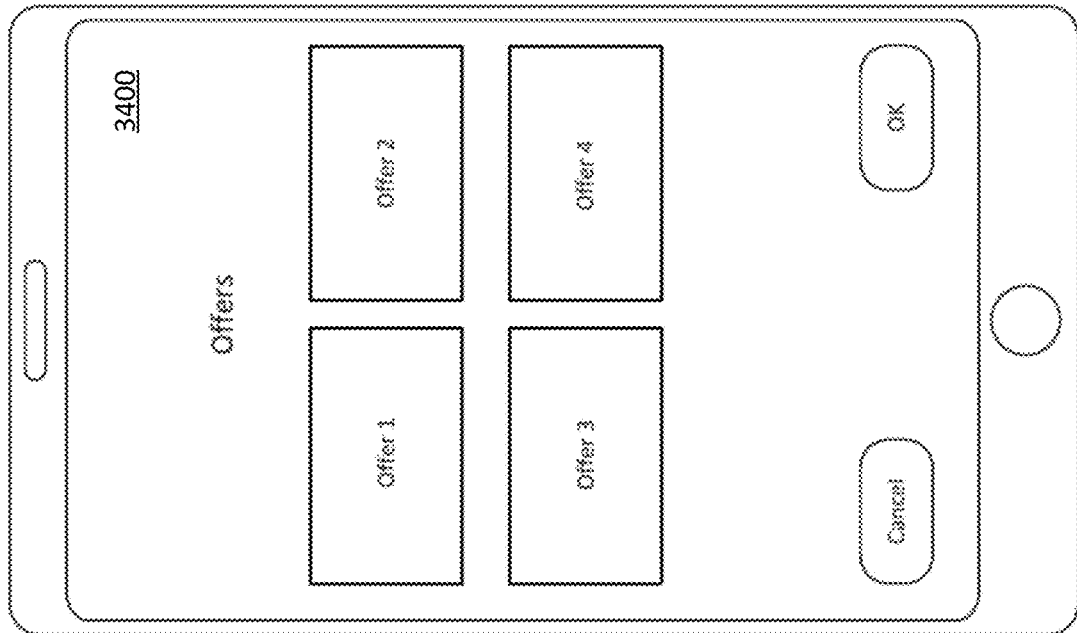

FIG. 34 illustrates one example user interface 3400 including example offers provided to the user. One or more offers for products, services, incentives, or the like, may be generated based on the user data and may be presented to the user via a user interface, such as interface 3400. Selection of one or more offers may prompt the offer generation computing platform 710 to process the selected offer.

As discussed herein, data may be received from one or more sources, may be aggregated and analyzed to generated one or more offers or insights for a user. In some examples, data may be received from various sources, such as a third party storing location data captured by a user device such as a mobile device, a third party storing financial transaction data or purchase history data, data from one or more applications executing on a mobile device, such as ride share applications, public transportation applications, and the like, data from one or more social media sites (e.g., from third party or mobile device), data from one or more fitness tracking devices or fitness tracking applications executing on a mobile device, or the like. The data may be captured, stored, retrieved, and the like, with user permissions, via one or more aspects or arrangements described herein.

As discussed herein, in some arrangements, an application executing on the mobile device may facilitate communication with one or more third party systems, transfer of data, and the like. In some examples, a user may be required to authenticate himself to the third party prior to retrieving data. In such arrangements, the application executing on the mobile device may direct the user to the third party authentication systems or interfaces and may not store or capture authenticating data of the user when authenticating to the third party.

In some arrangements, the application may provide various options for user actions. For instance, the application may include a user interface, such as interface 2500 in FIG. 25, that provides options to capture, gather or retrieve data, generate or view generated insights, view or select offers, and the like. Although three options are provided, various other options may be provided without departing from the invention.

Gathering, capturing or retrieving data may include selecting one or more types or sources of data. For instance, a plurality of sources may be provided, such as location data from a third party, data from the mobile device (e.g., health of fitness data), data from a fitness tracker, data from one or more financial institutions, ride share or other application data, or the like. The user may select one or more sources of data for analysis. In some examples, selection of a particular sources of data (e.g., a third party storing location data, web browsing data, payment application data, and the like) may prompt the user to select one or more types of data from that particular source. Accordingly, a user may customize the data being analyzed not just by sources but by type of data within or stored by a particular source. The data or type(s) of data being shared may also be selected by the user and controlled by the user (e.g., throughout the data capture, insight generation, and the like, process).

In some examples, selection of sources and/or types of data may prompt generation of a new user archive of data. The archive may be stored for a predetermined time period and then deleted upon expiration.

Analyzing the data may cause generation of a data hologram. The data hologram may include a plurality of categories of data. Selection of each category may prompt display of one or more sources of data within the category. The selected category may then provide options to display captured data. Display of captured data may include displaying aggregated data, insights into data, and the like. For instance, viewing location data may include identification of sources of the data as well as identification of frequently visited locations, maps showing frequent routes, total numbers of miles driven, time spent within a certain distance of a location, and the like. In some examples, data may further include identification of time, miles, or the like, spent on public transportation (e.g., by matching location data to public transportation datasets including routes, schedules, and the like), ride share (e.g., by identifying execution of a ride share application on a user device), and the like. In some arrangements, location data may be used to identify time spent in one or more particular locations (e.g., by zip code) which may then be used for further processing, such as for identifying work locations for tax purposes.

In another example, selection of viewing financial data may identify sources of the data (e.g., particular banks, particular payment services, mobile payment services, and the like) as well as data related to amounts spent in particular categories (e.g., dining out, groceries, food delivery fees, subscription costs, vehicle maintenance, shared mobility costs, and the like). In some examples, financial data may be captured directly from a financial institution or payment service, and/or from another third party that may capture the data directly from the processor or from other user-specific sources (e.g., with user permission).

In still another example, selection of health data may identify sources of the data (e.g., fitness tracker (e.g., steps, miles, and the like), health and wellness data from, for instance, mobile device, or the like), and the like. Viewing the data may include display of average time spent being active, average daily steps or miles, or the like.

In still another example, selection of social data may identify sources of data (e.g., particular social media sites), as well as metrics associated therewith (e.g., time spent on sites, interactions, and the like).

Based on the collected data and analysis thereof, user insights may be generated. The user insights may include identification of characteristics of a user (e.g., pet owner, owns a vehicle, frequently uses food delivery services, or the like).

In some examples, the insights may include prediction of user behaviors. For example, browser history and location history may indicate you are shopping for a new car. Accordingly, one or more offers may be generated. Further, the system may evaluate user mobility patterns to understand average cost per trip on ride share rides, how many miles do they typically drive, how often on public transportation, total cost of vehicle ownership, and the like. This mobility pattern may indicate that it may be more beneficial to not own a car and simply rely on public transportation or ride share. This insight may then be presented to the user.

The above example is merely one example insight arrangement. Other insights or types of insights may be generated without departing from the invention.

For instance, in some example, user data analysis may indicate that the user spends most of his or her food budget on food delivery services. In some examples, an offer or insight may be generated identifying one or more cost effective food delivery services. An offer or incentive to try the newly identified service may be generated, provided to the user and, if the user accepts, may be processed.

In some examples, the offer or incentive may include a payment of cash or other funds to the user. Accordingly, a deposit of the identified funds may be deposited in a user account (e.g., as provided by the user), in a digital wallet, or the like. In some examples, a balance may be maintained in a user account or digital wallet and the user may elect to withdrawn funds at any time.

In some examples, the system may provide an option to the user to donate the payment of cash or other funds to one or more charities. Accordingly, the user may select this option and the system (e.g., offer generation computing platform 710) may facilitate payment of the donation amount to the charity in a name of the user (e.g., may transfer funds, identify donor, provide donor contact information, or the like).

In some examples, the generated insights or offers may include offers for services not currently used by the user. For instance, detection of pet ownership may prompt an offer for pet insurance.

In some examples, the entity implementing the offer generation computing platform 710 may receive payment from one or more advertisers to present one or more offers. In these arrangements, the entity may share or present some or all of the payment to the user.

In some examples, a user may have an option to add one or more data sources via one or more user interfaces. For instance, upon display of the data hologram, the user may be presented with an option to add one or more sources of data. In another example, an interface presenting data hologram data for a particular category may include an option to add data from a source for that category. Selection of the option to add a data source may cause display of one or more other user interfaces including additional options, sources for selection, and the like.

Further, in some examples, the data hologram may present data extracted from one or more other data sources. For instance, in some examples, a third party data source may scan, with user permission, one or more user data sources to extract other user data. For instance, a third party system may scan user emails to identify and/or extract financial transaction data, shipping or online purchase data, reservation data (e.g., meals, airfare, hotels, and the like).

In some examples, a user may upload or otherwise provide data to the system. For instance, a user may upload a file (e.g., a PDF) including a credit card statement to provide additional financial data (e.g., in lieu of or in addition to capturing data from the financial institution directly). In some examples, the user may capture a photo of the document or file (e.g., via screen shot, mobile device image capture device, or the like) and may upload the photo to the system. The photo may be analyzed (e.g., using optical character recognition or other data recognition techniques) to extract the data, format the data, store the data, aggregate the data, or the like.

As discussed herein, data associated with a user may be captured and analyzed to generate one or more user insights, digital hologram, and the like. In some examples, the insights and/or data provided via the digital hologram may include data related to various themes, such as information or data that is sensitive, such as contact information, employment history, educational history, email address, birthdate, relationship status, and the like. This data may be captured and analyzed, and insights generated, with the permission of the user.

Another example theme may include things a user like. One or more aspects may include capturing user data from various sources, as discussed herein. The data may be indicative of things the user likes or enjoys. In some examples, insights and the like may be generated based on this data (and, in some examples, using machine learning) and may be displayed via a digital hologram as discussed herein. This data may be captured and analyzed, and insights generated, with the permission of the user.

Yet another example theme may include things a user buys. For example, data captured may include data associated with one or more purchases (e.g., based on internet history, financial transaction history, and the like). A history of purchases may be provided to a user, recommendations for items a user may wish to purchase, and the like, may be generated, as discussed herein. This data may be captured and analyzed, and insights generated, with the permission of the user.

Still another example theme may include how companies view a user or profile a user. For instance, purchase history, behavior history, location data, and the like may be analyzed to generated an estimate or assessment of how companies view a user. For instance, if a user frequently returns purchases, the user may be labeled as a chronic returner. In other examples, if a user has a low credit score, the user may be viewed as a credit risk. Various other insights may be generated and displayed within this theme without departing from the invention. This data may be captured and analyzed, and insights generated, with the permission of the user.

Another example theme may include things a user does. For instance, data associated with activities based on, for example, health and fitness data, location data, social media data, and the like, may be analyzed and insights may be generated and displayed to the user as discussed herein. In some examples, recommendations may be generated for the user. This data may be captured and analyzed, and insights generated, with the permission of the user.

Yet another example theme may include locations visited. As discussed herein, location data may be analyzed to provide historical insights into places a user has travelled, predictions or recommendations for the user, and the like. This data may be captured and analyzed, and insights generated, with the permission of the user.

As discussed herein, different types of data or categories of data, or the like, may be processed and/or evaluated using different machine learning techniques or algorithms that may be suited to a particular type of data, enable scalability and/or provide additional control to the user. Further, intelligent labels and annotations may be used to classify data to enable quick retention of the context of the data.

For instance, in one example, user travel data may be analyzed using a first machine learning technique or algorithm to identify and/or understand a user's daily commute and/or other frequent trips. If a user visits a grocery store every Tuesday, this data may be ingested as training data and annotated and/or labeled for ease of classification, comparison, or the like. This information may then be used to identify any changes in a travel pattern of a user (e.g., visiting the grocery store on a day other than Tuesday) based on, for example, one or more external factors.

In another example, social media data may be analyzed using a second machine learning technique or algorithm different from the first machine learning technique or algorithm described in the above example with respect to travel patterns. Social media data in a professional context may have different labels and/or annotations than social media data in a casual or family context. Accordingly, different types of social media data may be analyzed or used for analysis differently based on context of the data.

In another example, user spending data and date and/or time data may be analyzed using yet another, different machine learning technique. In some examples, purchase data such as items purchased, location of purchase, date and time of purchase, and the like, may be labeled or annotated in data to identify patterns of purchases. This data may then be used to generate one or more outputs, insights or recommendations for a user. For instance, if a user frequently purchases a gallon of milk on a weekend day each week but misses one weekend, the system may flag the anomaly from the pattern and generate a recommendation that the user purchase milk. The recommendation may be transmitted and displayed on a user device.

In some examples, one machine learning algorithm or technique may be used for a first purpose while a second, different machine learning algorithm or technique may be used for a second purpose. For instance, a first technique, such as unsupervised learning, may be used to discover patterns, categorize data, and the like, while a second, different technique, such as supervised learning, may be used to generate a particular output, insight, or the like. In some examples, a use case, type of data, category of data, or the like may be identified or determined and an algorithm or technique may be selected, used or implemented based on the determined use case, type of data, category of data, or the like.

In some examples, efficiently analyzing location data in accordance with one or more aspects described herein may be improved by creating a monolithic graph database including data related to public transportation (e.g., bus routes, train routes, schedules, transfer points, and the like), road networks, trail ways, bike routes, and the like. The location data may be used to efficiently search the graph to quickly identify a mode of transportation of a user at a given time.

Further, as aspects described herein are scaled to accommodate additional users, interpolation to complete datasets may be used. For instance, some devices, applications, and the like, might not efficiently or consistently capture longitude and latitude data of a user. Accordingly, when location data files are received, they may include location gaps in which longitude and latitude data are missing. Accordingly, machine learning and interpolation may be used to compare patterns in data, identify common trips and fill in any location gaps in the data.

The various arrangements described herein, for example, with respect to FIGS. 1-34, may be used in combination with one or more arrangements described herein (e.g., with respect to other figures, arrangements, or the like), without departing from the invention.

One or more aspects of the disclosure may be embodied in computer-usable data or computer-executable instructions, such as in one or more program modules, executed by one or more computers or other devices to perform the operations described herein. Generally, program modules include routines, programs, objects, components, data structures, and the like that perform particular tasks or implement particular abstract data types when executed by one or more processors in a computer or other data processing device. The computer-executable instructions may be stored as computer-readable instructions on a computer-readable medium such as a hard disk, optical disk, removable storage media, solid-state memory, RAM, and the like. The functionality of the program modules may be combined or distributed as desired in various embodiments. In addition, the functionality may be embodied in whole or in part in firmware or hardware equivalents, such as integrated circuits, Application-Specific Integrated Circuits (ASICs), Field Programmable Gate Arrays (FPGA), and the like. Particular data structures may be used to more effectively implement one or more aspects of the disclosure, and such data structures are contemplated to be within the scope of computer executable instructions and computer-usable data described herein.

Various aspects described herein may be embodied as a method, an apparatus, or as one or more computer-readable media storing computer-executable instructions. Accordingly, those aspects may take the form of an entirely hardware embodiment, an entirely software embodiment, an entirely firmware embodiment, or an embodiment combining software, hardware, and firmware aspects in any combination. Furthermore, such aspects may take the form of a computer program product stored by one or more computer-readable storage media having computer-readable program code, or instructions, embodied in or on the storage media. In addition, various signals representing data or events as described herein may be transferred between a source and a destination in the form of light or electromagnetic waves traveling through signal-conducting media such as metal wires, optical fibers, or wireless transmission media (e.g., air or space). In general, the one or more computer-readable media may be and/or include one or more non-transitory computer-readable media.

As described herein, the various methods and acts may be operative across one or more computing servers and one or more networks. The functionality may be distributed in any manner, or may be located in a single computing device (e.g., a server, a client computer, and the like). For example, in alternative embodiments, one or more of the computing platforms discussed above may be combined into a single computing platform, and the various functions of each computing platform may be performed by the single computing platform. In such arrangements, any and/or all of the above-discussed communications between computing platforms may correspond to data being accessed, moved, modified, updated, and/or otherwise used by the single computing platform. Additionally or alternatively, one or more of the computing platforms discussed above may be implemented in one or more virtual machines that are provided by one or more physical computing devices. In such arrangements, the various functions of each computing platform may be performed by the one or more virtual machines, and any and/or all of the above-discussed communications between computing platforms may correspond to data being accessed, moved, modified, updated, and/or otherwise used by the one or more virtual machines.

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one or more of the steps depicted in the illustrative figures may be performed in other than the recited order, one or more steps described with respect to one figure may be used in combination with one or more steps described with respect to another figure, and/or one or more depicted steps may be optional in accordance with aspects of the disclosure.

Various aspects described herein can be embodied as a method, an apparatus, or as one or more computer-readable media storing computer-executable instructions. Accordingly, those aspects can take the form of an entirely hardware embodiment, an entirely software embodiment, or an embodiment combining software and hardware aspects. Any and/or all of the method steps described herein can be embodied in computer-executable instructions stored on a computer-readable medium, such as a non-transitory computer readable medium. Any and/or all of the method steps described herein can be embodied in computer-readable instructions stored in the memory of an apparatus that includes one or more processors, such that the apparatus is caused to perform such method steps when the one or more processors execute the computer-readable instructions. In addition, various signals representing data or events as described herein can be transferred between a source and a destination in the form of light and/or electromagnetic waves traveling through signal-conducting media such as metal wires, optical fibers, and/or wireless transmission media (e.g., air and/or space).

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one of ordinary skill in the art will appreciate that the steps illustrated in the illustrative figures can be performed in other than the recited order, and that one or more steps illustrated can be optional in accordance with aspects of the disclosure. Further, one or more aspects described with respect to one figure or arrangement can be used in conjunction with other aspects associated with another figure or portion of the description.

The invention claimed is:

1. A computing platform, comprising:
a processing unit comprising a processor;
a communication interface; and
a memory unit storing computer-executable instructions that, when executed by the processing unit, cause the computing platform to:
receive a request to generate a customized output;
generate an instruction to capture physical trait data of a user;
transmit the instruction to a mobile device of the user;
receive, from the mobile device, the captured physical trait data, wherein the physical trait data is captured via one or more sensors of the mobile device;
receive, from the mobile device, one or more mobility patterns of the user based on one or more patterns of driving location;
receive, from one or more sensors of a vehicle associated with the user, vehicle performance data corresponding to maneuvers performed by the vehicle while being driven by the user;
apply machine learning to the received captured physical trait data, the one or more mobility patterns of the user, and the received vehicle performance data to determine a pattern of decision making behavior made by the user while interacting with the vehicle at specific locations;
determine a risk profile based on the pattern of decision making behavior;
generate the customized output to include a set of options that correspond to the risk profile of the user;
generate a user interface including the customized output; and
transmit the user interface to the mobile device for display on a display of the mobile device.

2. The computing platform of claim 1, wherein the captured physical trait data is captured by one or more biometric sensors.

3. The computing platform of claim 1, wherein the instruction to capture physical trait data of the user includes a request for the user to perform an activity with the mobile device.

4. The computing platform of claim 1, wherein the set of options of the customized output includes one or more offers.

5. The computing platform of claim 1, further including instructions that, when executed, cause the computing platform to:
authenticate the user, including:
transmitting a request for the user to capture an image of a photographic identification;
receiving a captured image of the photographic identification, wherein the captured image is geo-tagged with a location;
transmitting a request for the user to self-capture an image;
receiving the self-captured image, wherein the self-captured image is also geo-tagged with a location; and
comparing the image of the photographic identification to the self-captured image using facial recognition to determine whether the user is authenticated.

6. The computing platform of claim 1, wherein the one or more patterns of driving location is based on at least location data including a plurality of location entries corresponding to movement of the user with the mobile device, and further comprising validating the physical trait data based on the location data.

7. The computing platform of claim 1, wherein additional user data to generate the risk profile includes at least one of: medical data of the user, prescription data of the user, sensor data, and device usage data associated with the user of the mobile device.

8. A computing device, comprising:
a processing unit comprising a processor;
a communication interface; and
a memory unit storing computer-executable instructions, which when executed by the processing unit, cause the computing device to:
execute an application on the computing device, executing the application including:
initiating a communication session with a computing platform via the communication interface;
displaying, by a display of the computing device, instructions for capturing one or more physical traits of a user;
capturing, via one or more sensors in the computing device, the one or more physical traits of the user and driving location;
transmitting, to the computing platform, the captured one or more physical traits of the user and one or more mobility patterns associated with the user based on one or more patterns of the driving location;
receiving, from the computing platform, a user interface including a generated customized output that includes a set of options corresponding to a risk profile based on a pattern of decision making behavior made by the user while interacting with a vehicle at specific locations, wherein the pattern of decision making behavior is determined based on the captured one or more physical traits, the one or more mobility patterns of the user, and vehicle performance data received from one or more sensors of the vehicle associated with the user corresponding to maneuvers performed by the vehicle while being driven by the user; and
displaying, by a display of the computing device, the received user interface.

9. The computing device of claim 8, wherein the one or more patterns of driving location is based on at least location data of the user including a plurality of location entries corresponding to movement of the user performed with the computing device, and further comprising validating the one or more physical traits based on the location data.

10. The computing device of claim 8, wherein the one or more physical traits of the user include one or more of: blood pressure, heart rate, and pulse.

11. The computing device of claim 8, wherein the instructions for capturing one or more physical traits of the user include instructions to capture one or more images of the user wherein the one or more images are geo-tagged with a location.

12. The computing device of claim 11, wherein capturing one or more images of the user includes executing the application to control an image capture device of the computing device.

13. The computing device of claim 8, wherein the instructions for capturing one or more physical traits of the user include instructions to perform a predefined activity for a predefined time period with the computing device.

14. The computing device of claim 13, wherein the instructions to perform the predefined activity for the predefined time period further including instructions to capture a heart rate of the user at a start of the predefined time period and at an end of the predefined time period.

15. A method, comprising:
by a computing device having at least one processor, a communication interface and a memory storing instructions that, when executed by the at least one processor, cause the processor to:
execute an application on the computing device, executing the application including:
initiating a communication session with a computing platform via the communication interface;
displaying, by a display of the computing device, instructions for capturing one or more physical traits of a user;
capturing, via one or more sensors in the computing device, the one or more physical traits of the user and driving location;
transmitting, to the computing platform, the captured one or more physical traits of the user and one or more mobility patterns associated with the user based on one or more patterns of the driving location;
receiving, from the computing platform, a user interface including a generated customized output that includes a set of options corresponding to a risk profile based on a pattern of decision making behavior made by the user while interacting with a vehicle at specific locations, wherein the pattern of decision making behavior is determined based on the captured one or more physical traits, the one or more mobility patterns of the user, and vehicle performance data received from one or more sensors of the vehicle associated with the user corresponding to maneuvers performed by the vehicle while being driven by the user; and
displaying, by a display of the computing device, the received user interface.

16. The method of claim 15, wherein the one or more patterns of driving location is based on at least location data of the user including a plurality of location entries corresponding to movement of the user performed with the computing device, and further comprising validating the one or more physical traits based on the location data.

17. The method of claim 15, wherein the one or more physical traits of the user include one or more of: blood pressure, heart rate, and pulse.

18. The method of claim 15, wherein the instructions for capturing one or more physical traits of the user include instructions to capture one or more images of the user wherein the one or more images are geo-tagged with a location.

19. The method of claim 18, wherein capturing one or more images of the user includes executing the application to control an image capture device of the computing device.

20. The method of claim 15, wherein the instructions for capturing one or more physical traits of the user include instructions to perform a predefined activity for a predefined time period with the computing device.

* * * * *